US012533523B2

(12) United States Patent
Stevenson et al.

(10) Patent No.: US 12,533,523 B2
(45) Date of Patent: Jan. 27, 2026

(54) HIGH-VOLTAGE ELECTRICALLY INSULATING DESIGNS FOR USE IN ACTIVE IMPLANTABLE MEDICAL DEVICES

(71) Applicant: Greatbatch Ltd., Clarence, NY (US)

(72) Inventors: Robert A. Stevenson, Canyon Country, CA (US); Christine A. Frysz, Orchard Park, NY (US); Keith W. Seitz, Clarence Center, NY (US); Thomas Marzano, East Amherst, NY (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 221 days.

(21) Appl. No.: 18/377,030

(22) Filed: Oct. 5, 2023

(65) Prior Publication Data

US 2024/0115867 A1 Apr. 11, 2024

Related U.S. Application Data

(60) Provisional application No. 63/414,102, filed on Oct. 7, 2022.

(51) Int. Cl.
*A61N 1/375* (2006.01)

(52) U.S. Cl.
CPC .................................. *A61N 1/3754* (2013.01)

(58) Field of Classification Search
None
See application file for complete search history.

(56) References Cited

U.S. PATENT DOCUMENTS

| | | | |
|---|---|---|---|
| 3,137,808 | A | 6/1964 | Coda et al. |
| 5,333,095 | A | 7/1994 | Stevenson et al. |
| 5,489,180 | A | 2/1996 | Ichihara et al. |
| 5,751,539 | A | 5/1998 | Stevenson et al. |
| 5,896,267 | A | 4/1999 | Hittman et al. |
| 5,905,627 | A | 5/1999 | Brendel et al. |
| 5,973,906 | A | 10/1999 | Stevenson et al. |
| 5,978,204 | A | 11/1999 | Stevenson |
| 6,529,103 | B1 | 3/2003 | Brendel et al. |
| 6,765,779 | B2 | 7/2004 | Stevenson et al. |
| 6,765,780 | B2 | 7/2004 | Brendel et al. |
| 6,882,248 | B2 | 4/2005 | Stevenson et al. |
| 7,797,048 | B2 | 9/2010 | Stevenson et al. |
| 7,878,747 | B2 | 2/2011 | Dean et al. |
| 7,957,806 | B2 | 6/2011 | Stevenson et al. |
| 8,047,753 | B2 | 11/2011 | Dean et al. |
| 8,095,224 | B2 | 1/2012 | Truex et al. |
| 8,179,658 | B2 | 5/2012 | Stevenson et al. |
| 8,195,295 | B2 | 6/2012 | Stevenson et al. |
| 8,321,032 | B2 | 11/2012 | Frysz et al. |

(Continued)

FOREIGN PATENT DOCUMENTS

EP 3449973 A1 3/2019

*Primary Examiner* — Michael W Kahelin
(74) *Attorney, Agent, or Firm* — Michael F. Scalise

(57) ABSTRACT

The high-voltage and/or high-frequency pulse dielectric breakdown strength (DBS) of an implantable medical device is increased by strategically positioning insulation materials on or adjacent to the external surfaces of a filter capacitor. Dielectric breakdown strength is further increased by adding polymeric or ceramic nanoscale metal oxide insulative powders to the insulation materials.

17 Claims, 92 Drawing Sheets

(56) References Cited

U.S. PATENT DOCUMENTS

| | | | |
|---|---|---|---|
| 8,433,410 B2 | 4/2013 | Dabney et al. | |
| 8,437,865 B2 | 5/2013 | Dabney et al. | |
| 8,483,840 B2 | 7/2013 | Stevenson et al. | |
| 8,604,341 B2 | 12/2013 | Barry et al. | |
| 8,653,384 B2 | 2/2014 | Tang et al. | |
| 8,670,841 B2 | 3/2014 | Dabney et al. | |
| 8,712,544 B2 | 4/2014 | Dabney et al. | |
| 8,761,895 B2 | 6/2014 | Stevenson et al. | |
| 8,855,768 B1 | 10/2014 | Dabney et al. | |
| 8,868,189 B2 | 10/2014 | Stevenson et al. | |
| 8,918,189 B2 | 12/2014 | Dabney et al. | |
| 8,927,862 B2 | 1/2015 | Barry et al. | |
| 8,938,309 B2 | 1/2015 | Marzano et al. | |
| 8,996,126 B2 | 3/2015 | Stevenson et al. | |
| 9,014,808 B2 | 4/2015 | Dabney et al. | |
| 9,031,670 B2 | 5/2015 | Dabney et al. | |
| 9,064,640 B2 | 6/2015 | Brendel et al. | |
| 9,071,221 B1 | 6/2015 | Stevenson et al. | |
| 9,233,253 B2 | 1/2016 | Stevenson et al. | |
| 9,352,150 B2 | 5/2016 | Stevenson et al. | |
| 9,427,596 B2 | 8/2016 | Brendel et al. | |
| 9,447,810 B2 | 9/2016 | Dean et al. | |
| 9,463,329 B2 | 10/2016 | Frysz et al. | |
| 9,492,659 B2 | 11/2016 | Brendel et al. | |
| 9,511,220 B2 | 12/2016 | Marzano et al. | |
| 9,521,744 B2 | 12/2016 | Barry et al. | |
| 9,757,558 B2 | 9/2017 | Stevenson et al. | |
| 9,764,129 B2 | 9/2017 | Stevenson et al. | |
| 9,889,306 B2 | 2/2018 | Stevenson et al. | |
| 9,895,534 B2 | 2/2018 | Stevenson et al. | |
| 9,931,514 B2 | 4/2018 | Frysz et al. | |
| 9,993,650 B2 | 6/2018 | Seitz et al. | |
| 10,016,595 B2 | 7/2018 | Stevenson et al. | |
| 10,016,596 B2 | 7/2018 | Stevenson et al. | |
| 10,046,166 B2 | 8/2018 | Stevenson et al. | |
| 10,080,889 B2 | 9/2018 | Marzano et al. | |
| 10,092,749 B2 | 10/2018 | Stevenson et al. | |
| 10,099,051 B2 | 10/2018 | Stevenson et al. | |
| 10,124,164 B2 | 11/2018 | Stevenson et al. | |
| 10,249,415 B2 | 4/2019 | Seitz et al. | |
| 10,272,252 B2 | 4/2019 | Seitz et al. | |
| 10,272,253 B2 | 4/2019 | Seitz et al. | |
| 10,306,848 B2 | 6/2019 | Chan et al. | |
| 10,350,421 B2 | 7/2019 | Stevenson et al. | |
| 10,420,949 B2 | 9/2019 | Seitz et al. | |
| 10,449,375 B2 | 10/2019 | Frustaci et al. | |
| 10,499,375 B2 | 12/2019 | Jung et al. | |
| 10,500,402 B2 | 12/2019 | Stevenson et al. | |
| 10,559,409 B2 | 2/2020 | Seitz et al. | |
| 10,561,837 B2 | 2/2020 | Stevenson et al. | |
| 10,589,107 B2 | 3/2020 | Seitz et al. | |
| 10,596,369 B2 | 3/2020 | Stevenson et al. | |
| 10,722,706 B2 | 7/2020 | Stevenson et al. | |
| 10,828,498 B2 | 11/2020 | Stevenson et al. | |
| RE48,348 E | 12/2020 | Stevenson | |
| 10,857,369 B2 | 12/2020 | Stevenson et al. | |
| 10,874,866 B2 | 12/2020 | Stevenson et al. | |
| 10,905,888 B2 | 2/2021 | Stevenson et al. | |
| 10,912,945 B2 | 2/2021 | Stevenson et al. | |
| 11,013,928 B2 | 5/2021 | Stevenson et al. | |
| 11,071,858 B2 | 7/2021 | Stevenson et al. | |
| 11,147,977 B2 | 10/2021 | Stevenson et al. | |
| 11,185,705 B2 | 11/2021 | Stevenson et al. | |
| 11,198,014 B2 | 12/2021 | Stevenson et al. | |
| 11,211,741 B2 | 12/2021 | Marzano et al. | |
| 11,241,581 B2 | 2/2022 | Stevenson et al. | |
| 11,344,734 B2 | 5/2022 | Stevenson et al. | |
| 11,406,817 B2 | 8/2022 | Stevenson et al. | |
| 11,633,612 B2 | 4/2023 | Frysz et al. | |
| 11,648,408 B2 | 5/2023 | Hussein | |
| 11,764,745 B2 | 9/2023 | Sahabi et al. | |
| 2009/0080140 A1 | 3/2009 | Iyer et al. | |
| 2014/0094885 A1* | 4/2014 | Meffin ................ | A61N 1/3754 29/874 |

* cited by examiner

BODY FLUID SIDE

ATTENUATION VS. FREQUENCY

DEVICE SIDE

BODY FLUID SIDE

TABLE 1

| Insulating Polymer | | Nanoparticle Filler | | | | | |
|---|---|---|---|---|---|---|---|
| neat epoxy (no filler) | | alumina/untreated | | alumina/APS modifed | | alumina/HPB modifed | |
| | | Particle Size (600 nm - 800 nm) | | Particle Size (100 nm - 200 nm) | | Particle Size (100 nm - 200 nm) | |
| Concentration (wt. %) | Insulating Polymer Breakdown Strength (kV/mm) | Concentration (wt. %) | Insulating Polymer Breakdown Strength (kV/mm) | Concentration (wt. %) | Insulating Polymer Breakdown Strength (kV/mm) | Concentration (wt. %) | Insulating Polymer Breakdown Strength (kV/mm) |
| 0 | 30.7 | 5 | 28.5 | 5 | 29.9 | 5 | 31.3 |
| 0 | 30.7 | 10 | 27.4 | 10 | 28.6 | 10 | 31.9 |
| 0 | 30.7 | 15 | 27.1 | 15 | 27.5 | 15 | 31.3 |
| 0 | 30.7 | 20 | 25.1 | 20 | 25.9 | 20 | 31.5 |

FIG. 53C

TABLE 2

| Alumina-Epoxy Composite Insulating Polymer<br>DBS = 156 kV/mm and Thermal Conductivity = 0.874 W/mK<br>(60 wt % alumina with 4 μm average alumina particle size) | | | | |
|---|---|---|---|---|
| Nanoparticle Filler | Avg. Particle Size (nm) | Concentration (Vol. %) | Insulating Polymer Breakdown Strength (kV/mm) | Insulating Polymer Thermal Conductivity (W/mK) |
| cubic boron nitride | 150 | 0.2 | 163 | 0.914 |
| hexagonal boron nitride | 70 | 0.2 | 193 | 0.904 |
| hexagonal boron nitride | 70 | 0.6 | 176 | 0.922 |

FIG. 53D

GRAPH 1

GRAPH 2

| Element No. | Description | Symbol |
|---|---|---|
| | | |
| 360 | No polymer insulating material in this location | 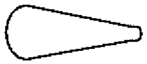 |
| | | |
| 353 | Uncured (flowable) insulating nanoparticle filled polymer insulating material | |
| 359 | Location for placing uncured (flowable) insulating nanoparticle filled polymer insulating material | 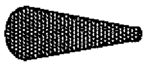 |
| 379 | Cured (solid) insulating nanoparticle filled polymer insulating material | |
| | | |
| 354 | Uncured (flowable) polymer insulating material without insulating nanoparticle fill | |
| 358 | Location for placing uncured (flowable) polymer insulating material without insulating nanoparticle fill |  |
| 378 | Cured (solid) polymer insulating material without insulating nanoparticle fill | |
| | | |

FIG. 64C (TOP VIEW OF DEVICE SIDE)

HIGH-VOLTAGE ELECTRICALLY INSULATING DESIGNS FOR USE IN ACTIVE IMPLANTABLE MEDICAL DEVICES

CROSS-REFERENCE TO RELATED APPLICATION

This application claims priority to U.S. provisional application Ser. No. 63/414,102, filed on Oct. 7, 2022, the content of which is fully incorporated herein by this reference.

FIELD OF THE INVENTION

The present invention generally relates to active implantable medical devices, including insulating components, hermetic seal terminal subassemblies, header connector blocks, AIMD circuit board connectors, and EMI filtered hermetic terminal subassemblies and various types of insulation, including the novel addition of nano-scale metal oxide or polymeric insulating powders to the insulation material. In general, the present invention teaches increasing the high-voltage dielectric breakdown strength of all the aforementioned AIMD parts and subassemblies.

Definitions

An "active implantable medical device (AIMD)" is defined as a special type of implantable medical device that is implanted within a human body and includes electronic circuits powered by an energy source, such as a primary or a secondary battery, energy induced by motion, thermal or chemical effects, or energy produced through external induction.

Regarding implantable medical devices, the term "active" means that the implantable medical device has at least one electronic circuit and an energy source, such as a primary battery, a secondary battery, a wireless energy source or a connected energy source.

An "implantable lead" refers to an electrically conductive structure having a distal electrode, a proximal terminal that connects to an implantable device, and a lead body that connects therebetween. The lead body consists of a flexible insulating tube or cylinder with at least one longitudinal lumen through which at least one implantable lead electrical conductor extends from the proximal terminal to the distal electrode. The at least one "implantable lead electrical conductor" allows electric current to flow.

A "conductive pathway" is defined as a conduction path for electrical current flow. The conductive pathway is an electrical conductor consisting of a lead, a wire, a lead wire, a terminal pin, a circuit trace, an electrical circuit, a fired electrically conductive structure, a co-fired electrically conductive structure, a paste filled via, a sintered filled via, a sintered paste filled via, a sintered electrically conductive material, a co-sintered filled via, a co-sintered paste filled via, a conductive co-sintered filled via, a composite conductive sintered paste filled via, and combinations thereof. Conductive pathways are typically hermetically sealed to a ceramic body by a brazing process, a co-firing process, or a co-sintering process.

The terms "lead", "wire", "lead wire", "terminal pin", and "terminal pin" are used interchangeably throughout this specification, and are further defined herein as electrical conductors having 100% density. In other words, they are solid electrical conductors. While each of the above may have unique structural features, they are all solid electrical conductors, each of which may be used alternatively to each other or in combination with each other, in any application requiring one or more conductive pathways, for example, but not limited to, a feedthrough for an implantable medical device. As such, the terms "lead", "wire", "lead wire", and "terminal pin", all being solid electrical conductors, are used interchangeably throughout this specification. It is understood that any number of the above named solid electrical conductors, in any combination, may be used in an application. Additionally, it is noted that the above solid electrical conductors are typically hermetically sealed to a ceramic body by either a brazing process or a co-firing process.

The terms "paste filled via", "sintered filled via", "sintered paste filled via", "sintered electrically conductive material", "co-sintered filled via", "co-sintered paste filled via" are all electrically conductive pathways formed using a co-sinter process. The fill material for the co-sintered filled via of the present patent application comprises an electrically conductive flowable medium selected from the group of a powder, an ink, a paste, a gel, or an otherwise electrically conductive sinterable material. During the co-sintering process, particles of the flowable medium densify and fuse without melting to the point of liquefaction (i.e., becoming a liquid) to form an electrical conductor having density <100%. In other words, they are a fused solid electrical conductor. While each of the above may have unique formulations, after co-sintering, they are all fused solid electrical conductors, each of which may be used alternatively to each other or in combination with each other, in any application requiring one or more conductive pathways, for example, but not limited to, a feedthrough for an implantable medical device. As such, the terms "paste filled via", "sintered filled via", "sintered paste filled via", "sintered electrically conductive material", "co-sintered filled via", "co-sintered paste filled via", and "conductive co-sintered filled via", all being fused solid electrical conductors, are used interchangeably throughout this specification. It is understood that any number of the above named fused solid electrical conductors, in any combination, may be used in an application. Additionally, it is noted that the above fused solid electrical conductors are typically hermetically sealed to a ceramic body by a co-sintering process.

Further regarding the term "conductive pathways", it is anticipated that solid electrical conductors and fused solid electrical conductors may be used in combination and in any numbers with each other for an application. For example, when both solid electrical conductors and fused solid electrical conductors are formed in a single ceramic body, the forming process includes co-firing the solid electrical conductors while at the same time co-sintering the conductive flowable medium to form a ceramic body comprising conductive paths, wherein at least one of the conductive paths is a solid electrical conductor, or at least one of the conductive paths is a fused solid electrical conductor. It is also anticipated that a solid electrical conductor and a fused solid electrical conductor may be integrated, which is herein defined as "a hybrid conductive pathway". Hybrid conductive pathways are formed by a co-firing process, whereby the conductive flowable medium sinters during the co-firing process, thereby capturing a solid electrical conductor in, on or adjacent to the resultant fused solid electrical conductor.

Regarding electrical connections, the term "active" refers to an electrically active conductive pathway as opposed to a system grounded connection. The electrically active conductive pathway extends through an AIMD feedthrough insulator to the feedthrough insulator body fluid and device sides in insulative relationship with either the ferrule or the housing of the AIMD. Active conductive pathways may conduct therapeutic pacing pulses, biological sensing signals or even high-voltage therapeutic shocks. For a neurostimulator application, such as, but not limited to, a spinal cord stimulator, electrically active conductive pathways may conduct, for example, AC, pulse, or triangular waveforms, in addition to many other different types of waveforms. The electrically active conductive pathway includes any of the solid and fused solid electrical conductors listed in the above definitions.

A feedthrough conductive co-sintered filled via passes through a feedthrough insulator. When the feedthrough insulator is hermetically sealed to a ferrule or a device housing, the conductive co-sintered filled via of the feedthrough insulator is in nonconductive relation with a feedthrough ferrule or a device housing. The conductive co-sintered filled via acts electrically in the same manner as the previously disclosed solid electrical conductors. The conductive co-sintered filled via may optionally incorporate a co-fired component, such as, but not limited to, a wire, a lead, a terminal pin, a ribbon, a screw, a connector, a nail head, or a custom designed attachment structure.

A "brazing process" is defined as a hermetic sealing process by which a solid electrical conductor is hermetically sealed to a ceramic body by means of a braze material.

A "braze material" is defined as a metal or alloy in the form of a wire, a preform, a compressed nano-material having a lower melting temperature than either of the parts to be sealed. Upon melting, the braze material metallurgically wets the surface of each part. Upon cooling, the braze solidifies to form a hermetic seal therebetween. The braze material may be selected from the group of gold, a gold-containing alloy, platinum, a platinum-containing alloy, palladium, a palladium-containing alloy, iridium, an iridium-containing alloy, germanium, a germanium-containing alloy, and combinations thereof.

A "co-fire process" is defined as a hermetic sealing process by which an entire ceramic body and any solid electrical conductors are fired at the same time in order to form a monolithic structure comprising at least one hermetically sealed electrically conductive pathway adhered directly to the ceramic body.

A "co-sinter process" is defined as a hermetic sealing process by which a green ceramic body and an electrically conducting flowable medium are sintered at the same time to form a monolithic structure comprising at least one hermetically sealed co-sintered conductive pathway adhered directly to the ceramic body.

A "flowable medium" generally refers to a dispensable medium such as a paste, an ink, a gel, a paint, a powder. The flowable medium may be electrically conductive, comprising a metal only, a metal and ceramic mixture, a metal, a ceramic, and an optional electrically conductive additive mixture, and combinations thereof. The flowable medium may alternatively be electrically insulative, comprising ceramic, polymeric, or a ceramic and polymeric mixture, and combinations thereof. The flowable medium can be injected, pressed, pulled, pushed, or otherwise moved into a via, a hole, a cavity, a pocket, a trough, a slit, or an orifice.

A "cermet" is defined as a composite material comprising a metal and a ceramic.

A "ceramic reinforced metal composite (CRMC)" is defined as a composition composite comprising a metal matrix composite and a ceramic matrix composite.

A "feedthrough conductive pathway" is defined as an electrical conductor through which current flows to a feedthrough insulator body fluid side and a feedthrough insulator device side. The feedthrough conductive pathway may be selected from a lead, a wire, a lead wire, a terminal pin, a sintered electrically conductive material, and combinations thereof. The feedthrough conductive pathway may be formed by one of a brazing process, a co-fire process, or a co-sinter process. For medical implantable devices, a feedthrough conductive pathway must be hermetic.

The term "hermetic" is defined as impermeable, that is, keeping gases, liquids, and solids from penetrating and/or permeating into or out of a sealed structure, device, or system. In the present invention, all hermetic metal, ceramic, glass, and glass-ceramic seals meet or exceed a leak rate no greater than $1\times10^{-7}$ std cc He/sec. Hermeticity is specifically a requirement when the performance and reliability of sensitive electrical and optical components can be compromised by a leaking seal. For example, it is well known that hermeticity is specifically required for implantable devices, such as, but not limited to, AIMDs, implantable sensors, implantable recorders, implantable monitors, leadless implantable devices, implantable bions, among others. That is because even very small amounts of a gas, a liquid or a solid (e.g., moisture, harmful gases, water vapor, chemicals, salts, nanosolids) within the housing of such devices have been shown to compromise electronics and photonics. Historically, therefore, to be considered "hermetic", the maximum internal moisture content allowed inside a hermetic package has been 5000 PPM or 0.5% water vapor. The rationale being that, at 5000 PPM, the water vapor dew point is well below the water vapor freezing point, therefore any moisture that would condense inside the package would be in the form of ice crystals and not be available for corrosion processes. Also, at the time the moisture limit was originally set, 5000 PPM represented the minimum repeatable detection limits of the then available equipment. However, it is now understood that, even at relatively dry moisture levels, condensation can and will form inside an enclosed hermetic package at a temperature of around 5° C. It is also known that materials internal of an enclosed hermetic package, particularly polymeric materials and plastics, outgas moisture over time. Additionally, it has been demonstrated that for implantable devices, even very small amounts of water vapor inside a sealed housing can harm the sensitive electronics and photonics enclosed therewithin. In fact, the effects of moisture levels ≥8000 PPM include not only corrosion, which can cause damage to metal interconnects, but also electrical leakage across conductors, such as leads, wires, terminal pins, traces, and connectors, among others, electrical shorts due to dendritic growth of electrically conductive materials, and light scattering or wavelength drift in photonic components. Additionally, analysis of devices that exhibit hermetic leaks have demonstrated that the leak can be severe, and, in some cases, not only cause component failure, but also complete device failure. Complete device failure can be catastrophic for a patient. For a pacemaker-dependent patient, complete device failure can be immediately life-threatening, as the patient's heart will not beat unless the pacemaker stimulates the heart.

Further regarding the term "hermetic", it is defined herein that only metal, ceramic, glass, and glass-ceramic seals are considered hermetic, as these materials are all inorganic, virtually non-aging, and inherently have very low permeation levels, which typically approach close to zero. That being said, polymeric materials and plastics, e.g., nylon, polyethylene, polyester, polytetrafluorethylene (PTFE), polyetheretherketone (PEEK), elastomers, epoxies, liquid crystal polymerics (LCPs), and the like, are defined herein as "non-hermetic". That is because they are organic in nature, thus have inherently high permeation rate. High permeation materials cannot, do not and will not ever impart hermeticity. Polymeric and plastic materials also naturally age over time, which means they eventually allow moisture to penetrate into a sealed device or system. The aging process for polymeric materials and plastics is also considerably accelerated under environmental influences such as high temperature, pressure, or chemicals. In addition to inherent high permeation rates, polymeric materials and plastics absorb and hold gases, liquids, residues, solids, and contaminants in their molecular structure. Such absorbed or held substances can outgas at elevated temperatures, such as during assembly processes (such as curing or welding), storage or transportation in an uncontrolled environment, or during functional operation, any of which can compromise the device/system ambient internal environment. Consequently, critical conditions of vapor pressure, moisture levels, and condensation can be induced. As a result, polymeric or plastic seals can develop serious, even catastrophic, loss of hermeticity leakage issues, which may be immediate or latent. Seal leakages due to latent loss of hermeticity are significantly more worrisome than are immediate hermetic losses, as they are unpredictable and often not discovered until months, even years, after being implanted in a human.

The term "hermetically sealed" ideally means that a structure is so tightly sealed that no gas, liquid or solid can leak in or out of the structure. However, as the definition infers, perfect hermeticity does not exist. Thus, all hermetically sealed enclosures and packaging have some finite leak rate. For example, the seal of every hermetically sealed implantable device is required to maintain hermeticity in a variety of harsh environments, such as, but not limited to, environments that exhibit high and low (even cryogenic) temperatures, corrosive conditions (including body fluids), high pressures, high vacuums, or combinations thereof. As such, the effectiveness of the hermetic seal is defined by a "leak rate", with industry standard rates generally determined by a helium (He) mass spectrometer leak detection tester. For AIMDs, leak rates are typically measured in std cc He/sec. Additionally, to facilitate helium leak detection when an AIMD is tested, helium is typically added to the AIMD when the AIMD is backfilled with nitrogen or argon. In the present invention, all hermetic seals described herein meet or exceed a leak rate no greater than $1\times10^{-7}$ std cc He/sec. The following are exemplary He leak rate limits for various AIMDs. Hermetically sealed feedthroughs for a typical cardiovascular implantable electronic device (CIED), such as, a pacemaker, an implantable cardioverter defibrillator (ICD), a cardiac resynchronization therapy (CRT) device, and various neurostimulators all require a leak rate no greater than $1\times10^{-7}$ std cc He/sec. For other types of AIMDs, for example, an ocular or cochlear implant, the required leak rate is no greater than $1\times10^{-10}$ std cc He/sec. For relatively small packages, such as a bion or a sensor, the leak rate is no greater than $1\times10^{-12}$ std cc He/sec.

The term "polymeric" refers to elastomers, polymers, plastic, epoxy, liquid crystal polymers (LCPs) and rubbers.

The universally accepted test to determine hermeticity is defined by MIL-STD-883, which was developed to test safety-relevant microelectronic components in military, aerospace, and class III medical implants. Today, MIL-STD-883 is also widely used as a reliability measure in applications that include automotive airbags, industrial, energy, and even consumer electronics. MIL-STD-883 also defines the standard leak rates for microelectronic devices with internal cavities. This standard is administered by the United States Department of Defense, Defense Logistics Agency, and is approved for use by all Departments and Agencies of the Department of Defense. Over time this standard has been updated at least 10 times, with the latest notice of change released in 2016, now MIL-STD-883K. At least eight methods of verifying device hermeticity given certain conditions are provided therein. For example, a maximum He leak rate of a hermetically sealed implantable medical device may be determined by a design size and free volume (METHOD 1014.15 of MIL-STD-883K). With the ability of defining a leak rate on the basis of design size and free volume, a maximum He leak rate of a hermetically sealed implantable medical device may range from no greater than $10^{-6}$ std cc He/sec to $\leq10^{-14}$ std cc He/sec. It is understood by one skilled in the art that $1\times10^{-14}$ std cc He/sec is a lower leak rate (in other words, a higher hermeticity level) than $1\times10^{-6}$ std cc He/sec (which is a higher leak rate, in other words a lower hermeticity level). It is also understood that the lower leak rate limit can only be determined by the sensitivity of the leak tester measurement range and capability.

Regarding polymeric materials and plastic seals, it is noted that a helium leak test method cannot provide reliable leak test results. That is because the helium leak test method only measures leakage and does not measure permeation. More specifically, the helium leak test method exposes polymeric and plastic seals to helium for only a short period of time, therefore the helium leak test method does not and cannot account for high permeation rates over time. In other words, polymeric materials and plastic seals may test to be "helium-tight" but will not sustain being "helium-tight" over time. Their inherently high permeation and absorbent nature can result in enclosed sensitive electronics and photonics being unpredictably subjected to catastrophic moisture levels in a matter of a few days, several weeks, or even after being implanted in a patient. It is noted that Military and Space standards prohibit the use of a polymeric "adjunct sealant" over a hermetic seal as it may mask the true leak rate.

A "feedthrough insulator" is defined as an electrically insulating body having at least one via for an electrical conductor. The feedthrough insulator may comprise one of a ceramic, a glass, a glass-ceramic, and combinations thereof. The feedthrough insulator does not comprise polymeric materials or plastics, as polymeric materials and plastics may not provide sustainable hermeticity.

A "hermetic seal feedthrough insulator" is defined as an electrically insulating body having at least one hermetically sealed conductive pathway. A hermetic seal feedthrough insulator may comprise one of a sintered ceramic, a fused glass, a fused glass-ceramic or combinations thereof. The hermetic seal feedthrough insulator can be a standalone component to be disposed on a ferrule surface, in a ferrule opening, or in a device housing opening, or the hermetic seal feedthrough insulator can be formed as an assembly with the ferrule or the housing.

A "hermetically sealed feedthrough" is defined as a hermetic terminal that is attachable to an AIMD, wherein, when the hermetic terminal is attached to an opening in a housing of an AIMD, the hermetic terminal body fluid side and device side reside outside and inside the AIMD, respectively.

A "feedthrough hermetic terminal" provides for an electrical connection between the hermetically sealed feedthrough body fluid and the device sides through at least one conductive pathway disposed therethrough. For example, the conductive pathway of a hermetically sealed feedthrough provides for an electrical connection between the electrical circuits inside a hermetically sealed device housing and a connector block assembly to which at least one implantable lead is connectable.

A "hermetically sealed filtered feedthrough" is defined as a hermetically sealed feedthrough to which an EMI filter is mounted either directly to the feedthrough or indirectly to the feedthrough by way of a filter circuit board. The hermetically sealed filtered feedthrough is attachable to an AIMD, wherein, when the hermetically sealed filtered feedthrough is attached to an opening in a housing of an AIMD, the hermetically sealed filtered feedthrough body fluid side and device side reside outside and inside the AIMD, respectively.

An "EMI filter" is defined herein as a passive component that filters electromagnetic interference (EMI), which is generally a first capacitor that is electrically connected between a hermetically sealed active conductive pathway of a hermetically sealed filtered feedthrough and a hermetically sealed implantable device housing. The EMI filter comprises at least one active electrode plate disposed parallel to and spaced from at least one ground electrode plate. The active and ground electrode plates are further disposed on or within a dielectric material. The terms "EMI filter", "EMI filter capacitor", "filter" and "filter capacitor" are used interchangeably throughout this specification.

The "EMI filter" is further defined herein as a first capacitor that is electrically connected between a hermetically sealed active conductive pathway of a hermetically sealed filtered feedthrough and a hermetically sealed implantable device housing. The EMI filter may be a three-terminal capacitor (such as a feedthrough filter capacitor or a flat-thru filter capacitor) or a two-terminal capacitor (such as an MLCC filter capacitor or an X2Y attenuator filter capacitor). Ideally, the role of the EMI filter is to freely pass low frequency biologic signals without significant attenuation, such as therapeutic pacing pulses, while, at the same time, diverting dangerous high-frequency EMI energy to the equipotential surface of the implantable device housing, such as the AIMD housing. The equipotential surface of the AIMD housing acts as a Faraday cage shield, which is defined herein as system ground. It is noted that when a ferrule is laser welded to an opening in an AIMD housing, the ferrule is then part of the system ground. When undesirable EMI energy is diverted to the system ground, the undesirable energy is dissipated harmlessly as a few milliwatts of heat energy. In the specific case of magnetic resonance imaging (MRI), even watts of heat energy, which can be induced by the MRI scanner environment, are dissipated harmlessly into surrounding body tissues, such as a pectoral pocket. In this manner, the dangerous EMI energy is prevented from entering the hermetically sealed AIMD, where the EMI could reach sensitive AIMD circuitry to seriously disrupt the proper operation of the AIMD. An EMI filter may be selected from the group: a feedthrough capacitor, an MLCC filter capacitor, an X2Y attenuator filter capacitor, a flat-thru filter capacitor, a stacked film filter capacitor, a tantalum filter capacitor, an EMI filter circuit board, and combinations thereof, which are disposed on, near or adjacent to the implantable device hermetically sealed feedthrough, for example, an AIMD hermetically sealed feedthrough. The EMI filter circuit board may further comprise one or more feedthrough capacitors, MLCC capacitors, X2Y attenuator capacitors, flat-thru capacitors, stacked film capacitors, or tantalum capacitors mounted on or within the EMI filter circuit board.

The term "system ground" is defined herein as an electrically conductive enclosed housing of an implantable medical device. The implantable medical device housing acts as an electromagnetic shield, a Faraday cage, and an energy dissipating surface. The system ground may also include an optional metallic electrically conductive feedthrough ferrule, which is mechanically and electrically attached to an opening in the implantable medical device housing, an optional pocket pad which is formed on a ferrule or a housing, or an optional metal addition which is electrically connected to a ferrule or a device housing. Many AIMDs are hermetically sealed in a titanium housing, which is both electrically conductive and biocompatible. The titanium housing acts as an electromagnetic shield. Some AIMDs have a ceramic hermetically sealed housing, which is an insulator. In order to provide a system ground in EMI shielding, they are generally coated on the inside with a conductive layer of metal, such as nickel, and the like. Since this metal layer is not exposed to body fluid, it does not have to be biocompatible or bioinert, such as is the case with titanium. If there is an EMI filter, the coating on the inside of the ceramic housing becomes the Faraday cage or EMI filter system ground.

An "insulator" is defined herein as a material that acts as a barrier to the flow of electrons. The atoms of the insulator are strongly bonded together which obstructs the flow of electrons. In other words, insulators are materials that do not conduct electricity in an electric field, as they do not have free electrons to do so. Throughout this specification, the term "insulator" applies to an implantable device feedthrough insulator.

A "dielectric material" is defined herein as a material that stores electrical energy in an electric field. The molecules of a dielectric material are weakly bonded; hence, a dielectric material polarizes in the presence of an electric field. Polarization is a material property in which positive and negative charges move in the opposite direction. In other words, a dielectric material polarizes so that the negative charges in the dielectric material orient themselves toward a positive electrode and the positive charges in the dielectric material shift toward a negative electrode. The more easily a material is polarized, then the greater the amount of charge that can be stored. Throughout this specification, the term "dielectric" applies to an implantable device EMI filter substrate. Insulators, as defined and used throughout this specification, have a low dielectric constant, but are not considered "dielectric materials". There is some small (stray) capacitance associated with insulators, insulating coatings and insulator substrates of the present specification, but not nearly enough to perform as the AIMD passive EMI filter. Such stray capacitance is typically only important for an RF telemetry terminal pin, which detects very small, radiated fields generally in the microvolt range. Too much stray capacitance would render the RF telemetry terminal pin inoperable. It is important that the RF telemetry terminal pin is not attached to any of the filters of the present specification. That would result in too much signal attenuation so that telemetry could not happen.

The "dielectric constant k" refers to the ability to store energy in an electric field. A material's degree of polarization is related to the dielectric constant k and the electric field strength. That being said, all dielectrics are insulators as dielectrics have high electrical resistance without an electric field but polarize in the presence of an electric field. All insulators, on the other hand, do not have dielectric characteristics. The tightly bound atoms of an insulator do not allow electrons to freely flow from atom to atom (will not conduct electricity). The dielectric constant of the filter capacitors of the present specification range from >0 to 200, more broadly from >0 to 1000, and still more broadly >1000k.

A "pocket pad" is a structure that embodies one or more cavities formed on or within a ferrule, or, alternatively, in a housing. The cavities may comprise one of a pocket, a pad, a trough, a slit, or a custom orifice. Throughout the present specification, the term "loaded pocket pad" is often referred to as a "gold pocket pad". It is understood, however, that the term "gold pocket pad" is not meant to be limiting to gold, but instead is inclusive of all of the loading material options as defined above. One or more pocket pads are each loaded with a preform (i.e., an oxide-resistant material, for example, but not limited to, gold), and the preform is reflowed at a temperature above the melting point of the preform. The preform may be a substantially pure gold body, a gold powder, an alloy of at least 50% gold, a gold nanoparticle, or a coil of fine gold wire. Throughout the present specification, the term "loaded pocket pad" is often simply referred to as a "gold pocket pad". It is understood, however, that the term "gold pocket pad" is not meant to be limiting as any oxide-resistant electrically conductive material can be used. The preform may also be of platinum, palladium, and any alloys thereof. The preform may be any material that can be metallurgically bonded to an oxidizable surface, such as, but not limited to, titanium. The term "metallurgical bonded" includes existing oxide burn-through and/or penetration. The end result is a substantially oxide-resistant electrical connection. It is noted that the pocket is an essential structure that creates a containment cavity (like a swimming pool) the preform material will not undesirably flow away from, outflow, seep or bleed to other areas or surfaces, thereby permitting the oxide-resistance material in the pocket to serve as an oxide-resistant attachment pad. As such, the pocket can be configured to be relatively thin in contrast to prior art structures. In an embodiment, the thickness of the gold pocket preform may be 1 mil thick (0.001 inch). In an embodiment, the gold pocket preform may be on the order of 5 to 10 mils thick (0.005 to 0.010 inch) to facilitate preform handling, including robotic placement of the preform into the pocket.

"Oxide-resistant" is herein defined as the ability to resist surface reactions that increase connection electrical resistance, introduce unstable connection resistance change, or disrupt electrical connection conductivity. Oxide-resistant materials include platinum, palladium, gold, rhodium, and their alloys. An oxide-resistant pocket-pad or metal addition may comprise an oxide-resistant material selected from the group of gold, gold alloys, rhodium, rhodium alloys, platinum, platinum alloys, platinum-iridium alloys, palladium, palladium alloys, nitinol, titanium nitride, cobalt-chromium alloys, and combinations thereof.

The term "metallurgical bond" is a type of chemical bond between atoms in a metallic element, including any bonding that involves oxide burn-through and/or penetration. Metallurgical bonds provide substantially oxide-resistant electrical connection.

A "header block" is a biocompatible AIMD component that attaches between an AIMD housing and an implantable lead. The term "header block connector assembly" refers to the header block and its connector ports. The proximal terminal of an implantable lead plugs into the header block connector port to provide a conductive path extending from the distal electrode of the implantable lead, through the implantable lead conductors to the header block connector ports, through the hermetic terminal subassembly electrical conductors, and into the electronics residing inside the AIMD housing.

While header blocks are disclosed within this specification, it is understood that some AIMDs do not have a header block or a header block connector assembly. It is also understood that some AIMDs are leadless devices. As such, it noted that the inventions disclosed herein apply to all AIMDs, i.e., AIMDs with or without header blocks and AIMDs with or without implantable leads.

The term "voltage stand-off" is understood to mean a minimum dielectric strength or breakdown voltage, whereby avalanche breakdown, microcoulomb discharge, flashover or arc-over will not occur between active and system ground or between active terminal pins.

An "active-to-system ground stand-off distance" is defined as the distance between an active terminal electrical conductor and the system ground.

A "dielectric breakdown strength (DBS)" is defined as the maximum electrical potential that a material can resist before electrical current breaks through the material and the material is no longer an insulator. As such, the dielectric breakdown strength of one or more filter capacitor insulation materials is further increased by adding very small insulating particles such as, but not limited to, metal oxides, and in particular, nanoscale metal oxide insulating powders, to the insulation material. Example of suitable insulation materials include elastomers, polymeric materials, or plastics. The insulation materials may be an epoxy, a liquid silicone rubber, a polycarbonate, a polyester, a polyether, a polyurethane, a polyimide, or a polyamide. Nanoscale metal oxides may be selected from one of: alumina, baria, calcia, ceria, magnesia, silica, strontia, titania, and zirconia ceramic families. Non-limiting examples of some nanoscale metal oxides that can be used in the described invention include: $Al_2O_3$, BaO, CaO, $CeO_2$, MgO, $ZrO_2$, $SiO_2$, $TiO_2$, $Al_2SiO_{53}$, $BaTiO_3$, $SrTiO_2$, and combinations thereof. Various stabilized or partially stabilized zirconia may be used including zirconia toughened alumina (ZTA) and alumina toughened zirconia (ATZ), yttrium stabilized zirconia (YSZ), yttrium-toughened zirconia (YTZP), and combinations thereof. Additionally, some nitrides may also be used, such as, AlN, $Si_3N_4$, BN, and combinations thereof.

The term "dielectric breakdown strength (DBS)" also refers to a level of insulation wherein flashover, avalanche discharge, carbon tracking, catastrophic failure, or microcoulomb discharge does not occur during high-voltage testing.

A "microcoulomb discharge" refers to a charge (electron) pool that can form on any external surface of a filter capacitor when it is subjected to a high voltage. These charge pools can form in random locations resulting in a relatively high electric field leading to a "microcoulomb discharge". In general, microcoulomb discharges do not have enough energy to damage a capacitor, but they is very dangerous, nonetheless. In the test laboratory, a microcoulomb discharge can be heard as an unexpected and very random snapping sound. In a darkened test laboratory, the microcoulomb discharge can be seen under a microscope and resembles a tiny winking light that usually flashes only once or may flash repetitively at an applied high-voltage (HV) pulse repetition rate. A reoccurring microcoulomb discharge can take place in a different location each time. Moreover, microcoulomb discharges tend to be random and unpredictable events. A microcoulomb discharge becomes very dangerous when it occurs in a region of very high electric field stress. Should a microcoulomb discharge occur, the microcoulomb discharge can initiate a stringer, which becomes an avalanche arc that intensifies, culminating in enormous energy that is usually very destructive to an EMI filter capacitor. Destruction of the EMI filter capacitor can result in the catastrophic failure of an AIMD, which for certain patients, can be immediately life threatening. Microcoulomb discharges are similar to corona events and can be detected by carefully monitoring current flow into a filter capacitor as voltage is raised linearly. Sharp or sudden filter capacitor charging current non-linearities are test indications of a microcoulomb discharge. Microcoulomb discharges can occur without causing damage on filter capacitor surfaces during high-voltage testing, such as the application of an ICD high-voltage pulse. In the present specification, insulation improvements are disclosed with one of the goals being to prevent microcoulomb discharge. When a microcoulomb discharge or a corona event occurs, for example, when standing under a high-voltage power line, one can hear crackling and popping. However, the distance above ground for powerlines is so great that these discharges cannot lead to a catastrophic breakdown or streamer between the wires high in the air and the distant ground. In a similar manner, if sufficient insulation is provided, as will be described herein, a microcoulomb discharge does not have to be dangerous for the filter capacitors of the present inventions.

The term “nano” is broadly used to describe microscopic particles that are not visible to the naked eye. Accordingly, the term “nanoscale” is defined herein as an insulating particle having a size that is measured in nanometers or microns.

A “nanoparticle” refers to “nano-size to micron-size” insulating microscopic particles that are specifically added to the polymeric material, plastic insulator, or an insulating material of an implantable medical device in order to increase the dielectric breakdown strength (DBS) of the polymeric material, plastic insulator or insulating material. Increasingly, the DBS of a polymeric material, a plastic insulator, and an insulating material translates into an increased stand-off voltage, which is particularly important for high-voltage applications. By increasing the stand-off voltage between an active electrical conductor and system ground, microcoulomb discharge, avalanche breakdown, flashover and/or arc-over are not likely to occur. However, increasing the DBS of a polymeric material and a plastic insulator does not in and of itself prevent surface flashover between conductors of opposite high-voltage polarity that are too close to each other. Accordingly, increasing the dielectric breakdown strength of a material assumes that there is sufficient physical distance between conductors of opposite high-voltage polarity across the surfaces of such insulator so that a surface flashover does not occur.

Further regarding the term “nanoparticle”, in general, the smaller the nanoparticles, the higher the increase in insulator DBS (assuming a sufficient quantity of nanoparticles and uniform distribution of them throughout the polymeric material, plastic insulator or insulating material. The nanoparticles of the present invention range in size from 1 nm (0.001 μm) to 40,000 nm (40 μm). The nanoparticles of the present invention may further have at least one dimension less than or equal to 100 nm. A nanoparticle size range for a polymeric material, plastic insulator or insulating material can be determined by the maximum voltage of the application.

The terms “nano-dielectric”, “nano-dielectric additive”, “nano-insulating material” and “nano-insulating additive” refer to nanoparticles and are used interchangeably with the term “nanoparticles”. “Insulating nanoparticles” are essentially filler materials that may be configured as particulates, short fibers, long fibers, spheres, flakes, and submicron fibers, which are isotropically dispersed within the base polymeric material. Such insulating nanoparticles may polymeric, ceramic, or combinations thereof.

The term “thermoplastic” refers to any plastic or polymeric material that becomes pliable or moldable at a certain elevated temperature and solidifies on cooling. Thermoplastic or polymeric materials may be transformed into thermosetting plastic and polymeric materials by free radical crosslinking using techniques, such as, but not limited to, redox initiators or high energy radiation.

The term “thermosetting” refers to any plastic or polymeric material that forms an irreversible chemical bond during the curing process and, thus, do not melt when heated. Thermosetting can be performed at elevated temperature or at room temperature. Composite or hybrid thermoplastic or thermosetting polymeric insulating components may be made by coating either a homogeneous thermoplastic material or a thermosetting material with a thermoplastic or a polymeric material. A thermoplastic coating can be used to bond AIMD components, such as an EMI filter and a feedthrough insulator or, alternatively, the coating may be used to increase the electrical stand-off distance and/or the electrical breakdown strength of AIMD electrical components.

As referred to herein, all compositional percentages are by weight of the total composition, unless otherwise specified.

As used herein, the word “include,” and its variants, is intended to be non-limiting, such that recitation of items in a list is not to the exclusion of other like items that may also be useful in the materials, compositions, devices, and methods of the inventions that are described in this specification.

Similarly, the terms “can” and “may” and their variants are intended to be non-limiting, such that the recitation that an embodiment can or may comprise certain elements or features does not exclude other embodiments of the present inventions that do not contain those elements or features.

“A” and “an” as used herein indicate “at least one” of the item is present or a plurality of such items may be present, when possible. “About” when applied to values indicates that the calculation or the measurement allows some slight imprecision in the value (with some approach to exactness in the value, approximately or reasonably close to the value, or nearly). If, for some reason, the imprecision provided by “about” is not otherwise understood in the art with its ordinary meaning, then “about”, as used herein, indicates at least variations that may arise from ordinary methods of measuring or using such parameters. In addition, disclosure of ranges includes disclosure of all distinct values and further divided ranges within the entire range.

The term “adjacent to” means adjoining a structure, attached to a structure, or near a structure. As used herein, the term “adjacent to” is not limited to touching. The term “adjacent to” includes being near a structure, being mounted directly onto a structure, being spaced from a structure, for example, by an air gap or by a spacer, such as a washer or an adhesive between two structures.

BACKGROUND OF THE INVENTION

FIG. 1 illustrates various types of active implantable and external medical devices 100 that are currently in use. FIG. 1 is a wireframe diagram of a generic human body showing a number of implanted medical devices.

Numerical designation 100A is a family of external and implantable hearing devices, which include the group of hearing aids, cochlear implants, piezoelectric sound bridge transducers and the like.

Numerical designation 100B includes the complete family of neurostimulators and brain stimulators. For example, neurostimulators are used to stimulate the Vagus nerve to treat epilepsy, obesity, and depression. Brain stimulators are similar to a pacemaker-like device and include electrodes implanted deep into the brain for sensing the onset of a seizure and also providing electrical stimulation to brain tissue to prevent the seizure from actually happening. The leads that come from a deep brain stimulator are often placed using real time imaging. Frequently, such leads are placed real time during MRI.

Numerical designation 1000 shows a cardiac pacemaker, which is well-known in the art and may have either endocardial or epicardial leads. Implantable pacemakers may also be leadless (meaning without a lead or leads). The family of cardiac pacemakers 1000 includes the cardiac resynchronization therapy devices (CRT-P pacemakers) and leadless pacemakers. CRT-P pacemakers are unique in that, they pace both the right and left sides of the heart. The cardiac device family also includes any and all types of biologic monitoring and/or data recording devices and all types of implantable loop recorders (ILR) or other such monitors and records biologic activity, for example, an ILR that records the electrical activity of the heart.

Numerical designation 100D includes the family of left ventricular assist devices (LVAD's) and artificial hearts.

Numerical designation 100E includes an entire family of drug pumps, which can be used for dispensing of insulin, chemotherapy drugs, pain medications and the like. Insulin pumps are evolving from passive devices to active devices that have sensors and closed loop systems, which can, for example, monitor blood glucose levels in real time. Such active pump devices tend to be more sensitive to EMI than passive pumps, which have no sense circuitry or externally implanted leads.

Numerical designation 100F includes a variety of external or implantable bone growth stimulators for rapid healing of fractures.

Numerical designation 100G includes urinary incontinence devices.

Numerical designation 100H includes the family of pain relief spinal cord stimulators and anti-tremor stimulators. Numerical designation 100H also includes the complete family of neurostimulators used to block pain signals.

Numerical designation 100I includes the complete families of implantable cardioverter defibrillators (ICD) and congestive heart failure (CHF) devices, including cardio resynchronization therapy devices (CRT-D). A CRT-D, which is a special subcutaneous device for heart failure patients who are also at high risk for sudden cardiac death, can also provide high-voltage defibrillation. The devices of numerical designation 100I may have either endocardial or epicardial leads.

Numerical designation 100J illustrates an externally worn pack, such as, but not limited to, an external insulin pump, an external drug pump, an external neurostimulator, a Holter monitor with skin electrodes or a ventricular assist device power pack.

FIG. 2 illustrates a side cutaway view of a prior art cardiac pacemaker 1000. The pacemaker electronics reside within a hermetically sealed AIMD housing 116 (typically titanium), which provides an electrically conductive electromagnetic shield. There is an implantable lead connector header block 101 generally made from a thermosetting insulating plastic or compound, such as Tecothane®. The header block 101 houses one or more connector assemblies, generally in accordance with ISO Standards IS-1, IS-2, IS4 or DF4. The header block port connector cavities (female connectors) are labelled 103, 103'. Implantable terminal pins 107, 107' have proximal plugs 105, 105' (male connectors), which are designed to be inserted into and mate with the header block connector cavities 103, 103'. In devices that do not have header blocks, the implantable terminal pins are built directly into the pulse generator itself.

Further regarding FIG. 2, the system ground 124 comprises the conductive AIMD housing 116, which, as noted above, provides the overall electromagnetic shield, and also functions as an energy dissipating surface. The AIMD also comprises a hermetically sealed feedthrough 120 to which a quadpolar feedthrough filter capacitor 132 is mounted. As the conductive ferrule 112 of the hermetically sealed feedthrough 120 is electrically connected to the AIMD housing 116, the ferrule 112 is also part of the system ground 124. Accordingly, as illustrated, the system ground 124 of FIG. 2 includes the ferrule 112 and the housing 116.

FIG. 3 illustrates a prior art isometric cutaway view of a unipolar (one filter capacitor passageway 134) feedthrough filter capacitor 132. The unipolar filter capacitor has an external ground capacitor metallization 142 and a passageway 134 active capacitor metallization 144. These metallizations can be applied by electroplating, physical vapor deposition or glass frit metallization bonding. In one embodiment, the filter capacitor metallizations may comprise silver, copper, platinum, palladium, platinum silver, palladium silver, and combinations thereof. After the external ground capacitor metallization 142 and passageway active capacitor metallization 144 are applied, the filter capacitor 132 can then be electrically connected to a hermetically sealed feedthrough 120 using an electrical connection material 152, such as a solder, a thermosetting electrically conductive adhesive, an electrically conductive silicone, an electrically conductive polyimide, an electrically conductive epoxy, and the like. As illustrated, the unipolar feedthrough filter capacitor 132 comprises active electrode plates 148 and ground electrode plates 146. The ground electrode plates 146 are electrically connected in parallel to each other by the external capacitor metallization 142 and the active electrode plates 148 are electrically connected in parallel to each other by the passageway capacitor metallization 144.

Referring once again to FIG. 2, the electrical connection of the filter capacitor to system ground 124 can be better appreciated. When the external capacitor metallization 142 of the feedthrough filter capacitor 132 is electrically connected to the ferrule 112 of the hermetically sealed feedthrough 120, and the ferrule 112 is hermetically sealed (typically by welding, such as laser welding) to the conductive housing 116 of an AIMD, in this case, a cardiac pacemaker 1000, then the external capacitor metallization 142 is electrically connected to system ground 124. Hence, the external capacitor metallization 142, the ferrule 112 and the AIMD housing 116 are all at the same potential; that is, they are all at ground potential, and are all part of the overall AIMD equipotential surface (in other words, system ground 124). As such, the hermetically sealed enclosure of the AIMD blocks EMI, thus is commonly known as an EMI shield or a Faraday cage. Additionally, the feedthrough filter capacitor 132 can selectively redirect undesirable high-frequency energy as it enters the AIMD housing 116 to this equipotential surface for diversion and/or energy dissipation. Ideally, the role of the feedthrough filter capacitor 132 is to freely pass, without attenuation, low frequency biologic signals, such as therapeutic pacing pulses, while, at the same time, diverting dangerous high-frequency EMI energy to the AIMD housing 116 equipotential surface. When the undesirable EMI energy is diverted to the AIMD housing 116, the undesirable energy is dissipated harmlessly as a few milliwatts of heat energy. In this manner, the dangerous EMI energy is prevented from entering the AIMD housing 116 where it could reach sensitive AIMD circuitry and seriously disrupt the proper operation of AIMDs 100.

FIG. 3A is an isometric exploded view of the feedthrough filter capacitor of FIG. 3. Shown are ceramic cover sheets 147; active electrode plates 148 disposed on ceramic substrates 149, which form an active electrode layer; and ground electrode plates 146 disposed on ceramic substrates 149, which form a ground electrode layer. The active and ground electrode plates are interleaved and stacked, with one or more ceramic cover sheets 147 positioned at the top and bottom of the stack. The stack is then pressed and laminated. It is appreciated that blank ceramic cover sheets 147 can be disposed between the active electrode plates 148 and the ground electrode plates 146, thereby increasing the dielectric thickness, and increasing the voltage rating of the device. The electrode plates 146 and 148 are typically applied by silk-screening or equivalent waterfall processes.

FIG. 4 is a cross-sectional view showing the unipolar feedthrough filter capacitor 132 of FIG. 3 mounted to a ferrule 112 of a hermetically sealed feedthrough 120 forming a filtered feedthrough 210 for use in an AIMD 100. The external capacitor metallization 142 of the feedthrough filter capacitor 132 is electrically connected to the ferrule 112 by electrical connection material 152. Also illustrated, there are two gold brazes: gold braze 150 which hermetically seals the insulator 160 and the ferrule 112, and gold braze 162 which hermetically seals the feedthrough insulator 160 and the terminal pin 114, 111. In alternative embodiments, the feedthrough insulator may directly be hermetically sealed to ferrule 112 by a glass or a glass-ceramic using conventional sealing or glass fusion processes.

In order for the gold to wet the via hole and perimeter surfaces of the ceramic insulator 160, one or more metallization layers must be applied. FIG. 4 illustrates two metallization layers, a first metallization layer, which is an adhesion layer 153 directly applied to the surface of the ceramic insulator 160, and a second metallization layer, which is a wetting layer 151 applied on top of the adhesion layer 153. In an embodiment, the adhesion layer 153 is titanium and the wetting layer 151 is either molybdenum or niobium. Metallization layers may be applied by thin and thick film technologies, such as printing, painting, plating, and deposition processes. Metallization processes include screen printing, pad printing, brush coating, direct bonding, active metal brazing, Magnetron sputtering, physical vapor deposition, ion implantation, electroplating, and electroless plating. In an embodiment, both adhesion and wetting may be provided by a single metallization layer. It is noted that within the present specification, the adhesion layer 153 and wetting layer 151 are sometimes intentionally not shown for simplicity. It is understood, however, that even if not shown or described, both via hole and perimeter metallizations are present for ceramic feedthrough insulators 160.

One or more feedthrough insulators 160 may be disposed either on a ferrule surface or within a ferrule opening. The one or more feedthrough insulators 160 comprise at least one conductive pathway 126 that passes through the hermetically sealed feedthrough 120 to a body fluid side and a device side. The filter capacitor 132 of the hermetically sealed filtered feedthrough 210 comprises a dielectric material, which is also insulative. Therefore, the insulators 160 of the present inventions generally comprise one of a brazed ceramic insulator, a fused glass insulator, or a glass-ceramic sealed insulator. The dielectric of the EMI filters of the present inventions comprise an insulative polarizable dielectric material, also referred to in the present specification as dielectric layers, the insulative polarizable dielectric material being not only a dielectric but also an insulator.

Referring once again to FIG. 4, the feedthrough ferrule 112 is shown hermetically sealed to the housing 116 of the AIMD by laser weld 154. The external ground capacitor metallization 142 is electrically connected to the ferrule 112, thus is part of the overall equipotential surface of the hermetically sealed AIMD 100 (now consisting of the housing 116, the ferrule 112 and the capacitor metallization 142), defined herein as the system ground 124. As such, a Faraday cage is formed, which provides the AIMD 100 with both an effective electromagnetic interference (EMI) shield and an energy dissipating surface (EDS). The body fluid side terminal pin 114 of FIG. 4 is generally electrically connected to AIMD implantable leads (not shown). Such electrical connection is previously illustrated by the prior art pacemaker 100C of FIG. 2, which shows that the body fluid side terminal pins 114 are electrically connected to AIMD implantable leads 107 and 107' when they are inserted into the header block 101 connector ports 103 and 103'. Implantable leads 107 and 107', which are electrically connected to electrodes 109*a*, 109*b* and 109*a*', 109*b*', provide cardiac electrical therapy delivery to the human heart when implanted. FIG. 2 also illustrates that electromagnetic interference (EMI) can undesirably couple to these implanted leads and, in turn, can pass through the leads into the interior of the AIMD housing 116. It has been shown (and documented in numerous articles) that EMI can disrupt the proper operation of the AIMD 100, such as a cardiac pacemaker, which can lead to improper therapy or even complete inhibition of therapy. Inhibition of therapy for a cardiac pacemaker, can be immediately life-threatening to a pacemaker dependent patient.

Referring to the EMI signals of FIG. 4, since EMI may be conducted along terminal pin 114 to terminal 1 of the hermetically sealed feedthrough 120, a feedthrough filter capacitor 132 is electrically connected to the hermetically sealed feedthrough 120 forming a hermetically sealed filtered feedthrough 210. The feedthrough filter capacitor 132 diverts unwanted high-frequency EMI signals passing through the body fluid side terminal pin 114 to the device side terminal pin 111 so that by the time the EMI signal reaches terminal 2 (that is, the AIMD device side electronics), the EMI has been greatly attenuated and harmlessly diverted through feedthrough filter capacitor 132 to the AIMD housing 116. The effect of the EMI filter capacitor can further be appreciated by examining the electrical schematic of FIG. 4A. As the schematic shows, EMI enters terminal 1 of the three-terminal feedthrough filter capacitor 132 and is harmlessly diverted to ground terminal 3 (AIMD housing 116 of FIG. 4) before the EMI can reach the terminal 2 device side terminal pin 111.

Referring once again to FIG. 4A, in addition to attenuating and diverting undesirable EMI signals, the filter capacitor 132 must also pass low-frequency biologic signals without significantly attenuating them. For example, the AIMD 100 may sense biologic signals from the human body that enter at terminal 1. These sensed biologic signals should pass freely to terminal 2 without significant attenuation and diversion to terminal 3. Similarly, for low-frequency therapeutic pacing pulses that originate on the device side, the low-frequency therapeutic pacing pulses must also pass through the feedthrough filter capacitor 132 to the body fluid side and, in turn, to implanted terminal pins and electrodes without significant attenuation. Thus, the feedthrough filter capacitor 132, when properly installed, acts electrically as a continuous part of the titanium housing 116, which shields the AIMD 100. As such, the feedthrough filter capacitor 132 is a three-terminal coaxial device whose internal electrode plates "plug the hole" to both reflect and absorb EMI fields. The feedthrough filter capacitor 132 is unique in that it is a broadband low pass filter that allows desirable frequencies (like pacing pulses) to pass, while diverting potentially dangerous and/or disruptive high-frequency electromagnetic interference signals to system ground 124. Because filter capacitor 132 is a unique three-terminal coaxial device, effective attenuation, and diversion of undesired signals (EMI) is provided over a very broad frequency band (i.e., a broad frequency range of 10 MHz to 10 GHz). Furthermore, when designed and installed properly, feedthrough filter capacitors 132 are very low inductance devices that do not series resonate. It is very important that feedthrough filter capacitors 132 are installed in such a way that undesirable resistances, for example, due to oxide layers, such as titanium oxides, cannot occur at or in the ground connection.

FIG. 5 is similar to the electrical schematic of FIG. 4A, except in this case, an oxide $R_{OXIDE}$ is illustrated. This undesirable $R_{OXIDE}$ results from the oxidation of the metal from which ferrule 112 is made (for example, oxidation of a titanium metal ferrule). As FIG. 4 illustrates, the electrical connection material 152 is directly connected to the surface of the ferrule 112. When direct electrical connection is made to an oxidizable surface, for example, titanium, undesirable oxides can form. The undesirable oxides impart a resistive component that can substantially reduce the EMI filtering efficacy of the feedthrough filter capacitor 132.

FIG. 6A is prior art taken from FIG. 21 of U.S. Pat. No. 5,333,095, the contents of which are fully incorporated herein by this reference. FIG. 6A illustrates a bipolar (two passageways instead of one) feedthrough filter capacitor 132 mounted on a ferrule 112 of a hermetically sealed feedthrough 120. In this embodiment, the diameter of the bipolar feedthrough filter capacitor 132 overhangs the ferrule 112. A filter capacitor 132 ground connection using electrical connection material 152 is made between the ferrule 112 and the filter capacitor 132 ground metallization 142.

Similarly, to the electrical schematic of FIG. 5, the electrical schematic of FIG. 6B illustrates an undesirable oxide $R_{OXIDE}$ between the bipolar feedthrough filter capacitor 132 of the hermetically sealed filtered feedthrough 210 of FIG. 6A and system ground 124, which is due to direct electrical connection to an oxidizable metal, that is, a titanium housing 116, 116'. Such direct electrical connection to an oxidizable metal can seriously degrade EMI filter performance.

FIG. 7A illustrates a prior art quadpolar feedthrough filter capacitor 132 (i.e., a filter capacitor having four filter capacitor passageways 134). It is appreciated that the feedthrough filter capacitor 132 can have any number "n" of filter capacitor passageways 134. Similar to the unipolar feedthrough filter capacitor of FIG. 3, the quadpolar feedthrough filter capacitor 132 of FIG. 7A shows an external ground capacitor metallization 142 and four passageway active capacitor metallizations 144, one in each filter capacitor passageway 134. Active pathways may conduct therapeutic pacing pulses, biological sensing signals or even high-voltage therapeutic shocks. For a neurostimulator application, active pathways may include AC, pulse, triangular or many other different types of waveforms, for example, for a spinal cord stimulator.

FIG. 7B is a cross-sectional view generally taken along 7B-7B of prior art quadpolar feedthrough filter capacitor of FIG. 7A. Illustrated are ground electrode plates 146 disposed through the feedthrough filter capacitor dielectric. The ground electrode plates 146 are electrically connected to the external ground capacitor metallization 142. Also illustrated are active electrode plates 148 disposed through the feedthrough filter capacitor dielectric. The active electrode plates 148, however, are interleaved in a capacitive relationship with the ground electrode plates 146. Whereas the ground electrode plates 146 are electrically connected to the external ground capacitor metallization 142, the active electrode plates 148 are electrically connected to a passageway capacitor metallization 144. More particularly, the passageway capacitor metallization 144 of each filter capacitor passageway 134 is electrically connected to its own set of active electrode plates 148. The active electrode plates 148 overlap the ground electrode plates 146, thereby resembling a sandwich-type construction (i.e., the active electrode plates are between the ground electrode plates).

It is the combination of each filter capacitor passageway 134 having its own set of active electrode plate overlapping the ground electrode plates that creates individual feedthrough capacitors within a single feedthrough filter capacitor structure. In the filter capacitor embodiment of FIG. 7A, there are four individual filter capacitors within the quadpolar feedthrough filter capacitor shown. Thus, as each of the feedthrough filter capacitor passageways are associated with its own passageway capacitor metallization 144, when the feedthrough filter capacitor is electrically connected to the conductive pathways 126 (not labelled) of a hermetically sealed feedthrough, the four filter capacitors within the quadpolar feedthrough filter capacitor of FIG. 7A each effectively filter their respective conductive pathway.

FIG. 8 is an isometric exploded view of the quadpolar capacitor of FIG. 7A. Similar to the embodiment of FIG. 3A, shown are cover sheets 147; however, the active electrode layer of FIG. 8 shows four active electrode plates 148 disposed on a ceramic substrate 149, each of which are individually associated with one of the four filter capacitor passageways. As shown, the ground electrode plate 146 of the ground electrode layer extends in non-conductive relationship with the active filter capacitor passageways to the feedthrough filter capacitor outside diameter (OD). As previously disclosed, the active electrode plates 148 are interleaved in a capacitive relationship with the ground electrode plates 146 to form the quadpolar feedthrough capacitor 132.

FIG. 9 is an electrical schematic representative of the feedthrough filter capacitor 132 of FIG. 8 after being installed onto a hermetically sealed feedthrough 120 having four terminal pins 114$a$, 111$a$ through 114$d$, 111$d$. The external ground capacitor metallization 142 of the feedthrough filter capacitor 132 is directly connected to the ferrule 112 and/or the AIMD housing 116. The ferrule 112 and the housing 116 are made of an oxidizable metal, for example, titanium, hence are susceptible to undesirable surface oxidation. The effect of the undesirable surface oxidation is reflected in the electrical schematic as $R_{OXIDE}$ between each feedthrough filter capacitor 132 and system ground 124 (system ground 124 being the feedthrough ferrule 112 and/or the AIMD housing 116).

Referring again to FIG. 9, $R_{OXIDE}$ is highly undesirable, as $R_{OXIDE}$ directly results in increased resistance, which degrades EMI filtering performance pf the feedthrough filter capacitor 132. In other words, the presence of $R_{OXIDE}$ means that the ability of the feedthrough filter capacitor 132 to divert high-frequency EMI from terminal 1 to terminal 3 is considerably reduced to a level below the designed AIMD EMI requirements. Accordingly, in the presence of $R_{OXIDE}$, undesirable EMI energy can now freely enter terminal 1, proceed unfiltered through terminal 2 to the inside of the AIMD housing 116, where the EMI can cause extremely dangerous, even life-threatening situations for an implant patient.

Surface oxides resulting in $R_{OXIDE}$ can form either immediately or latently. Latent formation is unpredictable, as an oxides can form during filtered feedthrough assembly and manufacturing, after filtered feedthrough manufacturing, or after high temperature operations, such as laser welding the filtered feedthrough to an AIMD housing. Worse yet, oxides can continue to increase in thickness over time, which results in slow degradation of EMI filter performance. Accordingly, it is generally very poor practice to make an electrical connection directly to an oxidizable surface, such as a titanium surface.

FIGS. 10A, 10B, 10C, and 10D, are taken from FIGS. 26, 28, 29 and 30, respectively, of U.S. Pat. No. 6,765,779, the contents of which are fully incorporated herein by this reference.

FIG. 10A is a cross-sectional view of a prior art filtered feedthrough taken from FIG. 26 of U.S. Pat. No. 6,765,779. As used herein, element numbers in parentheses are original element numbers of the '779 patent, while element numbers without parentheses are the actual element numbers of the present application.

Referring to FIG. 10A, illustrated is a feedthrough filter capacitor 132 (500), which is disposed inside a ferrule opening. The surface of the inside diameter (ID) wall of the ferrule surface has an oxidation layer, which is not labelled, but is shown in the cross-sectional view as a thin cross-hatched element on the surface of the ferrule inside diameter (ID) wall. The external ground capacitor metallization (also not labelled) of the feedthrough filter capacitor 132 (500) is directly electrically connected to the oxidization layer on the surface of the ID of the ferrule 112 (518) by an electrical connection material 152 (532). Because the bottom surface of the feedthrough filter capacitor 132 (500) is completely covered by an insulating material 212 (550), it is not possible for the electrical connection material 152 (532) to reach the gold braze 150 (530) to provide an oxide-resistant electrical connection. As previously disclosed, electrical connections to an oxidized surface are highly undesirable.

FIG. 10B is a cross-sectional view of a prior art filtered feedthrough taken from FIG. 28 of the '779 patent. Illustrated is an insulating washer 212 (748) designed to expose gold brazes 150 (730) and 162 (728) so that electrical connection materials 152 (732) and 156 (744) can be used to electrically connect the filter capacitor directly to these gold brazes. By direct electrical connection to a gold braze, a low resistance low impedance oxide-resistant electrical connection is made, which permanently remains unaffected by any immediate or latent oxides that can form on either the ferrule 112 (718) inside diameter surface or the terminal pin 111 (716) outside diameter surface. In this way, the insulating washer 212 (748) of FIG. 10B no longer requires that the terminal pin 111 (716) be restricted solely to platinum or other non-oxidizing materials. As a result, lower cost oxidizable terminal pins 111 (716), such as of niobium or tantalum, may be used. While only one polymeric insulating washer 212 (748) is illustrated, it is understood that 1, 2, or even "n" washers may be stacked and adhesively bonded to each other.

FIG. 10C is taken from FIG. 29 of the '779 patent. FIG. 10C is a blown-up partial view taken from 10C of FIG. 10B, illustrating the electrical connection material 152 (732) directly contacting a gold braze 150 (730) hermetically sealing the feedthrough ferrule 112 (718) and insulator 160 (724). In this blown-up view, an oxide layer 164 (734) is visible on most of the surface of the inside diameter wall of the ferrule 112 (718) but does not exist on the ferrule wall that is metallurgically bonded to the gold hermetically sealing the ferrule and the insulator. Importantly, the open space 140 between the feedthrough ferrule 112 (718) and the polymeric insulating washer 212 (748) allows electrical connection material 152 (732) to directly contact the gold braze 150 (730). Since gold metallurgically bonds to titanium during the brazing process, oxides do not form there. Thus, electrical attachment to the gold braze 150 (730) hermetically sealing the feedthrough insulator 160 (724) and the ferrule 112 (718) provides a stable oxide-resistant low resistance low impedance electrical connection. Gold and similarly oxide-resistant metals are highly resistant to oxidation, thus electrical connections made to such oxide-resistant materials have very low contact resistance. As such, oxide-resistant materials provide highly desirable electrical connections, and in particular, highly desirable electrical connections for diverting undesirable high-frequency RF signals that pass through an EMI filter.

FIG. 10D is taken from FIG. 30 of the '779 patent. FIG. 10D is a blown-up partial view taken from 10D of FIG. 10B, illustrating an electrical connection material 156 (744) directly contacting a gold braze 162 (728). The circular washer opening 115 is sized to the outside diameter of the gold braze 162 (728) hermetically sealing the terminal pin 111 (716) and the feedthrough insulator 160*m* (724). Similar to FIG. 10C, in this blown-up view, an oxide layer 164 (734) is visible on most of the surface of the terminal pin 111 (716). Because the gold metallurgically bonds to the terminal pin 111 (716) during the brazing process, oxides do not form there, thereby providing a stable oxide-resistant, low resistance, low impedance electrical connection between the passageway active capacitor metallization 144 (710) and the gold braze 162 (734) hermetically sealing terminal pin 111 (716) and the insulator 160 (724). Such electrical connections are particularly beneficial for high-frequency applications. Additionally, since the gold braze 162 (728) is metallurgically bonded to the terminal pin 111 (716), more economical biocompatible electrically conductive material options for the AIMD feedthrough conductive pathway 126 (not labelled) may be used, instead of the more costly precious metals generally used (e.g., platinum or platinum alloys). For example, terminal pin 111 (716) may be an oxidizable material, such as niobium, titanium, tantalum, or even a platinum-iridium or a palladium-iridium alloy, as the iridium in these alloys tend to oxidize. Thus, the embodiment of FIG. 10D illustrates that even an oxidizable terminal pin can have a low resistance low impedance electrical connection when attachment is made to the gold hermetically sealing the terminal pin and the insulator instead of directly to the terminal pin itself.

FIG. 10E is an oblique view of the polymeric insulating washer 212 of FIG. 10B having a washer thickness 104, which is generally thin in comparison to the thickness of an EMI feedthrough capacitor 132. Polymeric insulating washer 212 has a circular washer opening 115 that is sufficiently sized for receiving a feedthrough terminal pin 111 and exposing the gold braze 162 hermetically sealing the terminal pin 111 and the feedthrough insulator 160 so that the electrical connection material 156 directly contact gold braze 162, thereby electrically connecting the passageway active capacitor metallization 144 of the EMI filter capacitor 132 and the gold braze 162. The electrical connection and the circular washer opening 115 is best seen in FIG. 10D.

FIG. 11 illustrates a prior art rectangular EMI filter capacitor 132, which has the same number of poles (4, quadpolar) as previously illustrated in the discoidal EMI filter capacitor 132 of FIG. 7A. Accordingly, EMI filter capacitors may be round (such as the discoidal EMI filter capacitor of FIG. 7A), rectangular (as shown in FIG. 11), oval, elliptical, among other shapes, including custom shapes. While four filter capacitor passageways 134 (not labelled) are shown, as previously mentioned, the EMI filter capacitor 132 may have any number of filter capacitor passageways, each passageway comprising a passageway capacitor metallization 144.

Regarding the external ground capacitor metallization 142 of FIG. 11, only a portion of the long rectangular edge of the ceramic substrate 149 has external ground capacitor metallization 142. The external ground capacitor metallization 142, however, can alternatively extend around the entire perimeter of the rectangular EMI filter capacitor. The quadpolar rectangular EMI filter capacitor 132, as illustrated by FIG. 11, is ready for mounting to the hermetically sealed feedthrough 120 of FIG. 12.

FIG. 12 illustrates a prior art quadpolar hermetically sealed feedthrough 120. The hermetically sealed feedthrough 120 comprises a metallic ferrule 112, typically titanium, a feedthrough insulator 160, typically alumina, and four terminal pins 111, 114. The hermetically sealed feedthrough 120 also comprises two gold brazes: gold braze 150 which hermetically seals the feedthrough insulator 160 and the ferrule 112, and gold braze 162 which hermetically seals terminal pins 111, 114 and the feedthrough insulator 160.

FIG. 13 is a cross-sectional view generally taken along 13-13 of FIG. 11 showing four active electrode plates 148 on a ceramic substrate 149. Each of the four active electrode plates 148 is correspondingly associated with one of the active terminal pins 111, 114.

FIG. 14 is a cross-sectional view generally taken along 14-14 of FIG. 11 showing one ground electrode plate with four filter capacitor passageways 134. FIG. 14 illustrates that the ground electrode plates 146 of the EMI filter capacitor 132 extend to opposing edges of the filter capacitor ceramic substrate 149. The width of each electrode plate extension corresponds with the embodiment of FIG. 11, illustrating the external capacitor metallization 142 applied to only a portion of the long edges of the rectangular EMI filter capacitor. As such, depending on the ground electrode plate design, the external capacitor metallization 142 can correspondingly be selectively applied to an EMI filter capacitor. In other words, while full perimeter metallization is always an option, the ground electrode design of FIG. 14 establishes that there is no need for full perimeter filter capacitor metallization in order to attach an EMI filter capacitor 132 to a system ground.

FIG. 15 illustrates EMI filter capacitor 132 of FIG. 11 mounted on the hermetically sealed feedthrough 120 of FIG. 12, which thereby forms filtered feedthrough 210 Electrical connection material 152 electrically connects external ground capacitor metallization 142 directly to the ferrule 112. Electrical connection material 156 electrically connects passageway active capacitor metallization (not visible) directly to terminal pins 111, 114.

FIG. 16 is a cross-sectional view generally taken along 16-16 of FIG. 15. FIG. 16 illustrates gold braze 162 hermetically sealing terminal pins 111, 114 and feedthrough insulator 160, and gold braze 150 hermetically sealing feedthrough insulator 160 and ferrule 112. Visible on the surface of ferrule 112 is an oxide layer 164. It is understood that since titanium metal is highly reactive and has an extremely high affinity for oxygen, oxide layer 164 will exist on all titanium surfaces of the titanium ferrule 112. However, for simplicity, oxide layer 164 is only illustrated in FIG. 16 between electrical attachment material 152 and ferrule 112.

Regarding FIG. 16, in this embodiment, the EMI filter capacitor 132 is larger in diameter than the diameter of the gold braze 150 hermetically sealing the ferrule 112 and the insulator 160. Thus, FIG. 16 illustrates electrical connection material 152 electrically connecting external ground capacitor metallization 142 directly to the ferrule surface oxide layer 164. Electrical connection to the oxide layer 164 is highly undesirable. Such oxide layers can dangerously increase equivalent series resistance (ESR) of the EMI filter capacitor 132 so much so that EMI filtering is significantly compromised or even fails. Such potentially unsafe ESR increases are particularly observable at frequencies above 10 MHz.

Referring once again to FIG. 16, the ferrule 112 has a capture flange, also known as a ferrule H-flange shape 163, which captures the AIMD housing halves (not shown) for subsequent joining, typically by laser welding. Also illustrated is a polymeric insulating washer 212 positioned between the EMI filter capacitor 132 and the feedthrough insulator 160. In the embodiment illustrated, the polymeric insulating washer 212 precludes migration of electrical connection materials 152 and 156 so that they cannot contact each other. The polymeric insulating washer 212 generally comprises epoxies or polyimides. Polyimides are often preferred since they are higher temperature materials. Prior art polymeric insulating materials are either a dispensed liquid that is then cured to form a solid, a formed solid washer, for example, an adhesive-backed polyimide washer, or a B-staged epoxy, which is partially cured so it can be placed with tweezers and then fully cured in a subsequent high-temperature curing operation.

FIG. 17 is an electrical schematic illustrating the effect of an undesirable oxide layer 164 within the ground path of the filtered feedthrough 210 of FIG. 16. Similar to FIG. 9, oxide layer 164 of FIG. 17 causes an undesirable resistance $R_{OXIDE}$, which can increase the ESR of the EMI filter capacitor 132 to a dangerous level, whereby EMI filtering is either significantly compromised or the filter fails completely, and no EMI filtering can occur at all.

FIG. 18 is a prior art hermetically sealed feedthrough 120 taken from U.S. Pat. Nos. 6,765,779 and 9,427,596 (FIG. 20 and FIG. 18 respectively), the contents of which are fully incorporated herein by these references. The ferrule 112 of FIG. 18 has been modified to include a ferrule attachment area that, after brazing, becomes oxide-resistant bond pads 165. The oxide-resistant bond pads 165 are continuous extensions of gold braze 150 formed at the same time that the feedthrough insulator 160 and the ferrule 112 are hermetically sealed. During the brazing process, the oxide-resistant material, for example, gold, melts and flows about the feedthrough insulator 160 and into the ferrule attachment area, hermetically sealing the feedthrough insulator 160 and the ferrule 112, while at the same time forming the oxide-resistant bond pads 165 as a continuous extension of the hermetic seal 150 between the feedthrough insulator 160 and ferrule 112. The shape of the ferrule attachment area, while being an extension of the insulator-to-ferrule hermetic seal 150 may resemble a pocket, a cavity, a trough, a slit, an orifice, or similar such structures that capture and prevent unrestricted flow of an electrically conductive flowable oxide-resistant material. The EMI filter capacitor 132 can then conveniently be electrically connected to the oxide-resistant bond pads 165, thereby providing an oxide-resistant low resistance, low impedance electrical connection.

FIG. 19 is prior art taken from FIG. 21 of the '779 patent illustrating an EMI filter capacitor 132 mounted on the hermetically sealed feedthrough 120 forming a filtered feedthrough 210. Using electrical connection material 152, the external ground capacitor metallization 142 of the EMI filter capacitor 132 is directly electrically connected to the gold braze oxide-resistant bond pads 165 that extend from the gold braze 150 hermetically sealing the ferrule 112 to the insulator 160 of the hermetically sealed feedthrough 120 (labelled 150, 165).

FIG. 20 is a cross-sectional view generally taken along 20-20 of FIG. 19, illustrating that the gold braze oxide-resistant bond pad 165 is continuous with the gold braze 150 that hermetically seals feedthrough insulator 160 and ferrule 112, and that electrical connection material 152 electrically connects the external ground capacitor metallization 142 and the gold braze oxide-resistant bond pad 165.

FIG. 21 is a prior art isometric view taken from FIG. 23 of the '779 patent, illustrating a quadpolar filtered feedthrough 210. This embodiment shows a discoidal EMI filter capacitor 132 mounted on the hermetically sealed quadpolar feedthrough 120. The external ground capacitor metallization 142 of the EMI filter capacitor 132 is directly electrically connected to a gold braze oxide-resistant bond pad 165 circumscribing the entire diameter of the insulator-to-ferrule hermetic seal gold braze (not visible in this view).

FIG. 22 is a cross-sectional view taken from 22-22 of the quadpolar filtered feedthrough 210 of FIG. 21, illustrating an electrical connection material 152 directly electrically connecting the external ground capacitor metallization 142 of the EMI filter capacitor 132 and the gold braze oxide-resistant bond pad 165. Similar to FIG. 19, the oxide-resistant bond pad 165 of FIG. 22 extends from the hermetic seal gold braze 150. FIG. 22 further shows that the direct electrical connection to gold braze oxide-resistant bond pad 165 enables an electrical connection to an EMI filter capacitor 132 being larger in diameter than the diameter of the hermetic seal gold braze 150. FIG. 22 also illustrates that the gold braze oxide-resistant bond pad 165 may have various structural shapes including the rectangular and rounded cavity structures illustrated. As previously disclosed, electrical connection material 152 can be a thermosetting conductive adhesive, a solder, and the like. By electrically connecting directly to at least a portion of the gold braze oxide-resistant bond pad 165, a reliable oxide-resistant, low resistance, low impedance electrical connection (i.e., free of titanium oxides) is made. Such reliable oxide-resistant electrical connections are robust at high-frequencies, ensuring that the EMI filter capacitor 132 effectively diverts unwanted high-frequency EMI energy to the ferrule 112 and, in turn, to system ground 124.

FIG. 23 is an electrical schematic representative of the quadpolar filtered feedthrough 210 of FIG. 22 showing that the undesirable $R_{OXIDE}$ of FIG. 17 is no longer present. The absence of $R_{OXIDE}$ in the schematic of FIG. 23 is specifically due to the direct electrical connection of the external capacitor metallization 142 of the EMI filter capacitor 132 to the oxide-resistant bond pad 165. Moreover, not only is $R_{OXIDE}$ no longer present in the electrical schematic of FIG. 23, but also, when an electrical connection is made to the oxide-resistant bond pad 165 of the titanium ferrule 112, the unpredictable and dangerous formation of latent oxides thereon is also no longer possible. Additionally, such high reliability oxide-resistant electrical connections are resistant to both thermal and mechanical shocks, as well as piezoelectric mechanical stresses.

FIG. 24 is an attenuation vs. frequency graph comparing the filtering performance of an ideal feedthrough filter capacitor to a feedthrough filter capacitor electrically connected to an oxidized surface. More specifically, the attenuation vs. frequency graph of FIG. 24 compares insertion loss (i.e., attenuation) curves of a feedthrough filter capacitor having undesirable $R_{OXIDE}$ present in its electrical connection and a feedthrough filter capacitor having an ideal electrical connection (i.e., does not have undesirable $R_{OXIDE}$ in its electrical connection). Examining the insertion loss curve of the ideal feedthrough filter capacitor C,132, a slight self-resonance is observed above 1 GHz. Nonetheless, as the curve demonstrates, the ideal feedthrough filter capacitor C,132 continues its filtering function. Thus, the ideal feedthrough filter capacitor C,132 is a broadband three-terminal filter as previously disclosed. The electrical schematic of the broadband three-terminal filter is provided to the left of the ideal feedthrough filter capacitor C,132 insertion loss curve of FIG. 24. Compelling is that the insertion loss curve of the ideal feedthrough filter capacitor C,132 demonstrates over 30 dB of attenuation at all frequencies above 450 MHz. The above 450 MHz frequency is particularly significant because cell phones operate at frequencies above this 450 MHz level, and present grave concerns to AIMD implant patients. Cell phones are small and can be brought into very close proximity to the implanted device. For example, a cell phone can be placed in a shirt pocket of a pacemaker implant patient. A shirt pocket typically lies directly over the implanted pacemaker. Positioning a cell phone directly over the medical device allows maximum energy coupling to the implanted leads, which can interfere with pacemaker function. Historically, research has shown that interference may even be caused by holding a cell phone within 150 mm (6 inches) of an implanted device.

Referring once again to the insertion loss (attenuation) curves of FIG. 24, the insertion loss curve represents that a feedthrough filter capacitor C,132 undesirably attached to an oxidized surface demonstrates the effect $R_{OXIDE}$ has on EMI filtering performance. The electrical schematic showing an $R_{OXIDE}$ presence in the EMI filter capacitor's ground electrical path is included to the right of the feedthrough filter capacitor C,132 with the undesirable resistive oxide insertion loss curve of FIG. 24. This insertion loss curve demonstrates that the EMI filter capacitor with the resistive oxide $R_{OXIDE}$ has greatly reduced attenuation across a broad frequency band. In fact, the attenuation degraded so much that feedthrough filter capacitor C,132 provides less than 30 dB of attenuation at frequencies above 450 MHz (in other words, EMI filtering performance degrades sufficiently when $R_{OXIDE}$ is present, essentially rendering the EMI filter capacitor useless). Such dangerously degraded filter performance is of serious concern because, if a closely held emitter, such as a cell phone, interferes with, for example, a pacemaker sense circuit, it can undesirably cause the pacemaker to inhibit. Inhibit means that an implanted medical therapy delivery device fails to provide life-saving therapeutic pulses. One might ask, why are pacemakers designed to inhibit? Well, there are two reasons: Many patients who suffer from bradycardia (a very low heart rate) are not bradycardic all-day long. In other words, they can come in and out of bradycardic (life-threatening) condition. Therefore, demand pacemakers were developed such that when a patient's normal sinus rhythm returns, the pacemaker will inhibit. This is to not only save battery life, but also prevents a condition called rate competition. Rate competition is when you do not want the pacemaker to provide a pulse that is out of sync or competitive with a patient's intrinsic rhythm. Furthermore, if EMI is undesirably detected as a normal cardiac pulse in a pacemaker dependent patient, and the pacemaker is caused to inhibit by this erroneous interference of the pacemaker, the inhibition (which means the device does not deliver electrical therapy to the heart) is immediately life-threatening for a pacemaker dependent patient who needs the therapy for the heart to beat.

FIGS. 25, 26 and 27 are prior art views taken from FIGS. 48, 49 and 50 respectively of U.S. Pat. No. 9,427,596, the contents of which are fully incorporated herein by this reference.

FIG. 25 illustrates rectangular pockets 248 formed in the ferrule 112 (or, alternatively, formed in a housing 116, not shown) into which a preform, such as a gold braze preform, is inserted to form an oxide-resistant pocket pad 250, such as a gold braze pocket pad.

FIG. 26 illustrates round pockets 248 instead of the rectangular pockets of FIG. 25. Hence, the pockets 248 can be any shape or size to meet an applications' requirements. The pockets 248 may even be a cavity, a continuous groove, a slot, or a channel.

FIG. 27 illustrates two rectangular areas 248*a* and 248*b*, each area having an oxide-resistant pocket pad 250*a* and 250*b*. The oxide-resistant pocket pads 250*a* and 250*b* in this embodiment comprise a gold preform and a thin layer of a slightly longer and wider platinum or equivalent oxide-resistant material (longer and wider than the underlying gold). The gold preform is positioned on each ferrule surface rectangular area and the thin platinum or equivalent oxide-resistant material is placed on top of each gold preform. The thin platinum or equivalent oxide-resistant material becomes a metal addition to the underlying gold preform, and during brazing, the gold preform metallurgically bonds with the thin metal addition, which prevents uncontrolled gold flow (i.e., gold flowing, bleeding, or seeping all over the titanium surface).

The alternative embodiment of FIG. 27 shows the replacement of the thin metal addition with rectangular ferrule pockets 248*a* and 248*b* formed in the ferrule 112. An oxide-resistant material placed within each pocket 248*a* and 248*b* can be, for example, a gold wire, preform, low temperature solder or even a pressed powder. Pockets 248*a* and 248*b* confine the gold therewithin, mitigating uncontrolled gold reflow, bleeding or seeping. Pockets 248*a* and 248*b* can be relatively shallow or reasonably deep. By confining the gold within the pocket, oxide-resistant pocket pads 250*a* and 250*b* are formed without the need for a metal addition. During high-temperature furnace processing, the melted gold does not uncontrollably escape either pocket 248*a* or 248*b*, remaining fully contained, walled, or dammed therewithin. Such gold braze oxide-resistant pocket pads 250*a* and 250*b* provide reliable oxide-free electrical connections for the EMI filter capacitor 132 and the ferrule 112.

Referring again to FIG. 27, in the specific embodiment of gold, the depth of the pockets 248*a* and 248*b* define an appropriate gold thickness. Accordingly, the appropriate thickness for gold in the oxide-resistant pocket-pads 250*a* and 250*b* is greater than 1 μm (0.001 mm or 0.00004 inch). Thus, migration of metals, for example, titanium migration, are prevented from penetrating to the surface of the gold to then oxidize and introduce an electrical resistance $R_{OXIDE}$ into the electrical connection. When robotic handling of a gold preform is intended, the thickness of the gold preform for placement into the pocket may be at least 1 mil thick (0.0254 mm or 0.001 inch). To further facilitate robotic placement, the gold preform may be on the order of 5 to 10 mils thick (0.127 mm to 0.254 mm or 0.005 inch to 0.010 inch).

Gold preforms, gold brazes, and gold braze hermetic seals can be substantially pure gold, alloys containing gold, platinum, palladium, iridium, germanium and even nano-type structures, or structures comprising titanium nitride (TiN) and/or various conductive carbons. In other words, the oxide-resistant pocket-pads 250 of the present inventions can be any oxide-resistant material that can be brazed or metallurgically bonded to an oxidizable surface, such as titanium, to provide an oxide-resistant, low resistance, low impedance electrical connection.

Referring again to FIG. 27, two pocket-pads (labelled 248*a*, 250*a* and 248*b*, 250*b*) are shown on the ferrule 112 of the filtered feedthrough 210. There are also two pocket-pads that are not visible on the opposite side of the ferrule 112. Additionally, the spaced pockets at both ends of the ferrule allow less gold therewithin. It is appreciated that the four discrete pockets of FIG. 27 may alternatively be disposed along only the long side of the ferrule 112 instead of the ferrule shorts sides, or there can be either one continuous pocket on each side or one continuous cavity, trough, or channel about the entire perimeter of the ferrule 112.

FIG. 28 is a cross-sectional view generally taken along 28-28 of FIG. 27 that illustrates the ground electrode plates 146 of EMI filter capacitor 132. The ground electrode plate 146 extends to the edge metallizations 142 on both ends of the electrode plate and is electrically connected by the ground capacitor metallization 142 on each side. It is appreciated that the ground capacitor metallizations 142 need not be placed across the entirety of the edge of the ceramic substrate 149. In other words, ground capacitor metallizations 142 will be electrically effective even if only a portion of the metallization 142 contacts the ground electrode plate 146.

FIG. 29 is a cross-sectional view generally taken along 29-29 of FIG. 27 illustrating four (quadpolar) active electrode plates 148 disposed on a ceramic substrate 149, each of which is individually associated with a filter capacitor passageway for receiving terminal pins 111 Similar to other quadpolar EMI filter capacitors 132, the four active electrode plates 148 are electrically isolated one from the other with each active electrode electrically connected to a respective active terminal pin 111, as shown.

FIG. 29A is a cross-sectional view generally taken along 29A-29A of FIG. 27 illustrating a filtered feedthrough 210. The feedthrough terminal pins 111, 114 extend through the EMI filter capacitor passageways. In the cross-section of FIG. 29A, gold braze 162 hermetically seals terminal pins 111, 114 and the ceramic insulator 160, while gold braze 150 hermetically seals the insulator 160 and the ferrule 112. Electrical connection material 152 electrically connects the ground capacitor metallization 142 to the oxide-resistant pocket pads 248, 250 of the ferrule 112 of the hermetically sealed feedthrough 120. Regarding terminal pins 111, 114, the active passageway capacitor metallization 144 is electrically connected to the gold braze 162 hermetically sealing terminal pins 111, 114 to the insulator 160 using electrical connection material 156. Electrical connection materials 152 and 156 may be either a thermosetting conductive adhesive or a solder. Terminal pin 111, 114 on the left side is a continuous terminal pin to the device and body fluid sides, while terminal pin 111, 114 on the right is a two-part terminal pin having a joint located within the gold braze 162 of the hermetic seal 120. The two-part terminal pin 111, 114 may optionally be joined at location 145 before brazing or brazed together during the brazing process. The two-part terminal pin allows use of an oxide-resistant terminal pin 114, for example, platinum, palladium or similar on the body fluid side, and a lower cost oxidizable terminal pin 111, such as tantalum, niobium, titanium, among others on the device side. Terminal pin 111 on the device side may also comprise platinum-iridium or palladium-iridium or other such alloys. As the electrical connection material 156 electrically connects the active metallization 144 of the feedthrough capacitor 132 to the gold braze 162 for the terminal pin 111, 114, a reliable low impedance, low resistance electrical connection can be accomplished regardless of the material choices made to form the two-part terminal pins 111, 114. Two-part terminal pins are more thoroughly described in U.S. Pat. No. 10,272,252, the contents of which are fully incorporated herein by this reference.

Referring again to FIG. 29A, the electrical connection material 152 is shown contacting not only the gold pocket pad 248, 250, but also a portion of the ferrule surface 113. Both testing and high frequency modeling have demonstrated that as long as a portion of an oxide-resistant bond surface is electrically connected to the ground capacitor metallization 142, any additional contact of the electrical connection material 152 directly to an oxidizable ferrule surface 113 will not compromise filter performance or introduce $R_{OXIDE}$ in the oxide-resistant electrical connection. This validates that a low impedance, low resistance electrical connection suitable for high frequency performance is reliably achieved and maintained for the life of the implanted device.

FIG. 29B is a cross-sectional view generally taken along 29B-29B of FIG. 27 illustrating that the insulator 160 of the hermetically sealed feedthrough may alternatively be a fused glass or a fused glass-ceramic. While an air gap 135 is illustrated in FIG. 29B, it is understood that, depending on the needs of a particular application, a polymeric insulating material 208 or a polymeric insulating washer 212 may alternatively be used.

FIG. 30 is a cross-sectional view of a filtered feedthrough 210 illustrating alternative conductive pathway design options. The left side conductive pathway illustrates three lead segments (a three-part terminal pin), and the right-side conductive pathway illustrates two lead segments (a two-part terminal pin). Regarding the three-part terminal pin 111*a*, 117*a*, 114*a*, gold braze 162 hermetically seals terminal pin segments 114*a* and 117*a* to the insulator 160 and also electrically connects terminal pin segments 114*a* and 117*a* together. Electrical connection material 156 electrically connects passageway active capacitor metallization 144 to gold braze 162 and also electrically connects terminal pin segments 111*a* and 117*a* together. Regarding the two-part terminal pin, 111*b*, 114*b*, the gold braze 162 hermetically seals the terminal pin segment 114*b* to the insulator 160. Electrical connection material 156 electrically connects the passageway active capacitor metallization 144 to the gold braze 162 and electrically connects the terminal pin segments 111*a* and 114*a* together. As previously disclosed, the electrical connection material 156 may comprise of solder or a thermosetting conductive adhesive. As shown in FIG. 29B, the material of the terminal pin segments can be uniquely made for each segment depending on an application's needs. For more detail regarding these embodiments and other multi-segment terminal pin embodiments, reference is made to U.S. Pat. Nos. 10,272,252 and 10,499,375, the contents of which are fully incorporated herein by reference.

Referring again to FIG. 30, the external ground capacitor metallization 142 of the EMI filter capacitor 132 is shown electrically connected to the gold braze pocket pads 248, 250 using electrical connection material 152. This provides an oxide-resistant, low impedance, high-frequency electrical connection that ensures proper broadband low pass filtering.

FIG. 31 is similar to the filtered feedthrough 210 of FIG. 27, except in this embodiment, the EMI filter capacitor 132 is substantially wider than the ferrule 112 (i.e., overhangs the ferrule). Overhanging EMI filter capacitors are disclosed in U.S. Pat. No. 10,912,945, the contents of which are fully incorporated herein by this reference. The EMI filter capacitor width 268 is substantially wider than ferrule width 266 while the EMI filter capacitor length 272 is relatively shorter than the ferrule length 270. The external ground capacitor metallization 142 is therefore at least partially positioned over the gold braze pocket pads 248, 250 to electrically connect the external ground capacitor metallization 142 to the gold braze pocket pads 248, 250 using electrical connection material 152.

Referring again to FIG. 31, the width 268 of the EMI filter capacitor, which is greater than the width 266 of the ferrule provides a tremendous amount of EMI filter volumetric efficiency. In general, the EMI filter capacitor active electrode plates 148 (not visible) follow a square law. That is because electrode plates have an area, which depending on plate shape, either has a diameter, a square side length and width or a rectangular length and width. By making the EMI filter capacitor wider, the electrode plates are correspondingly wider, and the effective capacitance area (ECA) greatly increases which results in a much more volumetrically efficient EMI filter capacitor 132. In other words, significantly more capacitance can be introduced into a relatively thin area, which is very important for conserving space within an AIMD internal construction without compromising EMI filtering efficacy. Additionally, as previously disclosed, the ferrule 112 is designed to be laser-welded into an opening of an AIMD housing 116 (not shown). During laser welding, the localized area of the ferrule 112 gets very hot. Importantly, as shown in FIG. 31, the external ground capacitor metallization 142 of the EMI filter capacitor 132 is thermally connected to only a relatively small amount of electrical connection material 152 at both capacitor edges. The part of the EMI filter capacitor 132 that overhangs the ferrule 112 does not contact any electrical connection material and is thereby, thermally "free to float". In other words, during laser welding, very little to no thermal stress is imparted underneath the overhanging EMI filter capacitor length 272 to the EMI filter capacitor 132. It is appreciated that thermosetting conductive adhesive and solder electrical connection materials 152 have a very high metal content so that they are highly electrically conductive. Along with high electrical conductivity typically comes relatively high thermal conductivity. It follows then that the smaller the amount of electrical connection material 152, the lower the thermal conductivity (electrical conductivity remains uncompromised). The thermal stress to a wider overhanging EMI filter capacitor 132 due to laser welding therefore will be greatly reduced.

Referring again to FIG. 31, it is noted that an overhanging capacitor configuration allows the EMI filter capacitor 132 to be substantially larger without increasing its height, which is critically important for low k dielectric EMI filter capacitors. Low k dielectrics are disclosed in U.S. Pat. Nos. 9,014,808 and 9,757,558, the contents of which are fully incorporated herein by these references. The low k dielectrics can be used for an AIMD primary EMI filter capacitor 132, which is generally disposed at or near the point of entry of terminal pins into the housing of the AIMD, i.e., electrically connected to the feedthrough conductive pathway device side and one of the ferrule 112, the housing 116, or both. The primary EMI filter is a first EMI filter capacitor 132 electrically connected to the conductive pathway 126 coming from a body fluid side into the device side of the AIMD. The first EMI filter capacitor 132 may be selected from the group of a feedthrough capacitor, a monolithic ceramic capacitor, a flat-through capacitor, an MLCC chip capacitor, and an X2Y attenuator. Historically, high k dielectrics have been used for EMI filters, which, accordingly, have very low electrode plate counts. Low electrode plate counts, however, can result in relatively high internal ohmic loss, which increases the capacitor's equivalent series resistance (ESR).

Referring again to FIG. 31, it is appreciated that the EMI filter capacitor can be of a reversed geometry. That is, the EMI filter capacitor 132 can be terminated along its two long sides instead of its two short edges, such that the EMI filter capacitor 132 overhangs the two edges of the ferrule 112. A reversed geometry EMI filter capacitor can be important for patient comfort as it permits the housing for the AIMD to be relatively thin. An AIMD is generally implanted in a surgically created pocket. For example, cardiac pacemakers are typically implanted in a pocket formed just above the pectoral muscle. Early model pacemakers were quite uncomfortable for patients because they were so thick. Modern pacemakers are much thinner and more comfortable. Accordingly, by reversing the geometry, the EMI filter capacitor 132 remains relatively thin, which improves patient comfort.

FIG. 32A is a partially exploded view of a prior art filtered feedthrough 210 illustrating an internally grounded feedthrough filter capacitor 136 ready for mounting on a hermetically sealed feedthrough 120. The hermetically sealed feedthrough 120 in this embodiment has eight active terminal pins 111*a-h*, 114*a-h* (an octopolar feedthrough), one telemetry terminal pin T, and one centrally located internal ground terminal pin 111*gnd*. The ground terminal pin 111*gnd* is attached at a ferrule peninsula 139 that is electrically connected (grounded) to the ferrule 112. The internal ground terminal pin 111*gnd* can be either gold brazed, or laser welded to the ferrule peninsula 139. Electrical connections of the filter capacitor 132 to the active metallization 144 and the oxide-resistant terminal pin ensures that a low impedance, low resistance ground electrical connection to the ferrule 112 is present. The gold braze 150, which hermetically seals the feedthrough insulator 160 to the ferrule 112, mechanically and hermetically seals the active terminal pins 111*a-h*, 114*a-h* to the feedthrough insulator 160. The RF telemetry terminal pin T must not be filtered. Instead, it needs to freely pass high-frequency programming signals from a remote programmer. U.S. Pat. Nos. 5,905,627, 6,529,103, and 6,765,780 disclose internally grounded EMI filter capacitors, the contents of which are fully incorporated herein by these references.

FIG. 32B illustrates an isometric exploded view of a prior art octopolar internally grounded feedthrough filter capacitor 136 showing details of the active and ground electrode plates. There are eight active electrode plates 148*a-h* disposed on a ceramic dielectric 149 (there is no active electrode plate associated with telemetry terminal pin T). FIG. 32B also shows the structure of the ground electrode plate 146 disposed on ceramic substrate 149. As illustrated, the ground electrode plates 146 do not extend to the perimeter of the plate's ceramic substrate 149. Any number "n" of the ground electrode plates 146 can be interleaved in sandwiched construction with the active electrode plates 148 to achieve a desired filter capacitance value.

Referring once again to FIG. 32A, because the ground electrode plates 146 do not extend to the perimeter of the plate's ceramic substrate 149, there is no requirement for an external ground capacitor metallization 142.

FIG. 32C shows the internally grounded feedthrough capacitor 136 of FIG. 32A mounted to the ferrule 112 of the hermetically sealed feedthrough 120. Since there is no external ground capacitor metallization 142, there is no capacitor perimeter electrical connection to the ferrule 112. Grounding is achieved by electrical connection to only the internal ground terminal pin 111*gnd*, which can comprise an oxide-resistant material, such as platinum, palladium, or alloys thereof. Accordingly, the filter capacitor's ground electrode plates 146 can be electrically connected to the oxide-resistant ground terminal pin 111*gnd* to form a reliable low impedance, low resistance electrical connection to the feedthrough ferrule 112.

Regarding internal grounding, some feedthroughs are designed to have active terminal pins that can be relatively distant from the internal ground terminal pin 111*gnd*. In that case, the furthest active terminal pin from the ground terminal pin 111*gnd* can exhibit a buildup of undesirable inductance across the ground electrode plates 146. This inductance buildup can then undesirably appear in series with the capacitor's ground electrical path (known as a parasitic inductance). A parasitic inductance is highly undesirable since inductances at high-frequency will provide a conductive reactance in series with an EMI filter capacitor. Such an effect, which is represented by the electrical schematic of FIG. 32D, is analogous to an undesirable ohmic loss in this area.

FIG. 32D is an electrical schematic with parasitic capacitance in the filtered feedthrough 210 of FIG. 32C showing that the outermost (furthest) active terminal pins 111*a*, 111*b*, 111*g* and 111*h* can have parasitic inductance LP, L'P, while active terminal pins 111*c*, 111*d*, 111*e*, and 111*f* closest to the ground terminal pin 111*gnd* essentially have no (insignificant) parasitic inductance. Parasitic inductance LP, L'P can seriously degrade filter performance. A solution to this problem is an internally grounded hybrid filter capacitor, which has edge metallization ground electrical connections to the ferrule in addition to the internal ground terminal pin electrical connection. Internally grounded hybrid filter capacitors are disclosed in U.S. Pat. No. 6,765,780, the s of which are fully incorporated herein by this reference (see FIGS. 37 through 42).

FIG. 33 is prior art isometric view taken from FIG. 37 of the '780 patent illustrating a hybrid internally grounded filter capacitor 138 designed for both internal and external grounding. The hybrid internally grounded filter capacitor design is best understood by referring to the cross-sectional view of FIG. 34.

FIG. 34 is generally taken along 34-34 of FIG. 33 and illustrates a ground electrode plate 146 disposed on a ceramic substrate 149 with a central capacitor passageway for accepting a corresponding feedthrough centrally located ground terminal pin 111*gnd*. When the centrally located ground terminal pin 111*gnd* is electrically connected to the EMI filter capacitor 132, the feedthrough is then internally grounded. FIG. 34 also illustrates that the ground electrode plate 146 selectively extends to both edges of the ceramic substrate 149. When the external edge ground metallizations 142 (shown at the left and right edges of the rectangular hybrid internally grounded filter capacitor 138 of FIG. 33) are electrically connected to a hermetically sealed feedthrough, the feedthrough is then externally grounded. Such internal and external grounding (i.e., electrical connections of an EMI filter capacitor passageway to a ferrule ground terminal pin and at least one selectively located external ground capacitor metallization 142 to a ferrule oxide-resistant pad, pocket-pad or braze hermetic seal) defines hybrid internally grounded filter capacitors 138. A hybrid internally grounded filter capacitor is a multi-point grounding system, which is important for ensuring that each active terminal pin 111 has a high degree of filter performance (high insertion loss performance that shows EMI attenuation at high frequencies). As such, long and narrow feedthrough filter capacitors must not solely be grounded internally by electrical connection to terminal pin 111*gnd* alone. The furthermost terminal pin from the internal grounded terminal pin 111*gnd* will likely exhibit highly degraded insertion loss performance due to parasitic inductance that builds up across the internal ground electrode plates 146. In other words, by providing a multi-point grounding system, the hybrid internally grounded filter capacitor 138 is grounded internally at ground terminal pin 111*gnd* and at both external edge ground metallizations 142. In addition to the low inductance internal ground path, second and third low inductance edge ground paths are thereby provided. Accordingly, all of the terminal pins 111 of the hybrid internally grounded filter capacitor 138 will provide a high degree of filter performance.

FIG. 35 is a cross-sectional view generally taken along 35-35 of FIG. 33. This drawing illustrates eight active electrode plates 148 disposed on a ceramic substrate 149. Each of the eight active electrode plates 148 is configured to receive a corresponding feedthrough terminal pin 111.

FIG. 36 illustrates an isometric view of a prior art hermetically sealed feedthrough 120 that is ready for electrical connection to the hybrid internally grounded filter capacitor 138 of FIG. 33. This embodiment has two feedthrough insulators 160*a*, 160*b* separated by a ferrule bridge 141. Also illustrated are gold braze pocket pads 250 within a ferrule pocket 248. The ferrule pocket 248 is a cavity with side walls, which fully contain the gold during the brazing process, as previously disclosed. The left side of FIG. 36 illustrates that the ferrule pocket 248 can be discontinuous (two unconnected pockets). It is understood that, while only two discontinuous pockets are shown, any number "n" of discontinuous pockets 248 may be present. On the right side, one continuous pocket 248 is shown. The one continuous pocket 248 can be any length or it can even extend about the perimeter of the ferrule 112. In addition to an electrical connection to the central ground terminal pin 111*gnd*, electrical connection of the ground external metallizations 142 of the hybrid internally grounded filter capacitor 138 of FIG. 33 can be made to the gold braze pocket pads 248, 250. Such a hybrid electrical connection ensures broadband high-frequency filter performance, as the hybrid electrical connection arrangement overcomes any performance issues associated with the previously disclosed parasitic inductances. In other words, all of the filtered feedthrough terminal pins 111 provide proper broadband high-frequency filter performance (reliably effective attenuation and insertion loss performance). FIG. 36 demonstrates that a ferrule bridge 141 comprising a ground terminal pin 111*gnd* is an alternative feedthrough ferrule design to a ferrule peninsula. Both ferrule structures provide effective internally grounding of an EMI filter capacitor.

FIG. 37 illustrates the hybrid internally grounded filter capacitor 138 of FIG. 33 mounted onto the hermetically sealed feedthrough 120 of FIG. 36 to form a filtered feedthrough 210. This embodiment shows that the rectangular hybrid internally grounded filter capacitor 138 has a width 268 greater than the ferrule width 266. As previously disclosed, an EMI filter capacitor having a width greater than that of the ferrule can greatly improve EMI filter volumetric efficiency. It is understood that the filtered feedthrough 210 of FIG. 37 can optionally comprise one or more telemetry terminal pins similar to the telemetry pin shown in FIG. 32C. As previously disclosed, telemetry terminal pins are not associated with active electrode plates. A benefit of the embodiment of FIG. 37 is that the hybrid internally grounded filter capacitor 138 and the ferrule 112 have both been kept relatively long and narrow so that, even though the filter capacitor is wider than the ferrule, the filtered feedthrough will still fit into an AIMD without unduly increasing AIMD thickness. As previously disclosed, it is important that the AIMD be relatively thin so that it is comfortable for the patient after implant. It is understood that, while the terminal pin arrangement of FIG. 37 shows inline terminal pins, terminal pin arrangements may alternatively be staggered, as illustrated by FIG. 32C.

FIG. 38 is a cross-sectional view generally taken along 38-38 of FIG. 37. The ground terminal pin 111*gnd* of the filtered feedthrough 210 is electrically connected to the passageway ground metallization 142 of the hybrid internally grounded filter capacitor 138 using electrical connection material 156. The external ground metallization 142 on the right and the left-hand sides of the hybrid internally grounded filter capacitor 138 is shown being electrically connected to gold braze pocket pads 248, 250 using electrical connection material 152. As previously disclosed, such a hybrid electrical ground connection ensures that the end terminal pins (111*a*, 111*b*, 111 *g* and 111*h*) of the hermetically sealed feedthrough 120 are no longer relatively far from an electrical ground so that they will not exhibit substantial parasitic inductance. In other words, the multipoint electrical grounding of the hybrid internally grounded filter capacitor 138 can reliably provide significantly improved high-frequency filtering performance.

FIG. 39 illustrates a hermetically sealed feedthrough 120 having a ground terminal pin 111*gnd* mechanically and electrically connected to a ferrule peninsula 139. The ferrule peninsula 139 provides a feedthrough embodiment that has a single feedthrough insulator 160. In contrast, the ferrule bridge 141 of FIG. 36 provides a feedthrough embodiment that has two separate feedthrough insulators 160*a* and 160*b*. In either embodiment, the gold braze 150 hermetically seals each feedthrough insulator to the ferrule 112.

FIG. 40 illustrates a hermetically sealed feedthrough 120, wherein a conductive pathway of the feedthrough insulator 160 is filled with a conductive composite fill 185 and a conductive metallic fill 186. The conductive composite fill 185 may be either a conventional CERMET or CRMC (ceramic reinforced metal composite). The two end caps 186 may be substantially pure platinum or a similar oxide-resistant electrically conductive material. While FIG. 40 illustrates a conductive pathway with a composite fill and two metallic end caps, it is appreciated that the present invention applies to any type of co-sintered and/or co-fired filled conductive pathway, including a substantially pure metal fill. See U.S. Pat. Nos. 8,653,384, 8,938,309, 9,233, 253, 9,352,150, 9,463,329, 9,492,659, 9,511,220, 9,757,558, 9,764,129, 9,889,306, 9,993,650, 10,046,166, 10,080,889, 10,092,749, 10,249,415, 10,272,253, 10,350,421, 10,420,949, 10,449,375, 10,500,402, 10,559,409, 10,561,837, 10,589,107, and 10,596,369 for more details regarding various embodiment for providing electrically conductive pathways through an insulator. The contents of these patents are fully incorporated herein by these references. For example, the U.S. Pat. No. 10,272,253 teaches hybrid conductive pathways comprising a co-fired composite fill and a solid metal insert. U.S. Pat. No. 8,653,384 patent teaches an essentially pure platinum fill. U.S. Pat. No. 10,249,415 teaches a CRMC fill, either alone or with a platinum fill. It is also appreciated that the present invention is applicable to any of the embodiments disclosed in U.S. Pat. Nos. 5,333,095, 5,751,539, 5,896,267, 5,973,906, 5,978,204, 6,765,779, the contents of which are fully incorporated herein by these references.

FIG. 41 illustrates a filtered feedthrough 210 having an internally grounded filter capacitor 136 mounted to the hermetically sealed feedthrough 120 of FIG. 40. In this embodiment, the internally grounded filter capacitor 136 is electrically connected to a gold braze pocket pad 250 of the ferrule 112 using a BGA (ball grid array) dot electrical connection material 202. The gold braze pocket pad 250 provides an oxide-resistant electrical connection to a ferrule peninsula 139. FIG. 39 illustrates the ferrule peninsula 139 in more detail. The BGA dot electrical connection material 202 may be a dispensed solder or thermosetting conductive adhesive. A polymeric insulating washer 212 is also shown between the internally grounded feedthrough filter capacitor 136 and the feedthrough insulator 160. The polymeric insulating washer 212 prevents uncontrolled flow of the BGA dot 202 during filtered feedthrough assembly.

Referring once again to FIG. 41, solid filled filter capacitor passageways 119*a* and 119*gnd* are illustrated. The solid filled capacitor passageways permit a number of connection options to the AIMD electronics. For example, electrical connections 203 or 203*a* may be made by laser welding, brazing, thermal sonic bonding, ultrasonic bonding, or otherwise similar joining methods. On the right side of FIG. 41, an active electrical connection 203*a* is shown mechanically and electrically connecting the nail head of the solid filled capacitor passageway 119*a* to a ribbon terminal lead 113. On the left side of FIG. 41, a ground electrical connection 203*gnd* is shown mechanically and electrically connecting the nail head of the solid filled passageway 119*gnd* to a ground terminal pin 111*gnd*. It is understood that a flex cable or circuit board may alternatively be electrically connected to either solid passageway nail head. Alternatively, it is anticipated that electrical connections 203 and 203*a* may be made using an anisotropic conductive adhesive (ACA) or an anisotropic conductive film (ACF).

FIG. 41A illustrates an embodiment of an internally grounded feedthrough filter capacitor 136 that is significantly wider than the feedthrough insulator 160. The filter capacitor 136 extends beyond the gold braze 150 hermetically sealing the insulator 160 to the ferrule 112 but does not extend outwardly beyond the width of ferrule 112. Because the internally grounded feedthrough filter capacitor 136 extends beyond the gold braze 150, the ferrule comprises two gold braze pocket pads 250 on the right and left sides of the cross-section. The pocket pads 250 provide multi-point grounding of the ground electrode plates 146 of the filter capacitor. It is appreciated that, depending on the feedthrough design, one, two or "n" number of ferrule pocket pads 250 can be provided. It is also appreciated that the internally grounded feedthrough filter capacitor 136 of FIG. 41A can be wider than the width of the ferrule, thus overhanging the ferrule 112.

Referring once again to FIGS. 41 and 41A, while passageways 119*a*, 119*gnd* are shown as solid filled passageways, the passageways may be terminated but unfilled. In that embodiment, the passageways only comprise ground and active passageway metallizations 142 and 144, respectively. Additionally, as FIGS. 41 and 41A illustrate, the solid filled passageways 119*a*, 119*gnd* may make direct contact to the active and ground electrode plates 148 and 146, respectively. In other words, a direct electrical connection of the solid filled capacitor passageways 119*a*, 119*gnd* to the active and ground electrode plates 148 and 146, respectively, can be made without the need for active and ground metallizations 144 and 142, respectively. Direct connections to filter capacitor electrode plates are disclosed by U.S. Pat. No. 8,179,658, the contents of which are fully incorporated herein by this reference.

Referring again to FIG. 41A, it is appreciated that the internally grounded feedthrough filter capacitor 136 is disposed on the device side of the hermetically sealed feedthrough 120. As such, the internally grounded feedthrough filter capacitor 136 does not need to be biocompatible, non-toxic, or biostable. Accordingly, a number of different materials can be used for the solid filled filter capacitor passageways 119*a*, 119*gnd*, such as commercially available thermosetting conductive adhesives, conductive epoxies, conductive polyimides, or solders. Also, copper-containing solders or other electrically conductive commercially available solders that are not biocompatible can be used. Additionally, any type of electrically conductive metal paste can be used to form the solid filled filter capacitor passageways 119*a*, 119*gnd*. It is important that the fill material be sufficiently electrically conductive, particularly in the case of AIMDs that deliver high-voltage therapy, such as an implantable cardioverter defibrillator (ICD), where high electrical conductivity matters. An ICD must conduct very high current pulses to an implant patient's heart in order to properly cardiovert the heart to thereby restore its sinus rhythm. Accordingly, the resistivity or electrical resistance of ICD solid filled filter capacitor passageways must not exceed about 2 milliohms (mΩ) from top to bottom. On the other hand, for typical low voltage applications, such as a cardiac pacemaker, the resistivity or electrical resistance of pacemaker solid filled filter capacitor passageways can be as high as 8 mΩ to 10 mΩ. For neurostimulator applications, such as a retinal implant, extremely low currents are required, thus the resistivity or electrical resistance of the neurostimulator solid filled filter capacitor passageways can be in the range of 10 mΩ to 100 mΩ. Referring to conductive BGA dot electrical connection material 202, alternative electrical connection materials include, but are not limited to, electrically conductive adhesives, anisotropic conductive adhesives, anisotropic conductive films, anisotropic conductive pastes, conductive epoxies, conductive silicones, commercially available solders, and other similarly suitable materials.

FIG. 41B is a cross-sectional view of a prior art filtered feedthrough 210, illustrating that both the active co-sintered filled vias 185*a*, 186*a* and 185*b*, 186*b* and the ground oxide-resistant ferrule gold braze pocket pads 250*a*, 250*b* are electrically connected to active and ground capacitor passageway proud features 260. The proud feature 260 of FIG. 41B is a nail head proud feature; however, other proud configurations are anticipated. The electrical connections of FIG. 41B are made using an anisotropic conductive film (ACF) 261. Alternatively, an anisotropic conductive adhesive (ACA) or an anisotropic conductive paste (ACP) may be used for electrical connection.

FIG. 41C is a blown-up partial view taken from 41C-41C of FIG. 41B, illustrating in more detail uncompressed and compressed electrically conductive particles, 262 and 262' respectively. The electrically conductive particles 262 are only compressed within the area of the nail head proud feature 260. The compressed electrically conductive particles 262' provide electrical connection at the mating active or ground conductive pathways, allowing electrical conduction along the z-axis of each of these electrically connected filtered feedthrough conductors. Also shown in this embodiment is an oxide-resistant ground electrical connection between ground terminal pins 111*gnd* and gold braze pocket pads 250*a*, 250*b*, which, in turn, is also electrically connected to ferrule 112 and housing 116.

Regarding FIGS. 41B and 41C, anisotropic electrical connection materials generally have electrically conductive particles 262 that, when compressed (becoming compressed particles 262'), enable electrical conduction. For example, FIG. 41B illustrates ACF 261, which electrically connects the conductive pathways of the hermetically sealed feedthrough 120 and the conductive passageways of the filter capacitor 136 (or alternatively an EMI filter circuit board). The conductive pathways of the hermetically sealed feedthrough 120 has an electrically conductive composite fill 185*a* and 185*b* and metallic fills 186*a* and 186*b* at each end of the insulator vias (i.e., end caps). The conductive passageways of the filter capacitor 136 has a terminal pin with a nail head proud feature 260. FIG. 41C shows that when the nail head proud feature 260 compresses the ACF 261, as shown in FIG. 41C, the particles immediately within the ACF at the nail head are also compressed as indicated by electrically conductive particles 262'. The compressed electrically conductive particles 262' electrically connect the conductive pathways of the hermetically sealed feedthrough 120 and the conductive passageways of the filter capacitor 136 so that electrical conduction can occur therethrough. Away from the nail head proud feature 260, the electrically conductive particles 262 remain uncompressed such that the ACF 261 remains insulative. In other words, where the nail head proud feature 260 compresses the ACF electrically conductive particles 262', the filter conductive passageways are electrically connected to the feedthrough active conductive pathways, while, where the electrically conductive particles 262 are not compressed (i.e., away from the nail head proud feature 260), the ACF 261 retains insulation resistance. Anisotropic electrical connection materials (i.e., ACF, ACP, and ACA) offer two significant advantages: (1) the compressible particle 262 acts like a spring, whereby compression of the particle 262' extends the particle, thereby changing its shape, for example, from a sphere into an elongated ellipsoid; and (2) the contact resistance of the compressed particle 262' is lower due to the larger surface area resultant from the compressed particle in contact with the mating feedthrough conductive pathway. The attachment of EMI filter capacitors or EMI filter circuit boards using anisotropic electrical connection materials are disclosed in U.S. Pat. Nos. 10,596,369 and 10,905,888, the contents of which are fully incorporated herein by these references.

Regarding FIG. 41B, illustrated are filter capacitor passageways having passageway active and ground capacitor metallizations 144 and 142 respectively. As previously disclosed, nail head proud features 260, which may be co-formed, are provided for terminal pins 111*a*, 111*b* and 111*gnd*, and an ACF 261 is used between the hermetically sealed feedthrough 120 and the internally grounded feedthrough filter capacitor 136 (instead of the prior art polymeric insulating washer 212 previously shown). It is appreciated that, as previously disclosed, the passageway capacitor metallizations 144 and 142 can be applied using a variety of methods, including various plating operations, application of silver or palladium silver glass frits, sputtering and the like. It is important that the nail head is positioned at least partially proud of the capacitor surface, meaning that the nail head proud feature 260 protrudes to some extent above the surface of the EMI filter capacitor. Having the capacitor passageway nail heads protruding proud of the surface of the EMI filter capacitor facilitates crucial mating between the EMI filter capacitor 136 and the hermetically sealed feedthrough 120 ground gold braze pocket pads 250*a*, 250*b* and conductive pathways (active co-sintered filled vias 185*a*, 186*a* and 185*b*, 186*b*). The ACF 261 thus electrically connects the feedthrough and filter capacitor electrical conductors of the filtered feedthrough 210, while, at the same time, provides electrical insulation equivalent to polymeric insulating washer 212 (shown, for example, in FIGS. 41 and 41A) in one single component. The electrically conductive particles 262 may be rigid, such as, but not limited to, gold-plated nickel spheres, or elastic, such as, but not limited to, gold-plated polymeric spheres. Elastic electrically conductive particles are readily deformable under compression and/or during pressure curing operations.

FIG. 42 illustrates an isometric view of a prior art chip capacitor, also known as a multilayer ceramic capacitor 194 (MLCC). As shown, the MLCC chip capacitor 194 comprises a dielectric body with external edge capacitor metallizations labelled 142, 144 on opposite edges. The external capacitor metallizations are labelled 142,144 because an uninstalled MLCC chip capacitor 194 has no polarity, thus can reversibly be attached. In other words, the ground capacitor metallization 142 is only defined when the external capacitor metallization on one edge of the MLCC chip capacitor 194 is electrically connected to a ferrule 112 (thus becomes the external ground capacitor metallization 142). The external edge capacitor metallization on the opposite capacitor edge is left for active electrical connection (thus becoming the external active capacitor metallization 144). It is understood that EMI filter capacitors, may include in addition to MLCCs, but is not limited to, chip capacitors, stacked film capacitors, or tantalum chip capacitors. It is appreciated that circuit boards with one or more EMI filter capacitors mounted on circuit boards in any combination are also EMI filters, herein defined as EMI filter circuit boards.

FIG. 43 is a cross-sectional view generally taken along 43-43 of FIG. 42, illustrating interleaving electrode plates. Shown in this cross-section are electrode plates 146 interleaving electrode plates 148. Similar to the external capacitor metallizations of FIG. 42, the electrode plates of the uninstalled MLCC chip capacitor 194 of FIG. 43 are labelled 146, 148. Also, the ground and active electrode plates, 146 and 148 respectively, will not be defined until MLCC chip capacitor 194 is installed. Capacitors, such as the MLCC chip capacitor 194 of FIG. 42, are known as two-terminal chip capacitors. Two-terminal chip capacitors are not coaxial and are, generally, not effective broadband filters up to very high frequencies, as are three-terminal feedthrough filter capacitors. This is because two-terminal chip capacitors have internal inductance and will, at some frequency, self-resonate. However, when two-terminal chip capacitors are physically disposed very close to the point of AIMD terminal pin ingress into the AIMD housing, the two-terminal chip capacitors can and do exhibit effective EMI filtering.

FIG. 44 is a cross-sectional view generally taken along 44-44 of FIG. 43 illustrating an electrode plate electrically connected to a left side external capacitor metallization 142, 144.

FIG. 45 is a cross-sectional view generally taken along 45-45 of FIG. 43 illustrating an electrode plate electrically connected to a right-side external capacitor metallization 142, 144.

Regarding FIGS. 44 and 45, when the electrode plates electrically connected to the left side external capacitor metallization interleave with the electrode plates electrically connected to the right-side external capacitor metallization, the overlap of the two overlapping electrode plate areas form what is known as the effective capacitance area (ECA) of the MLCC or chip capacitor 194.

FIG. 46 illustrates two MLCC chip capacitors 194*a*, 194*b* directly mounted on top of a hermetically sealed feedthrough 120, thereby forming a filtered feedthrough 210. The filtered feedthrough 210 is shown in cross-sectional view. As illustrated, on the left side, the left external edge capacitor metallization is labelled 142. On the right side, the right external edge capacitor metallization is also labelled 142. Because the left and right external edge capacitor metallizations of the MLCC chip capacitors 194 on the left and right sides of the filtered feedthrough 210 respectively are both mechanically and electrically connected to gold braze pocket pads 248, 250 of the ferrule 112 using electrical connection material 152, then the left and right external edge capacitor metallizations of the MLCC chip capacitors 194 illustrated become external ground capacitor metallizations 142. Of significance is that electrical connection material 152 at least partially makes electrical contact to gold braze pocket pad 250 contained in pocket 248. Similarly, on the left side, the right external edge capacitor metallization is labelled 144. On the right side, the left external edge capacitor metallization is also labelled 144. Because the right and left external edge capacitor metallizations of the MLCC chip capacitors 194 on the left and right sides of the filtered feedthrough 210 respectively are both mechanically and electrically connected to gold braze 162 of the terminal pins 111*a* and 111*b* respectively using electrical connection material 156, then the right and left external edge capacitor metallizations of the MLCC chip capacitors 194 illustrated become external active capacitor metallizations 144.

FIG. 47A illustrates a prior art filtered feedthrough 210. In this embodiment, an MLCC EMI filter circuit board 155 is electrically connected to the hermetically sealed feedthrough 120. Disposed on the EMI filter circuit board 155 are six MLCC chip capacitors 194 of FIG. 42. The filtered feedthrough also has six active terminal pins 111*a*-111*f* (also known as active poles) hermetically sealed to the feedthrough insulator 160 (not visible) and two ground terminal pins 111*gnd*, 111'*gnd* electrically and mechanically connected to the feedthrough ferrule 112 (one on the left side and the other on the right side of the filtered feedthrough 210). The ground terminal pins 111*gnd*, 111'*gnd* each provide a ground connection to the MLCC filtered circuit board internal ground plates 161 (not visible). The circuit board internal ground plates 161 are extremely important in that radiated EMI is blocked from entering into the AIMD housing.

FIG. 47B is a plan view taken along 47B-47B of FIG. 47A, illustrating the layout of the MLCC chip capacitors 194*a*-194*f*. One external edge capacitor metallization 144 of each MLCC chip capacitor 194 is correspondingly electrically connected to an active terminal pin 111*a*-111*f* and the opposite external edge capacitor metallization 142 is correspondingly electrically connected to a circuit board ground filled passageway 265*gnd-a* through 265*gnd-f*. In this embodiment, the circuit board active filled passageways 111*a*-111*f* are each shown electrically connected to a circuit board active trace disposed on the surface of the MLCC EMI circuit board 155. It is anticipated that MLCC chip capacitor 194*a*-194*f* may alternatively be oriented to directly attach to the circuit board active filled passageways 111*a*-111*f* without the need of a circuit board active trace. The purpose of the MLCC chip capacitors 194*a*-194*f* is to provide high-frequency EMI filtering so that undesirable EMI may be diverted from active terminal pins 111*a*-111*f* to the ferrule 112.

Referring to FIG. 47A, terminal pins 111*a* and 111*f* are labelled terminal ① on the device side and terminal ② on the body fluid side. The ferrule 112 is labelled terminal ③. Each terminal pin 111*a*-111*f* acts as a three-terminal device when electrically connected to the MLCC EMI filter circuit board 155. The EMI filter circuit board 155 of FIG. 47A comprises at least one low impedance ground plate 161 (not visible in this view). Three-terminal devices, in general, attenuate undesirable EMI. When EMI enters at terminal ②, the EMI is diverted to an equipotential ground at terminal ③, so that by the time the EMI reaches terminal ①, the EMI is significantly attenuated and is no longer dangerous to AIMD circuit function.

FIG. 47C is generally taken along 47C-47C of FIG. 47A, illustrating an internal ground plate 161 residing within EMI filter circuit board 155. EMI filter circuit board 155 must have at least one ground plate 161. It is appreciated, however, that EMI filter circuit board 155 may alternatively have two or more ground plates 161, in other words, "n" number of ground plates 161. The "n" number of ground plates 161 are grounded to the ferrule 112 through the left and right-side ground terminal pins 111*gnd*, 111*gnd'*. These ground terminal pins 111*gnd*, 111*gnd'* can be gold brazed or laser welded directly to ferrule 112. Ground plate 161 provides a very low impedance extension of system ground so that the MLCC chip capacitors 194*a*-194*f* can act as three-terminal devices that divert undesirable EMI energy. Ground plate 161 also, at the same time, shields the feedthrough insulator 160 hermetically sealed to ferrule 112. The feedthrough insulator is transparent to high-frequency electromagnetic energy, acting like a physical opening in ferrule 112. Ground plate 161 "plugs" this "opening" at high frequencies by both reflecting and absorbing undesirable high-frequency energy. In other words, ground electrode plate(s) 161 act as a continuous part of the overall electromagnetic shield within which the AIMD electronic circuits are hermetically housed.

FIG. 47D is a cross-sectional view of a filtered feedthrough 210 having an EMI filter circuit board 155 comprising two ground plates: an internal ground plate 161 embedded within the EMI filter circuit board 155 and an external ground plate 161' located opposite the surface of the EMI filter circuit board 155 on which the MLCC chip capacitors 194 are mounted. In this embodiment, ground plates 161, 161' are grounded at external edge circuit board metallizations 143 electrically connected to oxide-resistant gold braze bond pads 165 at each end of ferrule 112. As previously disclosed, electrically connecting to oxide-resistant gold braze bond pads provide reliable low impedance low resistance electrical connections.

FIGS. 48 through 50 illustrate various filtered feedthrough active conductive pathway embodiments using filled vias and/or metal inserts in either the feedthrough conductive pathways or the EMI filter conductive passageways. Also, illustrated are various EMI filter ground conductive passageway embodiments. Not show in FIGS. 48 through 50 are the MLCC chip capacitors 194 ground connections, which are best understood by the ground circuit traces and connections of FIG. 47B 265*gnd-a* through 265*gnd-e*.

FIG. 48 is similar to FIG. 47D, except in this embodiment, the EMI filter circuit board 155 has only one internal circuit board ground electrode plate 161 and, instead of terminal pins 111, various types of co-sintered filled conductive pathways are shown. Co-sintered conductive filled pathways are more thoroughly disclosed in U.S. Pat. No. 10,272,253, the content of which is fully incorporated herein by this reference. The EMI filter circuit board 155 of FIG. 48 is grounded through filled circuit board passageways 265*gnd* that are electrically connected to corresponding gold braze pocket pads 250 (each pocket pad illustrated has a different pocket structure). Importantly, a polymeric insulating washer 212 is disposed between the EMI filter circuit board 155 and the feedthrough insulator 160 and ferrule 112. The polymeric insulating washer 212 is particularly important for high-voltage applications, as high-voltage flashover between adjacent terminal pins 111, or between any terminal pin 111 and system ground (in this case, the ferrule 112, the ground vias 265 and the gold pocket pads 250), can thereby be prevented.

FIG. 48A is similar to FIG. 48, except that now there are circuit board edge metallizations 143 at each end of circuit board 155. The circuit board edge metallizations 143 are electrically connected to circuit board ground plate 161 and corresponding oxide-resistant gold braze pocket pads 250. FIG. 48A also illustrates the co-sintered filled conductive pathway options of FIG. 48. Beginning on the left side, Option 1 illustrates a CRMC fill 185 having end caps comprising a metallic substantially pure platinum fill 186, as previously disclosed for FIG. 40. Option 2 illustrates an inner core of substantially pure platinum 186 surrounded by CRMC fill 185. Option 3 illustrates a solid metallic structure, such as a platinum wire 186W, which is co-fired with a CRMC fill 185. Option 4 illustrates a dumbbell-shaped metallic substantially pure platinum fill 186 surrounded by a CRMC fill 185 extended to the end cap portion of the dumbbell-shaped metallic substantially pure platinum fill 186. Option 5 illustrates a solid metallic structure, such as a platinum wire 186W surrounded by co-fired essentially pure platinum fill 186, which is then surrounded by a co-sintered layer of CRMC 185. The surrounding CRMC fill 185 may be a gradient surrounding CRMC fill 185, meaning that the ceramic content in the CRMC increases while the platinum content in the CRMC decreases as the CRMC extends further from the substantially pure platinum core.

FIG. 48B is similar to FIG. 48 except that an ACF 261 is disposed between the EMI filter circuit board 155 and the feedthrough insulator 160 and ferrule 112 instead of a polymeric insulating washer 212. In this embodiment, the terminal pins 111 are co-formed with a nail head proud feature 260. These nail-heads stand proud of the circuit board 155 device side surface, as shown. As previously disclosed, the proud feature 260 facilitates compression of electrically conductive particles 262' thereby providing a reliable electrical connection between the co-sintered vias and the nail head proud feature 260, forming a continuous electrically conductive path through the feedthrough insulator 160 and EMI filter circuit board 155 to the body fluid and device sides of the filtered feedthrough 210. Also illustrated are two ground pads 250 and 250', which permit multi-point grounding of the internal electrode plate of the circuit board 161. An additional via hole may be provided in the circuit board for a ground terminal pin 111*gnd*, which may then be routed to AIMD electronic circuit board (not illustrated).

FIG. 49 is similar to FIGS. 47 and 48, except that the circuit board has filled passageways 265*a* through 265*f* instead of terminal pins 111. The filled circuit board passageways 265 are electrically connected to filled feedthrough conductive pathways using a BGA dot or solder bump electrical connection material 202. The circuit board passageways 265 can be filled with a variety of electrically conductive materials, including solders, thermosetting conductive adhesives, conductive inserts and the like, to which a BGA dot or solder bump electrical connection material 202 can then be added, as FIG. 49 illustrates. Alternatively, the circuit board passageways 265 and the BGA dot or solder bump electrical connection material 202 may be disposed at the same manufacturing step, using the same electrically conductive materials.

FIG. 50 is very similar to FIG. 49, except that the filled circuit board passageways have proud features (now defined as nail head filled circuit board passageways 394*a*-394*f* and 394*gnd*) and the electrical connections between the EMI filter circuit board 155 and the hermetically sealed feedthrough 120 is an ACF 261. The proud features 260 disposed in the nail head filled circuit board passageways 394 compress the electrically conductive particles 262' in the ACF 261 so that the nail head filled circuit board passageways 394 and the feedthrough filled conductive pathways are electrically connected. The electrically conductive particles 262 away from the proud feature 260 are not compressed so that the ACF 261 correspondingly retains its insulative properties. There may also be a number of circuit board ground filled passageway 265*gnd*, which are ground plate stitching vias that reduce the inductance across the EMI filter circuit board 155. The circuit board ground filled passageway 265*gnd* are also examples of how the MLCC chip capacitors 194 can be electrically connected to system ground 124.

FIG. 50A is taken from section 50A-50A from FIG. 50 illustrating the proud feature 260 that is electrically connected to the nail head filled circuit board passageway 394*gnd* (which is electrically connected to the circuit board ground internal electrode plate 161). As can be seen, the conductive particles in the area of the nail head 260 are compressed ACF conductive particles 262', which results in electrical conductivity through the nail head filled circuit board passageway 394*gnd*, the oxide-resistant pocket pad 248, 250 and the ferrule 112.

Referring again to FIG. 50, it is appreciated that the nail head filled circuit board passageway 394*gnd* comprising a proud feature can instead be a circuit board passageway via hole eyelet, which are well known in the industry. In other words, the via holes could first be metallized by any type of metal plating or metal deposition and then a metallic eyelet, which can be of a compressed shape or a pop rivet construction, can be added. The benefit of the metallic eyelet is that the eyelet flange stands proud of the circuit board passageway. The metallic eyelets can alternatively be either solid eyelets or eyelets that are filled with solder and similarly electrically conductive materials. As the eyelets stand proud of the circuit board passageway surface, these eyelets accomplish the same purpose as the nail head proud feature 260.

Referring again to FIG. 50, it is anticipated that the end caps 186C' of feedthrough conductive pathway electrically connected to circuit board passageway 394*f* may be configured to stand proud of the feedthrough insulator 160 and ferrule 112, particularly in the mating area between the circuit board 155 and at least one of the insulator 160 and ferrule 112. The proud feature may further be custom configured to extend beyond the diameter of the insulator conductive pathway and/or with any shape or three-dimensional structure. With 186C' standing proud, either two proud surfaces may mate, i.e., 260 and 186C' to compress the ACF conductive particles 262', which provide highly conductive and reliable z-axis electrical connection, or the 186C' proud feature may be used in place of the proud feature 260 of the EMI filter circuit board filled passageway 394*f*. It is appreciated that the pads of the feedthrough conductive pathways mating with the circuit board filled passageways 394*a* and 394*d* can similarly be configured to stand proud with or without the circuit board proud feature 260. In other words, feedthrough conductive pathway proud features allow additional filtered feedthrough design options to ensure that the ACF uncompressed conductive particles 262 effectively transform into ACF compressed conductive particles 262' to enable optimal electrical conduction at the mating surfaces. In an embodiment, it is anticipated that metallic structures that provide a proud feature can optionally be embedded in ACF 261. For example, parallel metallic discs embedded so that they each stand proud on the body fluid and device sides of the ACF 261 can provide ACF compressed conductive particles 262', which will electrically connect the feedthrough conductive pathways and the circuit board conductive passageways achieving the desired electrical conduction through the filtered feedthrough 210 to its body fluid and device sides.

Referring once again to the various EMI filter capacitor and EMI filter circuit board embodiments illustrated throughout this specification, it is appreciated that electrical connection to a hermetically sealed feedthrough 120 using ACA, ACP, or ACF technologies, is deemed equally applicable to each. Also electrical connection of EMI filter capacitors or EMI filter circuit boards to implantable device feedthrough or housing oxide-resistant pads, pocket-pads, or other such oxide-resistant surface areas and/or making such electrical connections using ACA, ACP, or ACF are also anticipated applicable, wholly or in part, to each embodiment illustrated in U.S. Pat. Nos. 7,957,806; 8,195,295; 8,604,341; 8,927,862; 9,521,744; 9,895,534; and 10,306,848; the contents of which are fully incorporated herein by these references, including each of the patents previously incorporated herein by their references.

SUMMARY OF THE INVENTION

The present invention relates to a filtered feedthrough assembly that is attachable to an active implantable medical device (AIMD). The filtered feedthrough assembly comprises a feedthrough supporting a filter capacitor. The feedthrough comprises an electrically conductive ferrule having a ferrule sidewall defining a ferrule opening. The ferrule sidewall extends to a ferrule body fluid side spaced from a ferrule device side. An insulator is hermetically sealed to the ferrule in the ferrule opening. The insulator extends to an insulator body fluid side spaced from an insulator device side. That way, when the ferrule hermetically sealed to the insulator is attached to an opening in a housing of an AIMD, the ferrule body fluid side adjacent to the insulator body fluid side, and the ferrule device side adjacent to the insulator device side reside outside and inside the AIMD, respectively. At least a first terminal pin is hermetically sealed to the insulator in a first via hole by a first braze. The first terminal pin extends outwardly beyond at least the insulator device side.

The filter capacitor comprises a dielectric substrate having a dielectric substrate peripheral surface extending to a dielectric substrate first end surface spaced from a dielectric substrate second end surface. The dielectric substrate supports at least one active electrode plate interleaved in a capacitive relationship with at least one ground electrode plate. When its mounted on the feedthrough, the dielectric substrate first end surface is adjacent to the insulator and the ferrule device sides.

At least a first passageway extends through the dielectric substrate to the dielectric substrate first and second end surfaces. The first terminal pin extend through the first passageway and outwardly beyond at least the dielectric substrate second end surface and is electrically connected to one of the active and ground electrode plates in the first passageway.

Importantly, a polymeric insulating material comprising one or more layers is contacted to the dielectric substrate second end surface. The polymeric insulating material comprises insulating nanoparticles. In one embodiment, the dielectric substrate second end surface is recess below the ferrule device side, and the polymeric insulating material extends to an inner surface of the ferrule sidewall. In another embodiment, the dielectric substrate second end surface is spaced above the ferrule device side with the at least one ground electrode plate extending to the dielectric substrate peripheral surface. An external ground metallization is contacted to the ground electrode plate at the peripheral surface, and the polymeric insulating material contacted to the dielectric substrate second end surface also contacts the external ground metallization at the dielectric substrate peripheral surface.

Suitable polymeric insulating material are selected from silicone, polyurethane, polyester, polyethylene, polypropylene, polyimide, polyamide, acrylic, polyacrylates, perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), polytetrafluoroethylene (PTFE), ethylene tetrafluoroethylene (ETFE), polyoxymethylene (POM) polycarbonate (PC), epoxy, rubber, acetal, polyacetal, polyformaldehyde, phenolic, polysulfide, and combinations thereof.

Suitable nanoparticles are selected from $Al_2O_3$, BaO, CaO, $CeO_2$, MgO, ZnO, $ZrO_2$, $SiO_2$, $TiO_2$, $Al_2SiO_{53}$, $BaTiO_3$, $SrTiO_2$, zirconia toughened alumina (ZTA), alumina toughened zirconia (ATZ), yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof. The nanoparticles range in size from greater than about 100 nanometers (0.1 microns) to about 40,000 nanometers (40 microns) and have a loading in the polymeric insulating material that ranges from >0 to about 40%, by weight.

BRIEF DESCRIPTION OF THE DRAWINGS

The accompanying drawings illustrate the invention. In such drawings:

FIG. 48 is cross-sectional view of a filtered feedthrough, which is similar to the filtered feedthrough of FIG. 47A, except that the circuit board of FIG. 48 is grounded by BGA dots electrically connecting solid filled EMI filter circuit board passageways and corresponding oxide-resistant gold braze bond pads at each short end of the feedthrough ferrule.

FIG. 53C is TABLE 1 containing various alumina ($Al_2O_3$) nanoparticle filled epoxy composite polymeric insulating materials.

FIG. 53D is TABLE 2 containing various $Al_2O_3$-epoxy composite polymeric insulating materials having boron nitride (BN) nanoparticle fillers.

FIG. 54C-1 is taken along 54C-1-54C-1 of FIG. 54C illustrating a top composite polymeric insulating washing having thermoplastic coating on the insulating washer surface that bonds to the top surface of an EMI filter capacitor.

FIG. 54C-2 is taken along 54C-2-54C-2 of FIG. 54C illustrating a top composite polymeric insulating washing having thermoplastic coating on the polymeric insulating washer surface that bonds to the top surface of an EMI filter capacitor and an optional thermoplastic coating opposite polymeric insulating washer surface.

FIG. 54C-3 is taken along 54C-3-54C-3 of FIG. 54C illustrating a top composite polymeric insulating washer having at least two insulating washers with disposed thermoplastic coatings.

FIG. 54C-4 is taken along 54C-4-54C-4 of FIG. 54C illustrating a polymeric or an alumina or other ceramic insulating washer bonded to the thermoplastic coating of a top composite polymeric insulating washer.

Figure 54:
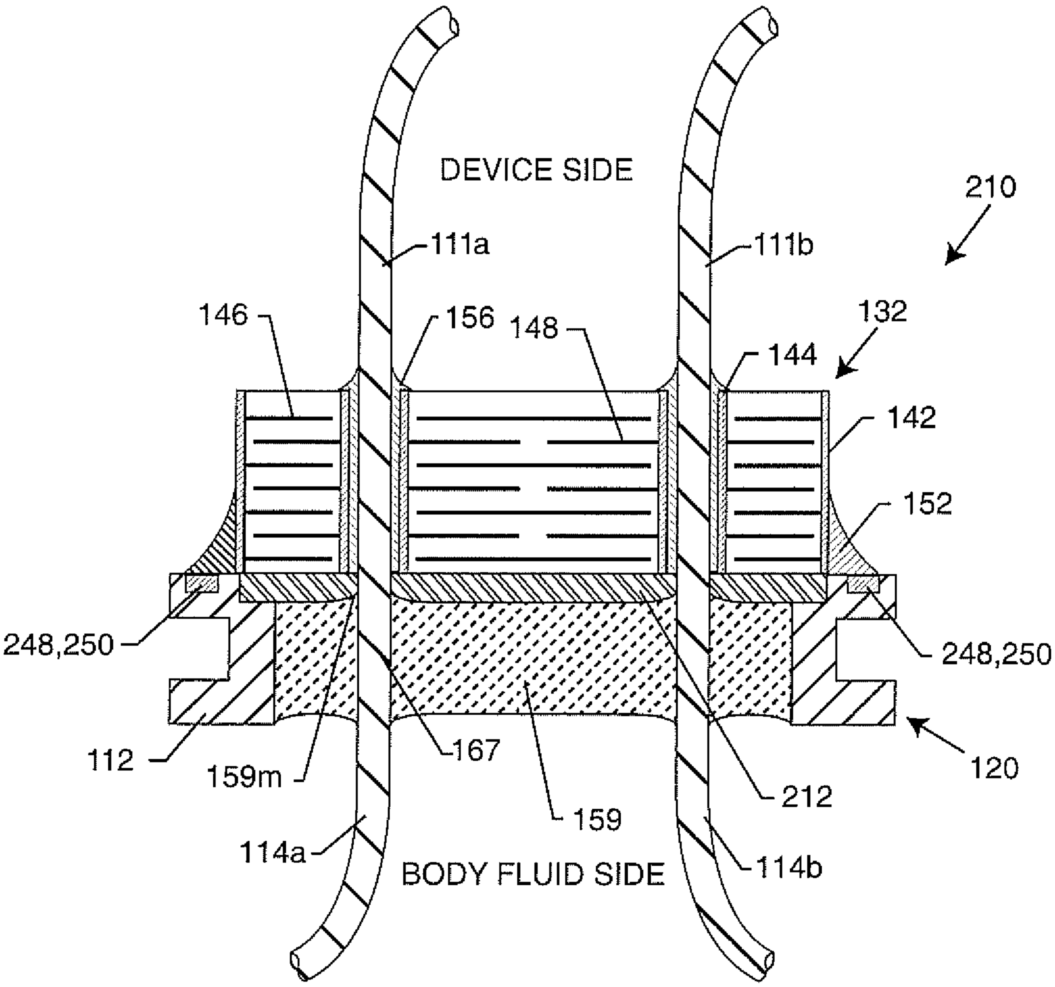
FIG. 54 is similar to FIG. 52, except that the insulator of the hermetically glass sealed feedthrough has terminal pins spaced further from the feedthrough ferrule and a thermoplastic coated polymeric insulating washer.
Figure 54A:
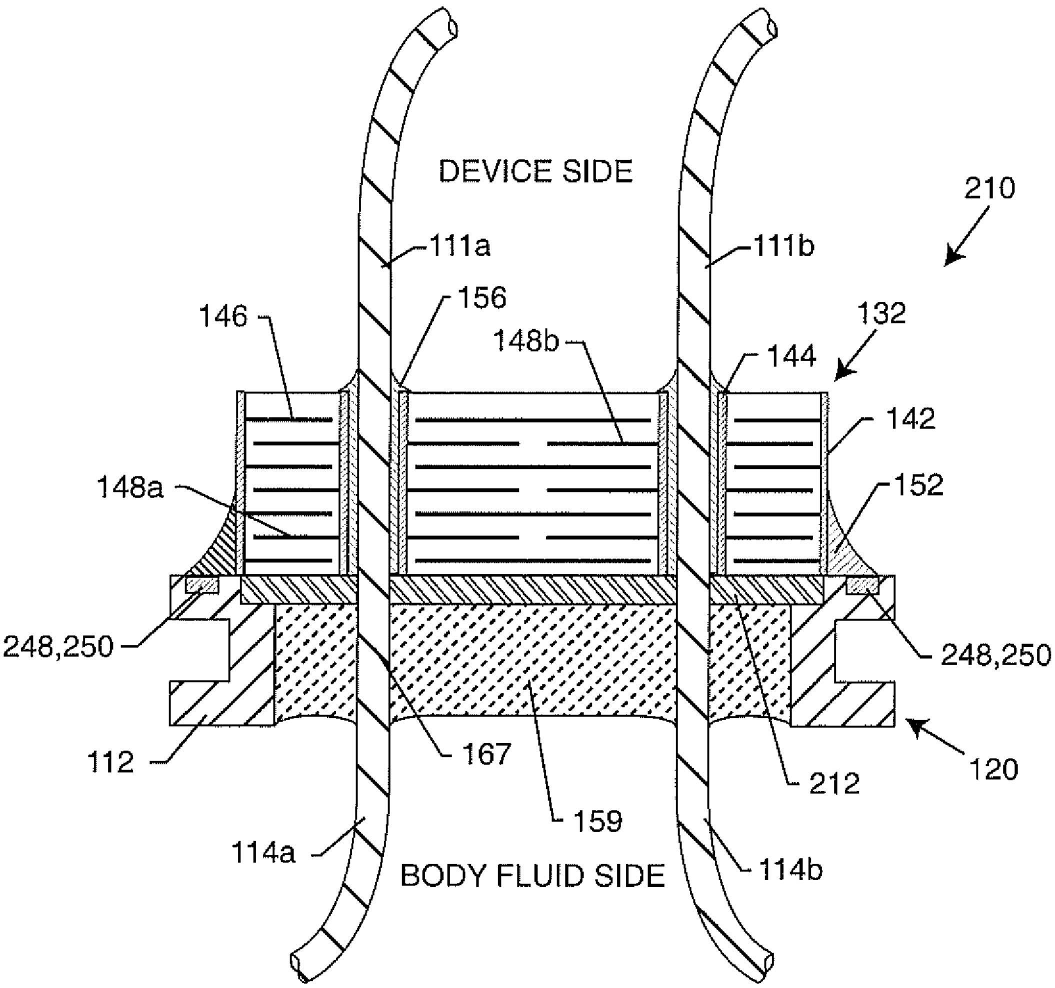
FIG. 54A is substantially equivalent to FIG. 54, except that the surface of the glass insulator is absent a lead menisci.
Figure 54B:
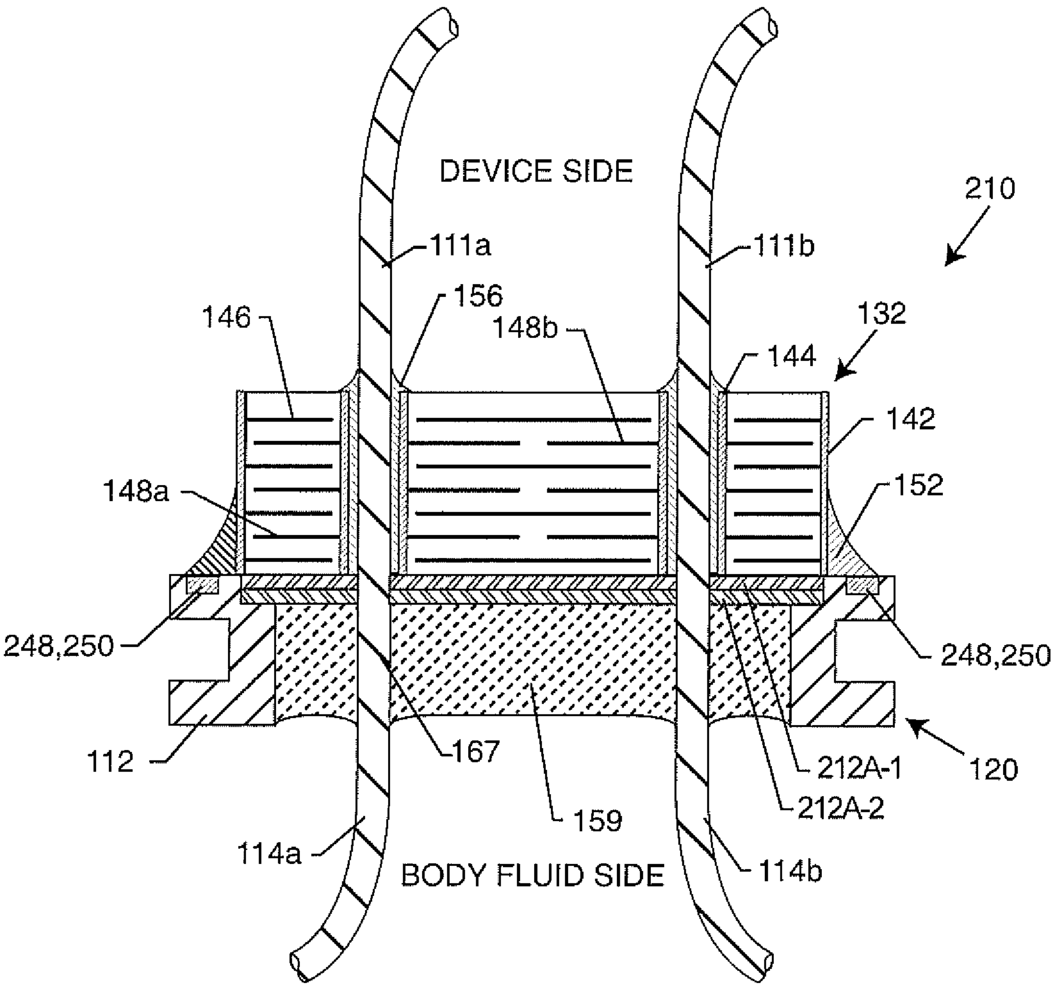
FIG. 54B is similar to FIG. 54, except that there are at least two insulating washer layers.
Figure 54C:
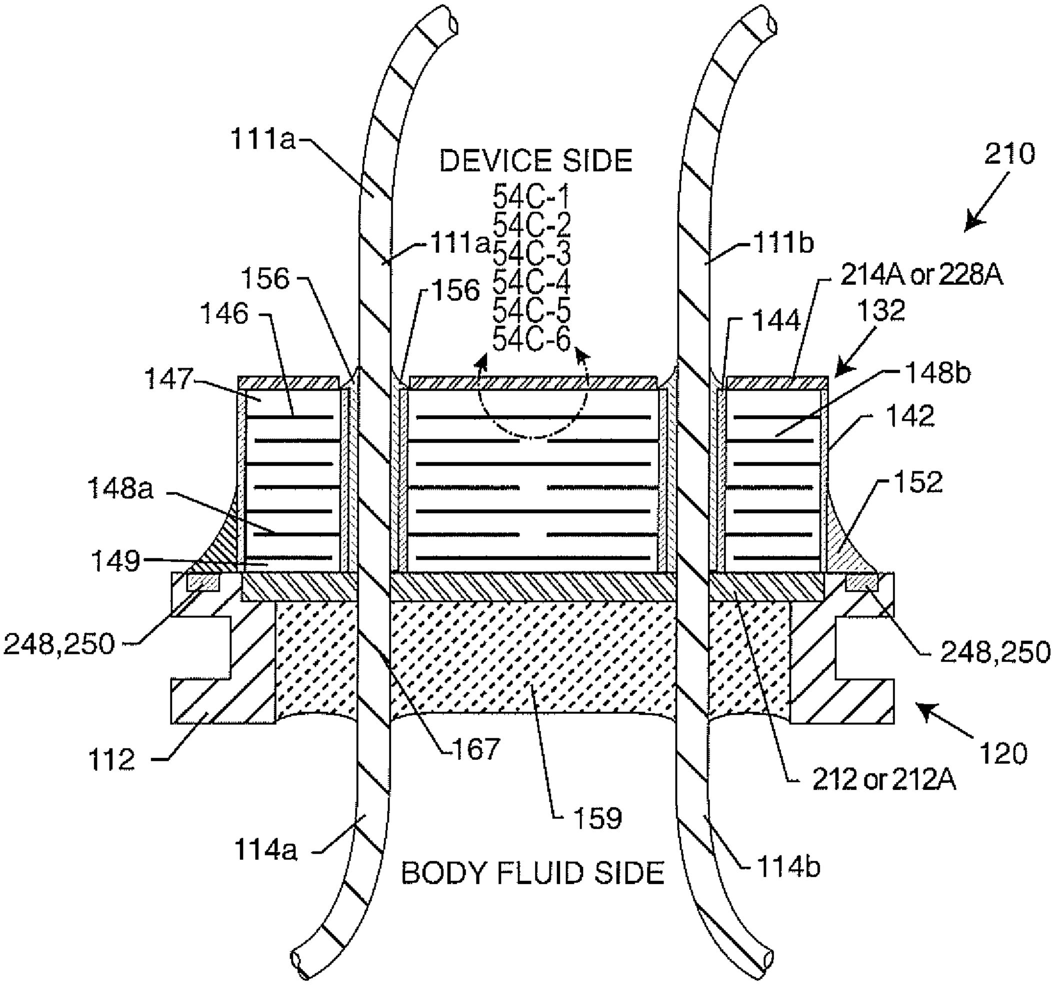
FIG. 54C is similar to FIG. 54, except that a top composite polymeric insulating washer or homogeneous polymeric insulating washer has been added.
Figures 1, 54C:
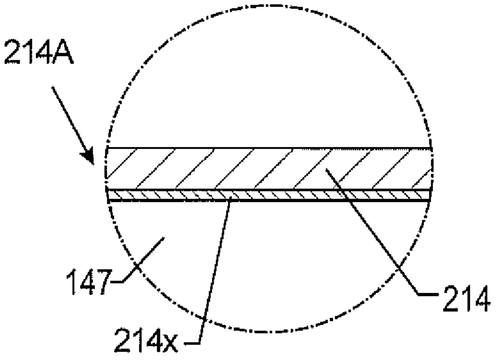
Figures 2, 54C:
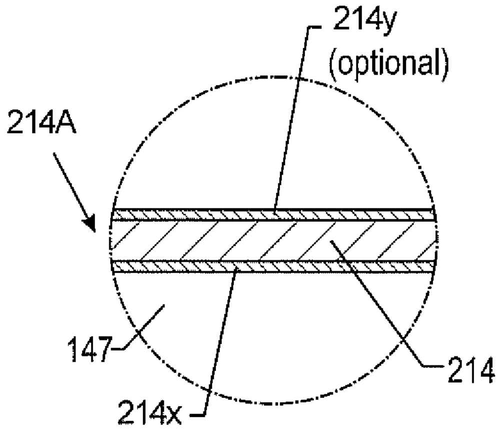
Figures 3, 54C:
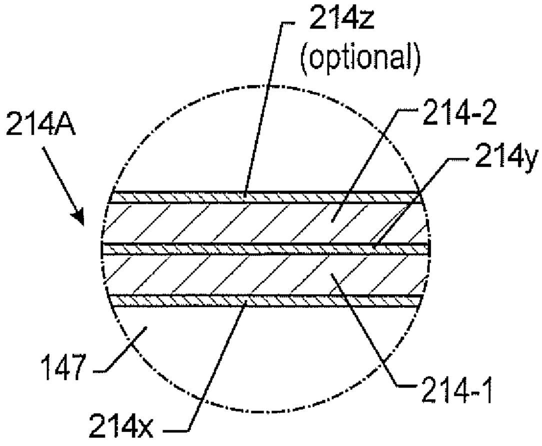
Figures 4, 54C:
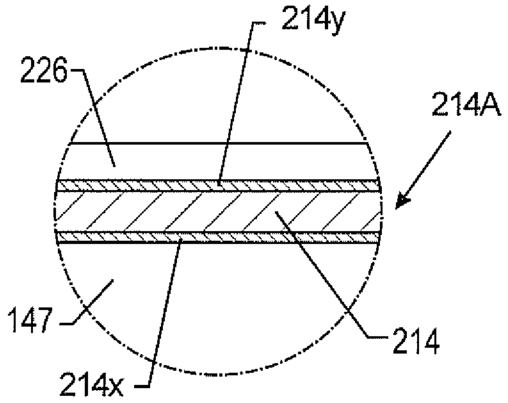
Figures 5, 54C:
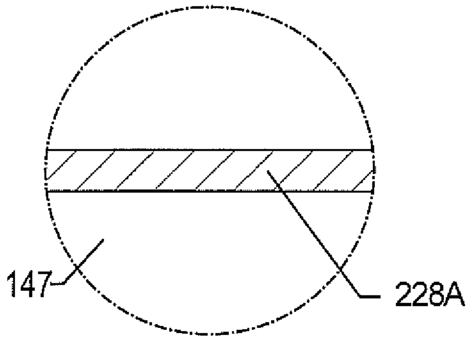

54C-5 is a blown-up partial view taken along section 54C-5 of FIG. 54C, illustrating a homogeneous polymeric insulating washer.

54C-6 is a blown-up partial view taken along section 54C-6 of FIG. 54C, illustrating a homogeneous nanoparticle-filled 264 polymeric insulating washer.

Figures 6, 54C:
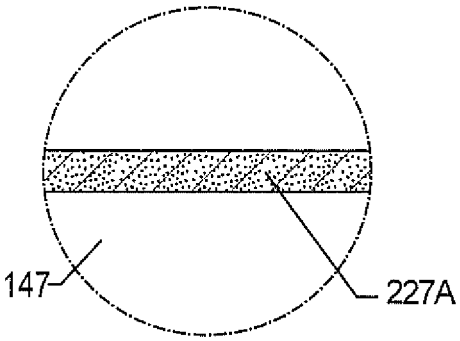
Figure 54D:
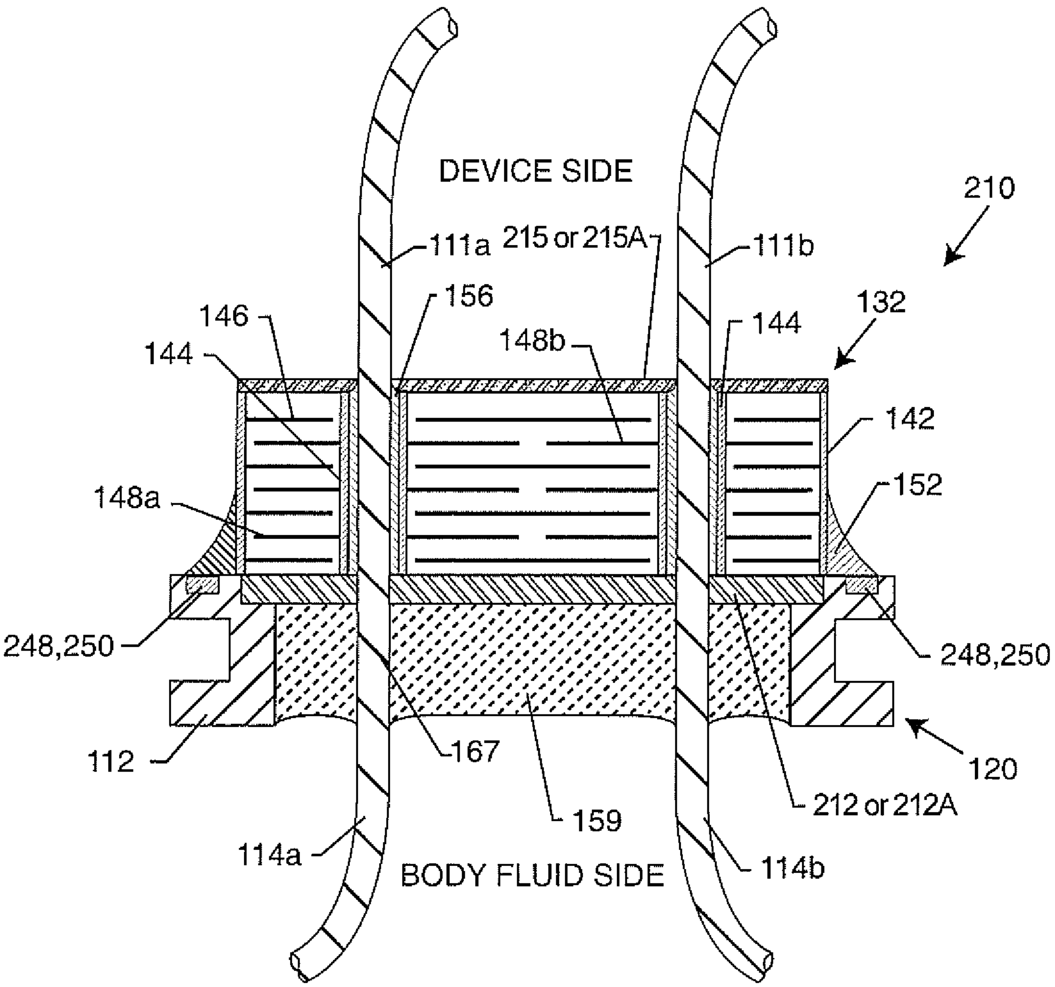

FIG. 54D is similar to FIG. 54C, except the top insulating washer or insulating material, which may comprise any insulating polymeric material including a thermoplastic, has filler insulating nanoparticles 264 uniformly dispersed therewithin.

Figure 54E:
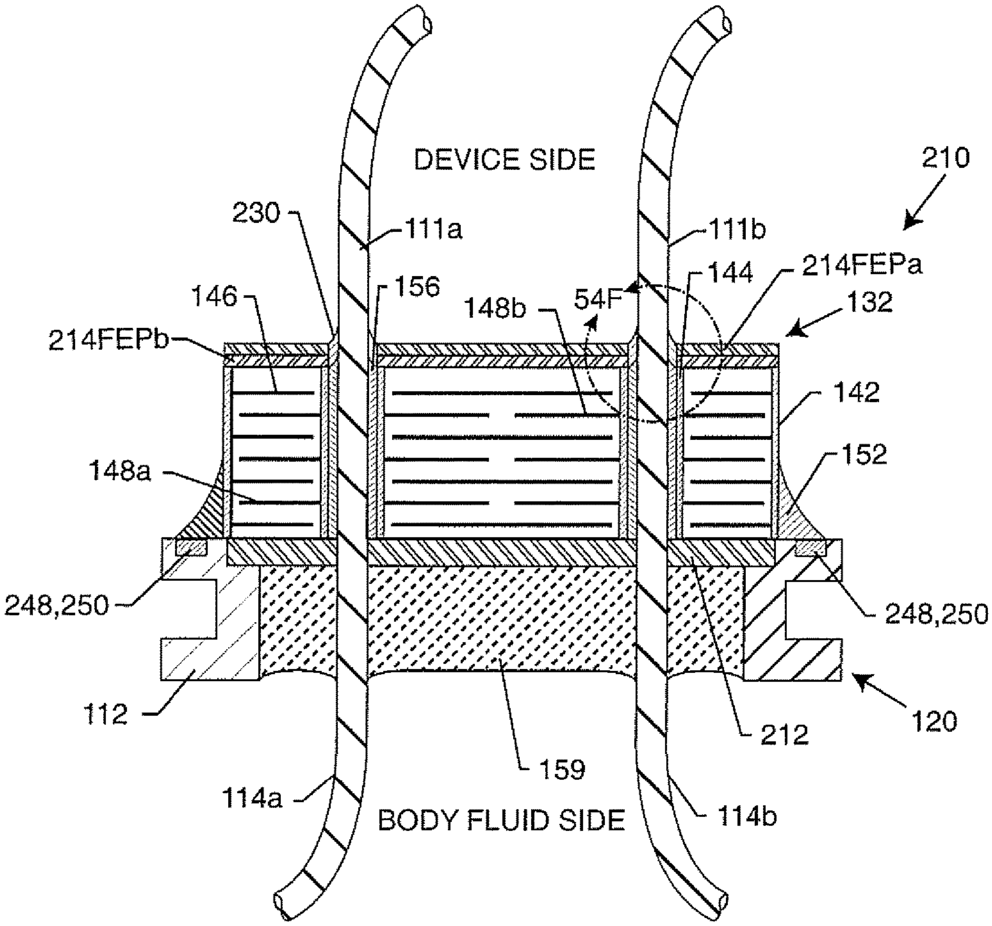

FIG. 54E is similar to FIG. 54C, except that there are at least two top thermoplastic insulating material or insulating washer layers.

Figure 54F:
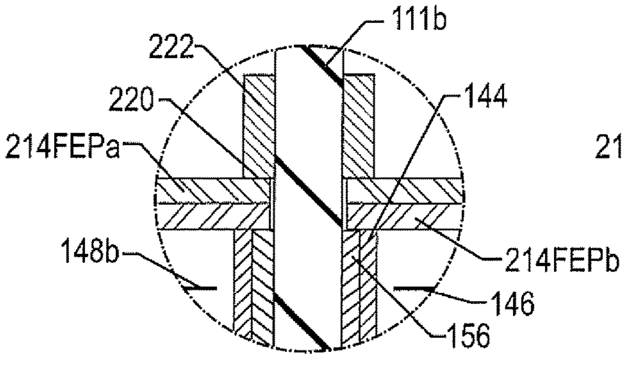

FIG. 54F is similar to FIG. 54E with the addition of insulating tubing disposed over the terminal pins on top of the thermoplastic coated insulating washers.

Figure 54G:
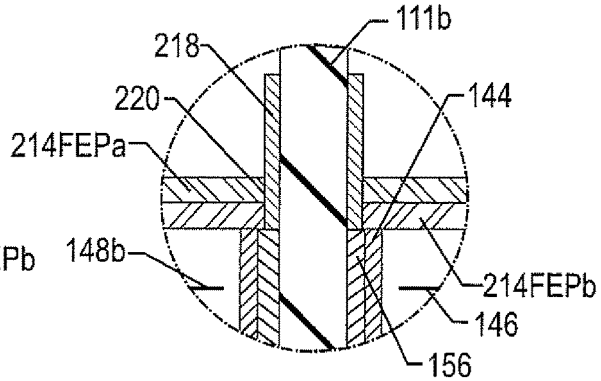

FIG. 54G is similar to FIG. 54E with the addition of insulating tubing disposed over the terminal pins and into openings in the thermoplastic coated insulating washers.

Figure 54H:
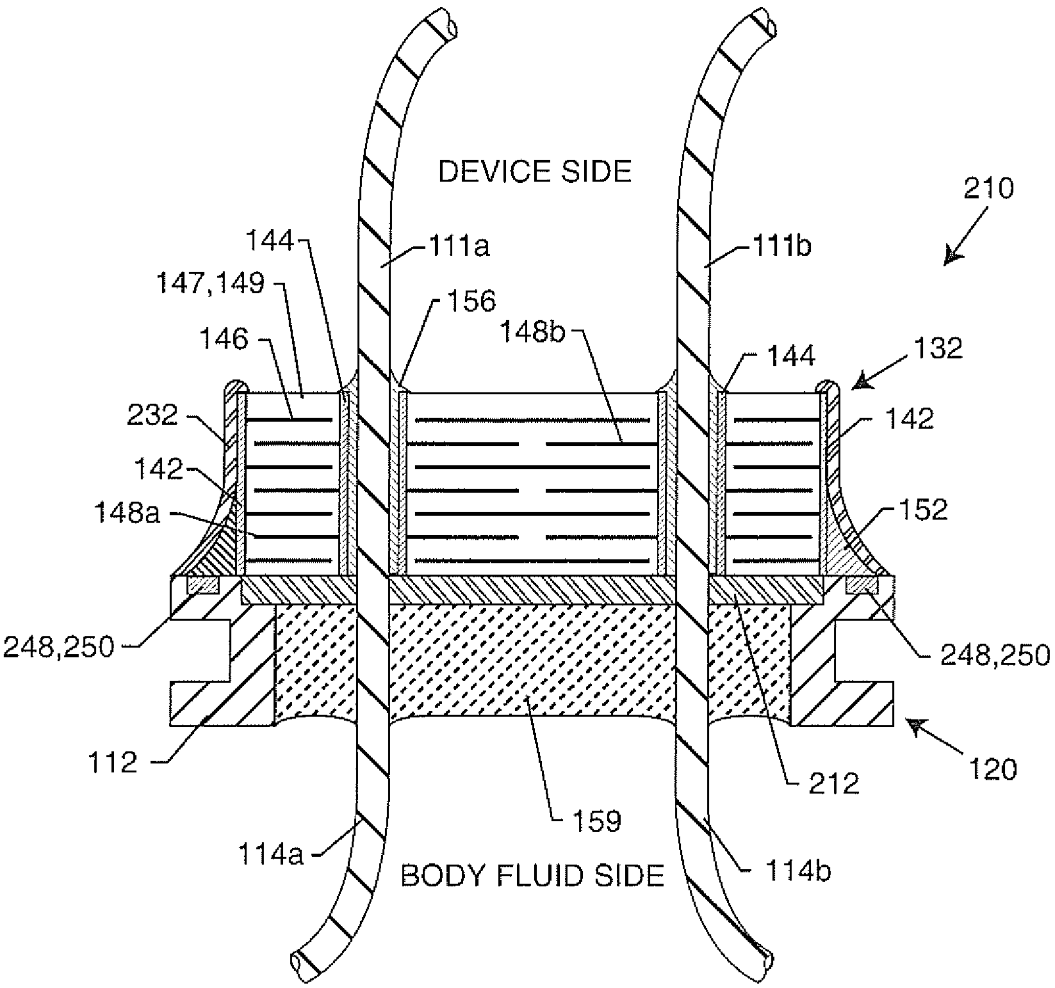

FIG. 54H is similar to FIG. 54, except that an insulating material has been added to the perimeter, diameter, or sides of the feedthrough filter capacitor.

Figure 54I:
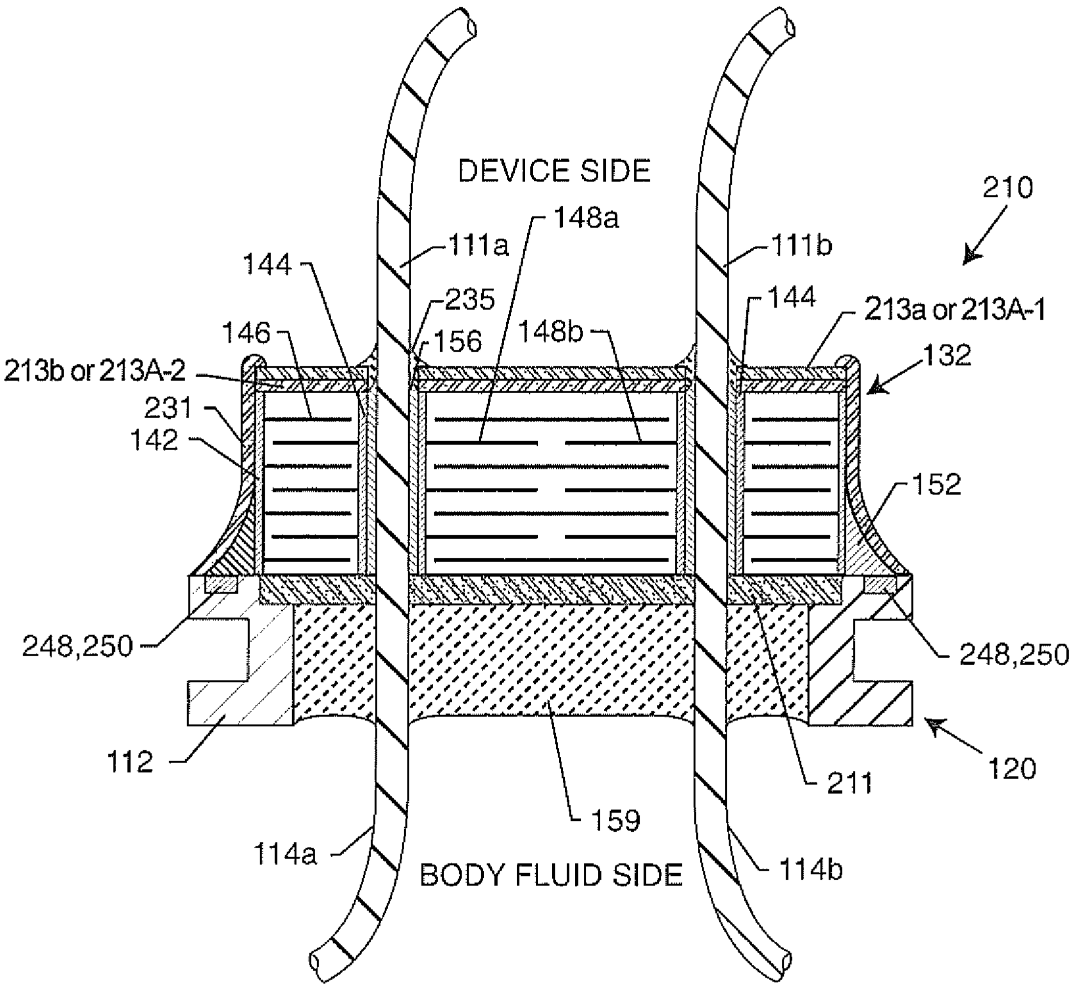

FIG. 54I is a cross-sectional view of a filtered feedthrough illustrating a feedthrough filter capacitor having insulating materials on the bottom, top and perimeter or sides.

Figure 21:
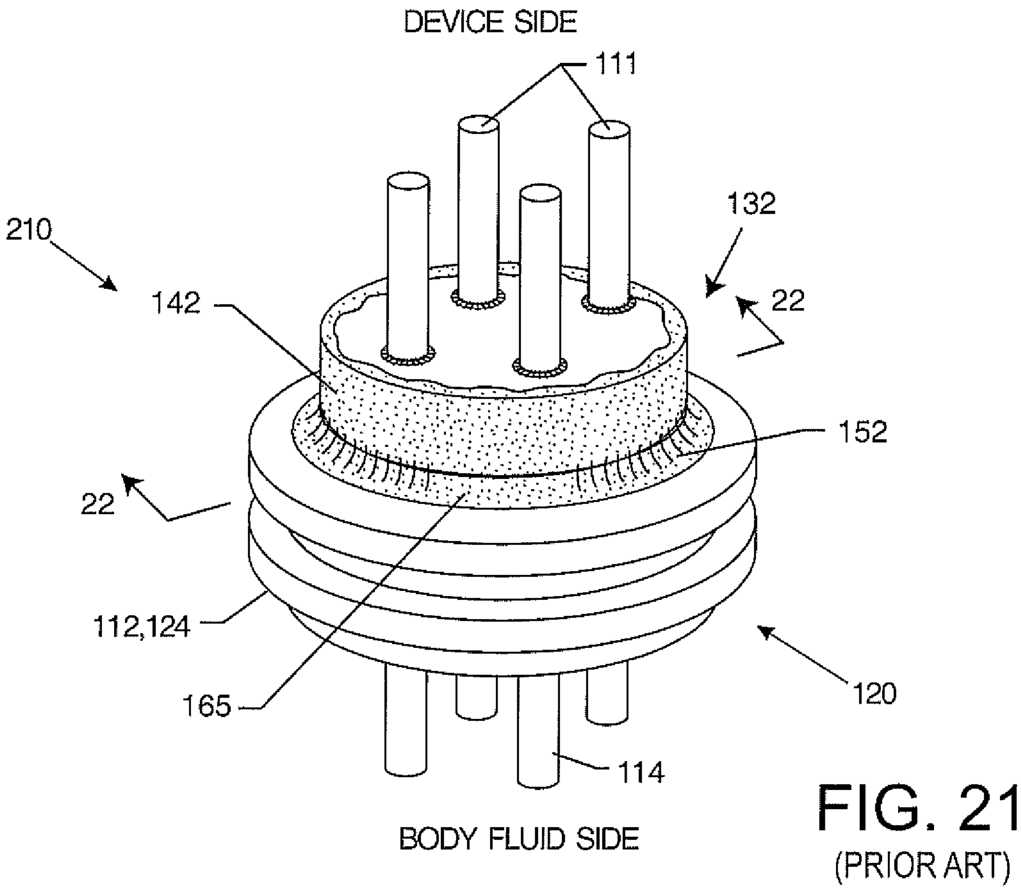
FIG. 21 (PRIOR ART)
FIG. 21 is prior art taken from FIG. 23 of U.S. Pat. No. 6,765,779, illustrating an isometric view of a hermetically sealed discoidal quadpolar filtered feedthrough.
Figure 55:
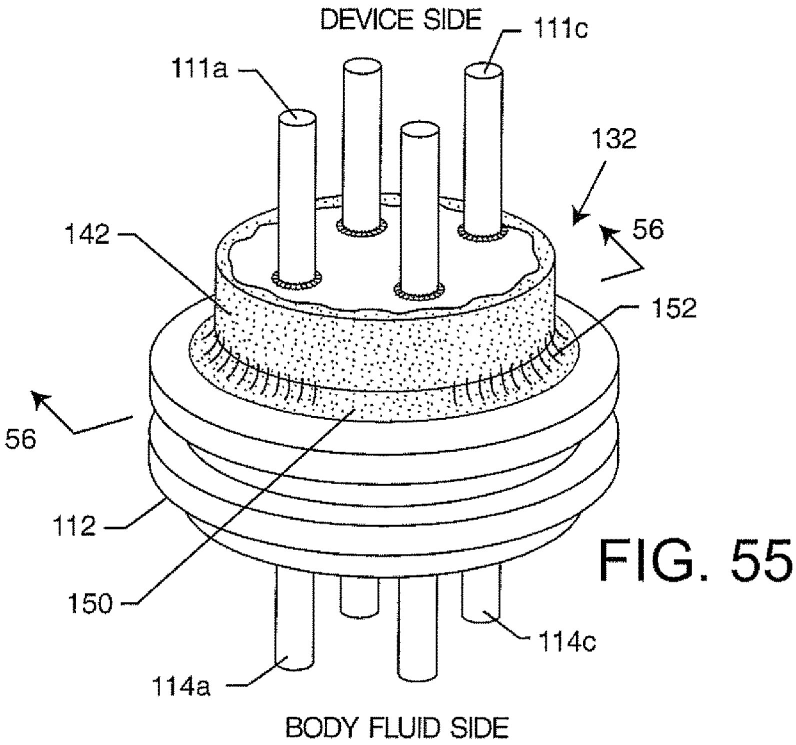
Figure 56A:
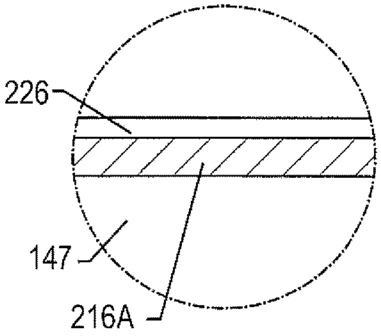
Figure 56:
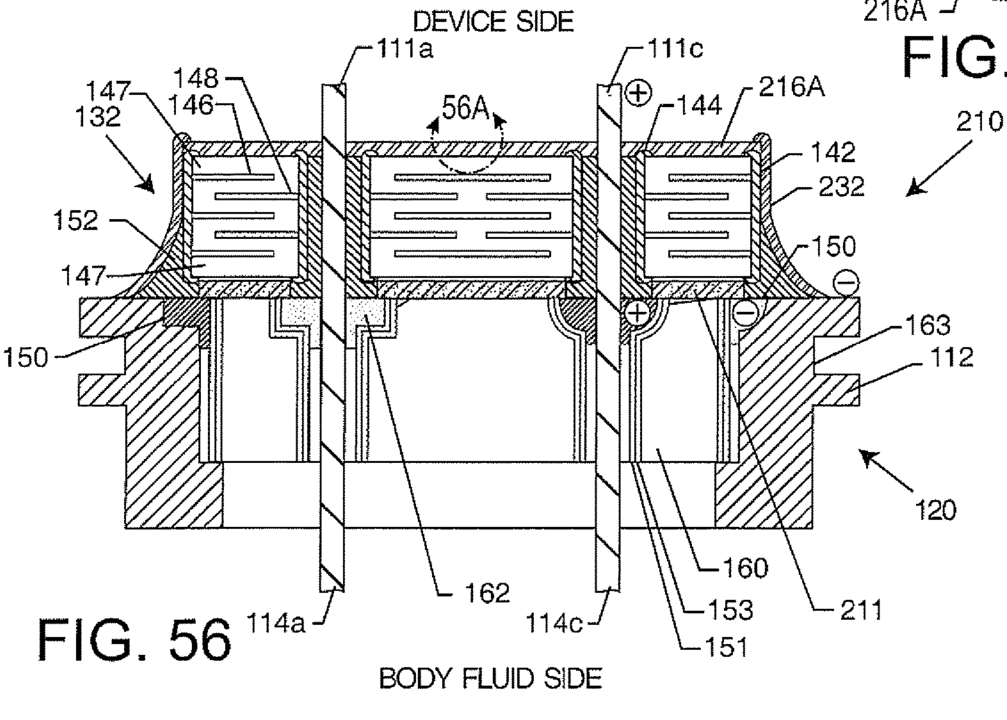

FIG. 55 is the quadpolar filtered feedthrough of FIG. 21, except section 56-56 is added for the purpose of illustrating several novel embodiments of FIG. 56.

FIG. 56 is a cross-sectional view generally taken along 56-56 of FIG. 55 illustrating a polymeric insulating material disposed about the perimeter and the top perimeter edge of the EMI filter capacitor and a nanoparticle-filled 264 insulating washer between the EMI filter capacitor and the hermetically sealed feedthrough.

FIG. 56A is taken along section 56A-56A of FIG. 56 illustrating a polymeric or an alumina or other ceramic insulating cover sheet bonded to the top surface of a homogenous thermoplastic insulating washer.

Figure 57:
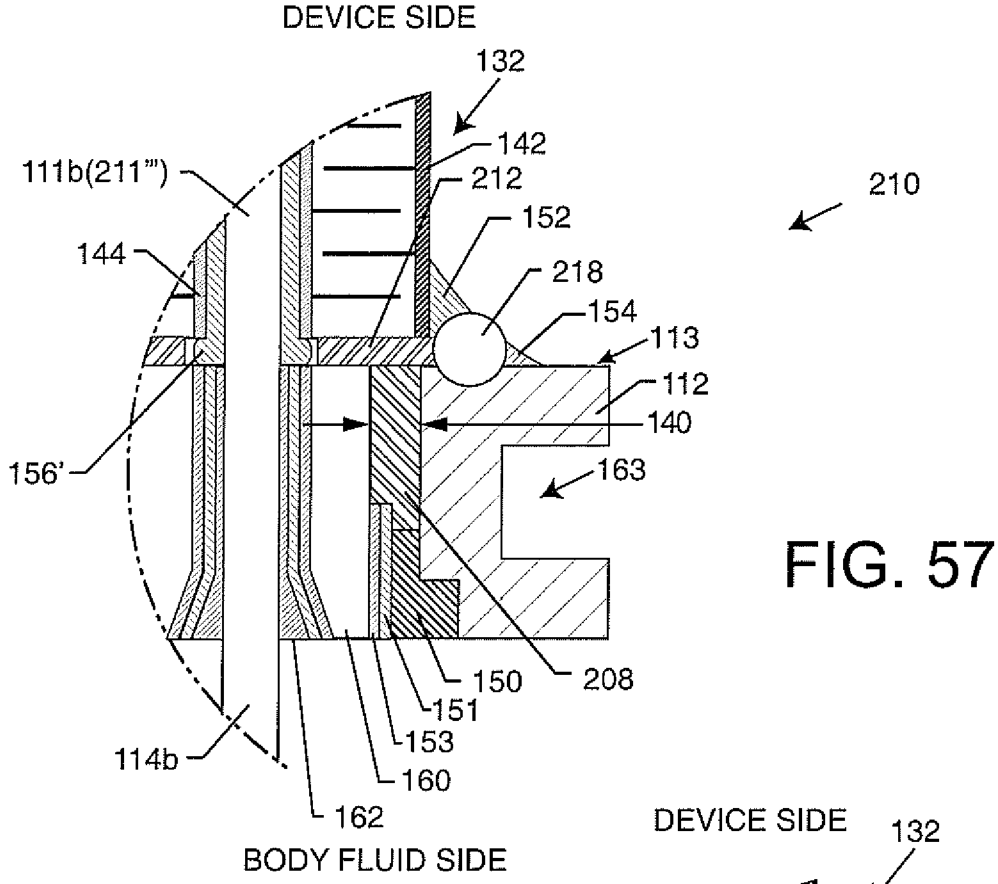

FIG. 57 is a cross-sectional view taken from FIG. 28A of U.S. Pat. No. 9,931,514, now illustrating that an insulating material that covers the gold braze has been added.

Figure 58:
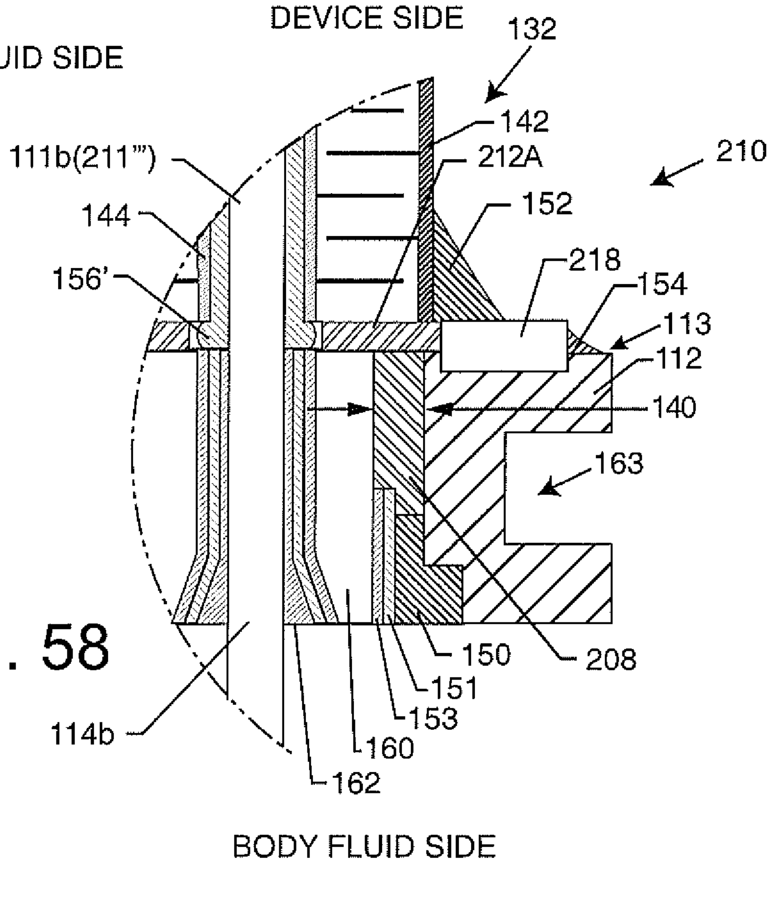

FIG. 58 is a cross-sectional view taken from FIG. 28B of U.S. Pat. No. 9,931,514 patent, now illustrating that a thermoplastic insulating washer has been added over the insulating material that covers the gold braze.

Figure 59:
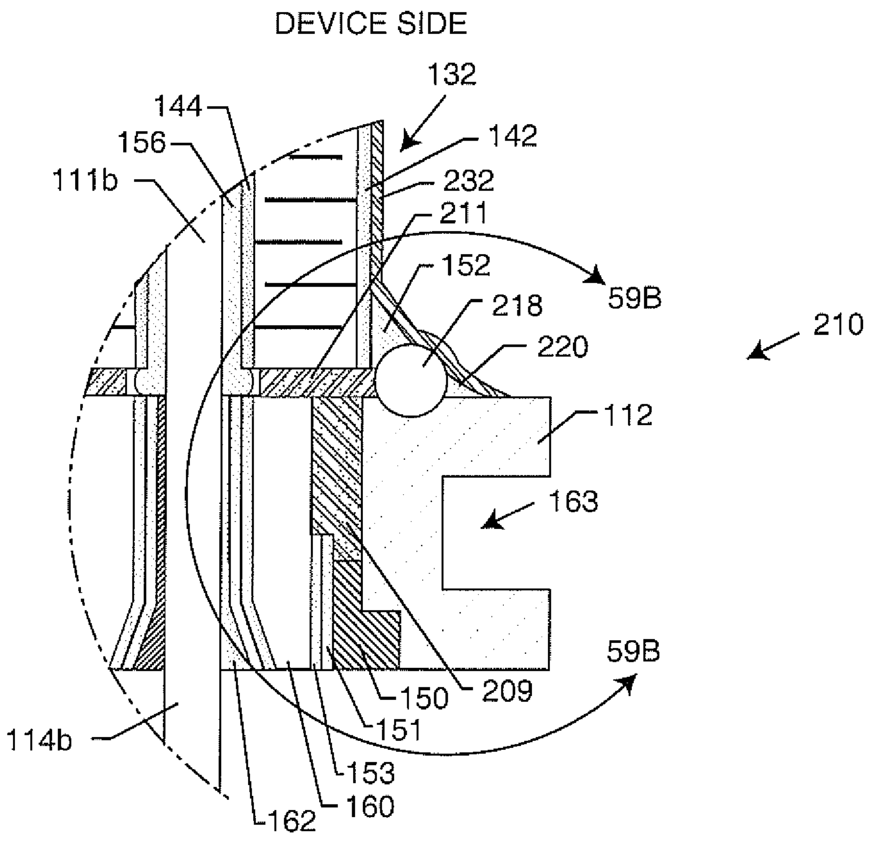

FIG. 59 is similar to FIG. 57, now illustrating that the novel filler insulating nanoparticles 264 have been added to the insulating washer or the insulating material or both the insulating washer and the insulating material.

Figure 59A:
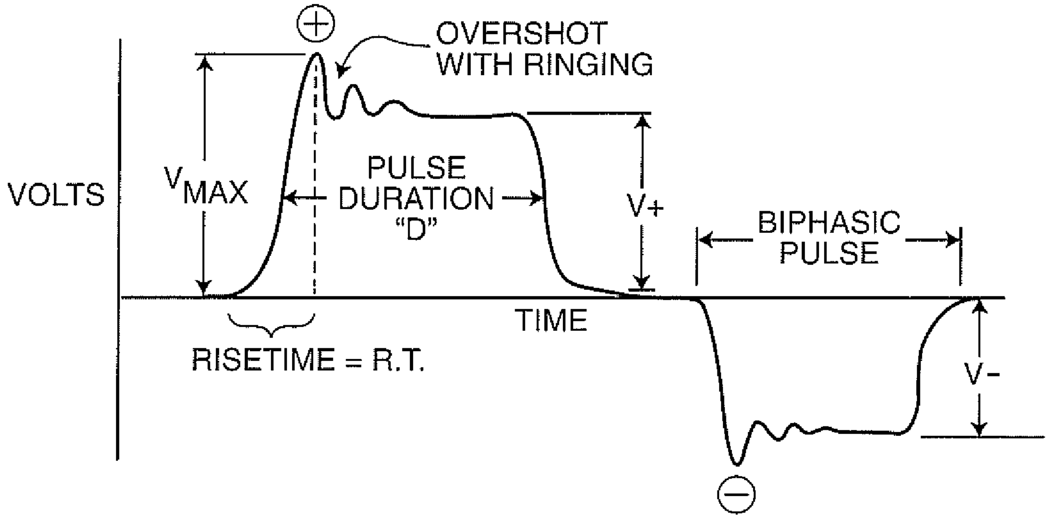

FIG. 59A is a illustrates a volts vs. risetime graph illustrating an ICD high-voltage biphasic pulse with overshoot and ringing.

Figure 59B:
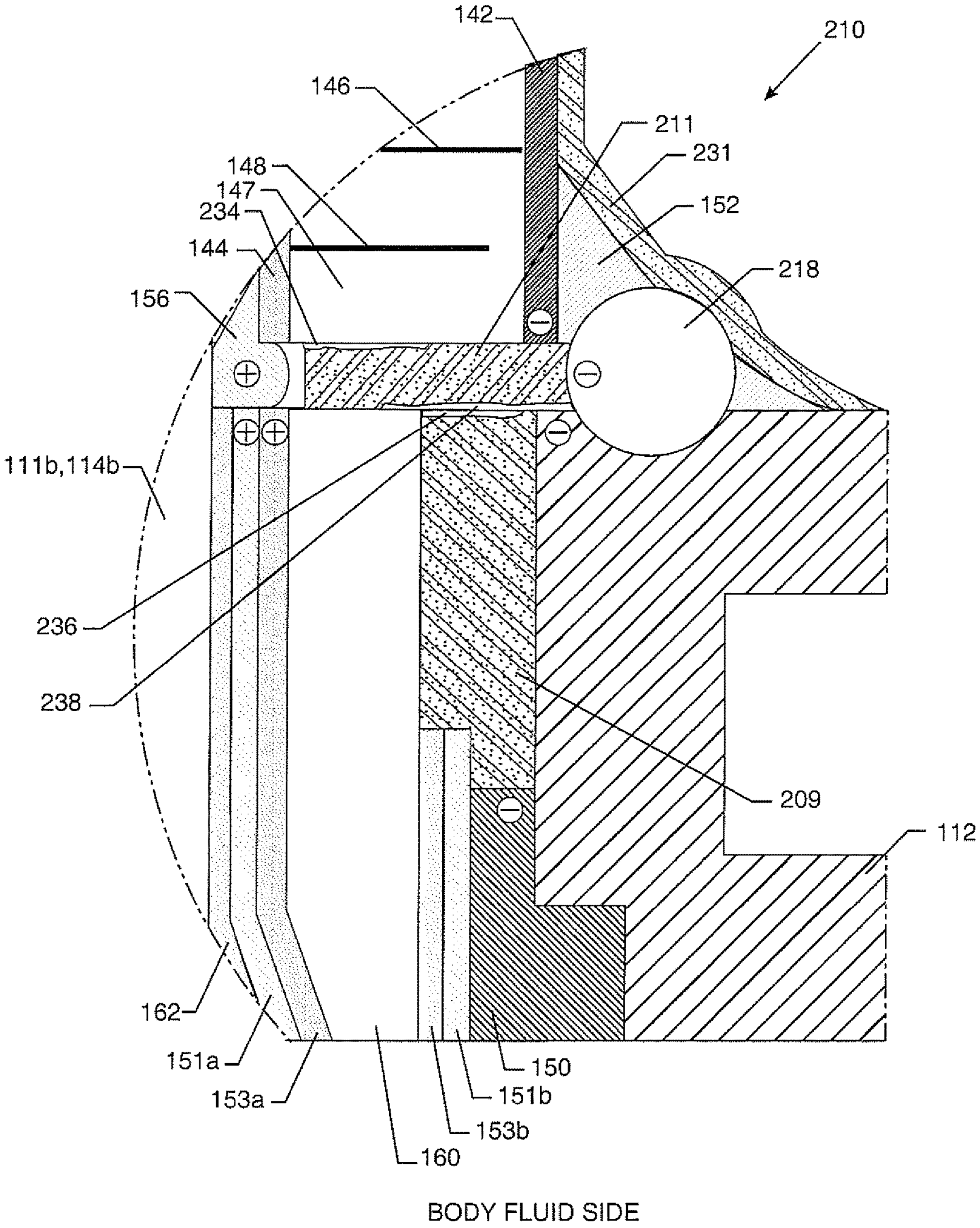

FIG. 59B is a blown-up partial view taken from 59B-59B of FIG. 59 illustrating undesirable gaps between the insulating washer and the filter capacitor and/or the insulating washer and the insulating material that covers the gold braze.

Figure 60:
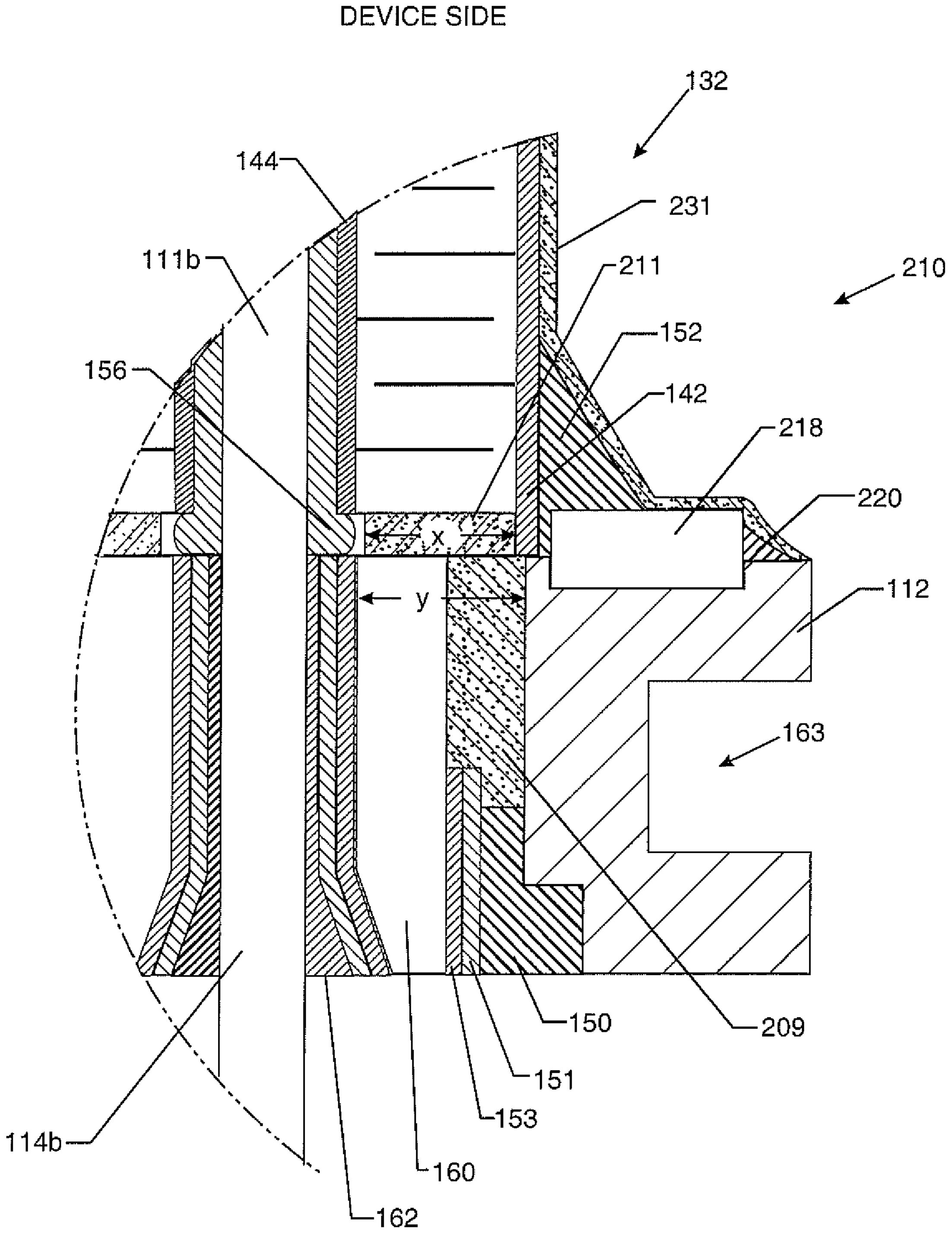

FIG. 60 is similar to FIG. 58, except the high-voltage stand-off distances x and y have been added.

Figure 48A:
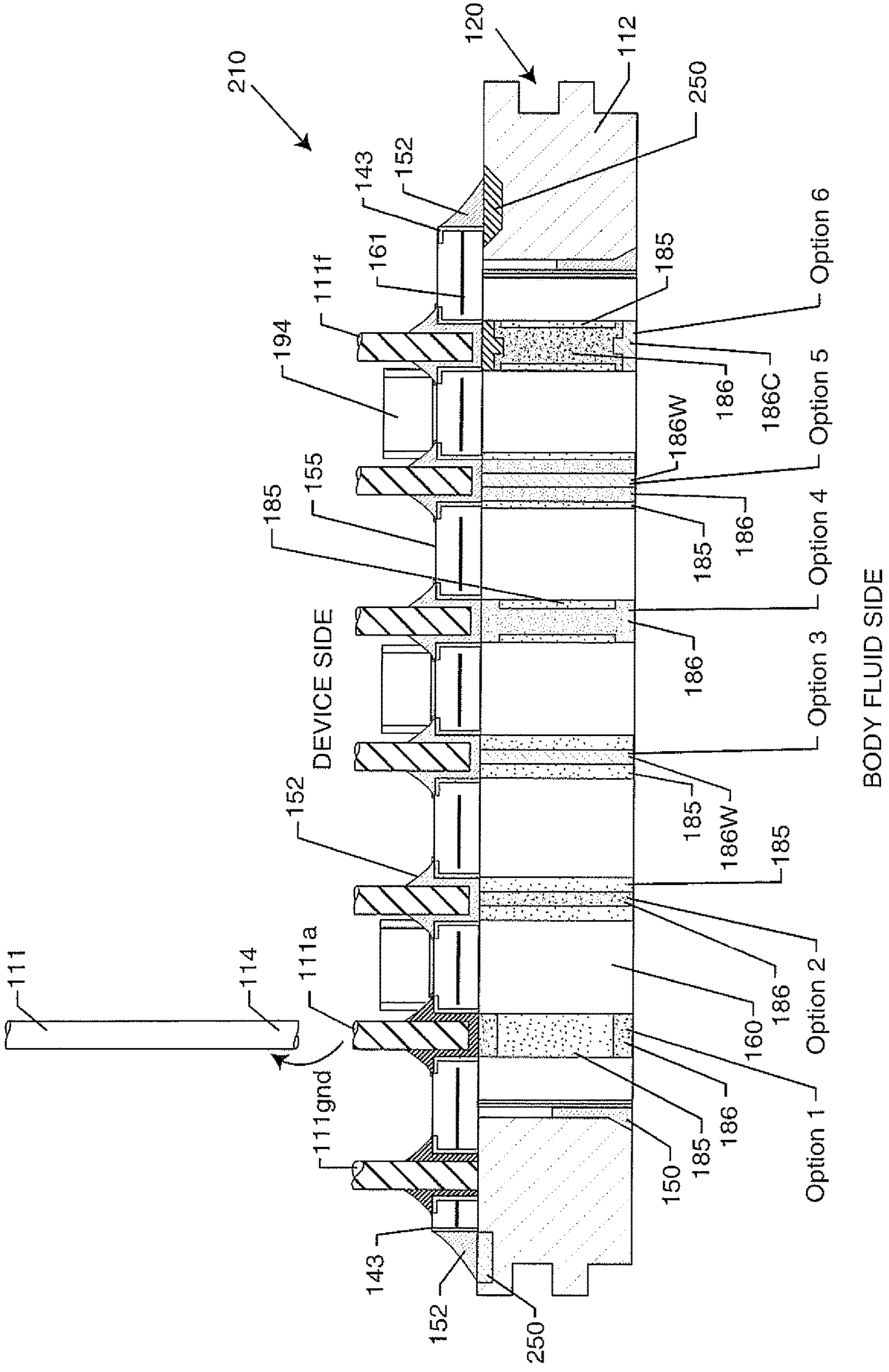
FIG. 48A (PRIOR ART)
FIG. 48A is similar to FIG. 48 except now each external ground circuit board metallization is electrically connected to a corresponding oxide-resistant gold braze bond pads at each short end of the feedthrough ferrule.
Figure 48B:
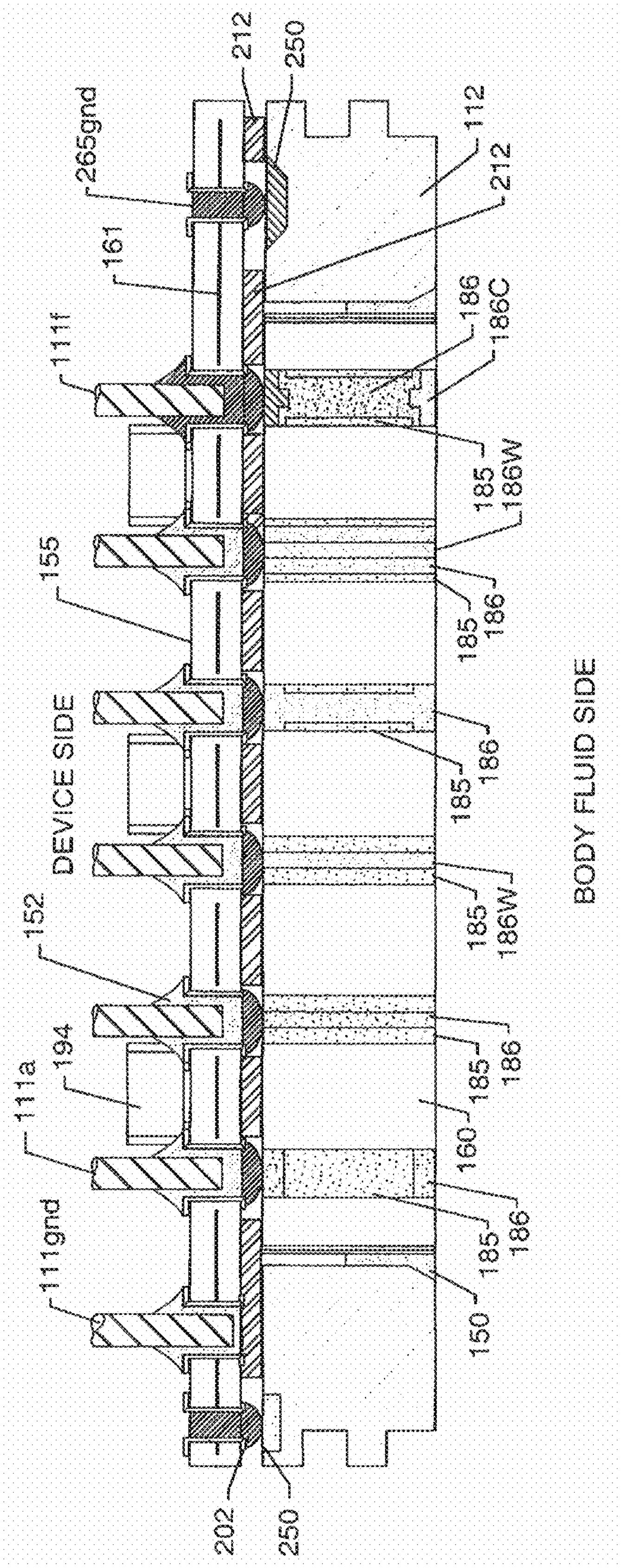
FIG. 48B (PRIOR ART)
FIG. 48B is a similar cross-sectional view to FIG. 48 except that now an anisotropic conductive film is used for electrically connecting the nail head electrical conductors of the EMI filter circuit board and the gold braze bond pads.
Figure 49:
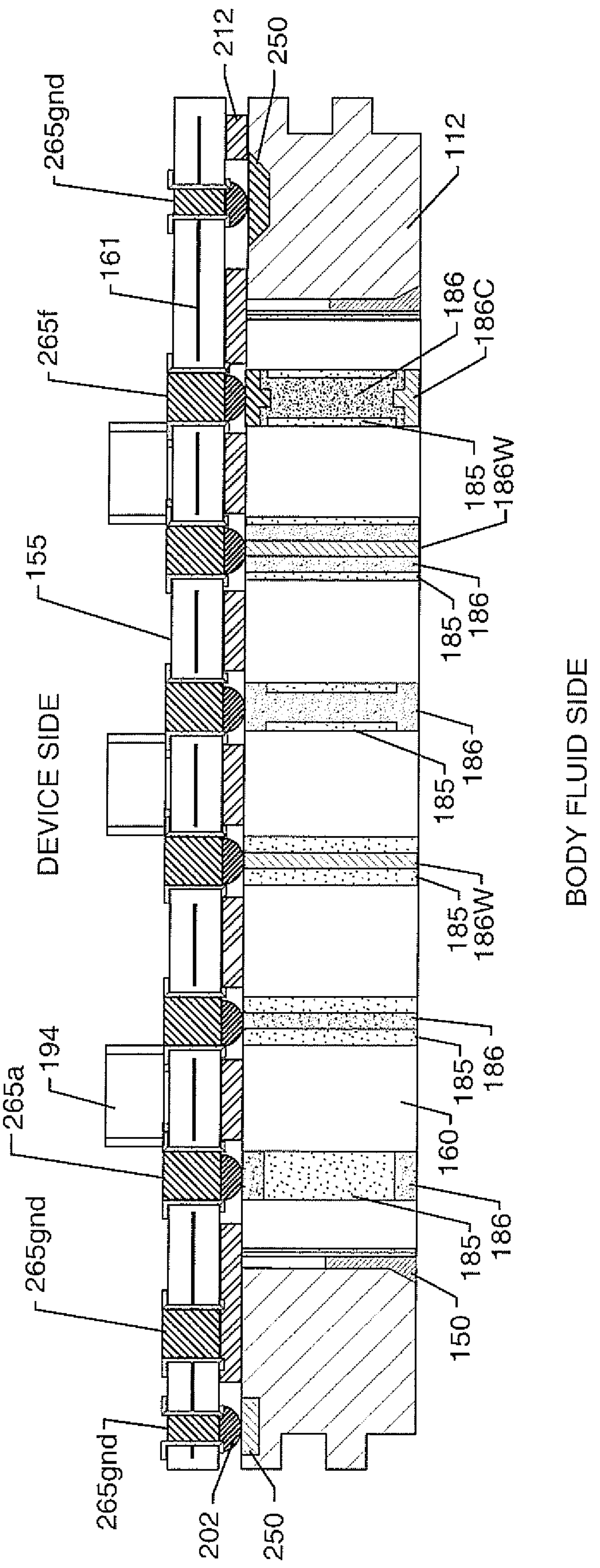
FIG. 49 (PRIOR ART)
FIG. 49 is a similar cross-sectional view to prior art FIGS. 47 and 48 except that now filled EMI filter circuit board conductive passageways with solder bumps, BGA bumps, or conductive polymeric bumps are used for making electrical connections.
Figure 61:
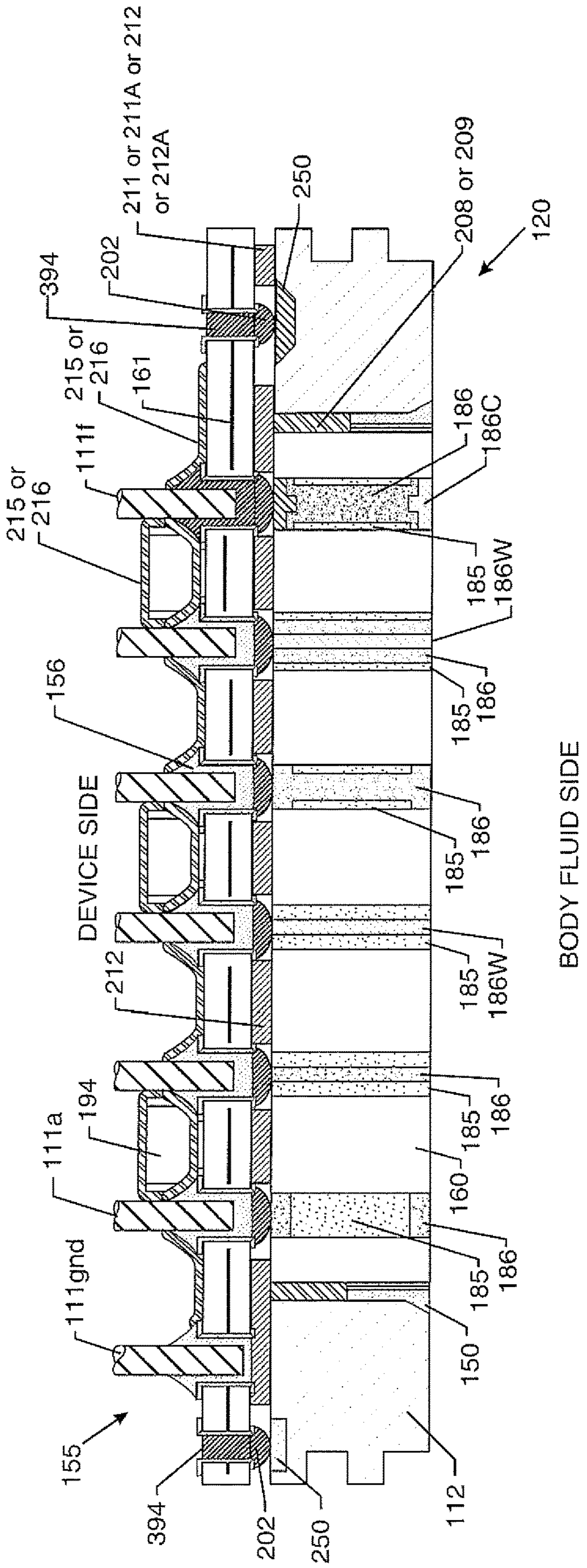

FIG. 61 is similar to FIG. 48, except that now an insulating material has been applied to cover the MLCC filter capacitors and the EMI filter circuit board surface between active conductive pathways and between the active and ground conductive pathways.

Figure 38:
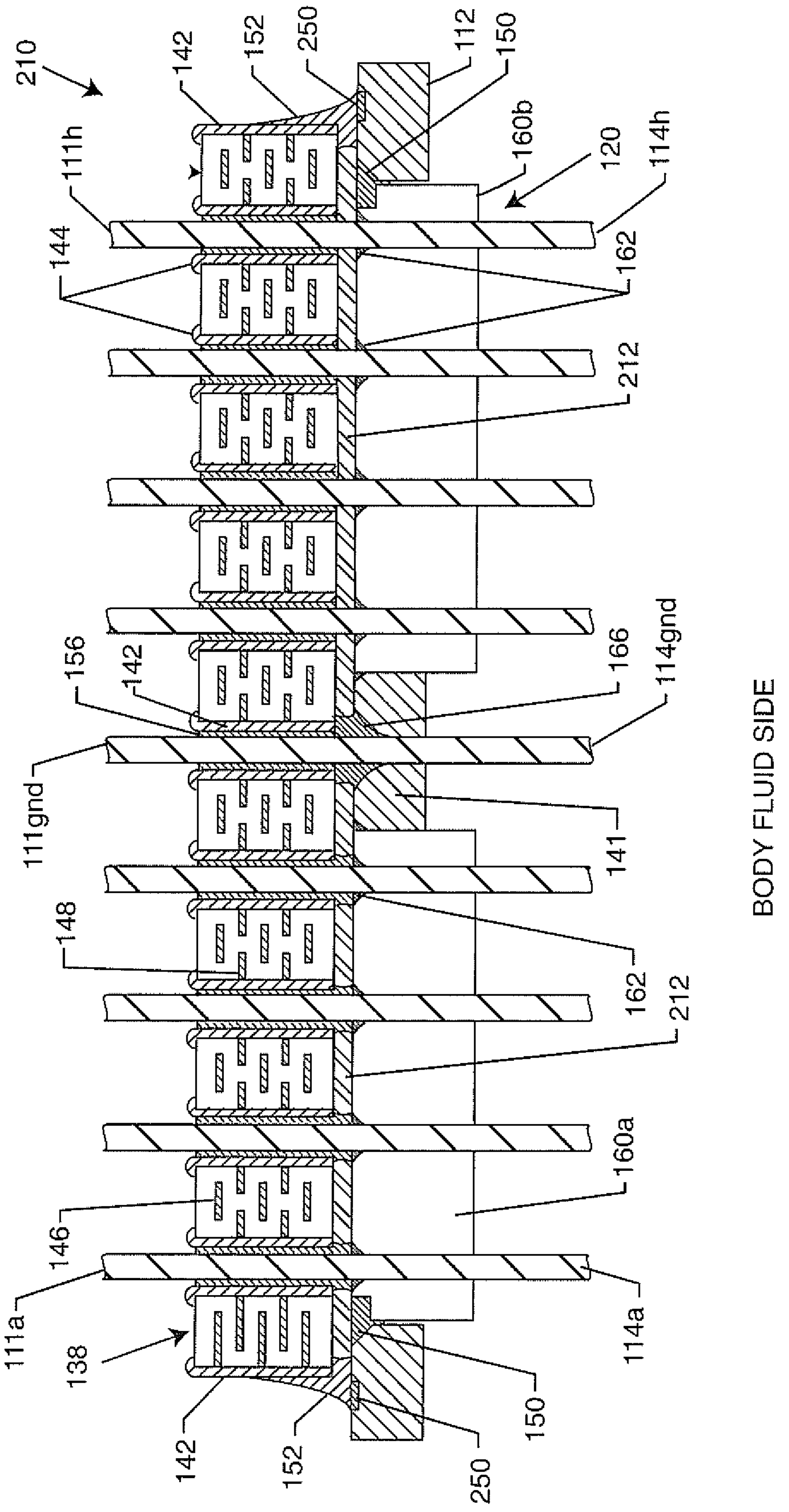
FIG. 38 (PRIOR ART)
FIG. 38 is a cross-sectional view generally taken along section 38-38 of prior art FIG. 37.
Figure 62:
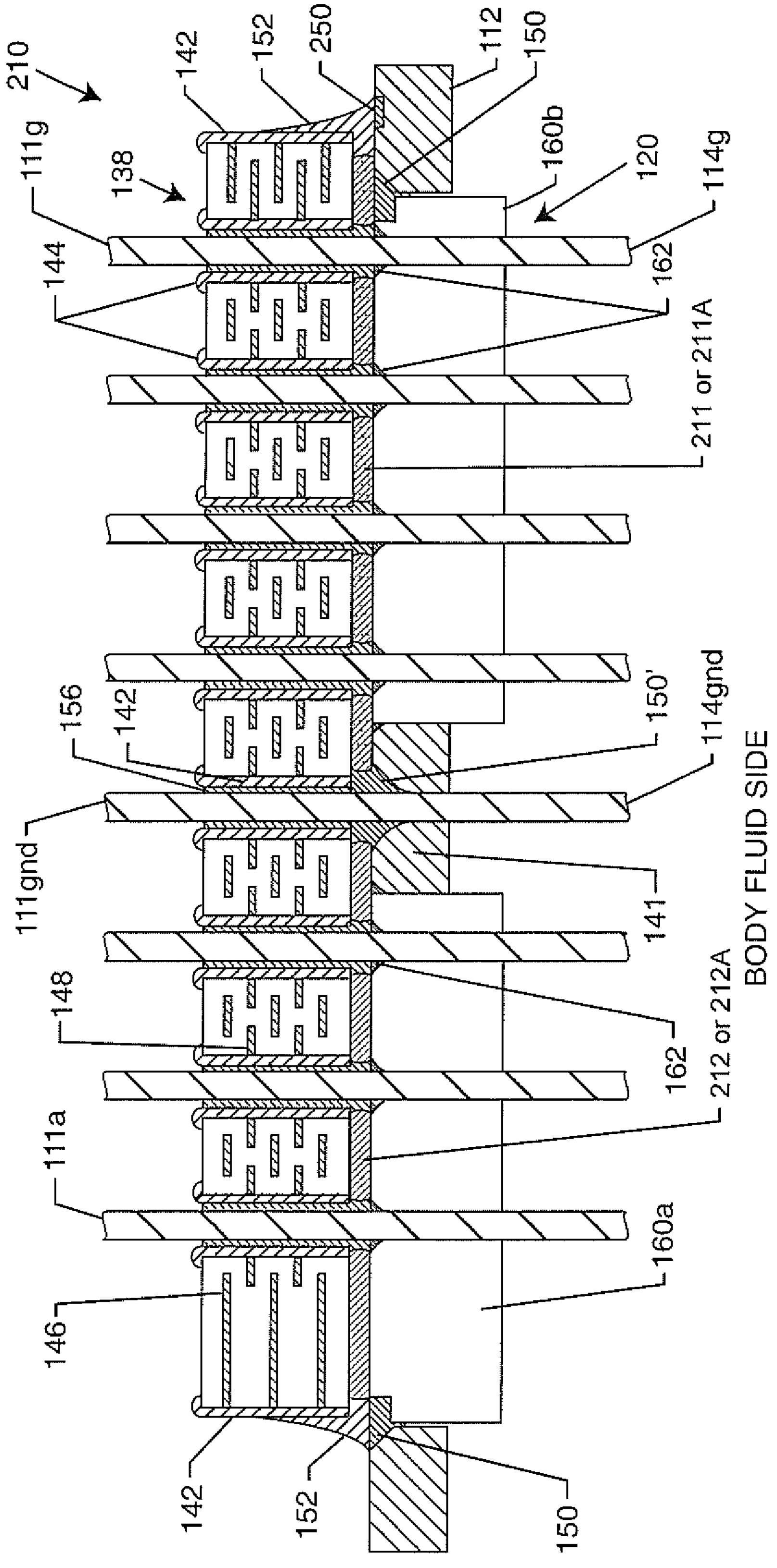

FIG. 62 is similar to prior art FIG. 38, except that the filter capacitor has a novel hybrid ground electrical connection, and the right side of the insulating washer has filler insulating nanoparticles 264 and the left side of the insulating washer does not have filler insulating nanoparticle.

Figure 62A:
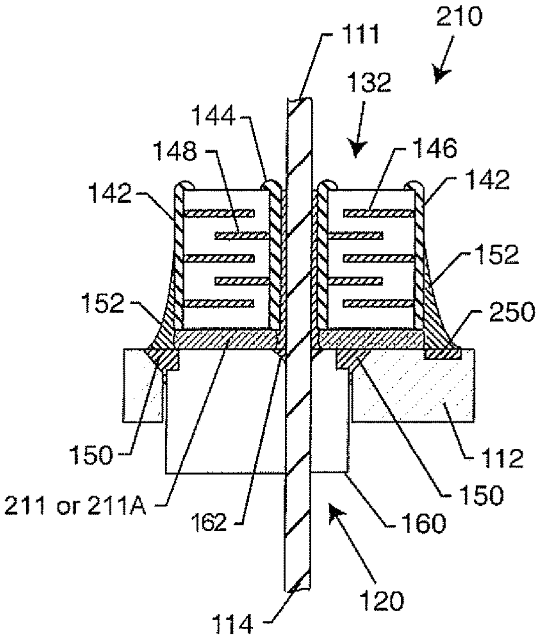

FIG. 62A is a cross-sectional view of a filtered feedthrough illustrating an asymmetrical hermetically sealed feedthrough insulating nanoparticle-filled 264 insulator and ferrule with the filter capacitor grounded to the novel hybrid ground electrical connection of FIG. 62.

Figure 62B:
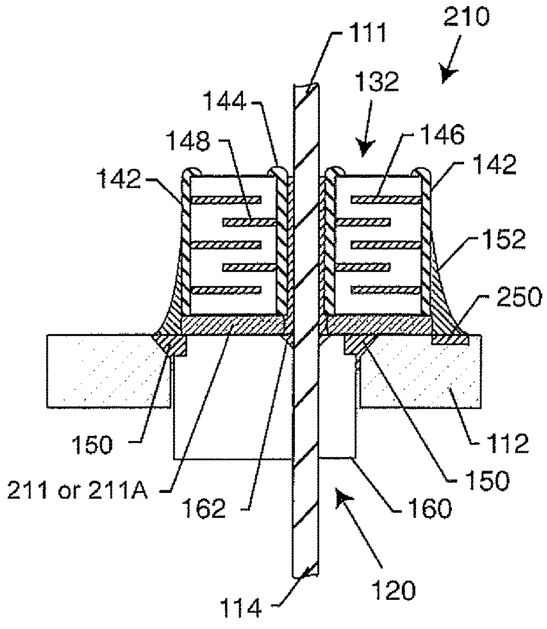

FIG. 62B is similar to FIG. 62A and has the novel hybrid ground electrical connection of FIG. 62, except that the polymeric insulating washer, which may be thermoplastic, does not have filler insulating nanoparticles 264 and the ferrule of the filtered feedthrough is substantially wider on the side.

Figure 62C:
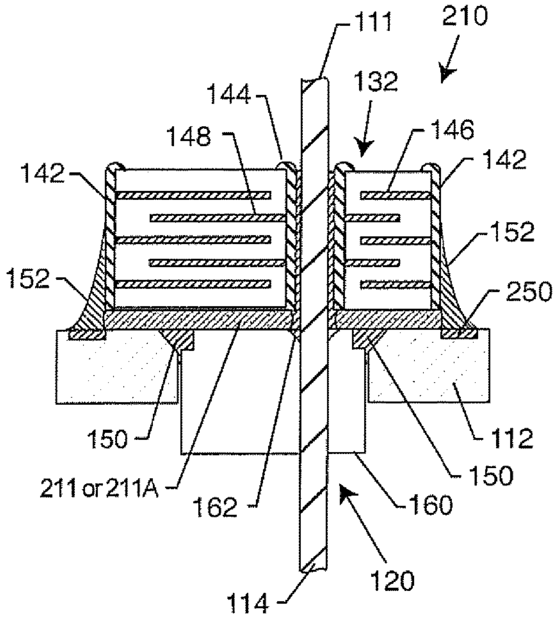

FIG. 62C is a cross-sectional view of a filtered feedthrough illustrating a filter capacitor that is substantially wider on the left side electrically connected to oxide-resistant pocket pads adjacent the ferrule edge, which increase HV stand-off distance, and the polymeric insulating washer, which may be thermoplastic, has filler insulating nanoparticles 264, which increase HV breakdown strength.

Figure 41:
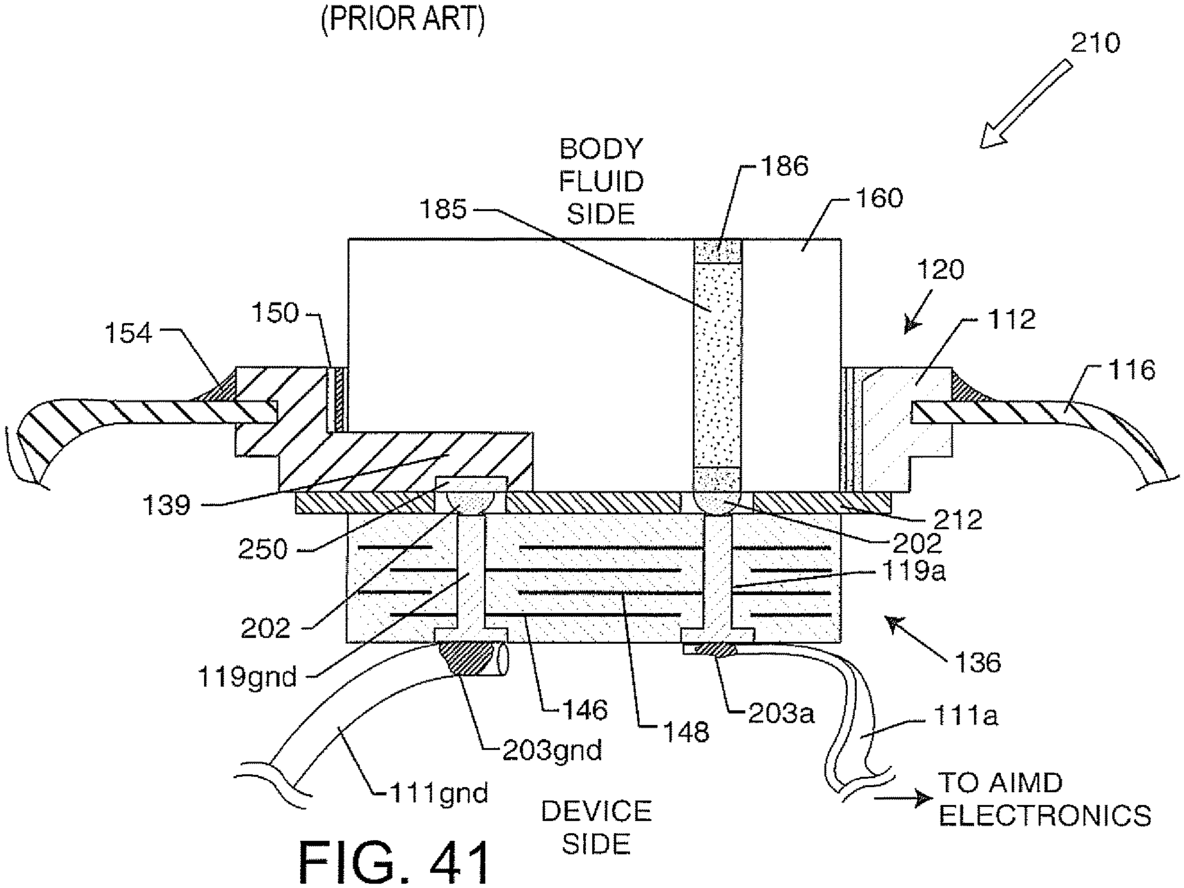
FIG. 41 (PRIOR ART)
FIG. 41 is a cross-sectional view illustrating a prior art internally grounded feedthrough filter capacitor mounted to the hermetically sealed feedthrough of prior art FIG. 40.
Figure 41A:
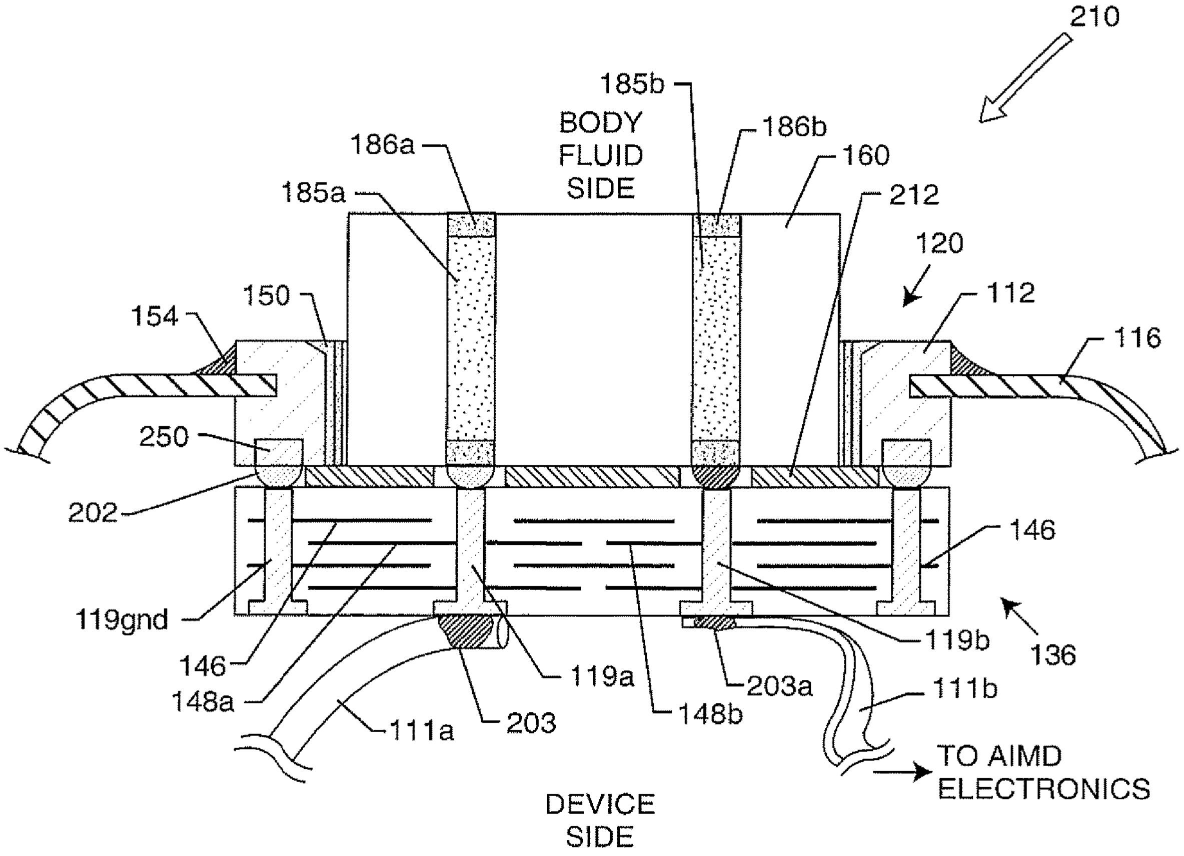
FIG. 41A (PRIOR ART)
FIG. 41A is a cross-sectional view illustrating a prior art internally grounded feedthrough filter capacitor that is as wide as the feedthrough ferrule.
Figure 41B:
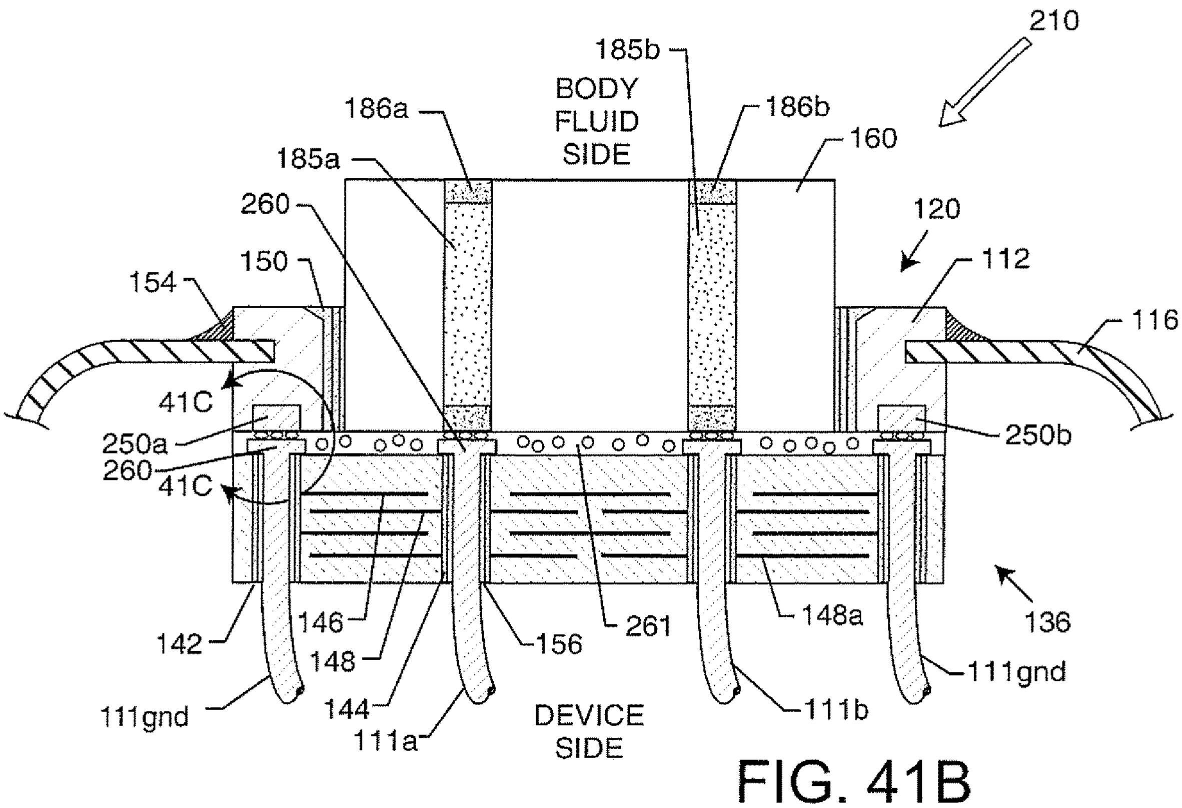
FIG. 41B (PRIOR ART)
FIG. 41B is a cross-sectional view of a prior art filtered feedthrough illustrating that active and ground connections comprise an anisotropic conductive film or an anisotropic conductive adhesive.
Figure 41C:
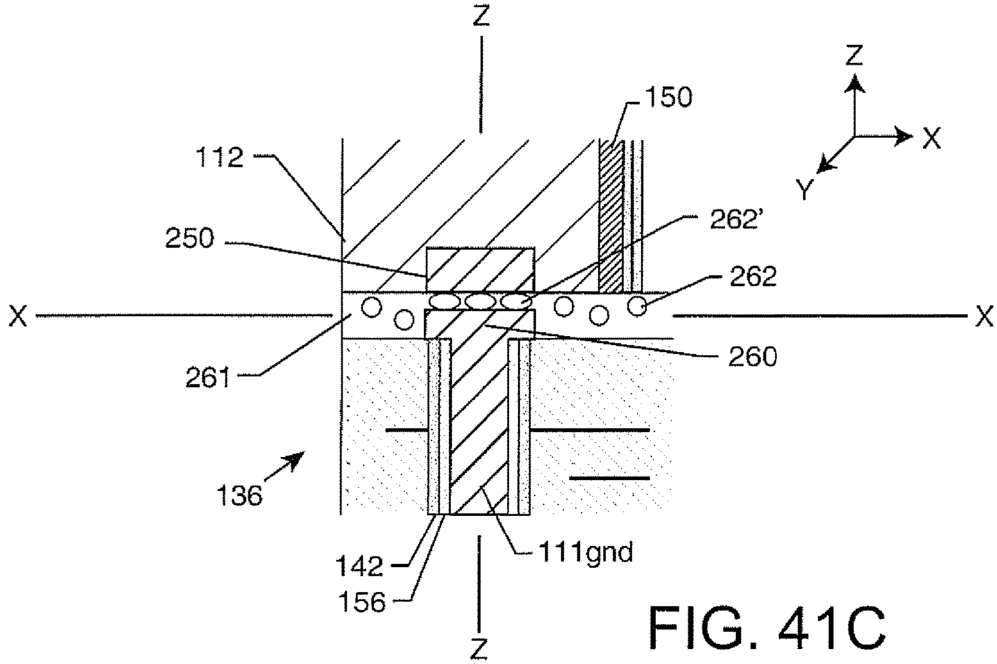
FIG. 41C (PRIOR ART)
FIG. 41C is a blown-up partial view taken from section 41C-41C of prior art FIG. 41B illustrating the compressed electrically conductive particles providing the electrical connection.
Figure 42:
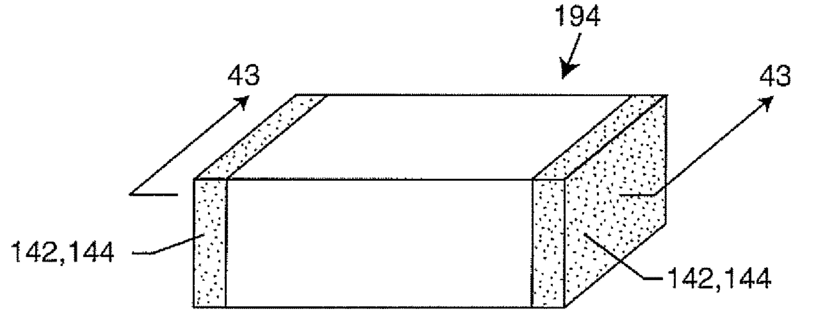
FIG. 42 (PRIOR ART)
FIG. 42 illustrates an isometric view of a prior art chip filter capacitor also known as a multilayer ceramic capacitor (MLCC).
Figure 43:
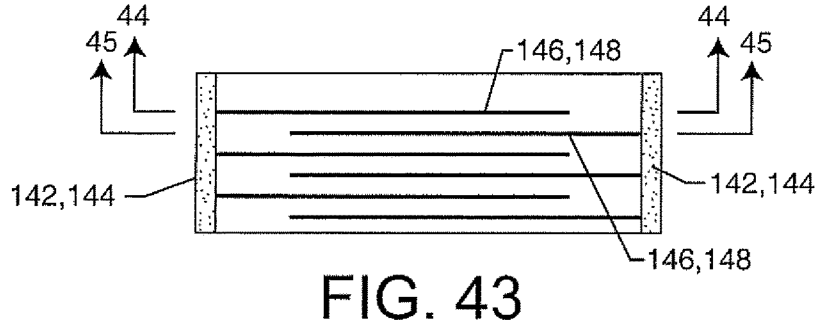
FIG. 43 (PRIOR ART)
FIG. 43 is a cross-sectional view generally taken along 43-43 of prior art FIG. 42 illustrating interleaving electrode plates.
Figure 44:
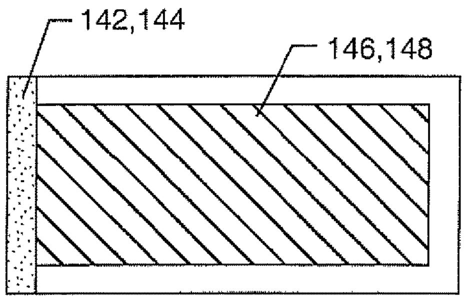
FIG. 44 (PRIOR ART)
FIG. 44 is a cross-sectional view generally taken along 44-44 of prior art FIG. 43 illustrating an electrode plate electrically connected to a left side chip filter capacitor edge metallization.
Figure 45:
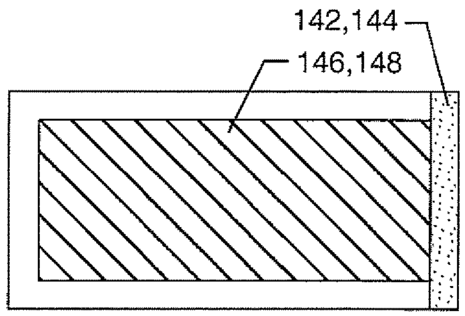
FIG. 45 (PRIOR ART)
FIG. 45 is a cross-sectional view generally taken along 45-45 of prior art FIG. 43 illustrating an electrode plate electrically connected to a right-side chip filter capacitor edge metallization.
Figure 46:
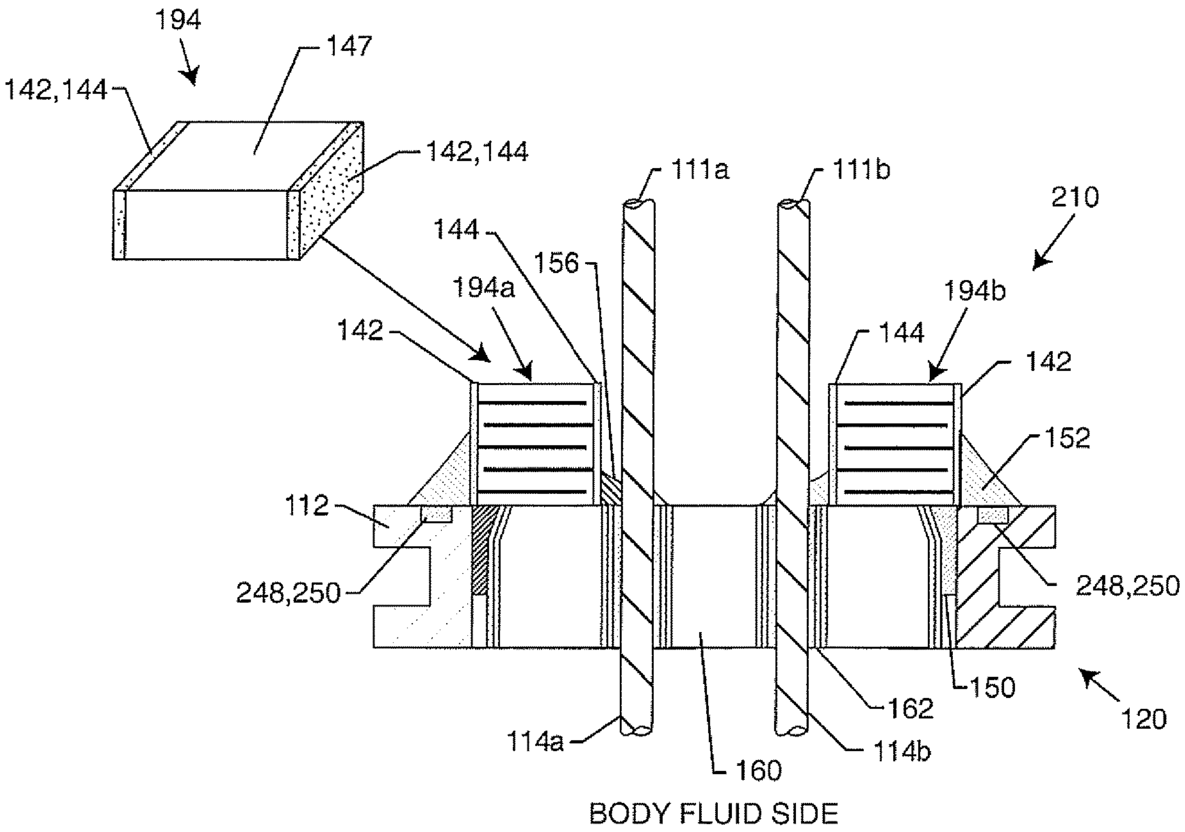
FIG. 46 (PRIOR ART)
FIG. 46 illustrates a cross-sectional view of two prior art FIG. 42 MLCC filter capacitors mounted directly on top of a prior art hermetically sealed filter feedthrough.
Figure 47A:
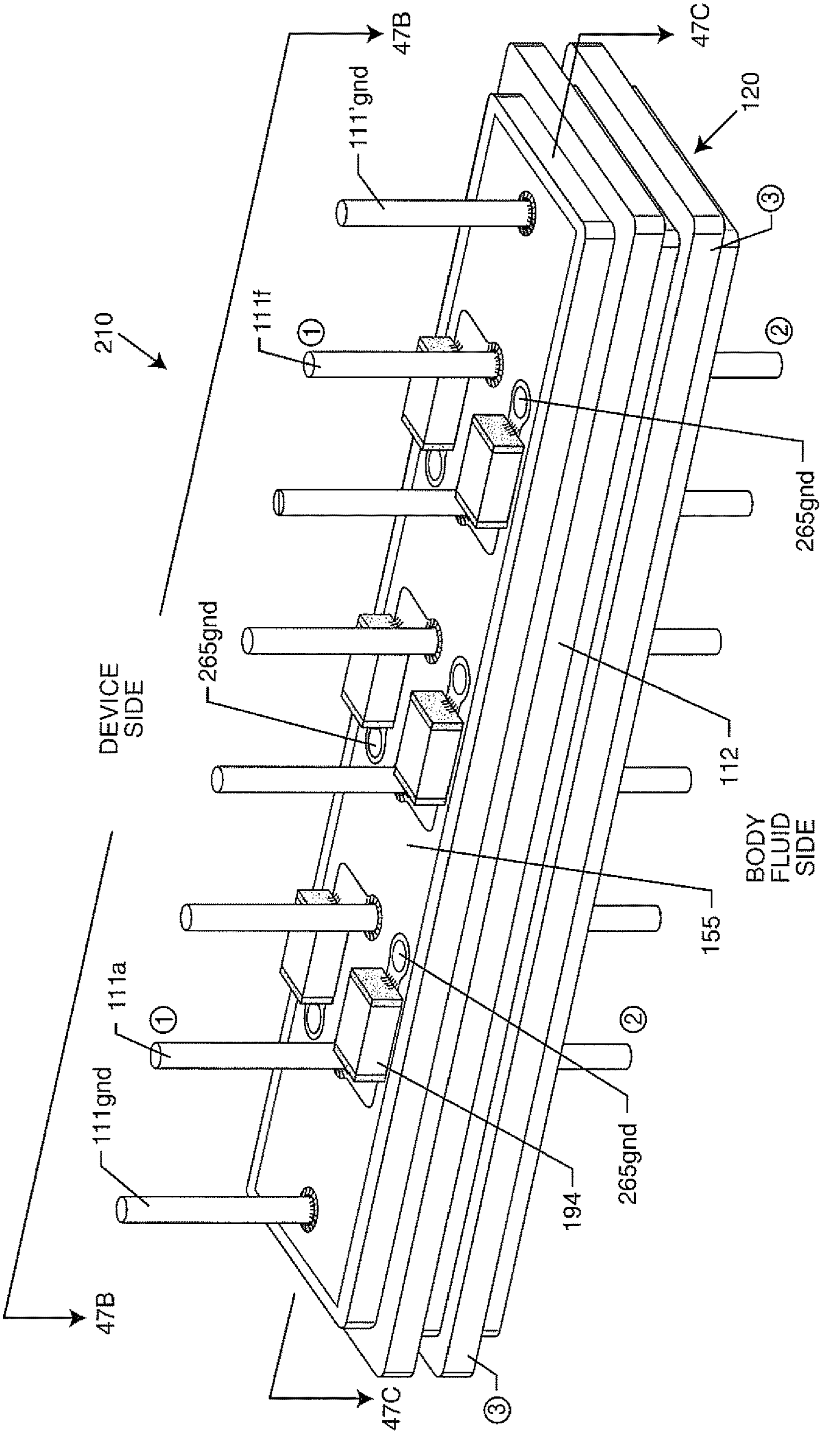
FIG. 47A (PRIOR ART)
FIG. 47A is an isometric view of a view of a prior art filtered feedthrough having an MLCC EMI filter circuit board electrically connected to an AIMD feedthrough ferrule an MLCC EMI filter circuit board.
Figure 47B:
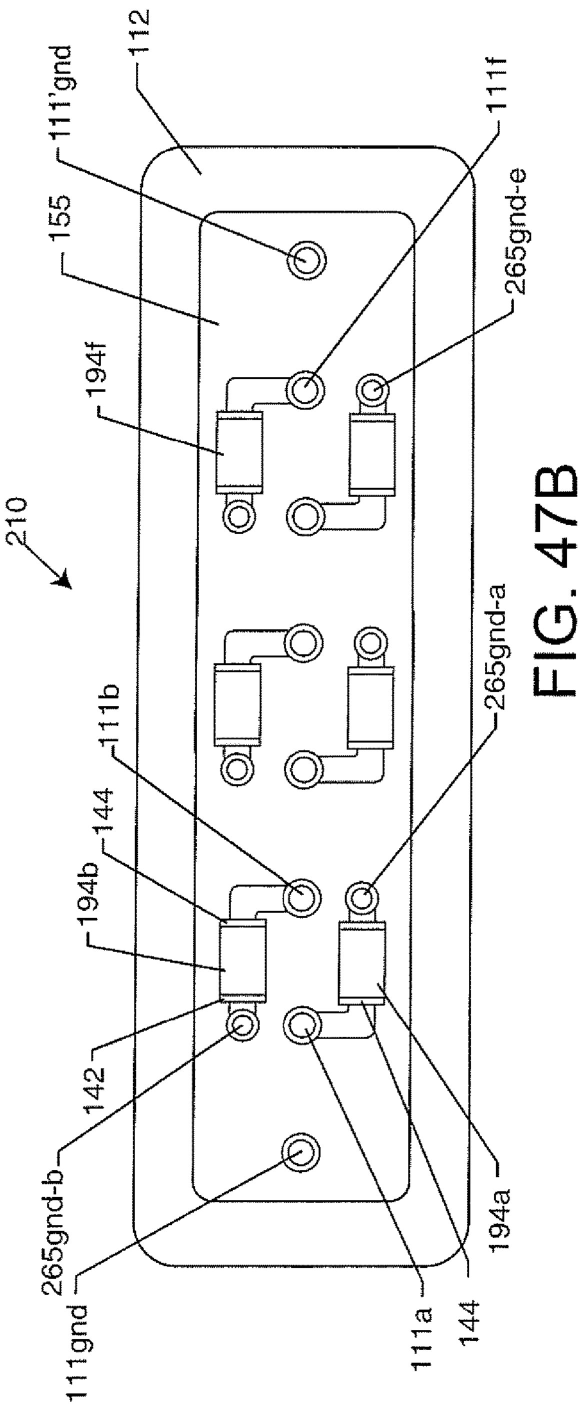
FIG. 47B is a plan view generally taken along 47B-47B of FIG. 47A showing the MLCC chip capacitor arrangement on the EMI filter circuit board of the filtered feedthrough of FIG. 47A.
Figure 47C:
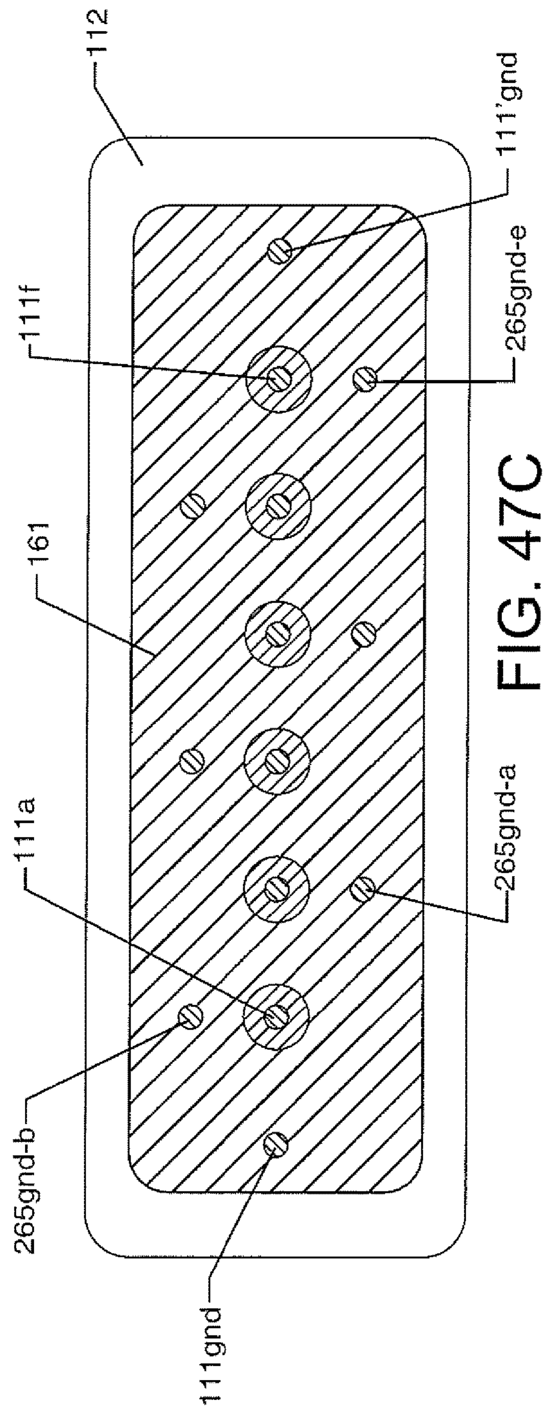
FIG. 47C is a cross-sectional view generally taken along 47C-47C of FIG. 47A illustrating a circuit board internal ground plate embedded within the MLCC EMI filter circuit board.
Figure 47D:
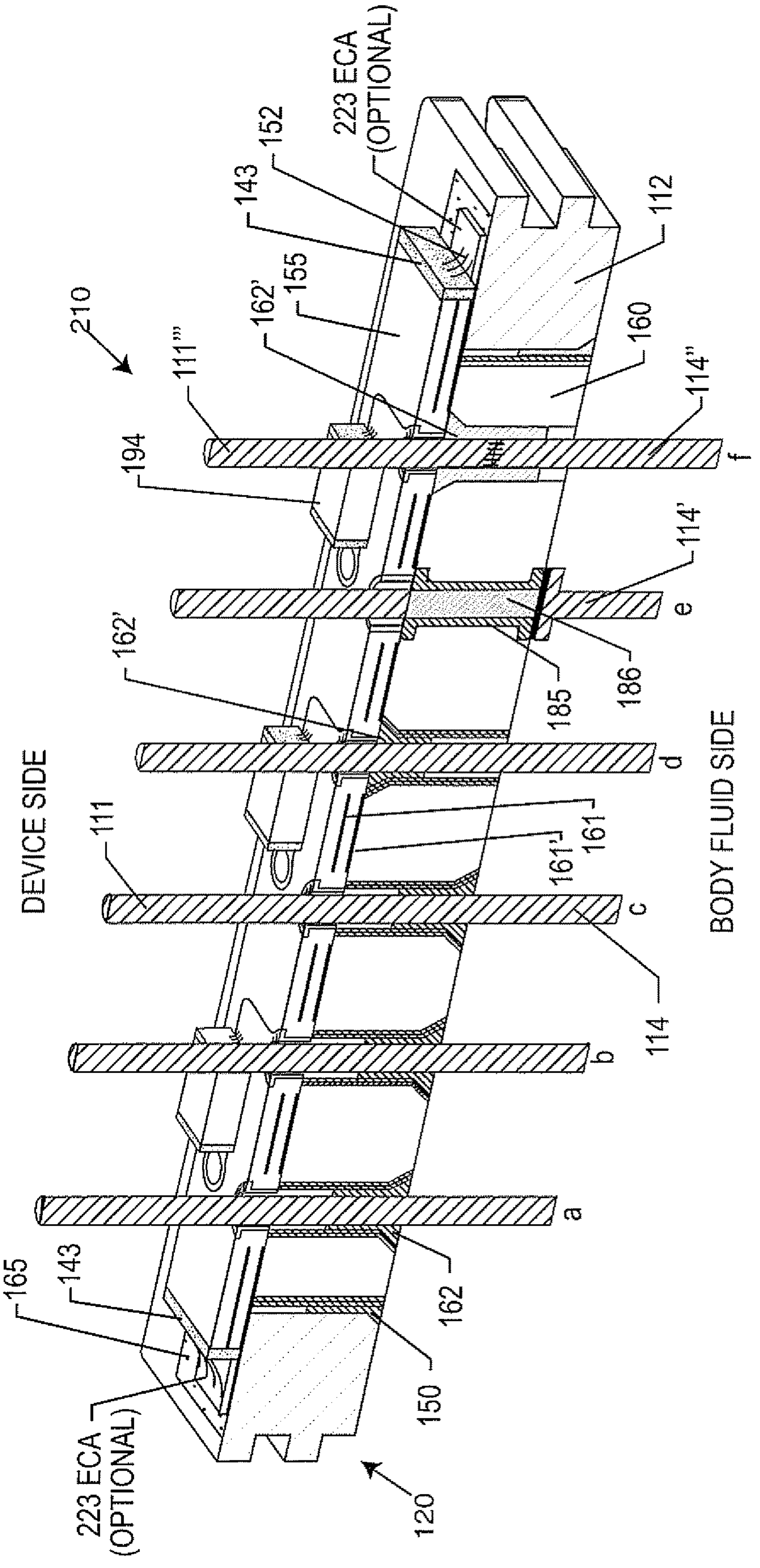
FIG. 47D is cross-sectional view of a filtered feedthrough, which is similar to the filtered feedthrough of FIG. 47A, except that the embodiment of FIG. 47D illustrates circuit board edge electrical connections at each external ground circuit board metallization to corresponding oxide-resistant gold braze bond pads at each short end of the feedthrough ferrule.
Figure 63:
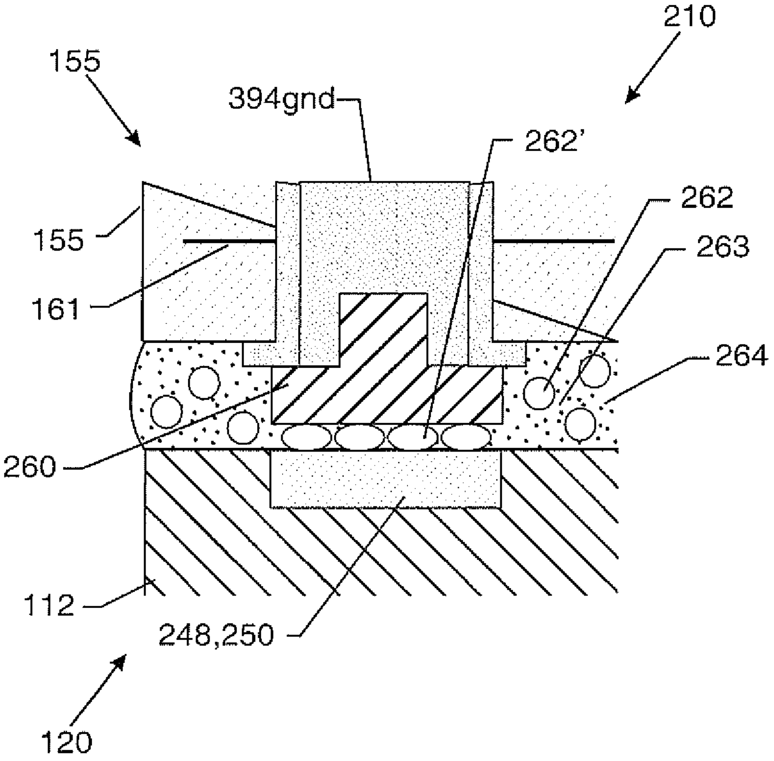

FIG. 63 is similar to FIG. 41C, except that the anisotropic conductive film comprises an insulating nanoparticle 264 fill of the present invention.

Figure 64:
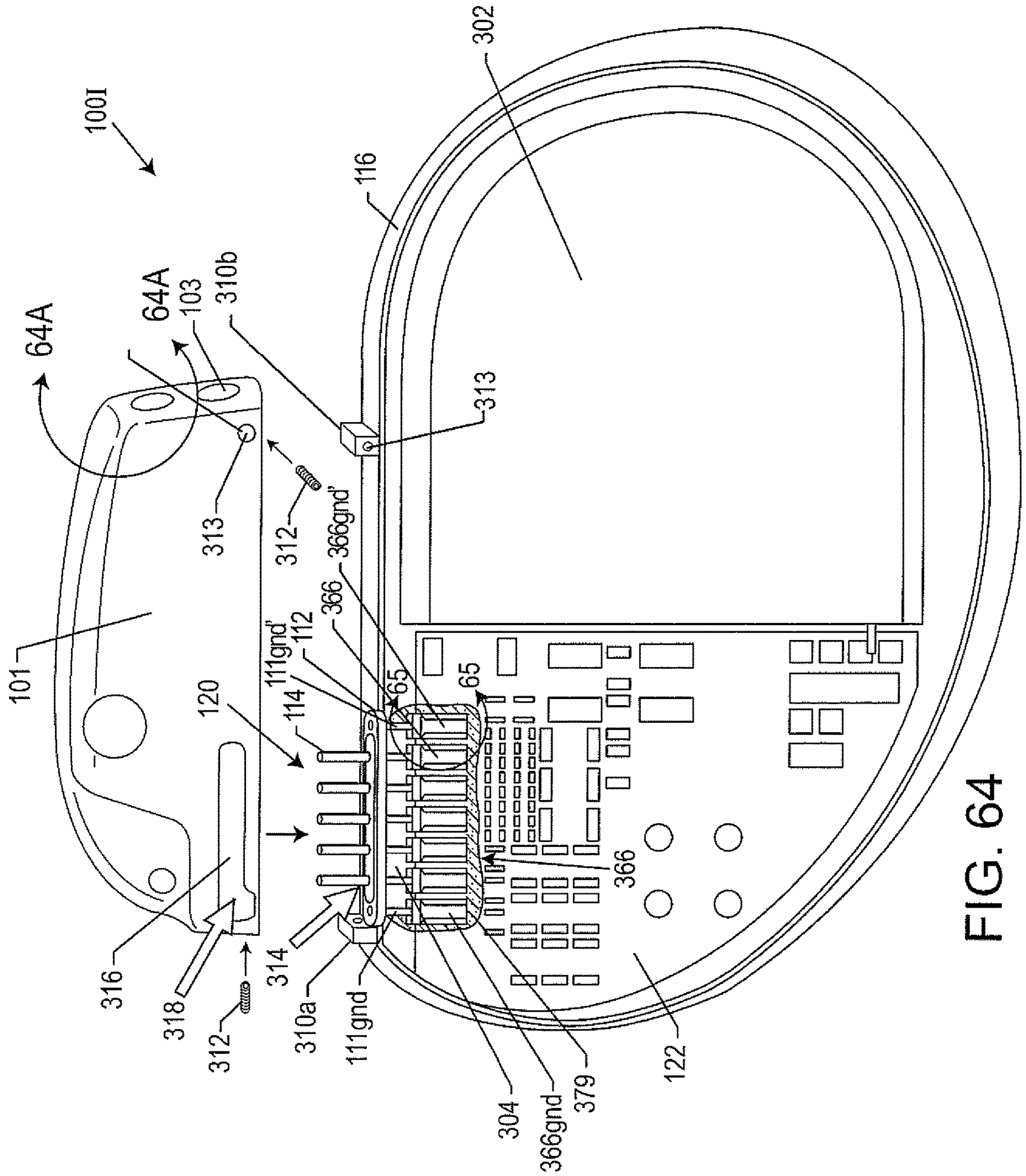

FIG. 64 is an exploded side view cutaway of an implantable cardioverter defibrillator (ICD) and a header block, wherein the device side circuit board connectors are electrically coated with a nanoparticle-filled 264 insulating material.

Figure 64A:
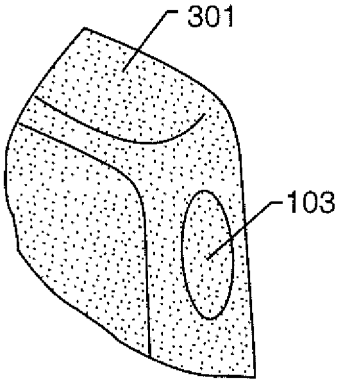

FIG. 64A is a blown-up partial view taken from 64A-64A of FIG. 64 illustrating that the polymeric header block comprises filler insulating nanoparticles 264.

Figure 64B:
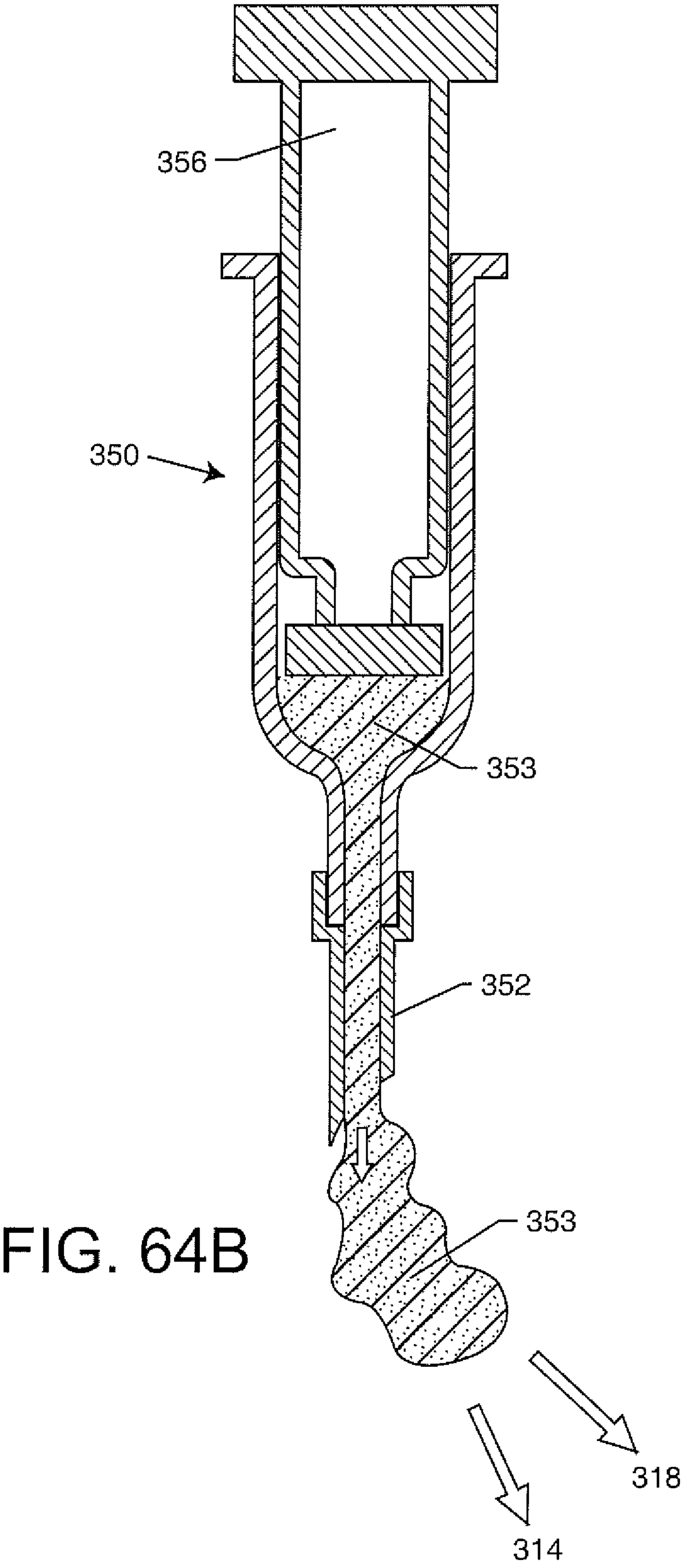

FIG. 64B illustrates a syringe dispenser, which may alternatively be a robotic dispenser, a spray, or the like, for application of insulating materials. The insulating materials may comprise conventionally used insulating materials and/or the nanoparticle-filled 264 insulating materials of the present invention.

FIG. 64C provides a table of insulating material types and symbols represented by a tear drop, the point of which is used to indicate a location, each having a fill that defines the type of insulating material.

Figure 65:
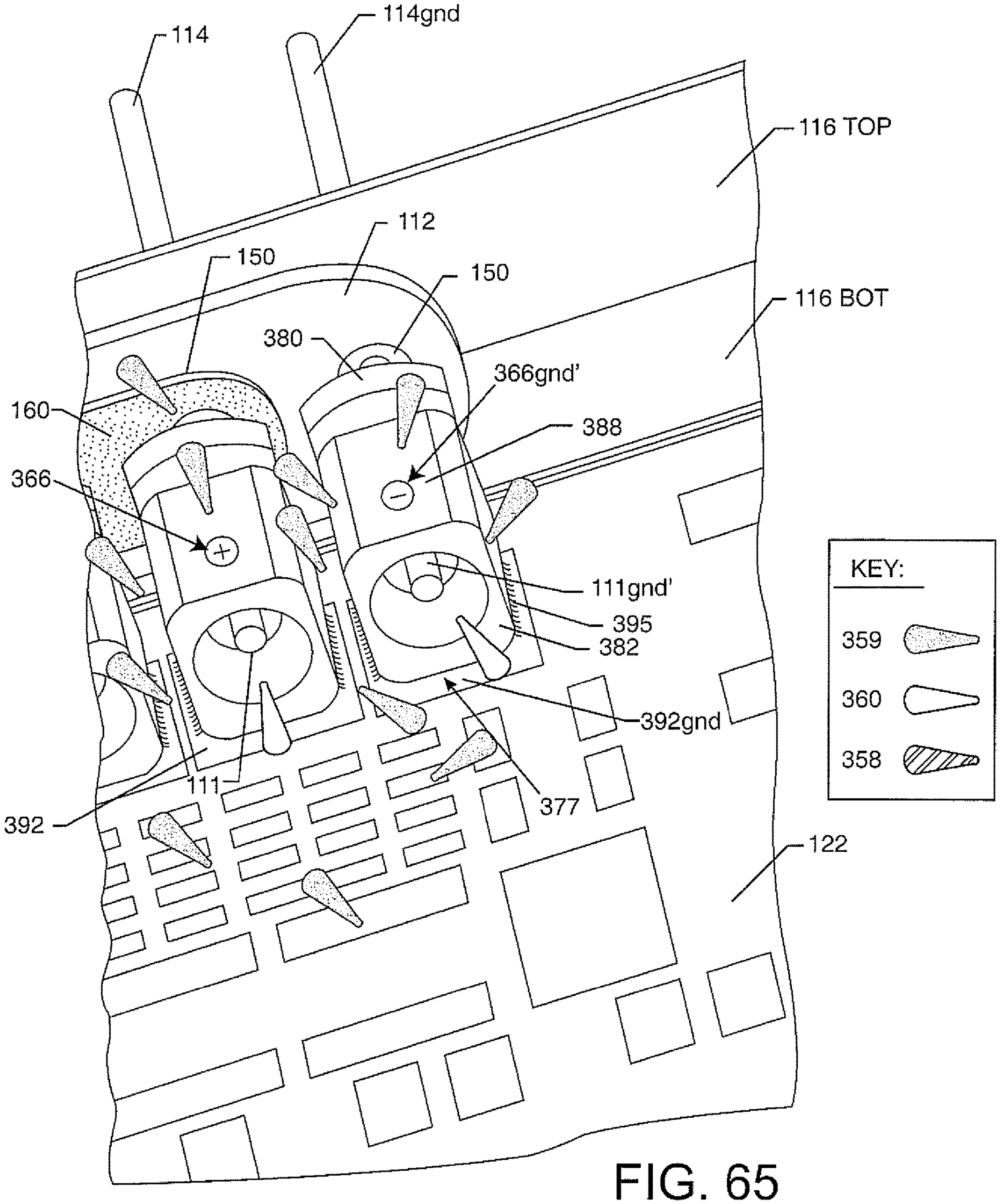

FIG. 65 is a blown-up partial view taken from 65-65 of FIG. 64, illustrating the locations for necessary placement of insulating material and the locations where the insulation material is undesirable.

Figures 65A, 65B, 65C:
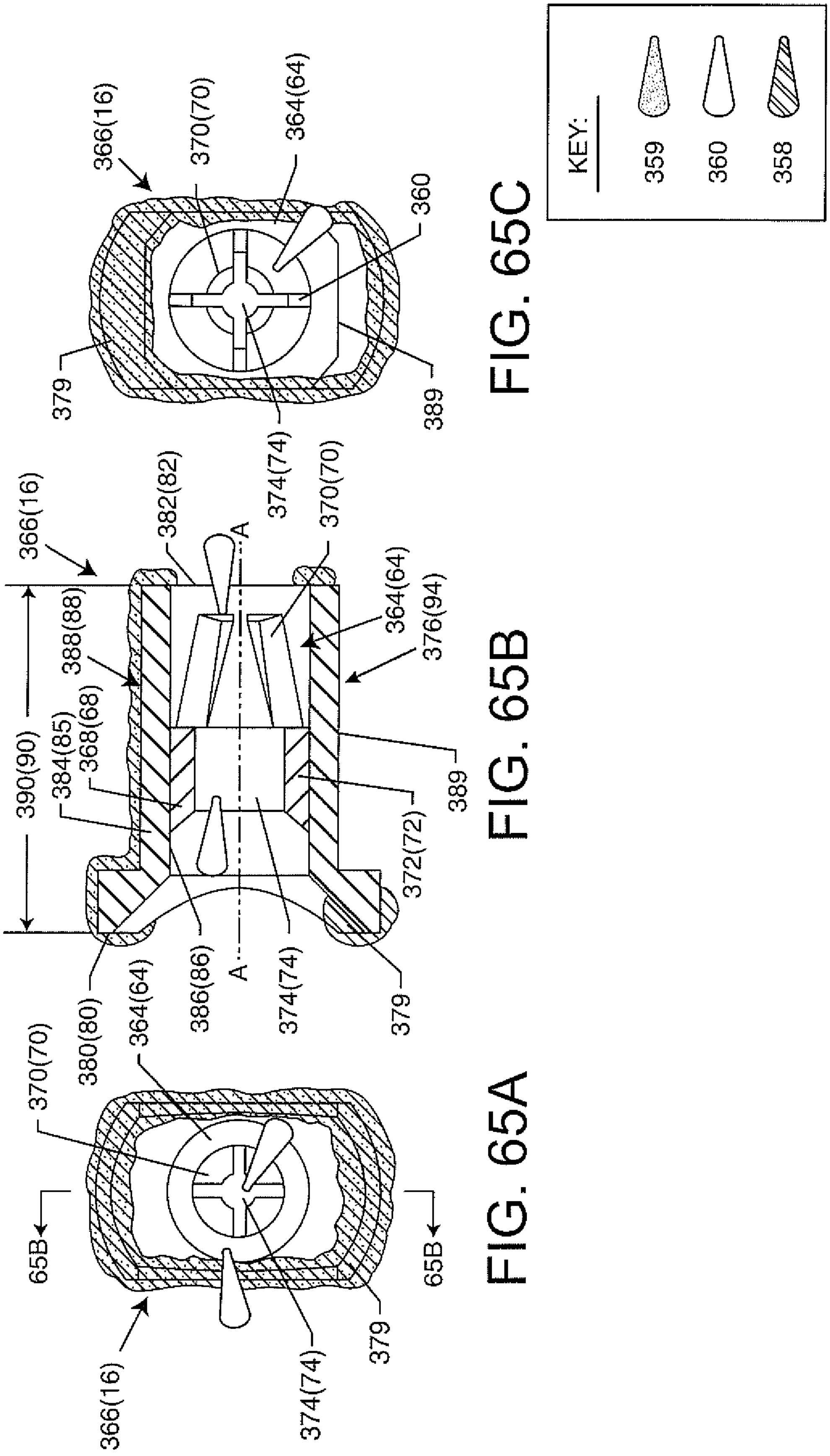

FIG. 65A is an end view of an AIMD circuit board connector flange surface, illustrating a nanoparticle-filled 264 insulation material disposed on the entire surface of the flange and the "no insulating material" symbols showing the locations that are not to be covered with insulating material.

FIG. 65B is a cross-sectional view of FIG. 65A illustrating locations where the nanoparticle-filled 264 insulation material is desirably disposed and the locations where the nanoparticle-filled 264 insulation material is not to be disposed.

FIG. 65C is similar to FIG. 65A illustrating the opposite end view of a circuit board connector surface, showing where the nanoparticle-filled 264 insulation material is disposed and the "no insulating material" symbols showing where the nanoparticle filled insulation material is not disposed.

Figure 66:
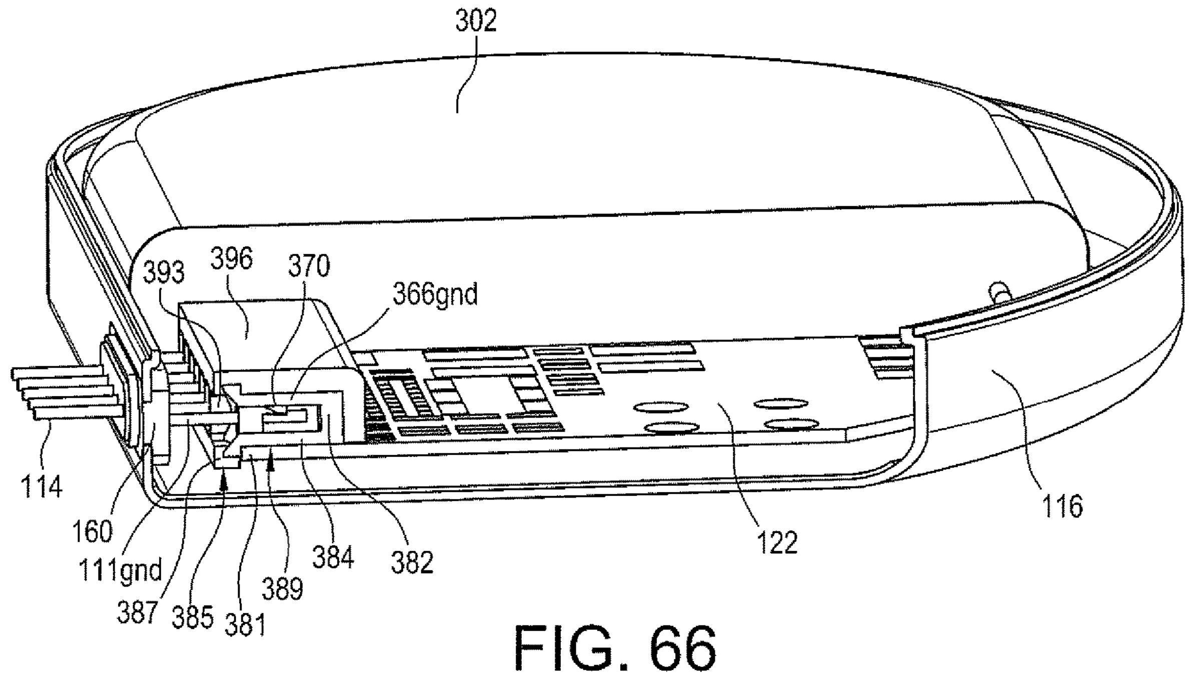

FIG. 66 is a pictorial cutaway view of an ICD having a connector cross-sectional view, the circuit board connectors being covered with an over-molded HV insulating block.

Figure 67:
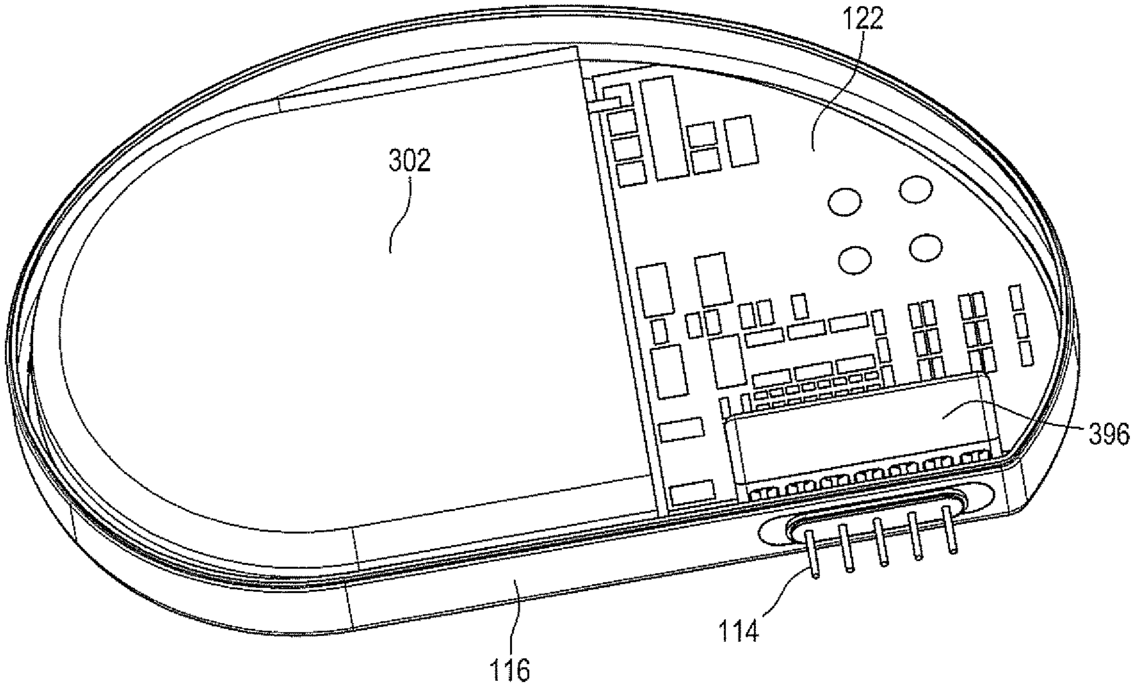

FIG. 67 is a rotated pictorial cutaway view of the ICD of FIG. 66.

Figure 68A:
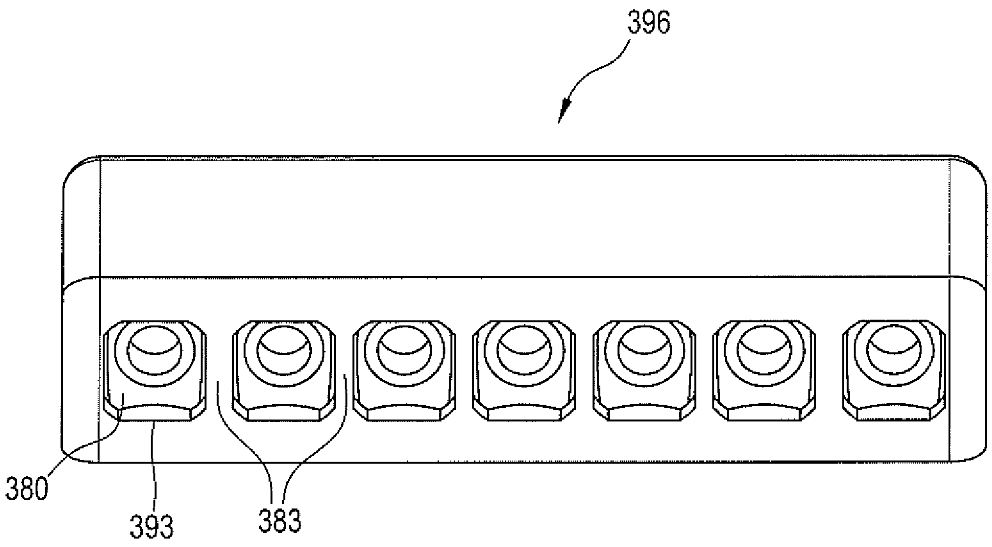

FIG. 68A is a pictorial view of a pre-molded HV insulating block into which the circuit board connectors of FIG. 66 are subsequently inserted.

Figure 68B:
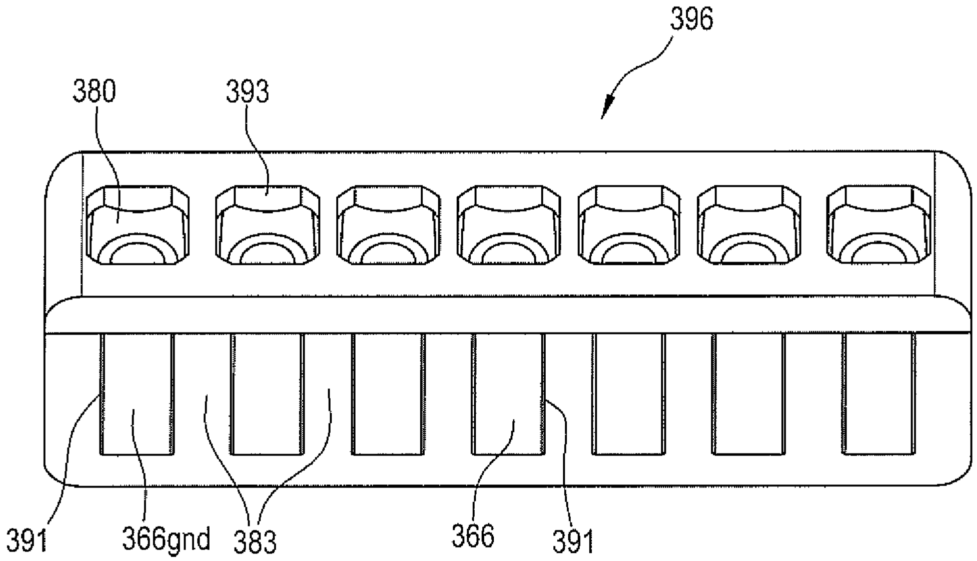

FIG. 68B is a pictorial view of FIG. 64A rotated to show that the insulating block has openings that expose the connector attachment surface for subsequent electrical connection to AIMD circuit board landing pads.

Figure 10A:
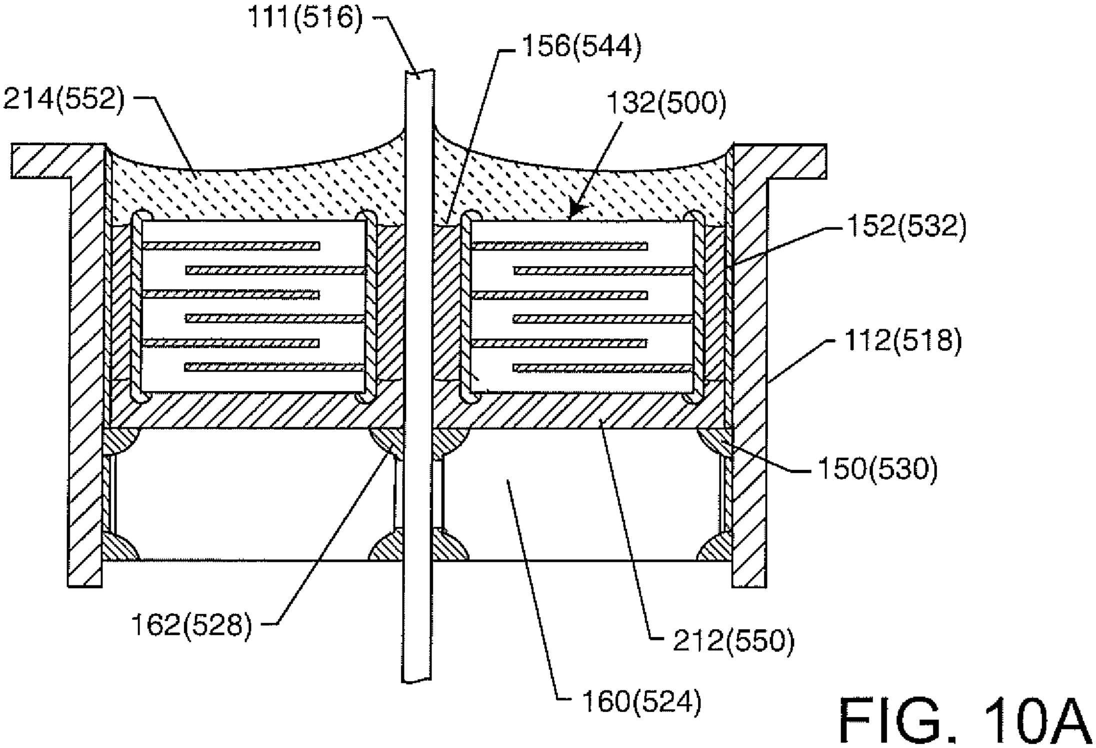
FIG. 10A (PRIOR ART)
FIG. 10A is a prior art filtered feedthrough taken from FIG. 26 of U.S. Pat. No. 6,765,779.
Figure 10B:
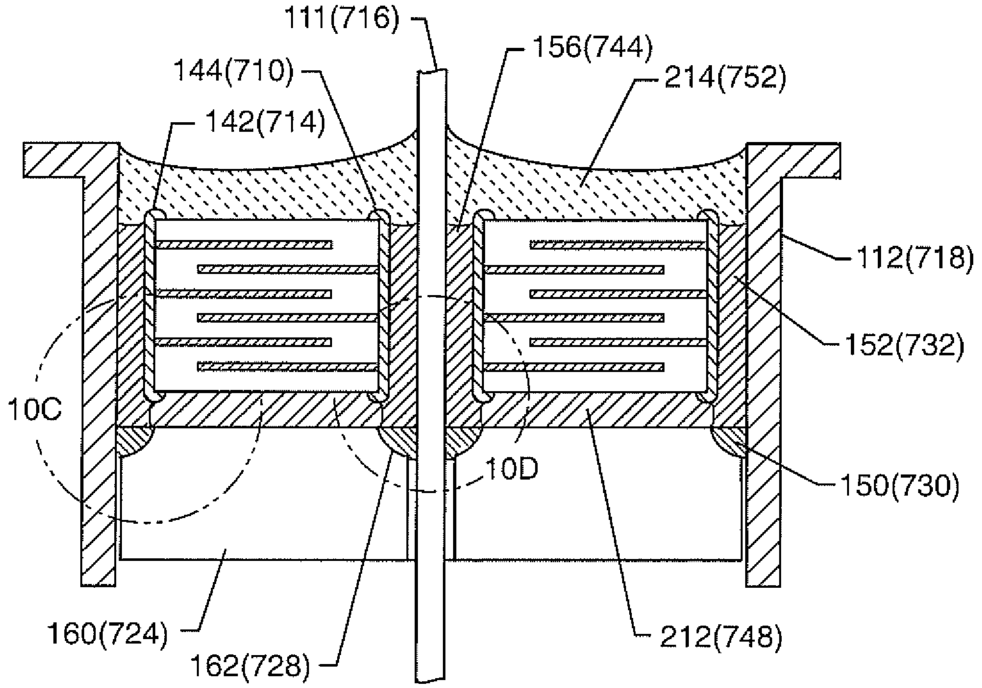
FIG. 10B (PRIOR ART)
FIG. 10B is a cross-sectional view of prior art filtered feedthrough taken from FIG. 28 of U.S. Pat. No. 6,765,779 patent.
Figure 10C:
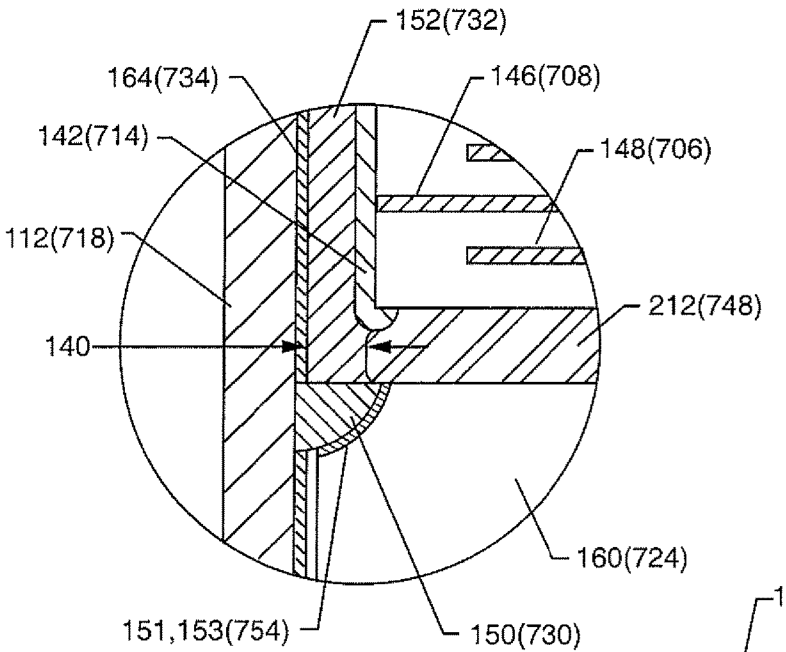
FIG. 10C (PRIOR ART)
FIG. 10C is a blown-up partial view taken from 10C of prior art FIG. 10B.
Figure 10D:
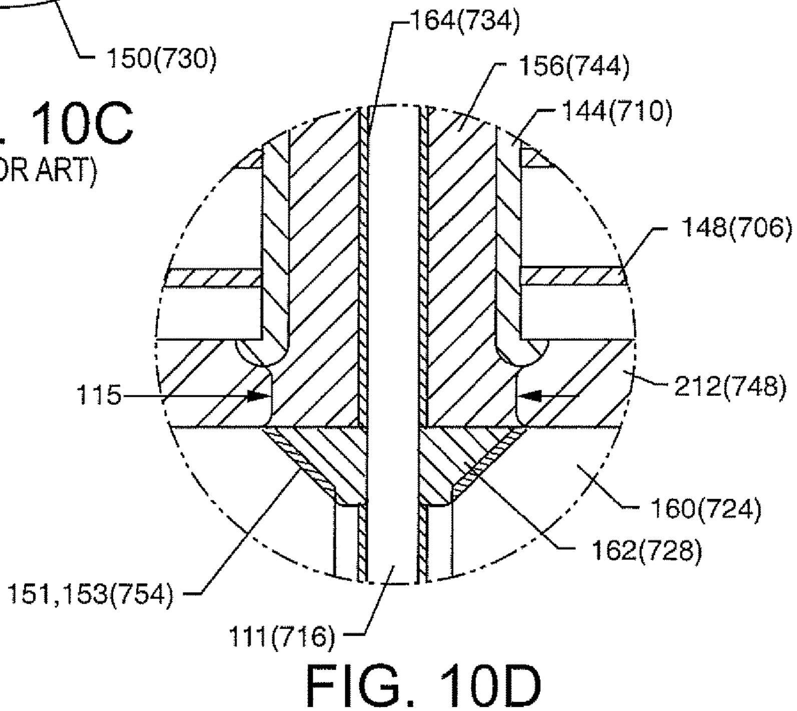
FIG. 10D (PRIOR ART)
FIG. 10D is a blown-up partial view taken from 10D of prior art FIG. 10B.
Figure 10E:
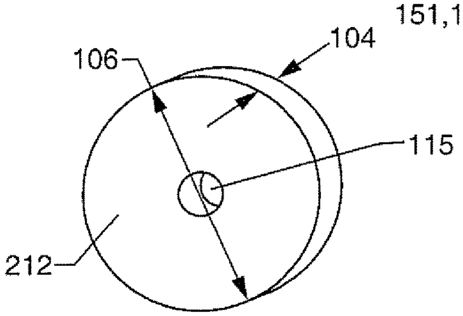
FIG. 10E is an oblique view of the insulting washer of FIGS. 10B through 10D.
Figure 11:
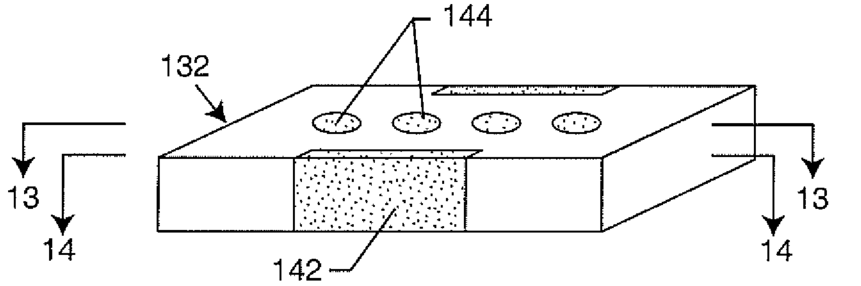
FIG. 11 (PRIOR ART)
FIG. 11 illustrates a prior art rectangular quadpolar feedthrough filter capacitor.
Figure 12:
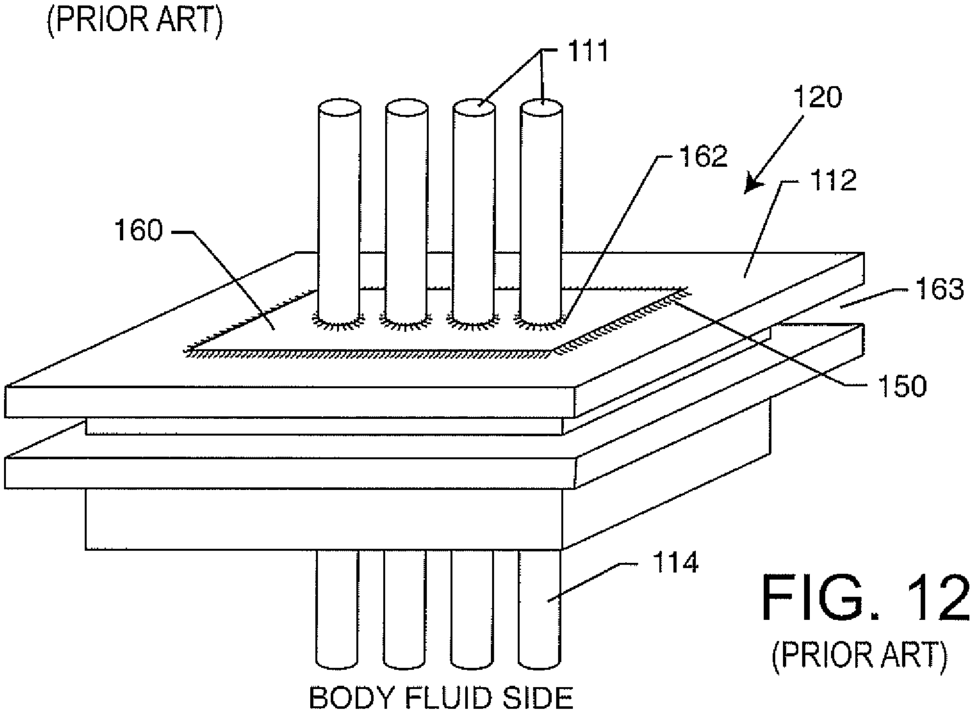
FIG. 12 (PRIOR ART)
FIG. 12 illustrates the hermetically sealed feedthrough, on which the prior art quadpolar feedthrough filter capacitor of FIG. 11 will be mounted.
Figure 13:
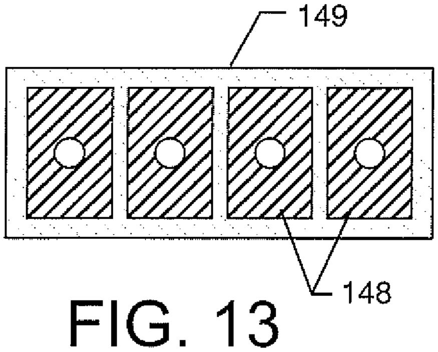
FIG. 13 (PRIOR ART)
FIG. 13 is a cross-sectional view of the active electrodes generally taken along section 13-13 of prior art FIG. 11 showing four active electrode plates on a single layer of a capacitor dielectric substrate.
Figure 14:
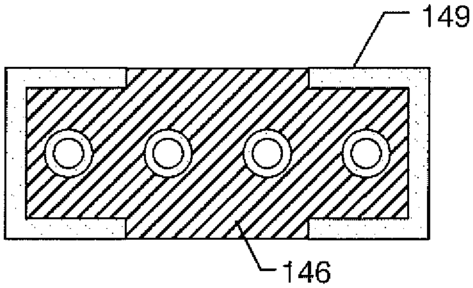
FIG. 14 (PRIOR ART)
FIG. 14 is a cross-sectional view generally taken along section 14-14 of prior art FIG. 11 showing one ground electrode plate with four filter capacitor passageways.
Figure 15:
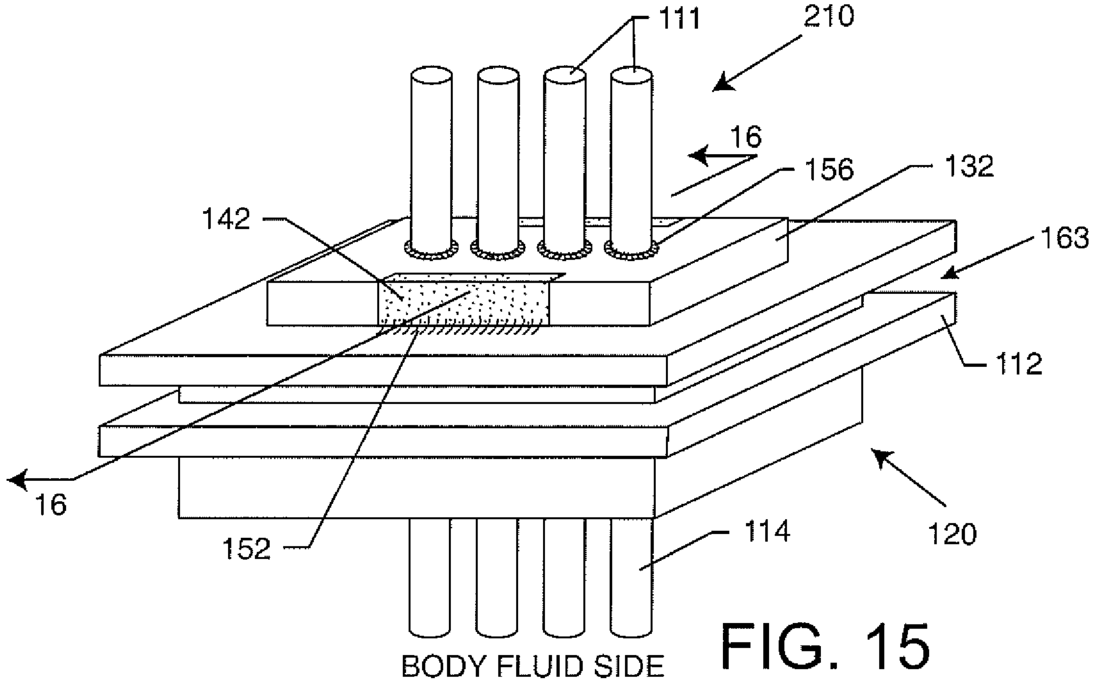
FIG. 15 (PRIOR ART)
FIG. 15 illustrates the prior art feedthrough filter capacitor of FIG. 11 mounted on the hermetically sealed feedthrough of FIG. 12.
Figure 16:
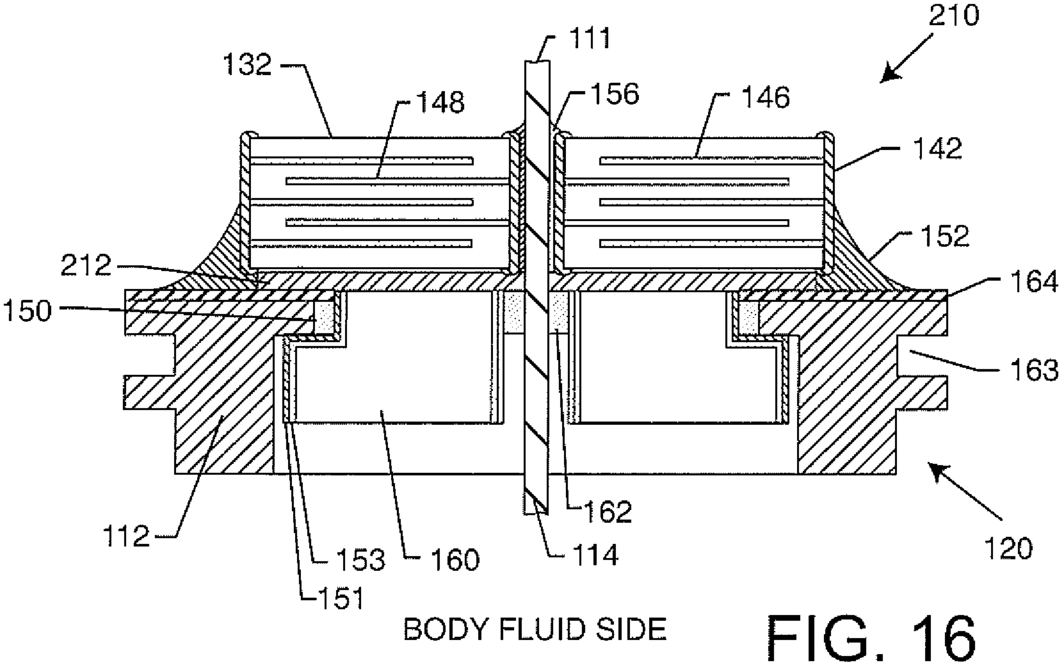
FIG. 16 (PRIOR ART)
FIG. 16 is a is a cross-sectional view generally taken along 16-16 of prior art FIG. 15.
Figure 17:
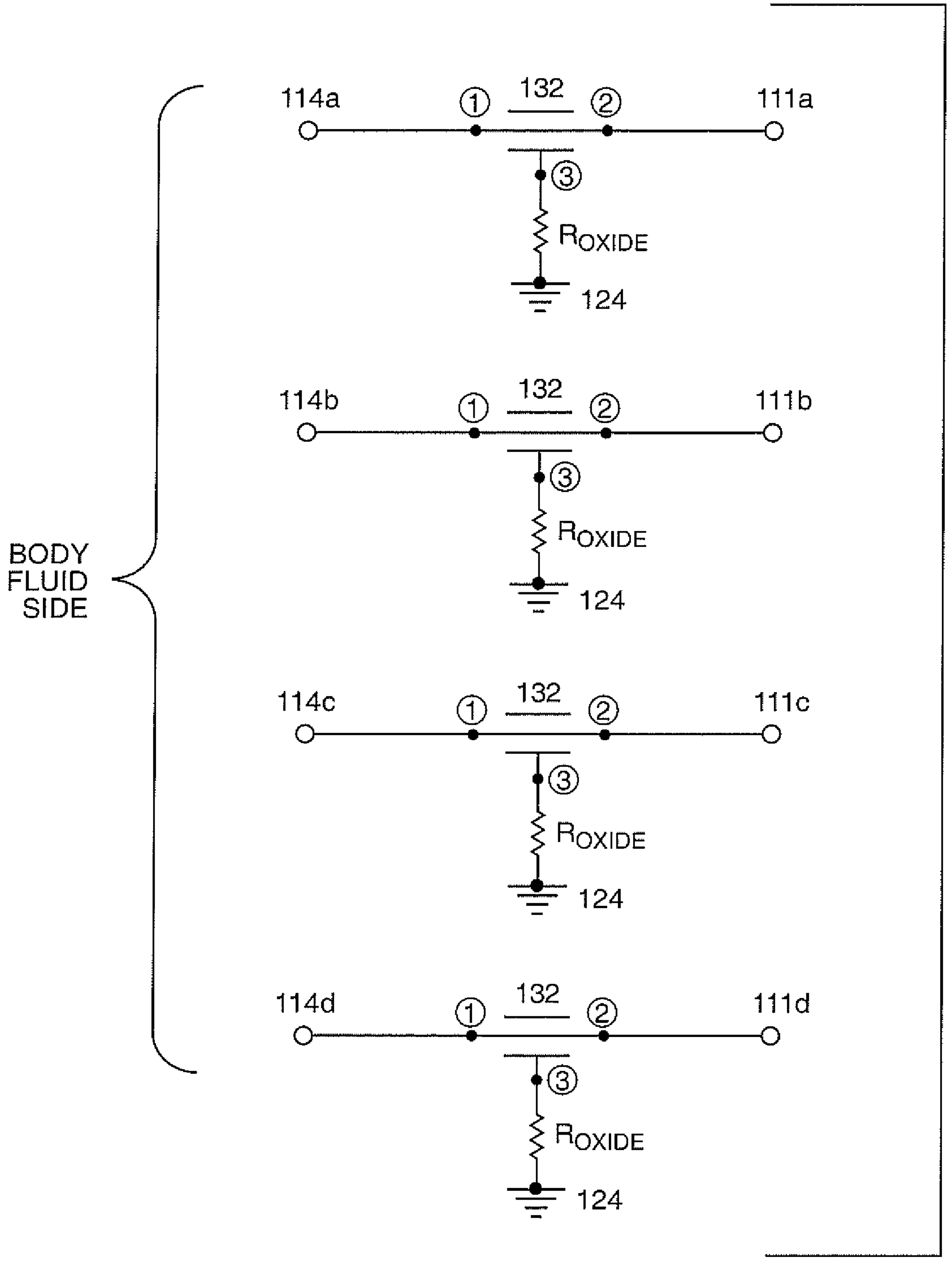
FIG. 17 (PRIOR ART)
FIG. 17 is an electrical schematic, which illustrates the effect of an undesirable oxide within the ground path of the prior art quadpolar feedthrough filter capacitor.
Figure 18:
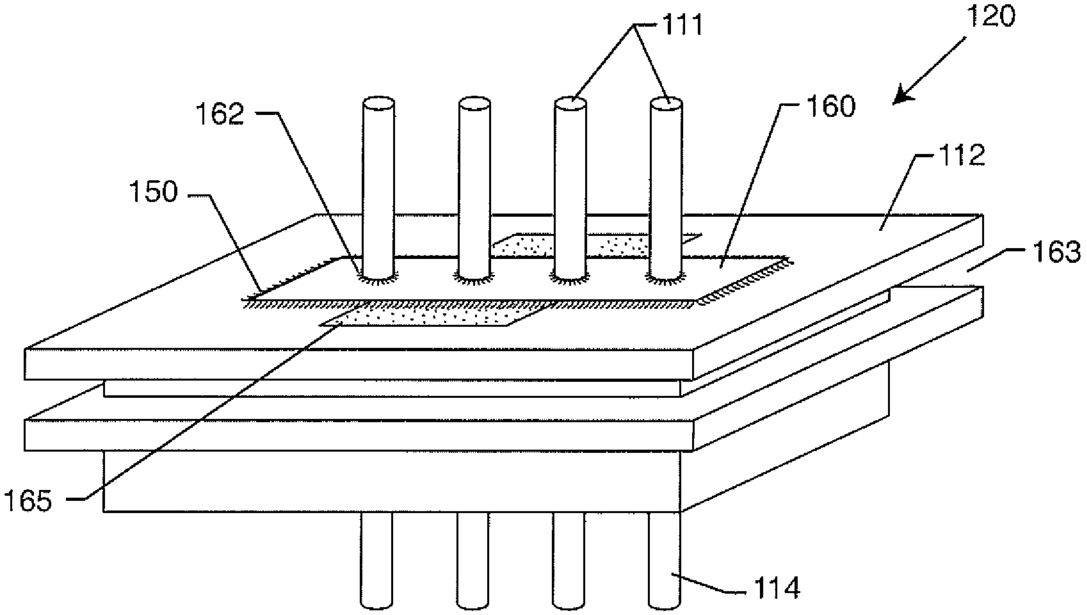
FIG. 18 (PRIOR ART)
FIG. 18 is prior art quadpolar hermetic feedthrough taken from FIG. 20 of U.S. Pat. No. 6,765,779 showing gold brazed bond pads.
Figure 19:
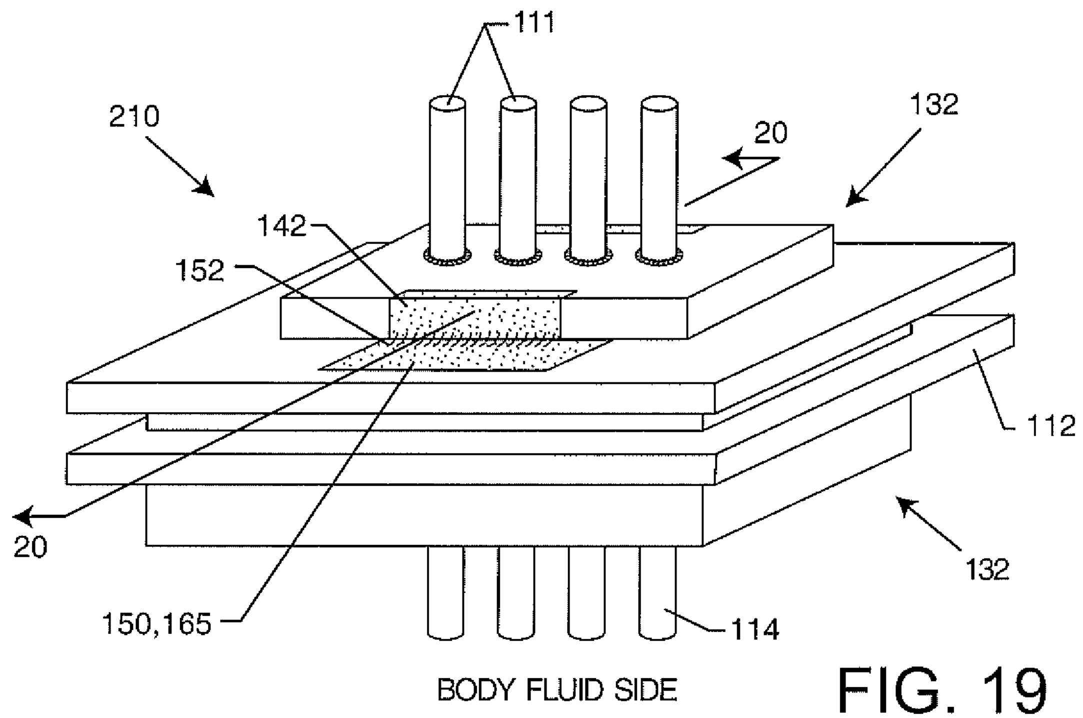
FIG. 19 (PRIOR ART)
FIG. 19 is prior art taken from FIG. 21 of U.S. Pat. No. 6,765,779 illustrating that the feedthrough filter capacitor ground metallization is electrically attached directly to the gold braze bond pads of prior art FIG. 18 by a thermosetting conductive adhesive.
Figure 69:
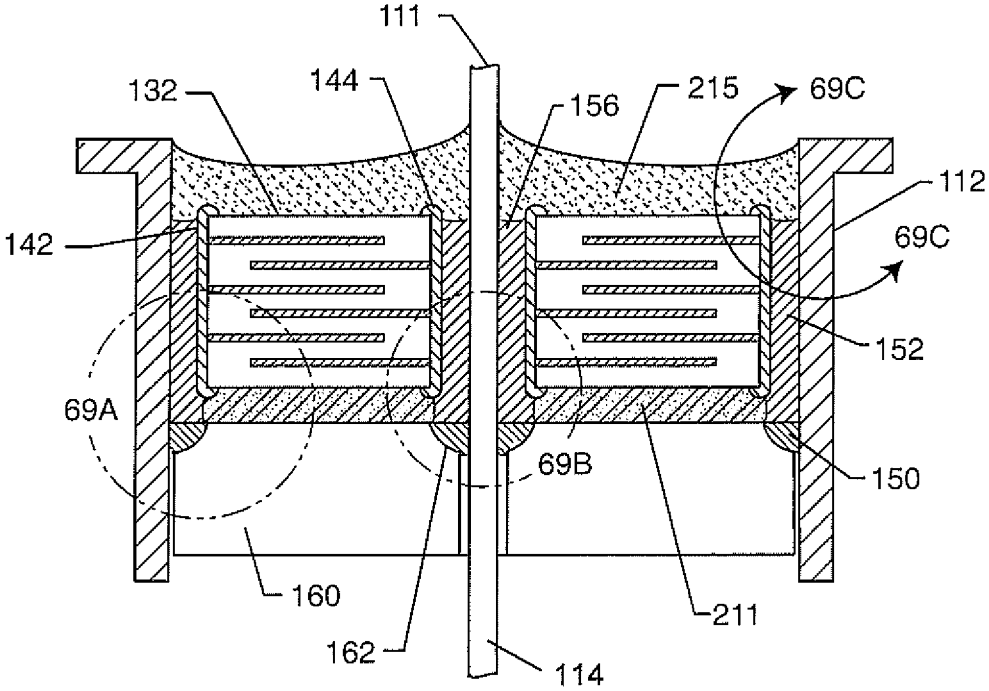

FIG. 69 is similar to prior art FIG. 10B, except that the insulating washer and insulating material is now a novel dielectric nanoparticle insulating material.

Figure 69A:
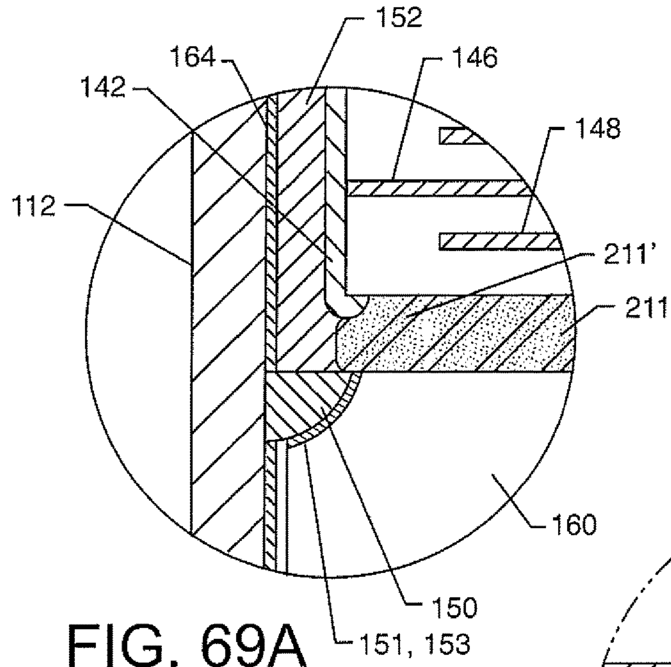

FIG. 69A is a blown-up partial view taken from 69A-69A of FIG. 69 showing that the uniformly dispersed dielectric nanoparticles 264 in a portion of the nanoparticle insulating washer between the feedthrough filter capacitor and the hermetically sealed feedthrough adjacent the feedthrough ferrule.

Figure 69B:
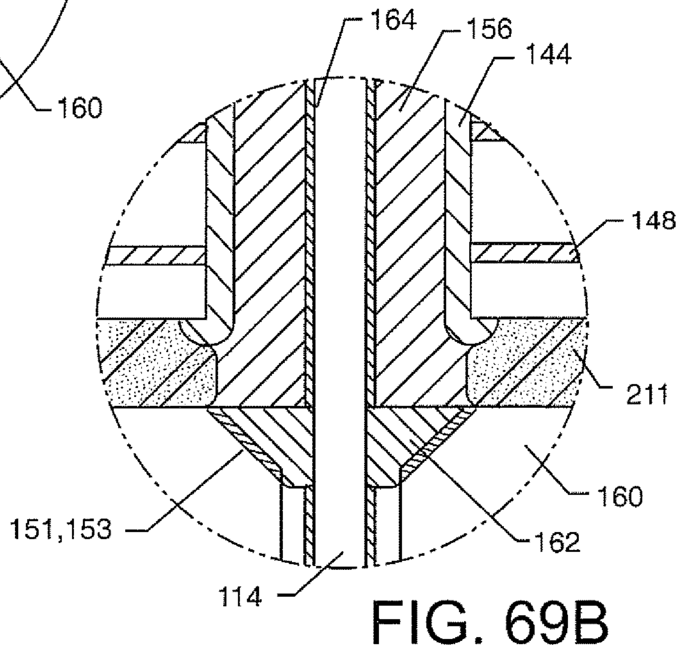

FIG. 69B is a blown-up partial view taken from 69B-69B of FIG. 69 showing the nanoparticle-filled 264 insulating washer between the feedthrough filter capacitor and the hermetically sealed feedthrough at the active terminal pin conductive pathway.

Figure 69C:
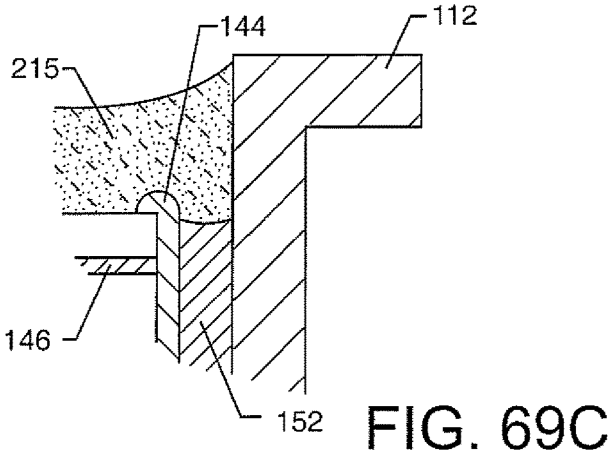

FIG. 69C is a blown-up partial view taken from 69C-69C of FIG. 69 showing the nanoparticle-filled 264 insulating material on the top of the feedthrough filter capacitor.

Figure 70:
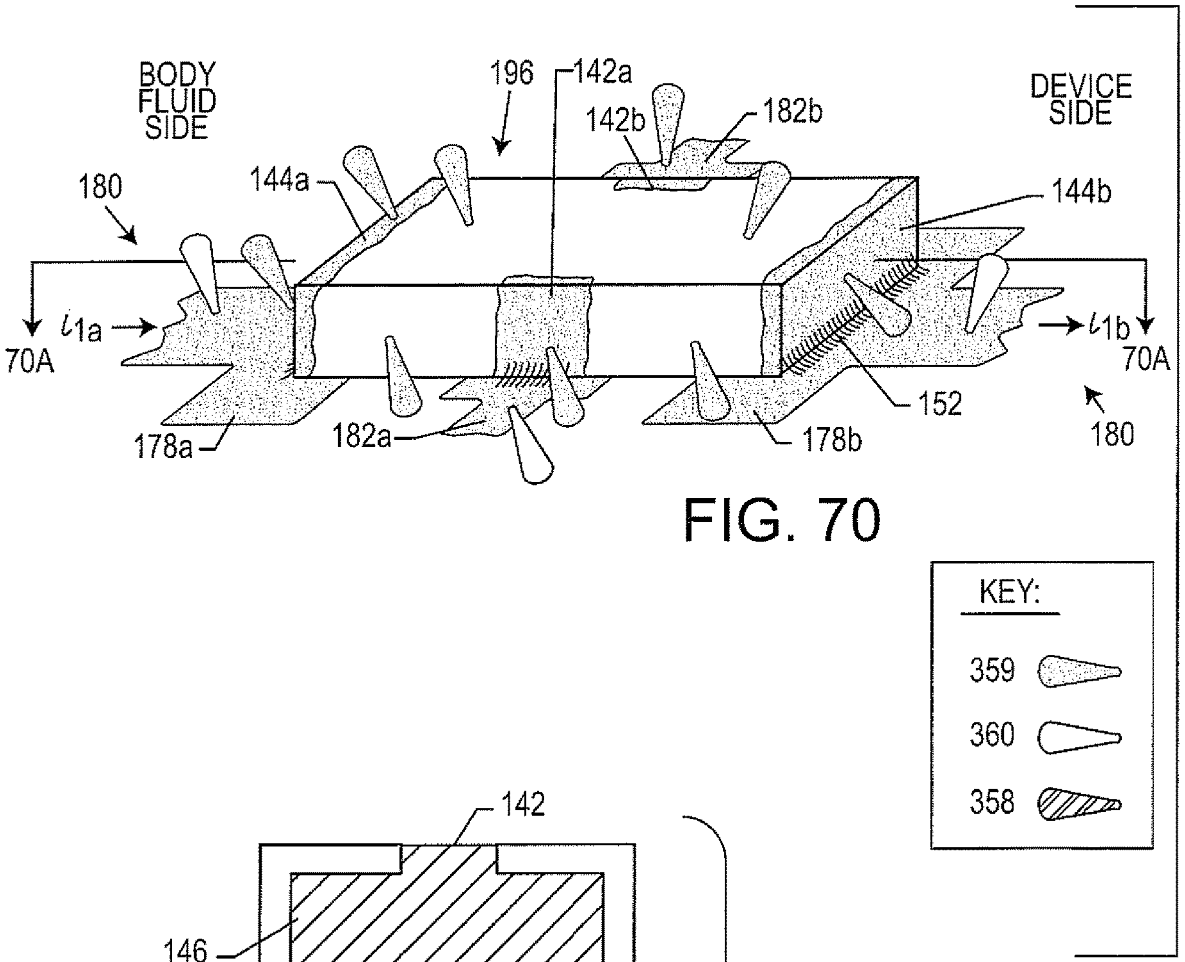

FIG. 70 is an isometric view of a prior art flat-thru filter capacitor with symbols indicating locations for placement of the novel nanoparticle-filled 264 insulating material.

Figure 70A:
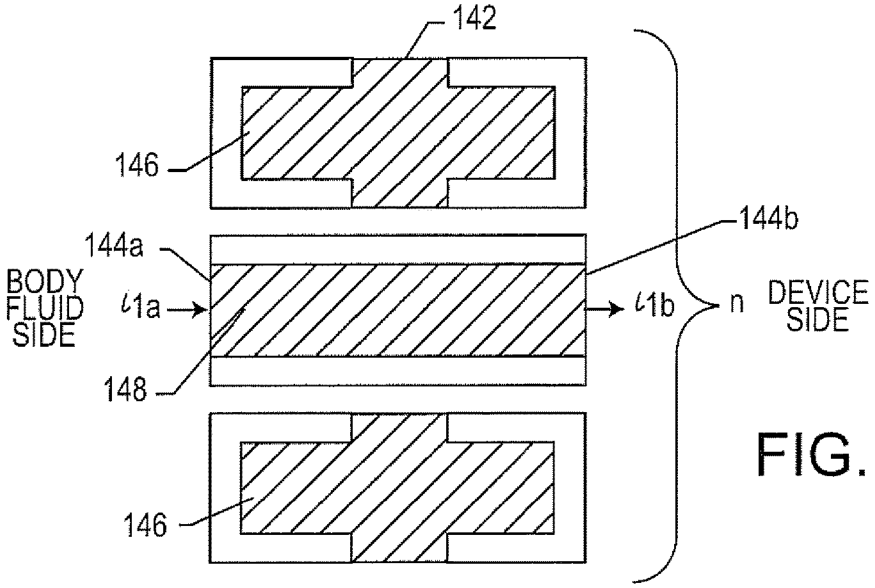

FIG. 70A is a cross-sectional view generally taken along 70A-70A of FIG. 70, illustrating the active and ground electrode plates of the flat-thru filter capacitor.

Figure 71:
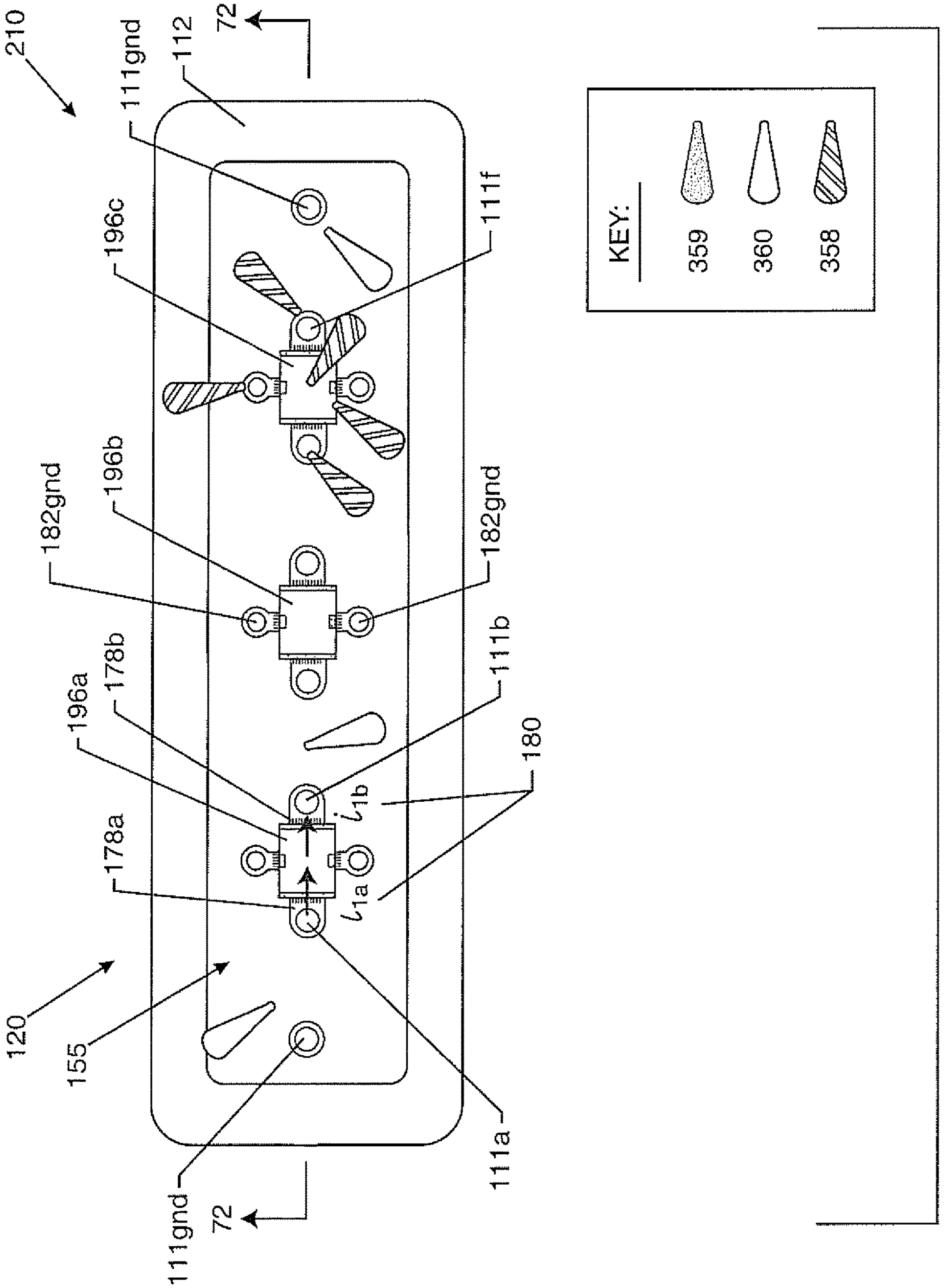

FIG. 71 is a plan view of the flat-thru filter capacitor of FIG. 70 mounted to an EMI filter circuit board including symbols for placement location for dispensing an insulating material. The locations where the insulation material is optional (not deemed necessary), are indicated by the "no insulating material" symbol.

Figure 72:
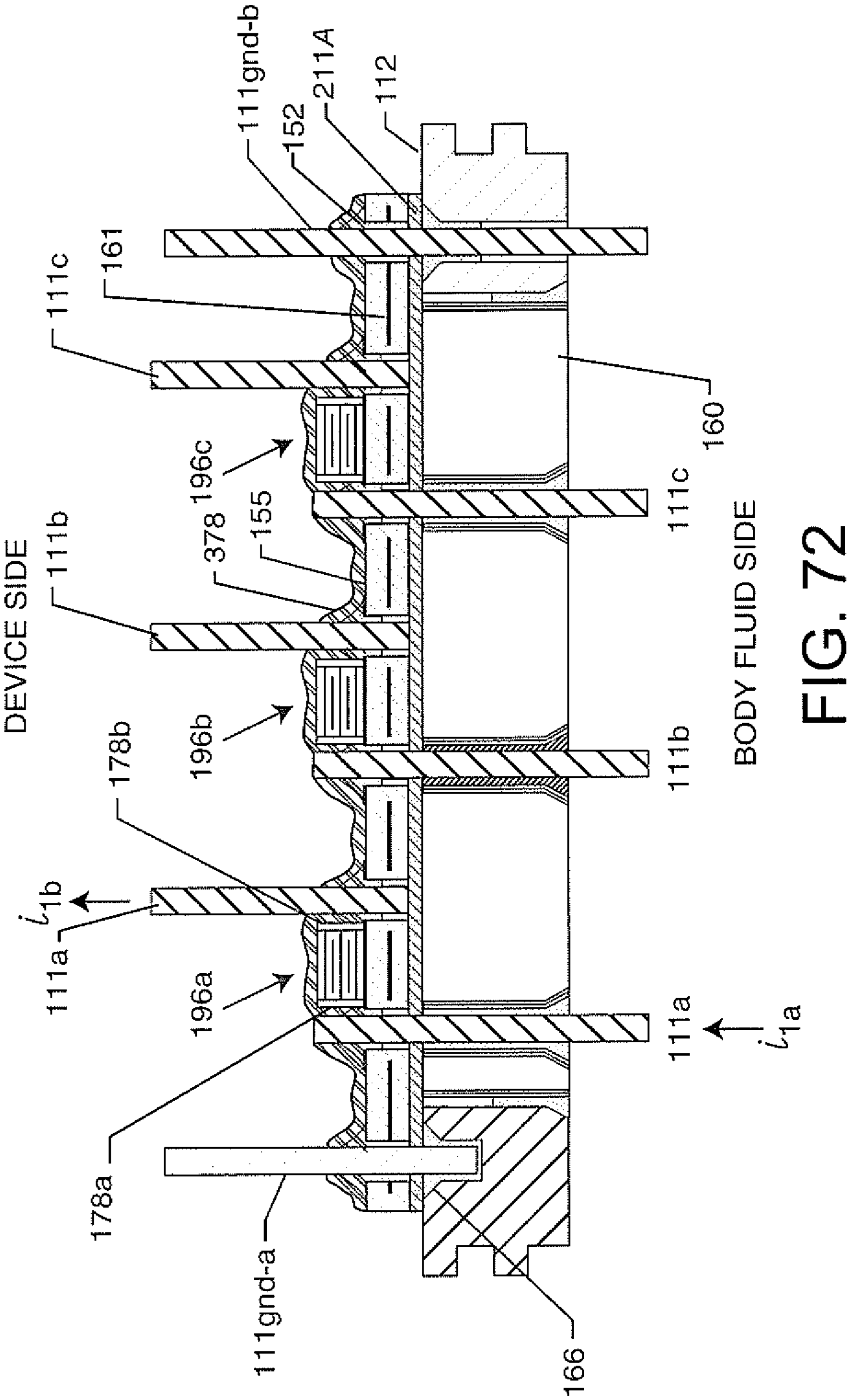

FIG. 72 is a cross-sectional view generally taken along 72-72 of FIG. 71, illustrating an insulating material applied to cover the flat-thru filter capacitors and the EMI filter circuit board surface between active conductive pathways, between the active and ground conductive pathways and between the ground conductive pathways and the feedthrough ferrule.

Figure 73:
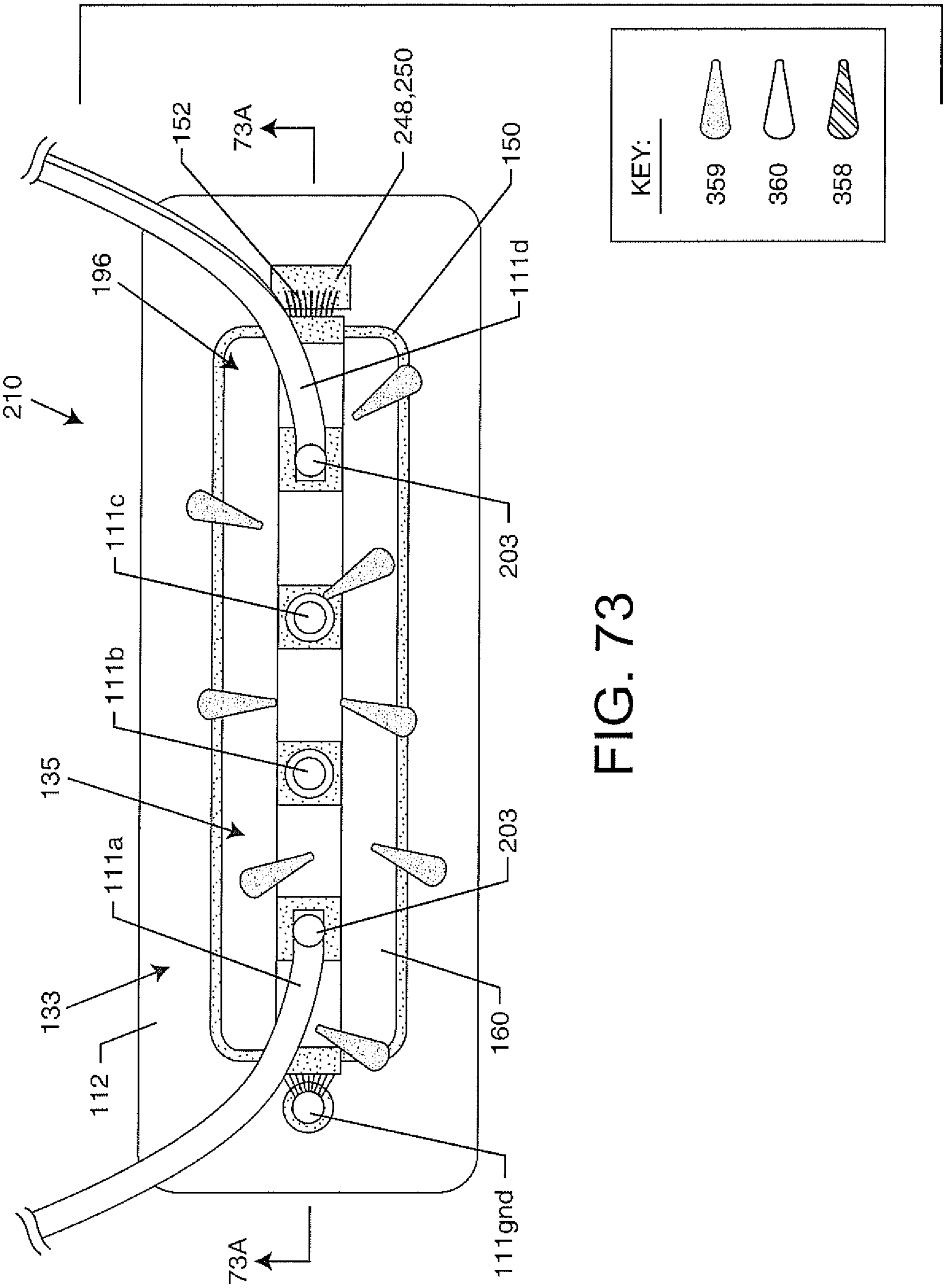

FIG. 73 is a plan view of a quadpolar flat-thru filter capacitor mounted in a tombstone position including symbols for the placement locations for dispensing a dielectric nanoparticle-filled 264 insulation material.

Figure 73A:
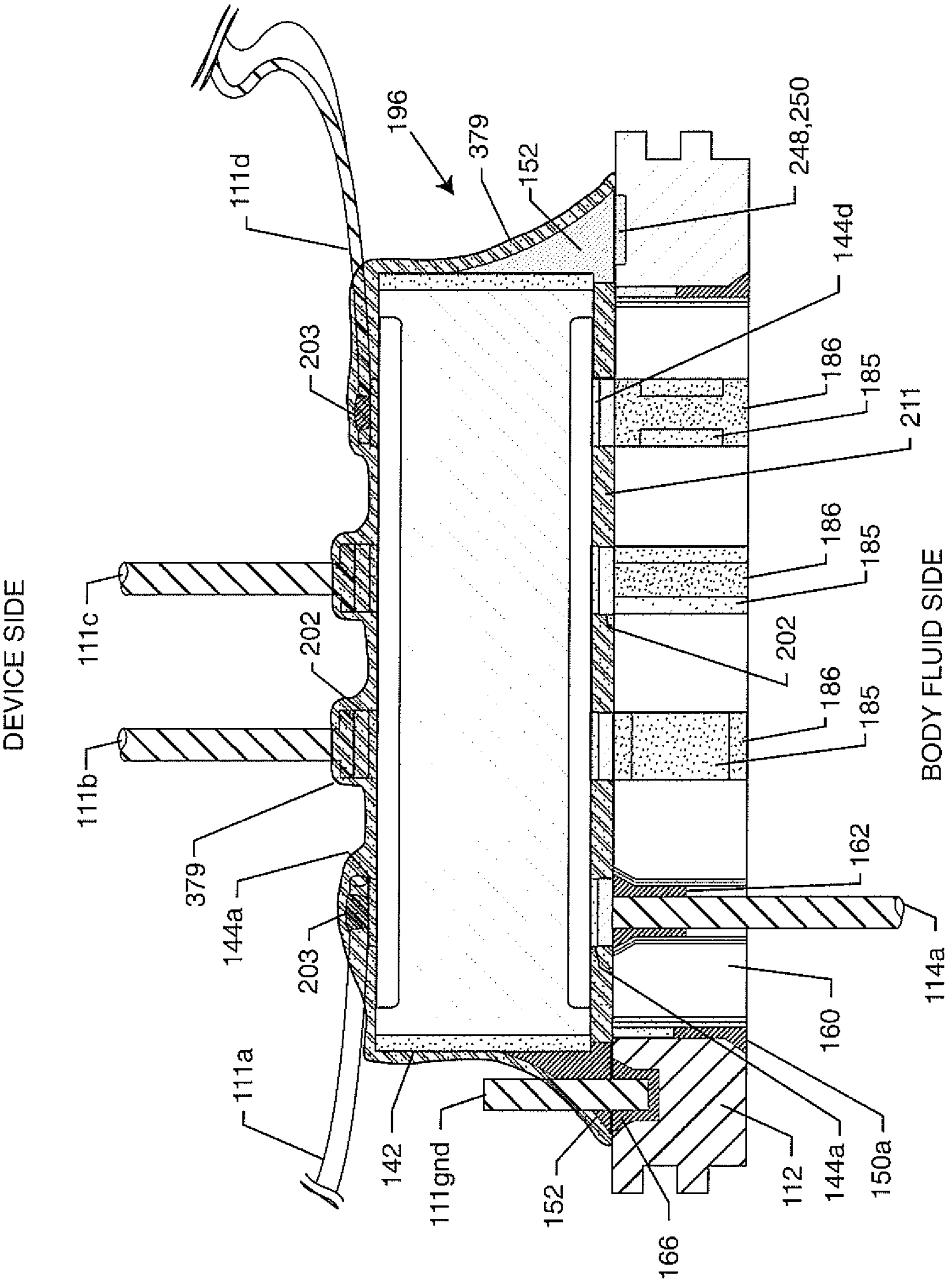

FIG. 73A is a cross-sectional view generally taken along 73A-73A of FIG. 73, illustrating surfaces covered by the dispensed nanoparticle-filled 264 insulation material.

Figure 74:
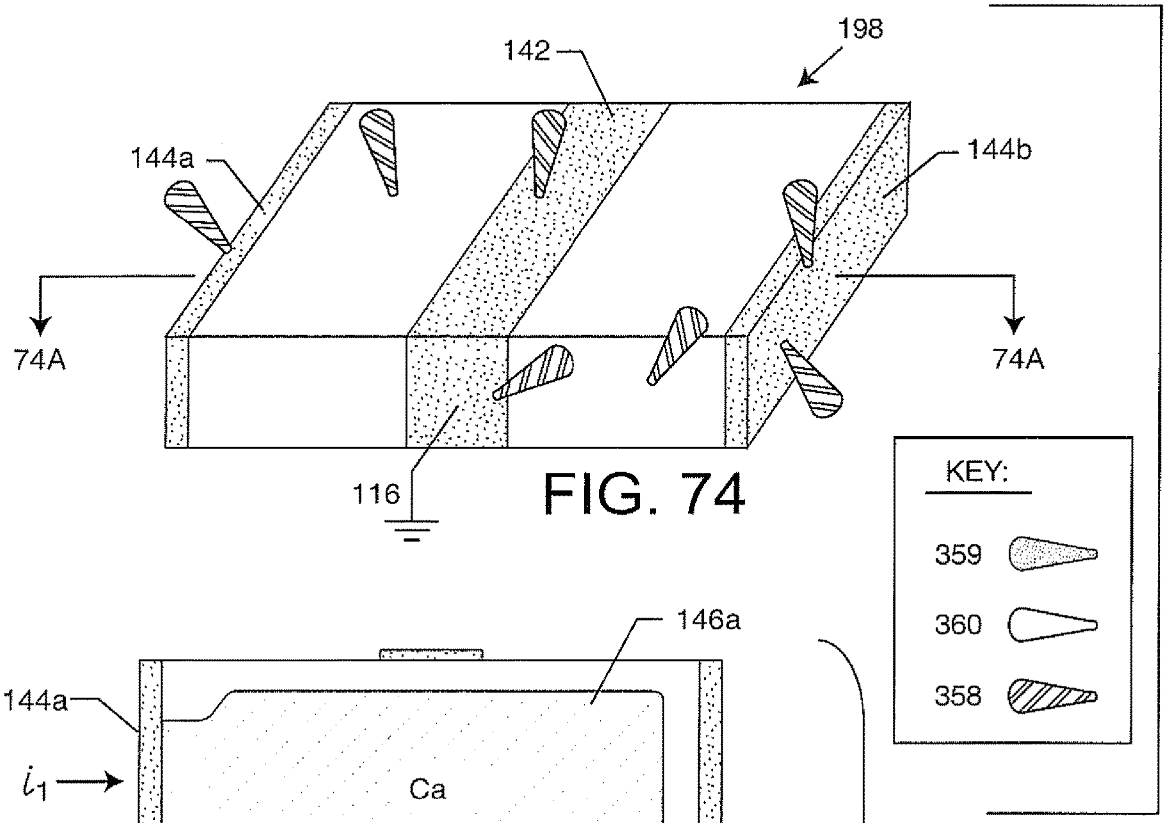

FIG. 74 illustrates a prior art X2Y attenuator filter capacitor illustrating placement locations for an insulating material in accordance with the present inventions.

Figure 74A:
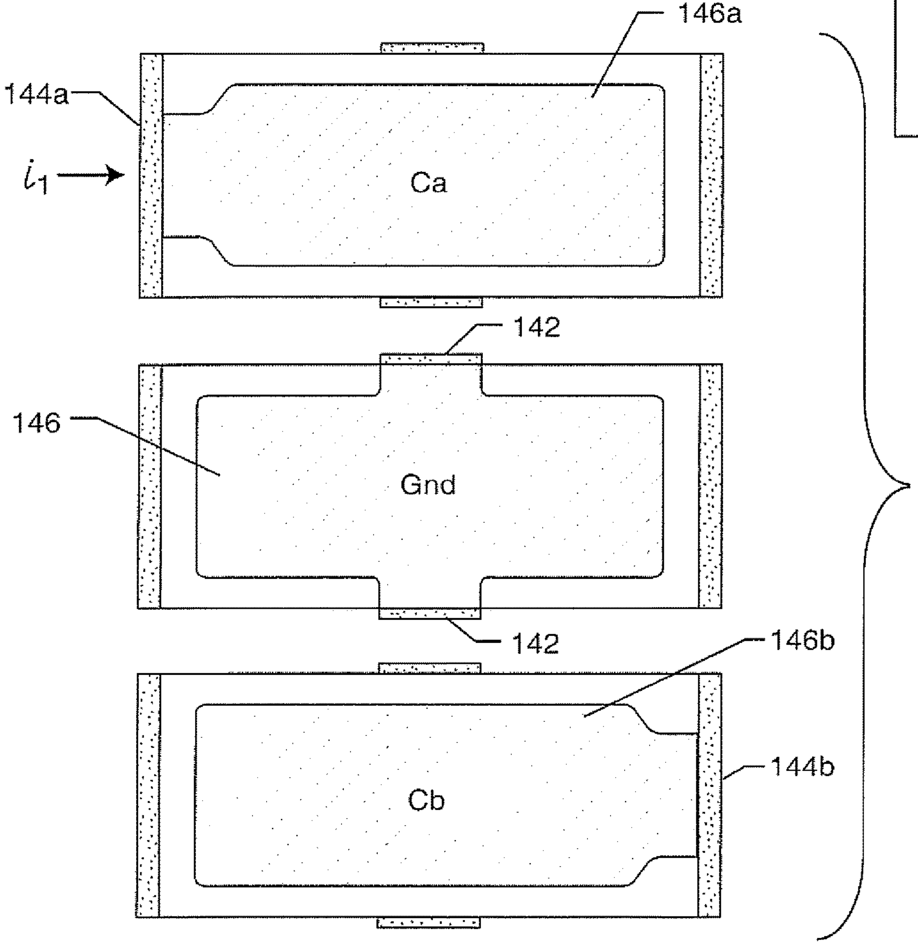

FIG. 74A is a cross-sectional view generally taken along 74A-74A of FIG. 74, illustrating the active and ground electrode plates of the X2Y attenuator filter capacitor.

Figure 75A:
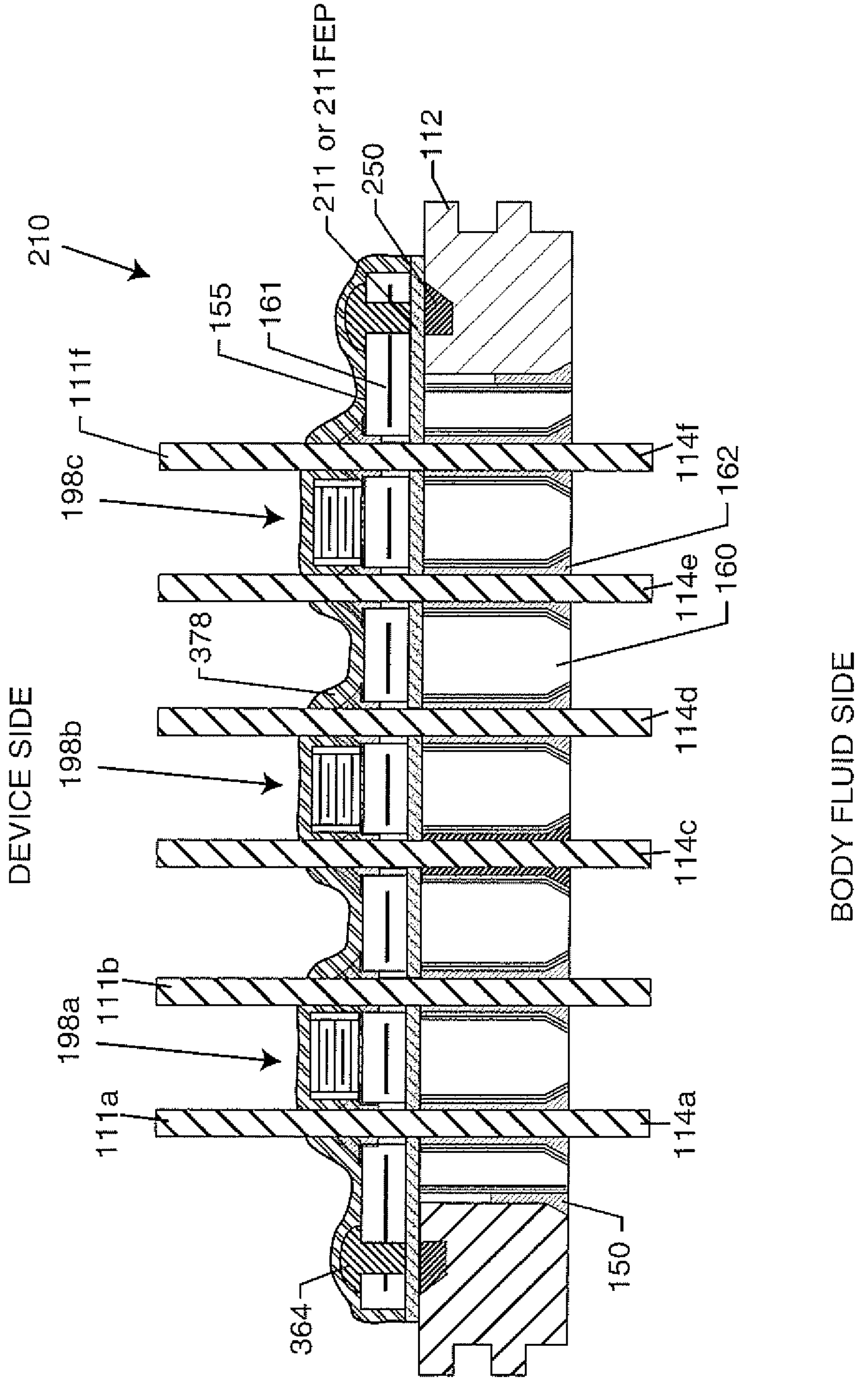

FIG. 75A is a cross-sectional view of the X2Y attenuator filter capacitors of FIG. 74 mounted on an EMI filter circuit board, both being covered by an insulating material, and an insulating washer disposed between the EMI filter circuit board and the feedthrough, which, in this embodiment, is with nanoparticles 264 and can be a thermoplastic.

Figure 76:
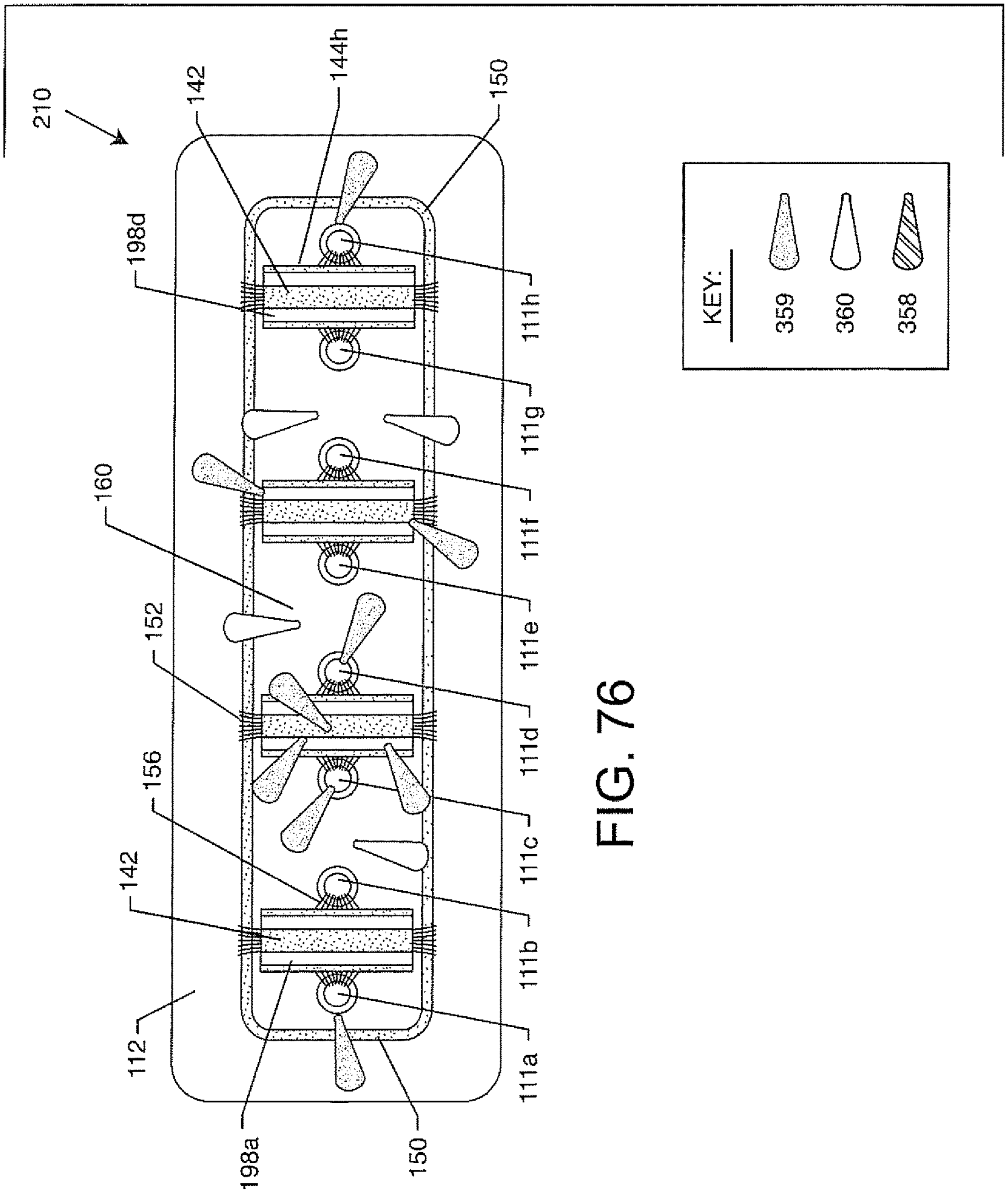

FIG. 76 is a plan view of a hermetically sealed feedthrough illustrating X2Y attenuator filter capacitors on top of the feedthrough insulator including strategic locations for dispensing nanoparticle-filled 264 insulation material to increase high-voltage stand-off. Locations where dispensed nanoparticle-filled 264 insulation material is optional is also indicated by the "no insulating material" symbol.

Figure 77:
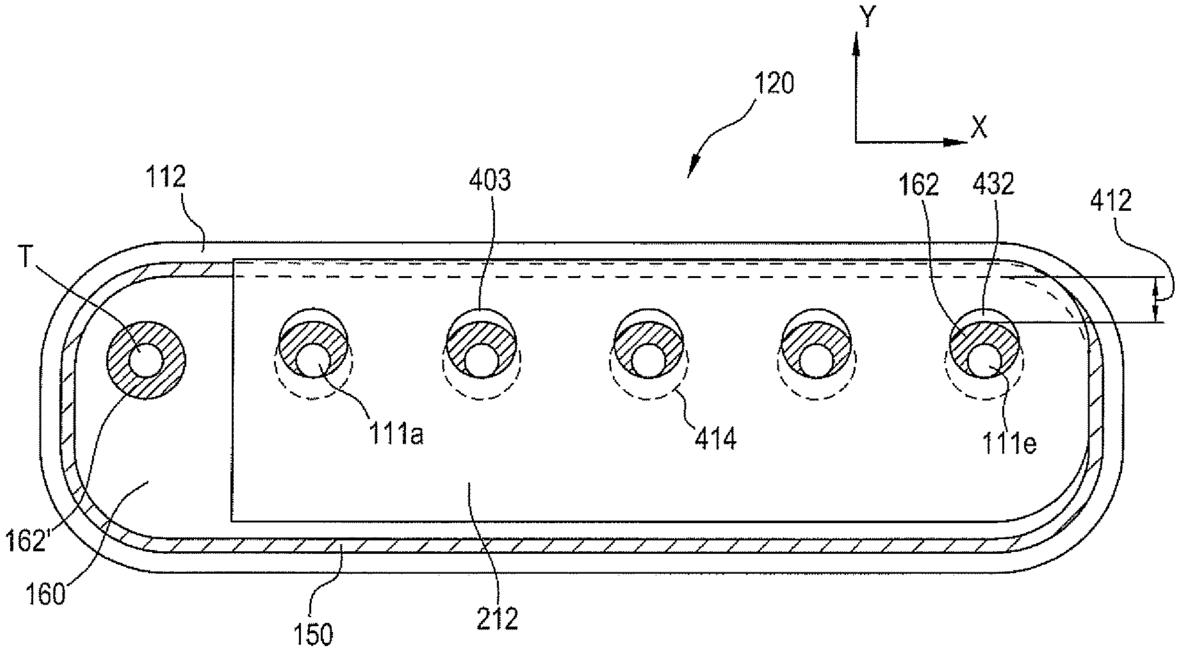
FIG. 77 (PRIOR ART)

FIG. 77 is a plan view of a hermetically sealed feedthrough on which an insulating washer is undesirably mislocated over gold brazes, whose outside diameter is shown by hidden lines. The insulating washer as illustrated has multiple round shaped insulating washer openings for receiving corresponding feedthrough terminal pins.

Figure 78:
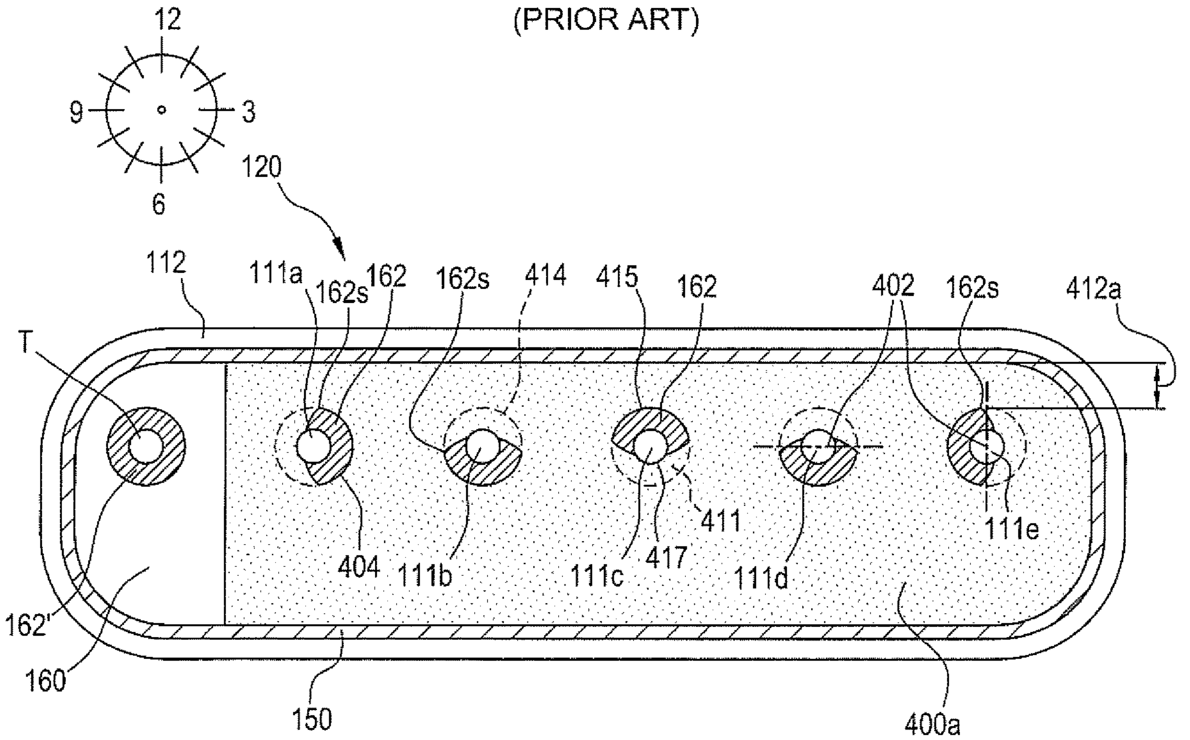

FIG. 78 is a plan view of a hermetically sealed feedthrough on which a self-centering insulating washer is desirably located. The self-centering insulating washer illustrated has individual baseball field-like insulating washer shaped openings that are clocked at various angles in accordance with the clock-face shown.

Figure 79:
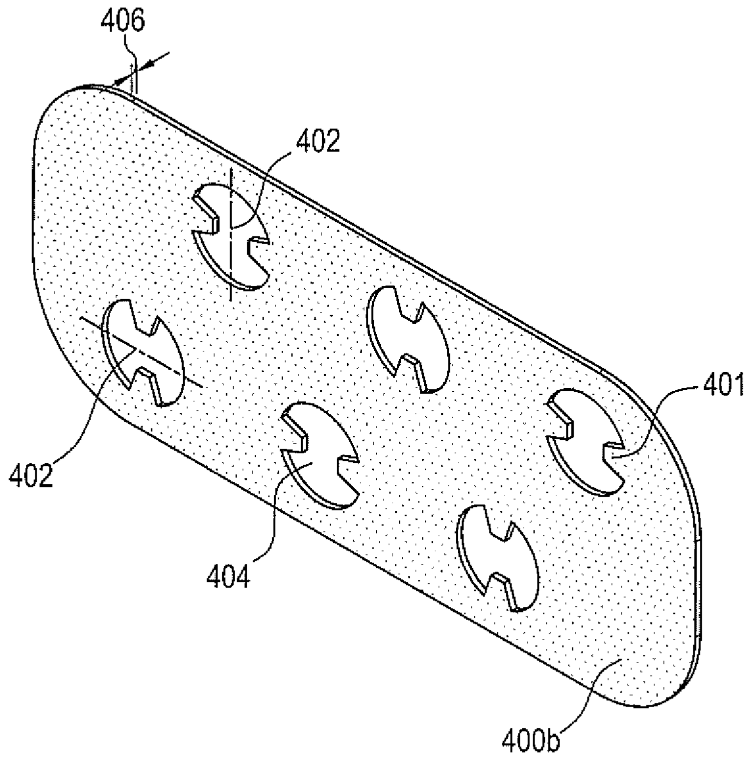

FIG. 79 is an isometric view of a novel self-centering insulating washer that has insulating washer shaped openings having two internal tooth-like structures.

Figure 80:
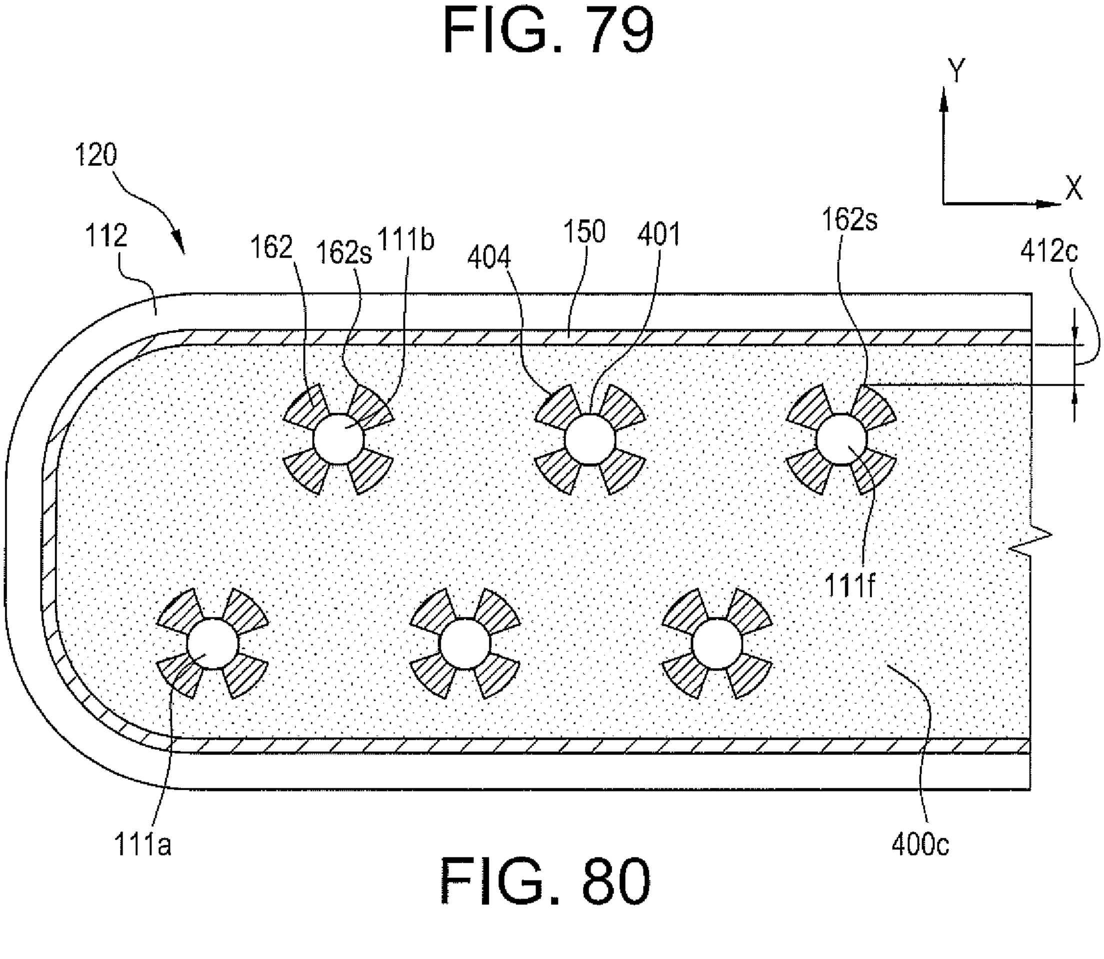

FIG. 80 is a plan view of a hermetically sealed feedthrough on which a novel self-centering insulating washer is desirably located. The self-centering insulating washer illustrated is similar to the self-centering washer of FIG. 79, except in this embodiment each insulating washer shaped opening has four internal tooth-like structures.

Figure 81:
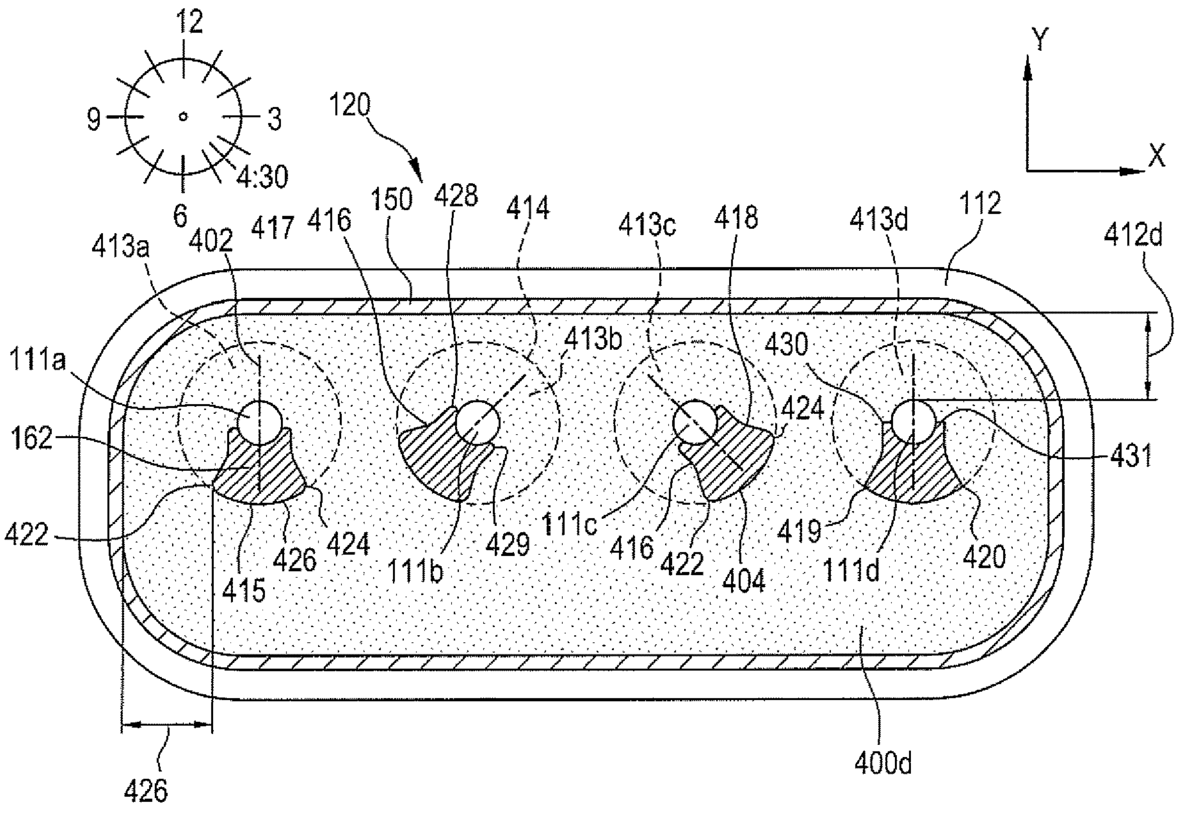

FIG. 81 is a plan view of a hermetically sealed feedthrough on which a self-centering insulating washer is desirably located so that the exposed insulator to terminal pin hermetic seal gold braze is outside of the high-voltage keep-out zones. The self-centering insulating washer illustrated has baseball field-like insulating washer shaped openings clocked in accordance with the clock-face shown.

Figure 81A:
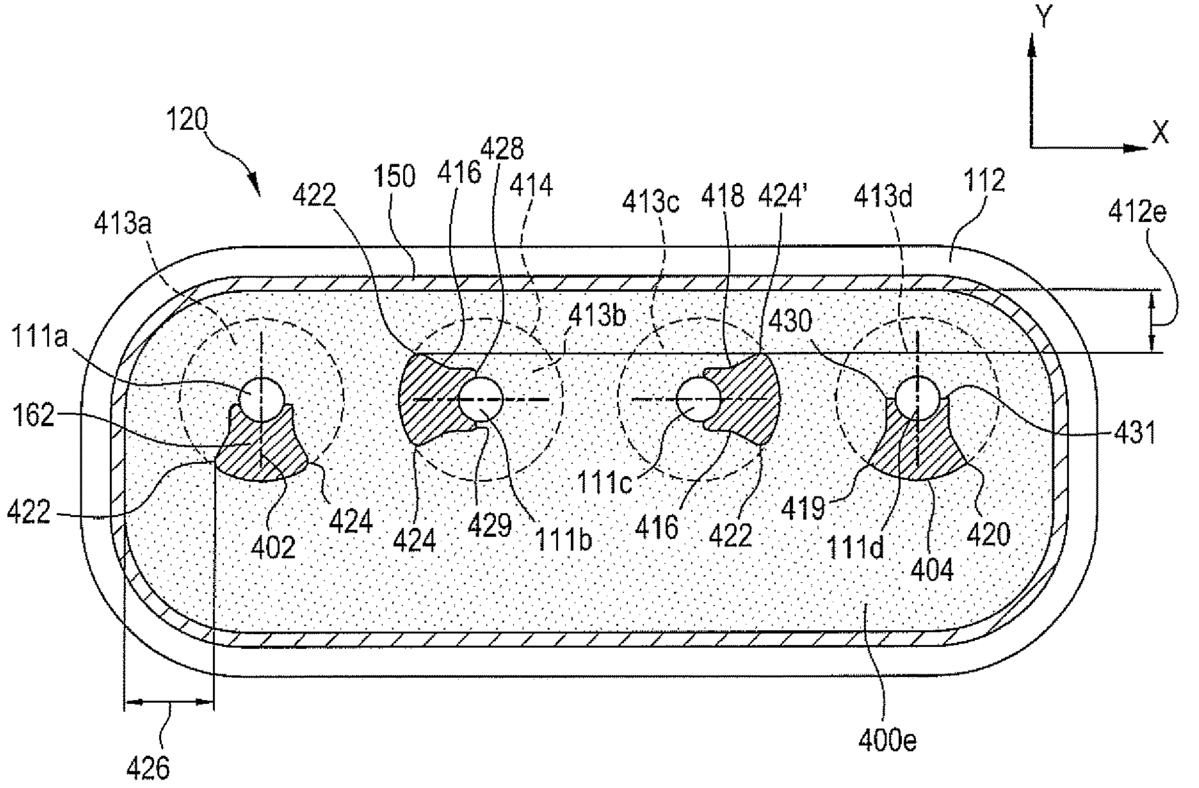

FIG. 81A is similar to FIG. 81, illustrating a plan view of a hermetically sealed feedthrough on which a self-centering insulating washer with baseball field-like shaped clocked openings so that the exposed insulator to terminal pin hermetic seal gold braze is outside a narrower high-voltage keep-out zones compared to FIG. 81.

Figure 81B:
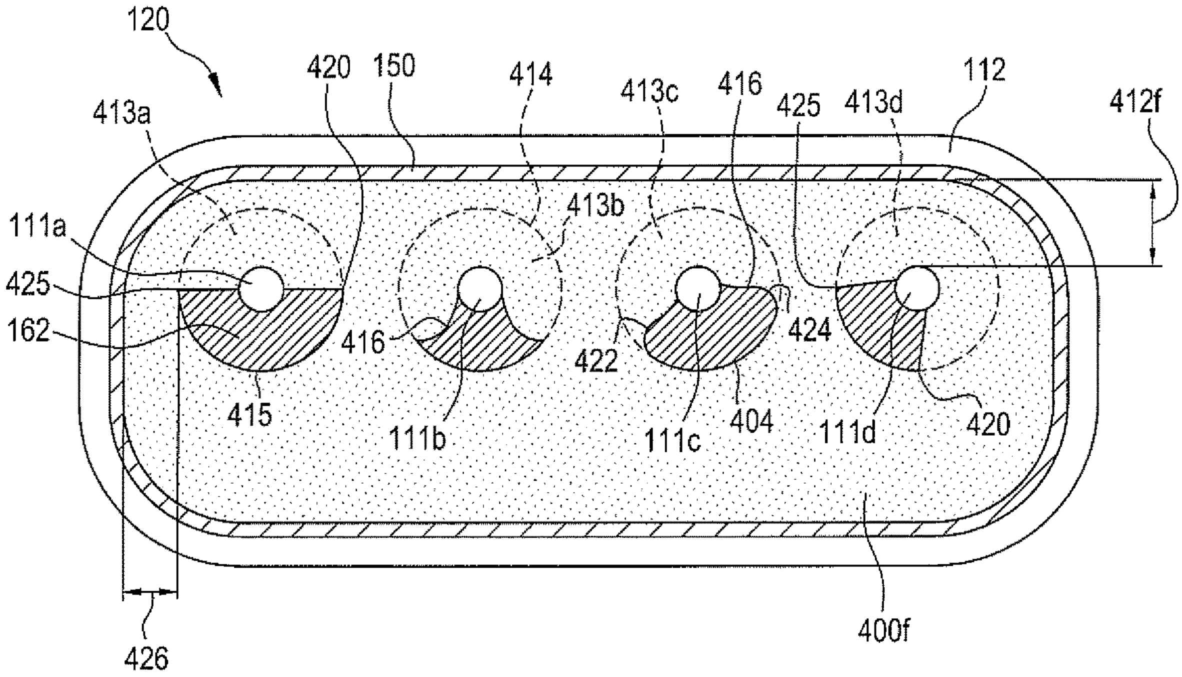

FIG. 81B is similar to FIG. 81 showing alternate washer shaped openings that expose the insulator to terminal pin hermetic seal gold brazes.

DETAILED DESCRIPTIONS OF THE PREFERRED EMBODIMENTS

The inventions disclosed herein apply to all the component embodiments in the literature and prior art patents incorporated by their reference. The electrically insulative materials used in the disclosed inventions may include any of the prior art materials currently in use, in addition to the novel thermoplastic/thermosetting polymeric embodiments of the present application. The polymerics of the present invention may be aromatic, semi-aromatic, aliphatic, partially fluorinated and combinations thereof. Suitable electrically insulative polymeric materials include acrylates, epoxies, elastomers, phenolics, polyimides, polyolefins and fluoropolymers. For example, the electrically insulative material may be selected from the group consisting of silicone, polyurethane, polyester, polyethylene, polypropylene, polyimide, polyamide (including synthetic polyamide, also known as nylon), acrylic or polyacrylates, and combinations thereof. Additional electrically insulative materials include perfluoroalkoxy (PFA), fluorinated ethylene-propylene (FEP), polyetheretherketone (PEEK), polyamide imide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl copolymers including ethylene-vinyl acetate (EVA) or polyethylene-vinyl acetate (PEVA), among others. The embodiments may include layers, laminar, coating structures. The embodiments may also comprise composite materials comprising two different materials, such as: a laminar composite structure comprising a core polymeric and a surface polymeric; a layered composite structure, wherein the layered composite structure comprises one of: a laminar composite layer, an insulating nanoparticle-filled 264 polymeric composite layer, a polymeric insulating layer, or combinations thereof. The insulative materials may be flexible, semi-rigid or rigid. The insulative materials may further be dispensable, curable, moldable, physically formed, or vapor deposited.

Figure 28:
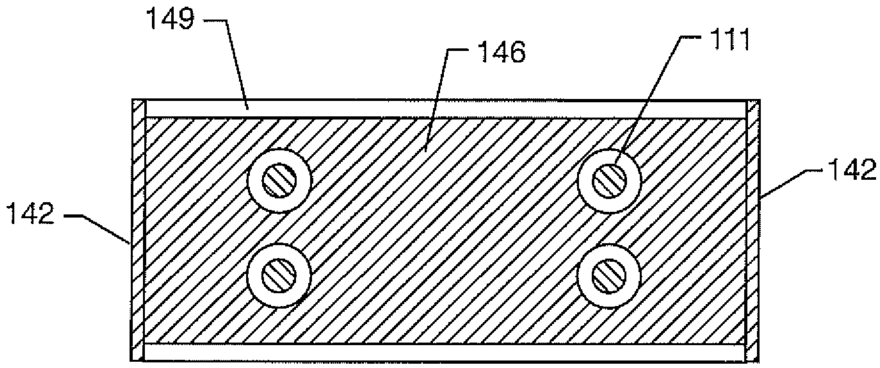
FIG. 28 (PRIOR ART)
FIG. 28 is a cross-sectional view generally taken along 28-28 of prior art FIG. 27 illustrating a ground electrode plate of the feedthrough filter capacitor. The ground plate has four capacitor passageways.
Figure 51:
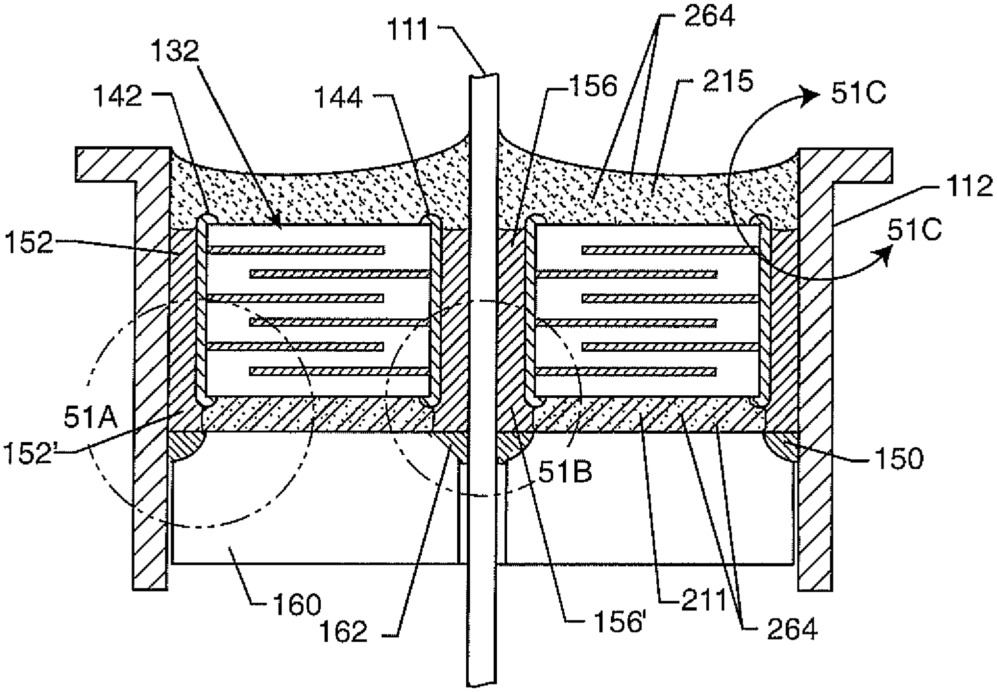
FIG. 51 is a cross-sectional view illustrating an embodiment of the present invention applied to the filtered feedthrough embodiment of prior art FIG. 10B. In this embodiment, both the insulating washer and the insulating material comprise uniformly dispersed filler insulating nanoparticles 264.

FIG. 51 illustrates the present invention applied to prior art FIG. 28 of U.S. Pat. No. 6,765,779, the contents of which are fully incorporated herein by this reference. This drawing shows a novel polymeric insulating washer 211 disposed between the EMI filter capacitor 132 and the feedthrough insulator 160. FIG. 51 also illustrates a novel insulating material 215 disposed on top of the EMI filter capacitor 132. Both the polymeric insulating washer 211 and the top insulating material 215 have a filler material comprising insulating nanoparticles 264. The polymeric insulating washer 211 of FIG. 51, better seen in the enlarged view of FIG. 51A, has a space 140 into which electrical connection material 152 is disposed to electrically connect the ground capacitor metallization 142 of the filter capacitor 132 to the ferrule-to-insulator gold braze 150. The polymeric insulating washer 211 of FIG. 51, better seen in the enlarged view of FIG. 51B, also has a washer opening 115, in which the feedthrough terminal pin 111 resides. An active capacitor passageway electrical connection material 156 electrically connects the active capacitor metallization 144 of the filter capacitor 132 to the terminal pin-to-insulator gold braze 162. Electrical connections to the gold brazes 150 and 162 provides reliable oxide-resistant low impedance filtered feedthrough ground and active connections, respectively. Also, the top insulating material 215 of FIG. 51 both cosmetically covers the filter capacitor 132 and, importantly, increases the high-voltage dielectric breakdown strength between the terminal pin 111 and the feedthrough ferrule 112.

While FIG. 51 shows that both the polymeric insulating washer 211 and the insulating material 215 have insulating nanoparticles 264, it is understood that one or the other may be absent of insulating nanoparticles 264. Additionally, one or more polymeric insulating washers 211 and/or insulating materials 215 may be used, either with or without insulating nanoparticles, and in any combination.

Further regarding the insulating nanoparticles 264, it is understood that the novel nanoparticle-filled 264 insulating washers 211 and/or insulating materials 215 of the present invention apply in their entirety to all of the embodiments of the prior art disclosed herein. For example, all of the polymeric insulating washers 212 (in general use in filtered feedthroughs of the medical implantable devices of FIG. 1 and including all of the prior art embodiments disclosed herein) may, instead, be nanoparticle-filled 264 polymeric insulating washers 211. By replacing polymeric insulating washer 212 with the novel nanoparticle-filled 264 polymeric insulating washers 211 of the present invention, the EMI filter capacitor 132 and, correspondingly the hermetically sealed feedthrough 120, may be downsized (made smaller) without compromising device therapy delivery performance. Typically, smaller filtered feedthroughs 210 have smaller filter and ferrule diameters (if discoidal) or lengths and/or widths (if oval, rectangular or square), which, for the prior art filtered feedthroughs, translates into closer active-to-ground spacing, for example, between an active terminal pin 111 and the ferrule-to-insulator gold braze 150 (the ferrule being part of system ground 124). The substantially increased dielectric strength of the nanoparticle-filled 264 polymeric insulating washer 211, which is substantially higher than the conventional polymeric insulating washer 212, thereby mitigates any potentially compromising effects of the closer active-to-ground spacing.

The polymeric insulating washer 211 of FIG. 51 may comprise a solid insulating structure like mica, nylon, polyimide (for example, Kapton®), polyamide (PA), polyurethane (PU), silicone, rubber, plastic, ceramic, glass, composite, polytetrafluoroethylene (PTFE), ethylene tetrafluoroethylene (ETFE), polycarbonate (PC), polyetherimide (PEI), polyoxymethylene (POM), polysulfide, acetal, polyacetal, polyformaldehyde, phenolic, and combinations thereof, and may also include other similar non-metallic materials. Kapton® is a DuPont registered brand name for polyimide films used as substrates for flexible printed circuits. The polymeric insulating washer 211 may further be a single or double-sided adhesive-backed polymeric insulating washer, the adhesive being a polyimide, a silicone polyimide, a polyurethane, a silicone, a polysulfide, and combinations thereof. It is understood that the adhesive backing and washer coatings may comprise polymeric materials that are thermoplastic, thermosetting, or both. It is anticipated that other similar adhesive materials may also be used. The polymeric insulating washer 211 and/or top insulating material 215 may be a cured liquid insulating material like epoxy, elastomer, polyester, liquid silicone rubber, polyurethane, or other similar materials, including combinations thereof.

The insulating nanoparticles 264 of the polymeric insulating washer 211 and the top insulating material 215 may be polymeric, ceramic or combinations thereof. Polymeric nanoparticle 264 may be selected from any of the insulating materials listed above for FIG. 51. Ceramic nanoparticles 264 may be selected from alumina, baria, calcia, ceria, magnesia, silica, strontia, titania, zirconia ceramic families and combinations thereof. Non-limiting examples of some nanoscale metal oxides that can also be used include $Al_2O_3$, BaO, CaO, $CeO_2$, MgO, $ZrO_2$, $SiO_2$, $TiO_2$, $Al_2SiO_{53}$, $BaTiO_3$, $SrTiO_2$, ZnO, $Si_3N_4$, AlN, BN and combinations thereof. Various stabilized or partially stabilized zirconia may also be used including zirconia toughened alumina (ZTA) and alumina toughened zirconia (ATZ), Yttrium stabilized zirconia (YSZ), yttrium-toughened zirconia (YTZP), and combinations thereof. Some nitrides may also be used, such as, aluminum nitride (AlN), silicon nitride ($Si_3N_4$), boron nitride (BN), carbon nitride (CN) and combinations thereof.

The nanoparticles 264 may be configured as particulates, short fibers, long fibers, spheres, flakes, submicron fibers, which are isotropically dispersed within the base polymeric material. It is understood that the insulating nanoparticles 264 may be the same material, or, alternatively, may be a combination of one or more materials. For example, a combination of various insulating nanoparticles 264 may be used. Insulating nanoparticle 264 material selection is defined by the specific electrical performance needs of an application and the physical, chemical, and electrical properties of the insulating nanoparticle material. The above nanoparticle materials and particle configurations are applicable to all polymeric insulating washer and insulating material embodiments disclosed herein.

The insulating nanoparticles 264 (low to near zero electrical conductivity) may alternatively be dielectric nanoparticles (insulators that are polarizable). For example, Yuxuam Chen, in his graduate thesis entitled ELECTRICAL BREAKDOWN OF GASES IN SUBATOMIC PRESSURE, dated Aug. 6, 2016, Auburn University, the contents of which are fully incorporated herein by this reference, states: "The materials made by adding nano-scale particulates into polymeric-based bulk are called nano-dielectrics." Chen's primary focus is gas discharge, including breakdown and flashover, however, Chen does not contemplate unique dielectric breakdown issues relative to AIMD components. Chen generally describes doping metal oxides such as alumina into epoxy to impart "surface insulation strength" but does not consider issues of AIMD component delamination or separation. Moreover, Chen does not contemplate improving the high-voltage insulation of AIMD components, for example, about and around feedthrough filter capacitors configured as the primary passive EMI filter for an Implantable Cardioverter Defibrillator (ICD). Chen's primary focus is simply gas discharge, breakdown, and flashover. Some AIMDs, like ICDs, have a fast-rise time pulse, which creates high-frequency components that increase the risk of both gas and dielectric discharge, which can start as a microcoulomb discharge. A microcoulomb discharge can result in a catastrophic medical device event. Chen does not seem to be aware of microcoulomb discharge, which can particularly occur on high dielectric constant surfaces, such as the filter capacitor 132 and a transition to air or another gas.

As previously defined, "nano-scale", "nano-sized", "nano-dielectric additives", "nano-insulating materials" and "nanoparticles", which are generally measured in nanometers or microns, all refer to particles (commonly known as fillers) that are added to a polymeric insulating component disposed on or adjacent to other components of an active implantable medical device, such as, an EMI filter capacitor or circuit board. The insulating nanoparticles 264 of the present invention are represented by small uniform dots evenly distributed in various polymeric insulating component embodiments. These nano-scale particles (nanoparticles 264) are defined by numerical designation 264. While small dots are used to indicate nanoparticles 264, in reality, the insulating nanoparticles 264 of the present invention are so small that they are actually not visible to the naked eye (requires microscopy techniques). The small dots are intended to distinguish the embodiments having nanoparticles according to the present invention from those embodiments that do not. The small dots are not an indication of particle size.

Regarding particle size, the insulating nanoparticles 264 of the present invention range from greater than 0 nanometers to about 40,000 nanometers. As such, the insulating nanoparticles 264 can range from greater than 0 nanometers to about 100 nanometers, which is the common industry range for "nano". The particle size range of the insulating nanoparticles 264 of the present invention, however, also includes fine and micron-sized particles, ranging from greater than about 100 nanometers (0.1 microns) to about 40,000 nanometers (40 microns). The about 40-micron size upper limit of the insulating nanoparticles 264 of the present invention is derived from an analysis of a worst-case ICD pulse, wherein an ICD high energy storage capacitor is first charged to a voltage greater than 800 volts and then discharged into the initially uncharged EMI filter capacitor 132, which is in parallel with the load of the human heart. When measured at the EMI filter capacitor 132, the HV ICD pulse may have a pulse rise time (PRT) of less than 100 nanoseconds (the pulse rise time is application and design specific). The about 40-micron upper limit of the added insulating nanoparticles 264 was determined using analysis and bench-top testing of high-frequency (HF) high-voltage (HV) pulse components measured at the EMI filter capacitor 132. The data showed a high-voltage pulse ring-up above 1200 volts at high frequencies, for example, in the 13-megahertz frequency range. Such high-frequency (fast rise time) high-voltage pulses are more prone to dielectric breakdown, gas discharge, flashover, or arc overs. Thus, the addition of the insulating nanoparticles 264 of the present invention, having a particle size ranging from greater than 0 nanometers to about 40,000 nanometers, to one or more implantable device polymeric insulating components disposed on or adjacent to an EMI filtering component, such as an EMI filter capacitor or EMI filter circuit board, significantly increases the high-voltage and high-frequency dielectric breakdown strength of the EMI filter capacitor or EMI filter circuit board.

More particularly, the addition of well dispersed insulating nanoparticles 264 of the present invention into AIMD polymeric insulating materials can reduce the probability of a high-voltage breakdown due to a high-voltage pulse of an implantable device, for example an ICD, against EMI filter breakdown or failure due to a high-voltage pulse. The inventors have found that very fast (less than 1 microsecond or even less than 100 nanoseconds) rise time HV ICD pulses greater than 800 volts are highly resistant to forming breakdown tracks (like carbon tracks) or breakdown paths due to the minefield of insulating nanoparticles 264 dispersed within the polymeric insulating material disposed on or adjacent to the EMI filter capacitor 132. When particles are larger than about 40,000 nanometers, high-voltage discharge tracks become possible.

Although the present invention is three-dimensional, the mechanism of breakdown protection may be better understood through a two-dimensional terminal pinball machine analogy. Think of shooting a terminal pinball through a field of very large terminal pins that are spaced out and evenly distributed in a specified area vs. shooting the same terminal pinball through a field of densely packed, much smaller terminal pins. The probability of the same terminal pinball getting through the latter more densely packed terminal pin area becomes extremely unlikely as there is no open path between the smaller but higher number of terminal pin). The terminal pinball is analogous to the fast rise time of the HV ICD pulse through a high-frequency component. Furthermore, the nanoparticle-filled 264 polymeric insulating materials of the present invention disposed on or adjacent to an EMI filter capacitor or an EMI filter circuit board is not just useful in protecting against HV breakdown due to ICD pulses. All AIMDs and CIEDs are subject to external high-voltage pulses, including induced high voltages on AIMD leads from Automatic External Defibrillators (AEDs), manual external defibrillators, electrostatic discharge, and the like. Thus, the nanoparticle-filled 264 polymeric insulating materials of the present invention provide a great degree of protection from these or similar HV sources.

Referring once again to FIG. 51, ground electrical connection material 152 and active electrical connection material 156 may comprise either a thermosetting conductive adhesive or a solder. The thermosetting conductive adhesive may be selected from the group of an electrically conductive polymeric, an electrically conductive elastomer, an electrically conductive epoxy, an electrically conductive silicone, an electrically conductive polyimide, and an electrically conductive polyamide. Two commonly available solders that may be used include, but are not limited to, AG1.5, which consists of 97.5% lead, 1% tin and 1.5% silver, and SN10 comprising 10% tin, 88% lead and 2% silver. Other suitable commercially available solders may also be used. When using a solder, ductile solders are preferable, as ductile solders limit potential thermal shock damage due to the soldering process.

Regarding thermosetting conductive adhesives, in order for the electrical connection materials 152 and 156 to thoroughly flow about terminal pin 111 and between the ferrule-to-insulator open space 140, a centrifuging process and/or very small syringe dispensers are often used. Centrifuging and syringe dispensing both tend to drive excess electrical connection materials 152' and 156' through the capacitor passageway and out into any open space between the EMI filter capacitor 132 and the feedthrough insulator 160 (also see FIGS. 51A and 51B). It is desirable that electrical connection materials 152' and 156' contact the gold brazes 150 and 162, respectively, so that an oxide-resistant electrical connection is made. In some cases, the terminal pin 111 may comprise oxidizable tantalum or niobium, both of which can have a highly oxidized surface, which, as previously disclosed introduces an undesirable $R_{OXIDE}$ into the electrical connection. Also, platinum (Pt) or palladium (Pd) terminal pins 111 are often alloyed, with iridium (Ir), which increases the hardness and stiffness of pure platinum and palladium, making iridium alloyed platinum and palladium terminal pins stronger and more resistant to repeated bending. Iridium, however, also can oxidize, which often results in Pt—Ir and Pd—Ir soldering issues. For example, solder dipping a terminal pin 111 typically results in splotchy areas where the solder does not readily wet. The splotchy areas comprise oxidized surface iridium. All solderability issues due to such oxidizable metals are resolved by placing the electrical connection materials 152 and 156 in direct contact with a portion of the oxide-resistant gold brazes 150 and 162, respectively, as direct contact with an oxide-resistant material creates a very low impedance conductive pathway to divert high-frequency EMI signals so that filtered feedthrough 210 can properly work.

Referring again to FIG. 51, if there is a delamination of the polymeric insulating washer 211 (either between the EMI filter capacitor 132 and the polymeric insulating washer 211 or between the polymeric insulating washer 211 and the feedthrough insulator 160), the excess electrical connection materials 152' and/or 156' can each undesirably flow into such delamination gaps (which is possible particularly under centrifuged induced pressure). Accordingly, the excess electrical connection materials 152' and 156' can thereby reduce the electrical stand-off distance between the active terminal pin 111/gold braze 162 and the ground ferrule 112/gold braze 150. In a worst-case scenario (complete delamination of the insulating washer), excess electrical connection material 152' or 156' or both can fill the entire delamination resulting in an undesirable active-to-ground electrical short. Furthermore, if the filtered feedthrough has two or more terminal pins 111, then one active terminal pin can be electrically shorted to another active terminal pin. Electrical testing during production, can detect and screen out such a total short. The bigger concern is a latent delamination defect, which could happen in the field if the electrical connection materials 152' and 156' continue to migrate. Then, an unpredictable electrical short can occur, which can be dangerous for an implant patient. Latent electrical shorts between the EMI filter capacitor 132 and the feedthrough insulator 160 are highly undesirable, as such short circuits result in a complete failure of the active implantable medical device. For example, if the electrical short is in the sense circuits of a cardiac pacemaker 100C, then the cardiac pacemaker 100C cannot sense biologic signals; thus, the pacemaker cannot and does not work properly. In the case of an electrical short across the low voltage therapy delivery electrodes of a cardiac pacemaker 100C, then low voltage therapy pacing pulses are suspended (which is immediately life threatening for a pacemaker dependent patient). In the case of an electrical short across high-voltage therapy delivery electrodes of an implantable cardioverter defibrillator (ICD) 100I, high-voltage defibrillation pulses are suspended, which can result in the ICD failing to cardiovert a patient. ICD failure to cardiovert can be immediately life threatening to a defibrillator patient. Moreover, such high-voltage ICD electrical shorts are exceptionally high in energy (on the order of 32 Joules or more) and likely to result in physical destruction of the EMI filter capacitor 132, including the surrounding areas of the ICD. In other words, the ICD 100I becomes destroyed beyond repair. As such, electrical shorts between the EMI filter capacitor 132 and the feedthrough insulator 160 of an active implantable medical device can be catastrophic.

Further, regarding unintended electrically conductive contact between the active terminal pin 111 or its associated gold braze 162 and the system ground 124, to produce a catastrophic failure it is not necessary for an ICD 100I that electrical connection material 156' completely connects (shorts) the active area (terminal pin 111 and/or gold braze 162) and system ground 124. In fact, for high-voltage devices, such as the ICD 100I, when the electrical connection material 156' flows sufficiently to reduce the distance between the active area and system ground 124 (that is, creates a gas gap, such as a nitrogen or an air gap 135 in FIG. 28B), then the reduced distance therein can be enough to result in a catastrophic avalanche breakdown, which essentially destroys the functionality of the ICD 100I. For an ICD implant patient, this translates into an immediately dangerous and life-threatening situation. During production manufacturing operations, high-voltage tests are typically performed in air. Once the filtered hermetic seal assembly 210 is installed and the AIMD housing 116 is laser-welded (hermetically sealed), it is normally exposed to a vacuum to evacuate the air through a small opening (not shown), and it is then backfilled with dry nitrogen. Other gases can be used, but for an ICD, dry nitrogen with a helium tracer gas is typical. Low-voltage devices, such as cardiac pacemakers, may be backfilled with argon. For example, if one were to remove the insulating washer 211 of FIG. 51 and the capacitor active electrode plate 144 is disposed at the bottom of the filter capacitor 132, delivery of a fast rise time ICD 100I high-voltage pulse could result in a gas gap avalanche (breakdown or arc) through the gas (air or nitrogen) in the space between the active area (terminal pin 111 and/or braze 162) and system ground 124. Accordingly, a polymeric insulating washer 212, as illustrated, or alternatively an insulating material as previously disclosed, not only fills the gas gap between the feedthrough filter capacitor 132 and the ceramic insulator 160 and/or ferrule 112 but also provides a high dielectric breakdown strength of at least 100 volts per mil thickness.

In a prior art embodiment, where polymeric insulating washer 212 is devoid of nanoparticle fill, it may have a dielectric breakdown strength of around 500 volts to 1000 volts per mil. In the prior art for washer 212, it was typical that the polymeric insulating washer 212 may comprise a polyimide, such as Kapton®, that was adhesively coated on both sides. It was also known in the prior art to use two of these washers that were adhesively bonded on top of each other. Importantly, there must not be any separation, delamination, disconnection, disjunction, holes, openings, breaks, cavities, spaces, gas bubbles, or interruptions that function as gas gaps (135 in FIG. 29B) between the bottom of the filter capacitor 132 and the polymeric insulating material 212 and/or between the insulating washer 212 and/or the ferrule 112. Proper bonding of polymeric insulating material 212 is therefore very important. Adjunct adhesives, epoxies, or polyimides (not shown) can facilitate and improve such bonding. By converting the insulator washer 112 to a nanoparticle-filled 264 polymeric insulating washer 211, the dielectric breakdown strength is increased dramatically, generally greater than about 5 to about 10 thousand volts per mil. For the novel nanoparticle-filled 264 polymeric insulating washer 211, it is very important that there must not be any separation or delamination.

Figure 51A:
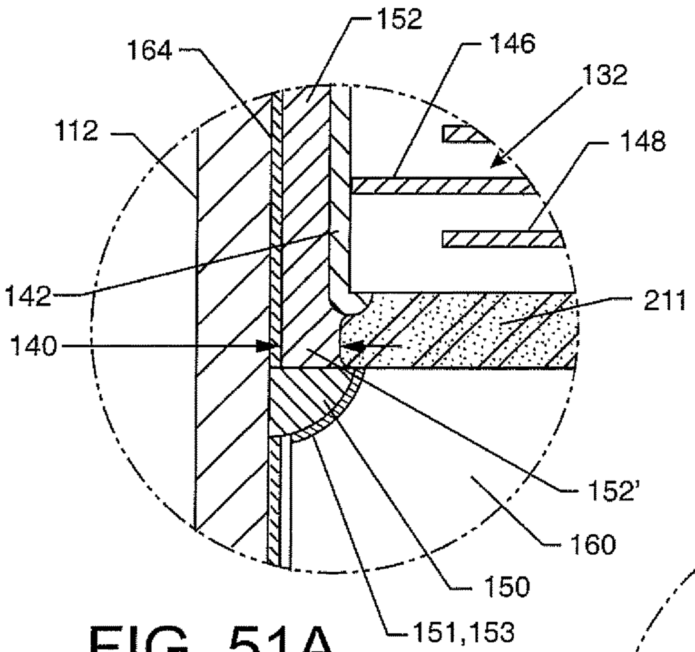
FIG. 51A is a blown-up partial view taken from section 51A-51A of FIG. 51 showing the uniformly dispersed filler insulating nanoparticles 264 in a portion of the insulating washer.

FIG. 51A is a cross-sectional view, generally taken along line 51A-51A of FIG. 51, illustrating an enlarged view that shows the space 140 between the EMI filter capacitor 132 and the feedthrough ferrule 112. The space 140 is defined by a specified insulating washer size (diameter if discoidal, major/minor diameters if oval, or length/width if rectangular or square) that is less than the opening size of the ferrule 112 in which the feedthrough insulator 160 is disposed and hermetically sealed. In this embodiment, the insulating washer 211 is filled with nanoparticles 264. By designing the washer to be smaller than the ferrule opening, the surface of gold braze 150 becomes exposed for electrical connection so that the electrical connection material 152 disposed within space 140 contacts the gold braze surface at 152', thereby electrically connecting the ground capacitor metallization 142 of EMI filter capacitor 132 to the feedthrough hermetic seal gold braze 150. As previously disclosed, electrical connections to oxide-resistant materials, like gold braze 150, provide sustainable low impedance low resistance oxide-resistant ground electrical connections.

Figure 51B:
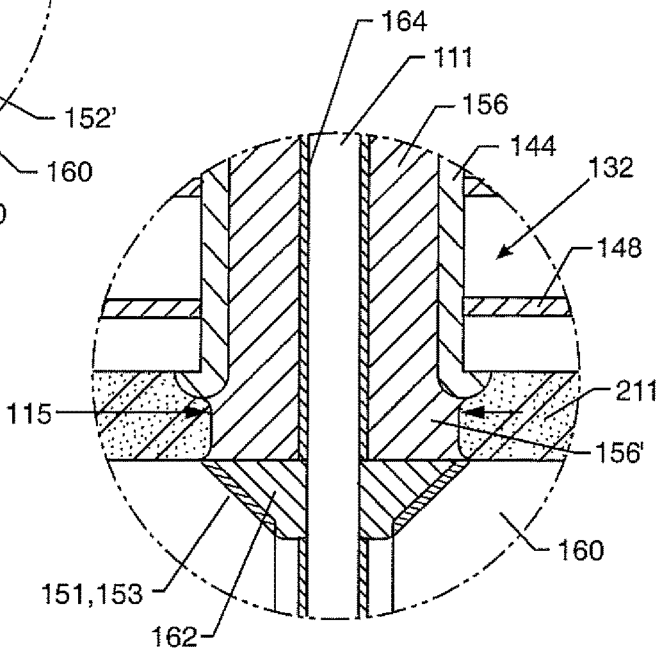
FIG. 51B is a blown-up partial view taken from section 51B-51B of FIG. 51 showing the uniformly dispersed filler insulating nanoparticles 264 in a portion of the insulating washer.

FIG. 51B is a cross-sectional view generally taken along line 51B-51B of FIG. 51 illustrating an enlarged view that shows the circular washer opening 115 of the nanoparticle-filled 264 polymeric insulating washer 211 into which feedthrough terminal pin 111 is received. The circular washer opening 115 allows electrical connection material 156 to contact the gold braze 162 at 156'. The electrical connection material 156 disposed in the active conductive passageway of the EMI filter capacitor 132 thereby electrically connects the filter capacitor's active conductive passageway metallization 144 to the feedthrough active terminal pin 111 hermetic seal gold braze 162. Again, electrical connections to oxide-resistant materials, like gold braze 162, provide sustainable low impedance, low resistance oxide-resistant ground electrical connections.

Figure 51C:
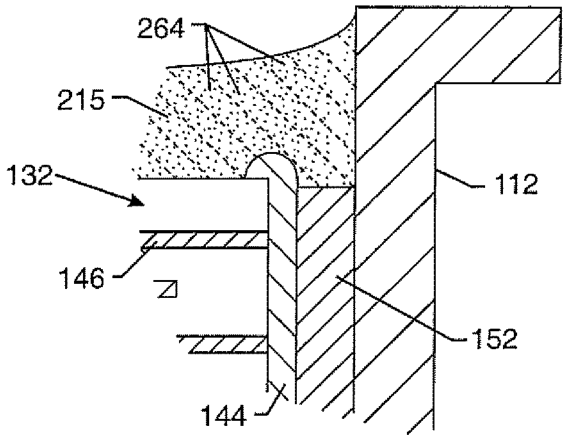
FIG. 51C is a blown-up partial view taken from section 51C-51C of FIG. 51 showing the uniformly dispersed filler insulating nanoparticles 264 in a portion of the top insulating material.

FIG. 51C is a cross-sectional view generally taken along line 51C-51C of FIG. 51 illustrating nanoparticle-filled 264 insulating material 215 on top of the EMI filter capacitor 132. As previously disclosed, insulating nanoparticles 264 are not actually visible to the naked eye and are used herein to simply establish their presence, thereby distinguishing insulating material 215 from other insulating material options that are devoid of nanoparticle 264 fill. FIG. 51C shows that insulating material 215 also extends to the ferrule 112, thereby increasing the dielectric breakdown strength between filtered feedthrough terminal pin 111 (not shown in this view) and the ferrule 112.

Figure 29:
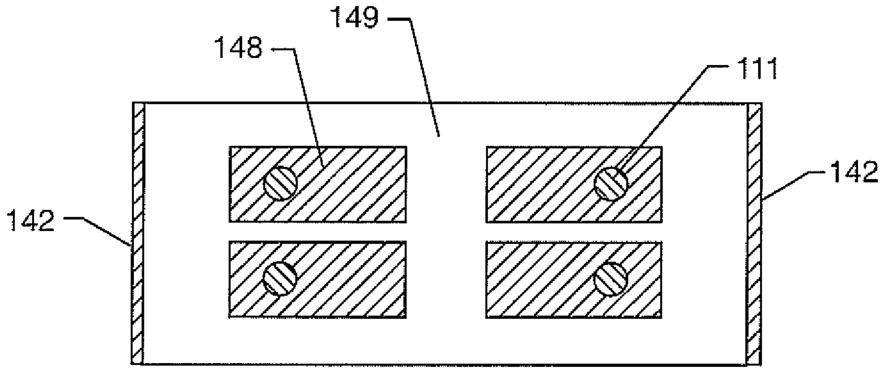
FIG. 29 (PRIOR ART)
FIG. 29 is a cross-sectional view generally taken along section 29-29 of prior art FIG. 27 illustrating four active electrode plates on a single layer of a capacitor dielectric substrate.
Figure 29A:
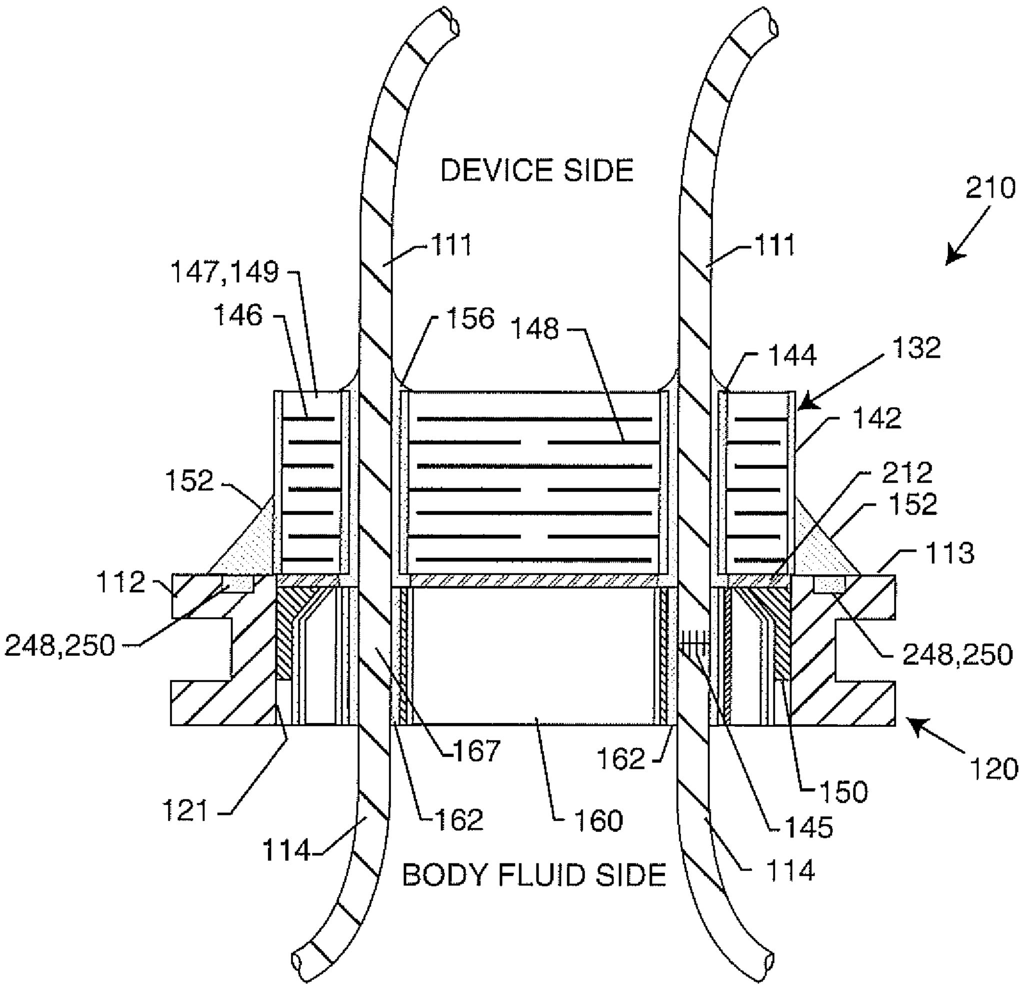
FIG. 29A (PRIOR ART)
FIG. 29A is a cross-sectional view generally taken along 29A-29A of prior art FIG. 27 illustrating the electrical attachment of the feedthrough filter capacitor metallization to the oxide-resistant pocket pads of the ferrule of the hermetically sealed feedthrough.
Figure 52:
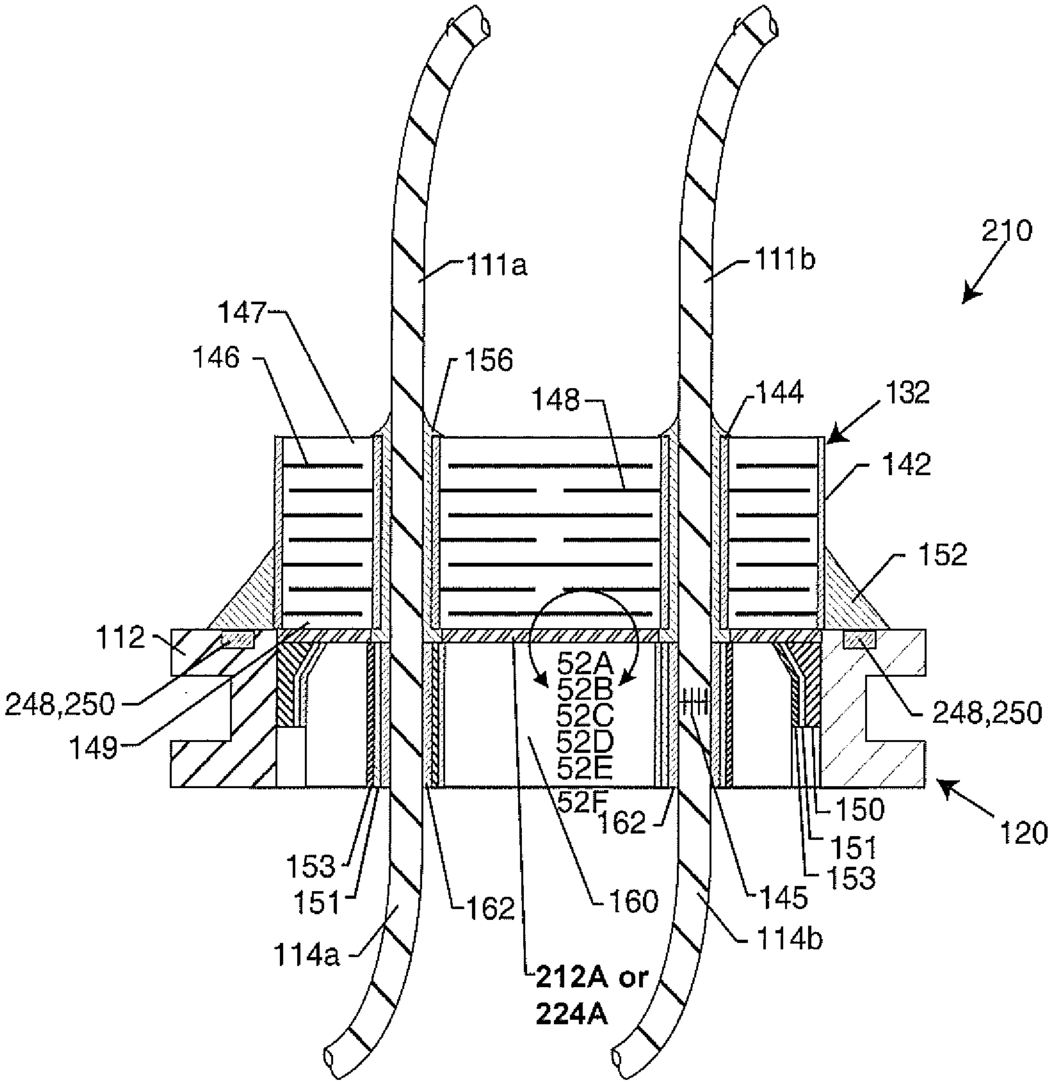
FIG. 52 is a cross-sectional view of a feedthrough filter capacitor bonded to the feedthrough insulator using a thermoplastic.

FIG. 52 illustrates the present invention applied to prior art FIG. 29A, except that the terminal pin pairs 111*a*, 114*a* and 111*b*, 114*b* have been moved closer to each other and farther from the ferrule-to-insulator gold braze 150. Moving terminal pin pairs 111*a*, 114*a* and 111*b*, 114*b* farther away from the gold braze 150 increases the stand-off distance between each terminal pin 111, 114 and the ferrule-to-insulator gold braze 150, thereby correspondingly increasing dielectric strength therebetween. At the same time, adequate high voltage distance between terminal pins 111*a* and 111*b* is maintained. An ideal high voltage distance balance is to have the distance between terminal pin pairs 111*a*, 114*a* and 111*b*, 114*b* be approximately the same as the distance between the ferrule-to-insulator gold braze 150 and terminal pin pairs 111*a*, 114*a* and 111*b*, 114*b* (not shown in this view).

FIG. 52 illustrates a polymeric insulating washer that can be either a composite polymeric insulating washer 212A or a homogeneous polymeric insulating washer 224A, either with or without insulating nanoparticles 264. Thermoplastic plastics and polymerics are softer than thermosetting plastics and polymerics that typically melt at relatively lower temperatures, hence are melt-processable. Because a melt-processable plastic or polymeric can be applied by standard dispensing methods, such as injection molding, robotic dispensing, or manual syringe dispensing, using thermoplastics alone or in combination with thermosetting plastics or polymerics provides component assembly, manufacturing and performance benefits that would otherwise not be available for an application need.

In an embodiment, the thermoplastic, thermosetting and composite thermoplastic/thermosetting plastic, and polymeric insulating components may comprise insulating nanoparticles 264. It is anticipated that homogeneous thermoplastic and thermosetting polymeric insulating washers and insulating materials including composite thermoplastic/thermosetting polymeric insulating washers and insulating materials with and without insulating nanoparticles 264 can be used in combination with each other in any number "n" and in any "n" combination variations. Furthermore, homogeneous thermoplastic and thermosetting insulating washers and insulating materials with and without insulating nanoparticle 264 composites thereof, and with and without insulating nanoparticles 264 may be used in combination with any of the prior art polymeric insulating washers and insulating materials in any number "n" and in any "n" combination variations.

Referring to FIG. 52, the composite polymeric insulating washer 212A generally comprises an insulating polymeric washer 212, which is coated with a thermoplastic on one or both bonding surfaces and, alternatively, the thermoplastic may be coated on one bonding surface of the insulating polymeric washer 212 with an insulating adhesive 204 (FIG. 52D) disposed on the opposite bonding surface of the washer 212. The thermoplastic coating may be applied to a film, a tape or equivalent insulating substrate, for example, a polyimide washer, film, tape, or equivalent insulating substrate. The thermoplastic coating may be disposed, deposited, dispensed, or laminated to the washer film, tape, or equivalent insulating substrate. The insulating polymeric washer 212 may be one of a flexible or semi-rigid film, tape, or equivalent insulating material (low plasticity, high elasticity), or may be a nearly rigid insulating material (high plasticity, low elasticity). The insulating polymeric washer 212 may comprise any insulating polymeric material previously disclosed, which includes the conventionally used prior art polymeric washer 212 materials. In a preferred embodiment, the washer 212 comprises a polyimide, such as Kapton®. In a more preferred embodiment, the polymeric insulating washer 212 comprises a natural aromatic polyimide having a coefficient of thermal expansion (CTE) that matches the CTE of an EMI filter dielectric ceramic 149 or an insulating ceramic cover sheet 147 for an EMI filter. More specifically, natural aromatic polyimide insulating washer 212 having a CTE that closely matches the CTE of the dielectric ceramic 149 or the insulating ceramic cover sheet 147 of an AIMD EMI filter capacitor 132, or the substrate of an AIMD EMI filter circuit board 155, is most preferred. It is understood that the natural aromatic polyimide may alternatively be a semi-aromatic, an aliphatic, an aromatic-aliphatic, a monocyclic aromatic, a heterocyclic aromatic, or temperature and/or strength stabilized polyimide. The thermoplastic coating may contain an additive that induces surface cross-linking between the polyimide and the coating without affecting the melt-processability of the thermoplastic coating. It is understood that AIMD EMI filter capacitors include a feedthrough EMI filter capacitor 132, an MLCC chip capacitor 194, a flat-thru filter capacitor 196, and an X2Y attenuator filter capacitor 198.

Generally regarding feedthrough EMI filter capacitor 132, the CTE of a ceramic feedthrough EMI filter capacitor is generally in the range of $9\times10^{-6}/°$ C. to $11\times10^{-6}/°$ C. The CTE of an EMI filter capacitor varies depending on its dielectric ceramic formulation. For example, a barium titanite ceramic feedthrough EMI filter capacitor generally has a CTE that is close to $10\times10^{-6}/°$ C. or $11\times10^{-6}/°$ C. The CTE of conventional commercially available polyimides, including Kapton®, is on the order of $20\times10^{-6}/°$ C. to $21\times10^{-6}/°$ C. Consequently, the CTEs of the conventional commercially available polyimides and the barium titanate undesirably mismatch significantly. In fact, when the inventors conducted experiments using commercially available conventional polyimides (for example, Kapton®) coated with a thermoplastic electrically bonded to the barium titanate ceramic feedthrough EMI filter capacitor, the relatively large CTE mismatch therebetween resulted in cracking of the ceramic feedthrough EMI filter capacitor during thermal shock tests from about −55° C. to +125° C. Thermal shock testing is required to qualify an AIMD filtered feedthrough 210. If even one AIMD EMI filter capacitor displays a crack, the filtered feedthrough qualification fails. Ceramic is a very brittle material, consequently, cracking can immediately or latently occur, particularly at the high stress concentration areas adjacent to the CTE mismatch. For example, a crack may initially only be confined to the capacitor's cover sheets bonded to the surface of the feedthrough, but then, over time, the cracking may propagate into the capacitor's electrode layers. Propagation of a crack between an active electrode plate and a ground electrode plate creates a gap that, during an ICD pulse, can cause an avalanche breakdown. Avalanche breakdown is a catastrophic ICD failure because the ICD becomes inoperable (unable to sense or deliver either low-voltage or high-voltage therapeutic pulses), which can be life-threatening to the implant patient. In contrast, when the inventors used the novel composite polymeric insulating washer 212A comprising a natural aromatic polyimide having a CTE on the order of $8\times10^{-6}/^{\circ}$ C. between the EMI filter capacitor 132 and the hermetically sealed feedthrough 120, no cracking of the EMI filter capacitor 132 occurred during thermal shock testing. Thus, the absence of any EMI filter capacitor cracking can be directly attributed to the closely matched CTEs of the EMI filter capacitor 132 and the composite polymeric insulating washer 212A of the present invention. In a preferred embodiment, the composite thermoplastic coated washer 212A of the present invention comprises a polymeric insulating washer 212 that has a CTE of approximately $8\times10^{-6}/^{\circ}$ C. at temperatures between 50° C. to 150° C. The CTE of the thermoplastic coated polymeric insulating washer 212A ranges from about $\geq 6\times10^{-6}/^{\circ}$ C. to $\leq 12\times10^{-6}/^{\circ}$ C. An embodiment of the present invention comprises a polymeric insulating washer 212 having high temperature stability (glass transition temperature of approximately 300° C.) and a ring molecule to absorb mechanical and thermal stresses. The ability to withstand mechanical and thermal stresses is important for both thermal shock and piezoelectric stress induced purposes in ceramic filter capacitors during fast risetime ICD pulses.

In the present invention, the preferred composite polymeric insulating washer 212A (or top composite polymeric insulating washer 214A as will be shown) comprises a thermoplastic coating thickness of approximately 2 mils (0.002 inch). The thickness of the thermoplastic coating of the present invention may vary from ≥0.1 mils to ≤10 mils.

Referring back to FIG. 52, the composite polymeric insulating washer 212A can alternatively be a homogenous polymeric insulating washer 224A. The homogenous polymeric insulating washer 224A can be a thermoplastic film that is disposed under pressure and at a high temperature above or near its thermoplastic melting point so that the washer bonds to an adjacent structure of the filtered feedthrough 210, such as between the EMI filter capacitor 132 and the hermetically sealed feedthrough 120. The CTE of the homogenous polymeric insulating washer 224A closely matches the CTE of the ceramic feedthrough EMI filter capacitor 132. The CTE of the thermoplastic material is about $12\times10^{-6}/^{\circ}$ C.

Referring either to the composite or homogeneous thermoplastic washer, by approximately matching the CTE of the thermoplastic coating/insulating polymeric washer material and the CTE of the ceramic for the filter capacitor, the temperature induced cracking or delamination of the EMI filter capacitor 132, including any crack or delamination propagation thereof, such as through the electrical connection materials and/or the thermoplastic coated polymeric insulating washer 224A, are significantly mitigated. Temperature induced cracking and delamination can occur during temperature cycle testing, exposure to temperature shocks during laser welding of the filtered feedthrough 210 into an opening in an AIMD housing or as a result of an ICD HV pulse, which induces piezoelectric mechanical movement of and stresses to the EMI filter capacitor 132 physically attached to the ICD hermetically sealed feedthrough 120. The thermoplastic coated polymeric insulating washer 224A of the present invention exhibits an excellent balance of physical, electrical, moisture, and chemical resistance properties and offers superior dimensional stability. While FIG. 52 shows only one thermoplastic coated insulating washer 212A or 224A, it is understood that one, two or “n” thermoplastic coated insulating washers 212A or 224A may be used. Each thermoplastic coated insulating washer may have a thickness ranging from about 12.5 μm (0.5 mil) to about 125 μm (5 mil).

In an embodiment, the thermoplastic coated polymeric insulating washer 212A is laminated on both of its top and bottom surfaces with a thermoplastic coating. As illustrated by FIG. 52, the top surface is the washer surface that mates with the EMI filter capacitor 132 and the bottom surface is the opposing washer surface that mates with the hermetically sealed feedthrough insulator 160.

FIGS. 52A through 52D illustrate various embodiments of the composite polymeric insulating washer 212A of FIG. 52. The insulating washer of FIG. 52 shows double cross-hatching, which is consistent for insulators. The insulative washers and/or adhesives of the blown-up sectional views of FIGS. 52A to 52F show single cross hatching for simplicity. While all of these embodiments illustrate washers without insulating nanoparticles 264, it is understood that any of the layers within each of these embodiments, individually or in combination, may optionally comprise the insulating nanoparticles 264 previously disclosed with respect to FIG. 51.

Figure 52A:
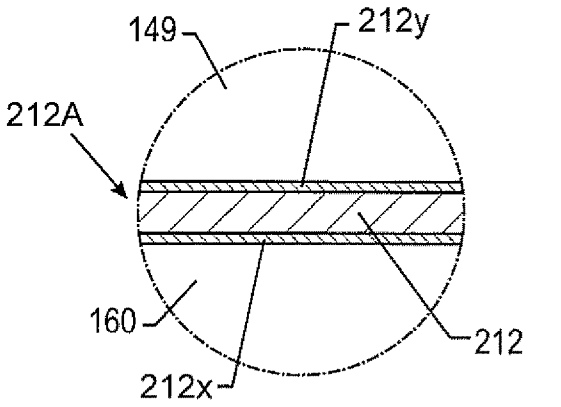
FIG. 52A is taken along 52A-52A of FIG. 52 illustrating a composite polymeric insulating washer having a thermoplastic coating disposed on both surfaces of a polymeric insulating washer.

FIG. 52A is a blown-up partial view taken along line 52A-52A of FIG. 52, illustrating an embodiment of the composite polymeric insulating washer 212A disposed between the EMI filter capacitor 132 and the hermetically sealed feedthrough 120 of FIG. 52. The composite polymeric insulating washer 212A has a core polymeric insulating layer 212 to which a top thermoplastic coating layer 212*y* and a bottom thermoplastic coating layer 212*x* are laminated. When the composite polymeric insulating washer 212A is placed between the EMI filter capacitor 132 and the hermetically sealed feedthrough 120, heat and pressure are applied to the assembly so that the top thermoplastic coating 212*y* and the bottom thermoplastic coating 212*x* melt, each acting like an adhesive that adheres to the adjacent surfaces of the filter capacitor ceramic substrate 149 and the feedthrough insulator 160, respectively.

Figure 52B:
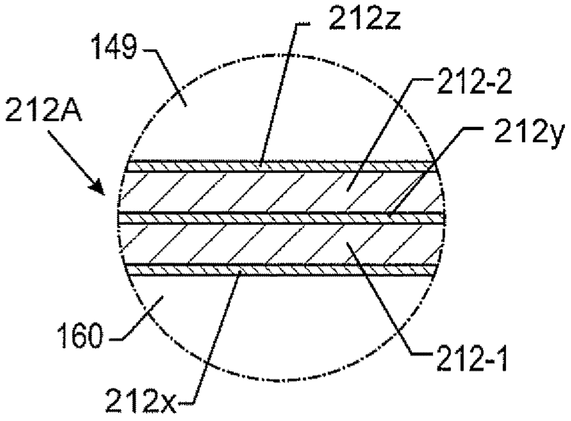
FIG. 52B is taken along 52B-52B of FIG. 52 illustrating a composite polymeric insulating washer having at least two insulating washers with disposed thermoplastic coatings.

FIG. 52B is a blown-up partial view taken along line 52B-52B of FIG. 52 illustrating another embodiment of the composite polymeric insulating washer 212A. In this embodiment, the composite polymeric insulating washer 212A has two polymeric insulating washer layers 212-1 and 212-2, each layer having a different laminated structure. It is understood that, while only two polymeric insulating washer layers 212-1 and 212-2 are shown, the filtered feedthrough 210 of FIG. 52 may include any number of polymeric insulating washer layers, including “n” layers. The polymeric insulating washer layer 212-1 has a laminated top thermoplastic coating layer 212*y* and a laminated bottom thermoplastic coating layer 212*x*. The polymeric insulating washer layer 212-2 has only a laminated top thermoplastic coating layer 212*z*. A first laminated polymeric insulting washer layer 212-1 is disposed on top of the hermetically sealed feedthrough 120 of FIG. 52. Then, a second laminated polymeric insulating washer layer 212-2 is disposed on top of the first laminated polymeric insulating washer 212-1 so that the surface without the thermoplastic coating layer contacts the surface of the first laminated polymeric insulating washer. The EMI filter capacitor 132 of FIG. 52 is then placed on top of the second laminated polymeric insulating washer layer 212-2 to complete the assembly. Heat and pressure are then applied to the assembly so that the thermoplastic coatings 212x, 212y and 212z all melt and adhere to their respective adjacent surfaces to thereby form the filtered feedthrough 210. It is understood that the order in which the laminated polymeric insulating washer layers 212-1 and 212-2 are disposed may be reversed; however, when layer 212-2 is the first disposed laminated polymeric insulating washer, the surface without the thermoplastic coating layer 212z must be oriented to contact the hermetically sealed feedthrough 120.

Figure 52C:
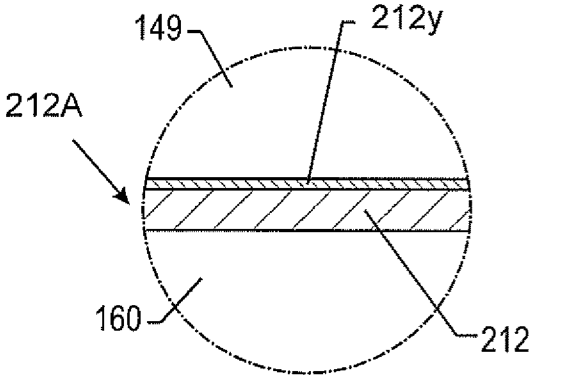
FIG. 52C is taken along 52C-52C of FIG. 52 illustrating a composite polymeric insulating washer having a thermoplastic coating disposed on only one surface of a polymeric insulating washer.

FIG. 52C is a blown-up partial view taken along line 52C-52C of FIG. 52 illustrating another embodiment of the composite polymeric insulating washer 212A. In this embodiment, the composite polymeric insulating washer 212A has a core polymeric insulating layer 212 to which only one thermoplastic coating layer 212y is laminated. The laminated thermoplastic coating layer 212y is adhered to the filter capacitor 149; however, there is no thermoplastic coating layer 212x on the bottom of the core polymeric insulating layer 212 adjacent to the feedthrough insulator 160. Accordingly, a very thin gap will be present between the composite polymeric insulating washer 212A and the feedthrough insulator 160. Such a thin gap is useful in that it facilitates detection of hermetic leaks during helium leak testing, which can otherwise go undetected when the polymeric insulating washer comprises the bottom thermoplastic coating layer 212x adhered to the feedthrough insulator 160. Additionally, without the thermoplastic coating layer 212x, the feedthrough insulator 160 is not physically bonded to the EMI filter capacitor 132, which means that the EMI filter capacitor 132 is free to expand and contact during heating so that capacitor ceramic cracking does not occur. Hermetic seal leak detection for an AIMD is typically performed with a helium tracer gas, which is a trace element of the gas backfill within the AIMD housing 16. This particular embodiment may be used in low-voltage applications, such as neurostimulators, as the gap is insufficient to catastrophically damage the relatively low voltage device. However, such gaps in high-voltage applications, such as for ICDs, are contraindicated as even a very thin gap between the composite polymeric insulating washer 212A and the feedthrough insulator 160 would concentrate high-voltage equipotential lines that could lead to catastrophic avalanche breakdowns therebetween.

Figure 52D:
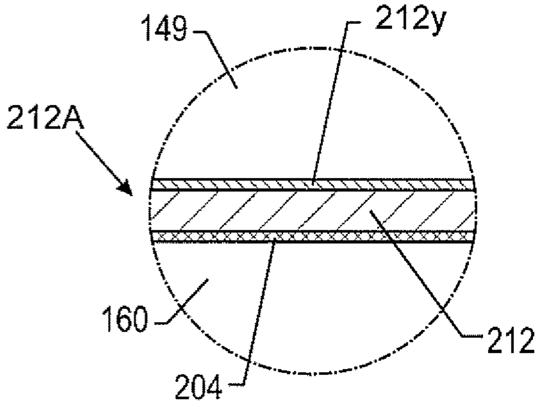
FIG. 52D is taken along 52D-52D of FIG. 52 illustrating a composite polymeric insulating washer having a thermoplastic coating disposed on one surface of a polymeric insulating washer and a thermoplastic adhesive of a different material than the thermoplastic coating disposed on the opposite surface of the polymeric insulating washer.

FIG. 52D is a blown-up partial view taken along line 52D-52D of FIG. 52 illustrating another embodiment of the composite polymeric insulating washer 212A. Washer 212A comprises a laminated structure having the core polymeric insulating layer 212 to which two different coating layers are disposed. The top coating is a laminated thermoplastic coating layer 212y and the bottom coating is a polymeric insulating adhesive layer 204. The adhesive layer 204 is of a different material than the top thermoplastic coating layer 212y. Any type of adhesive may be used as the polymeric insulating adhesive 204, including reactive, non-reactive, pressure-sensitive, synthetic or even natural adhesives selected from acrylics, acrylates, acrylonitrites, cyanoacrylates, polyurethanes, polyvinyl acetates, polyvinyl alcohols, polyvinyl chlorides, polyesters, phenol-formaldehydes, polyamides, polyethylenes, polypropylenes, polysulfides, polyvinyl pyrrolidones, epoxies, styrene-butadienes, styrene acrylic copolymerics, silicones, silyl modified polymerics, among others. The adhesive may also include biocompatible, biostable, and non-toxic materials in the family of polyimides, polyamides, polyethylene terephthalates (PET), polydimethylsiloxane (PDMS), polytetrafluoroethylene (PTFE), ethylene tetrafluoroethylene (ETFE), parylenes, polyether block amides (PEBAX), polyetheretherketones (PEEK), polystyrenes, polysulfones, polypropylenes, polycarbonates, polyvinyl chlorides (PVC), polyxylylene polymerics, silicones, including medical-grade adhesives and epoxies. Heat and pressure may be applied to the filtered feedthrough assembly so that the laminated thermoplastic coating layer 212y and the different material polymeric insulating adhesive layer 204 adhere to the filter capacitor ceramic substrate 149 and to the feedthrough insulator 160, respectively. It is understood that the laminated thermoplastic coating layer 212y and the different polymeric insulating adhesive layer 204 may be reversed so that the laminated thermoplastic coating layer 212y adheres to the feedthrough insulator 160 and the different polymeric insulating adhesive layer 204 adheres to the filter capacitor 149.

Referring again to FIGS. 52A through 52D, the core polymeric insulating layer 212 of the composite polymeric insulating washer 212A may be any of the previously disclosed suitable insulating polymeric materials. The composite polymeric insulating washer 212A may also be an insulating polymeric material having a coefficient of thermal expansion (CTE) that closely matches the CTE of the EMI filter capacitor 132. For example, the core polymeric insulating layer 212 may have a CTE of about $21\times10^{-6}/°$ C.

Figure 52E:
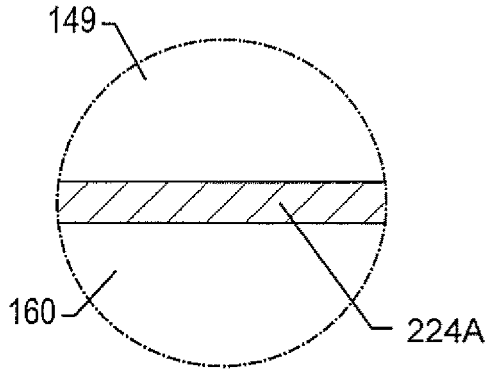
FIG. 52E is taken along 52E-52E of FIG. 52 illustrating a polymeric insulating washer comprising homogeneous thermoplastic.
Figure 52F:
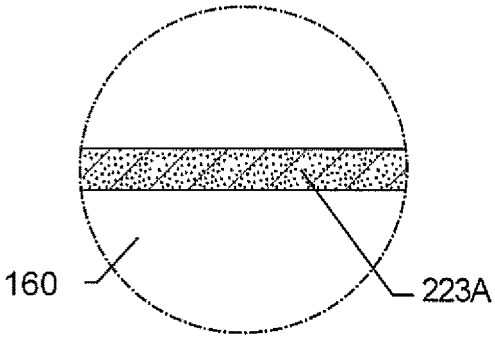
FIG. 52F is taken along 52F-52F of FIG. 52 illustrating an embodiment of the homogeneous polymeric insulating washer 223A shown in FIG. 52E but containing insulating nanoparticles.

FIG. 52E is a blown-up partial view taken along line 52E-52E of FIG. 52 illustrating a homogeneous polymeric insulating washer 224A without any top or bottom surface coatings. In a preferred embodiment, the homogeneous polymeric insulating washer 224A is a film or a tape, which is then heat and pressure processed to adhere to the bottom surface of the EMI filter capacitor 149 and to the top surface of the feedthrough insulator 160. While this embodiment of FIG. 52E illustrates a washer without insulating nanoparticles 264, it is understood that the homogeneous polymeric insulating washer can optionally comprise the insulating nanoparticles 264 as shown in FIG. 52F, which would then provide a nanoparticle-filled 264 homogeneous polymeric insulating washer 223A.

The thermoplastic coated polymeric insulating washer 224A may be applied to an adjacent surface using both heat and pressure. For example, the thermoplastic coated polymeric washer 224A may be disposed between the EMI filter capacitor 132 and the feedthrough insulator 160 of the filtered feedthrough 210 at a temperature of about 265° C. and a pressure of approximately 70 lbs. per square inch. In this example, the thermoplastic melting point is about 270° C. so that the thermoplastic coating softens and flows, thereby allowing the thermoplastic coated polymeric insulating washer 224A to firmly bond to the EMI filter capacitor 132 or to other surrounding feedthrough surfaces. The thermoplastic coated polymeric insulating washer of FIG. 52 is also semi-rigid, which means that it absorbs mechanical, thermal, and piezoelectric shocks that an AIMD EMI filter capacitor may experience during high voltage, fast rise-time electrical therapy delivery. Importantly, the thermoplastic coated polymeric insulating washer 224A acts not only as an excellent insulator having a relatively high-volume resistivity of greater than 1016 ohm-cm, but it also forms a critical protective intermediary layer for the feedthrough EMI filter capacitor 132 so that the high-voltage fields associated with therapy delivery (for example, from a fast-time HV ICD pulse) are relaxed. The intermediary protection by the thermoplastic coated polymeric insulating washer 224A is due to its intermediate dielectric constant material, which has a k value that is between that of the high dielectric constant of the feedthrough EMI filter capacitor 132 (k greater than 60, and in many cases, >1500) and air (with a k of 1). The thermoplastic coated polymeric insulating washer 224A of the present invention has a k value greater than 2.5 but less than 10. In a preferred embodiment, the k value is approximately 3.3. The intermediary k value of the thermoplastic coated polymeric insulting washer 224A thereby desirably redistributes (meaning, widely spreads or spreads out) the HV equipotential lines of an electric field, substantially reducing electric stress and, in turn, significantly relaxing high-voltage electric fields. Field relaxation means that the probability of a microcoulomb discharge, which can lead to a catastrophic HV breakdown and/or avalanche, is greatly reduced.

The fixture that is used to apply pressure to the thermoplastic coated polymeric insulating washer is a PTFE coated fixture, which is not melt-processable, which means that the fixture itself will not melt, soften, or stick to the thermoplastic coated polymeric insulating washer 224A as the thermoplastic coating softens and flows. Applying too much pressure to the thermoplastic coated polymeric insulating washer 224A while heating can cause the thermoplastic material to undesirably flow and run up the feedthrough terminal pins 111, 114. In the case where the thermoplastic coated polymeric insulating washer 224A is disposed between the feedthrough EMI filter capacitor 132 and the hermetically sealed feedthrough 120 of the filtered feedthrough 210, run-up on the feedthrough terminal pins is undesirable. If thermoplastic run-up extends too far upward, the run-up can interfere with the contact area of the electrical connection material 156 electrically connecting the passageway active capacitor metallization 144 of the EMI filter capacitor 132 to the gold braze 162 of the hermetically sealed terminal pins 111, 114. That is particularly the case when a conductive polyimide or a high temperature solder is used to produce the electrical connection.

The method of application of thermoplastic coated insulating washers, in general, requires the following steps:

1. Clean all surfaces.
2. Apply one or more thermoplastic coated insulating washers between the EMI filter capacitor 149 and the hermetic seal insulation 160 or on top of the EMI capacitor.
3. Place a layer of PTFE, such as Teflon™ or an alternative, with mating holes over the washers to be bonded so that the heated metal fixture of STEP 4 releases without sticking to the washer.
4. Apply pressure from a heated metal fixture, for example, a fixture made of aluminum or copper, which presses the composite thermoplastic coated polymeric insulating washers together while at the same time sufficiently heating the assembly above the melting point of the thermoplastic material. This combination of heat and pressure causes the thermoplastic material to bond or laminate to the adjacent surfaces, such as to the EMI filter capacitor 149 and to the insulating washer while at the same time bonding or laminating to the insulator and/or ferrule of the hermetically sealed feedthrough. The metal fixture may alternatively comprise a highly thermally conductive material instead of a metal, such as diamond, graphite, aluminum nitride, silicon carbide, among others.

The thermoplastic coated polymeric insulating washers 212A or 224A shown in the embodiment of FIG. 52 completely cover the gold braze 150 at or adjacent to a gold pocket-pad 248, 250, which increases both the low and the high-voltage electrical stand-off distances between the active terminal pins 111, 114 and system ground 124 (not labelled). The EMI filter system ground 124 of FIG. 52 consists of the feedthrough ferrule 112 and gold pocket pads 248, 250. It will be appreciated that system ground 124 is complete when the feedthrough ferrule 112 is installed into an opening in an AIMD housing 116, which is usually accomplished by a laser weld. It is also noted that while the feedthrough ferrule 112 is part of the system ground 124 due to it being electrically connected to the AIMD housing 116, the AIMD housing 116 is the "true" EMI filter system ground 124. That is because the housing creates both a shield, also known as a Faraday cage, and an RF energy dissipating surface. For simplicity, and as used herein, the high-voltage electrical stand-off distance between the active terminal pins 111, 114 and the system ground 124 will be referred to as the active-to-system ground 124 stand-off distance, in this case, an HV stand-off distance. The term "active-to-system ground" 124 also applies to increasing the stand-off distance for low voltage devices, such as a cardiac pacemaker and a neurostimulator. That is because low voltage devices are still exposed to high voltages, particularly, when a patient may require cardiac defibrillation therapy using an automatic external defibrillator (AED) or a manual defibrillator, which may induce a high-voltage energy on implanted leads. Such high-voltage energy can be coupled to the implanted leads to directly enter inside the AIMD causing the high voltage to occur in the area of the EMI filter capacitor. The thermoplastic coated polymeric insulating washers 212A or 224A can be a single washer or one or more "n" washers, as previously disclosed. High voltages can also be introduced into the system by handling the AIMD and its leads through electrostatic discharge.

A novel feature of the present invention is that nanoparticles 264 can be added to the thermoplastic coating before applying it to the polymeric insulating film or to the polymeric material before the insulating film is formed. The thermoplastic coated polymeric insulating washer of the present invention may therefore comprise one of: a non-nanoparticle thermoplastic coated polymeric insulating washer, a nanoparticle thermoplastic coated non-nanoparticle polymeric insulating washer, a non-nanoparticle thermoplastic coated nanoparticle-filled polymeric insulating washer, or a thermoplastic coated nanoparticle-filled polymeric insulating washer. The purpose of adding nanoparticles 264 to either the thermoplastic coating, the polymeric insulating film, or both, is to further increase the dielectric breakdown strength of the resultant thermoplastic coated polymeric insulating washer. It is anticipated that the melt-processable thermoplastic material, with or without nanoparticles 264, may be used alone as an insulation material on either the top surface, the bottom surface, or both surfaces of a hermetically sealed filtered feedthrough or between a feedthrough filter capacitor or filter circuit board and a hermetically sealed feedthrough. Similarly, it is anticipated that a polyimide film, such as Kapton®, with or without nanoparticles 264, may be used alone as a polymeric insulating washer on either the top surface, the bottom surface or both surfaces of a hermetically sealed filtered feedthrough or between a feedthrough filter capacitor or filter circuit board and a hermetically sealed feedthrough. It is further anticipated that melt-processable thermoplastic material with or without nanoparticles 264, and a polyimide film, such as of Kapton®, with or without nanoparticles 264, may be stacked with each other in any number or combination on either the top surface, the bottom surface, or both surfaces of a hermetically sealed filtered feedthrough or between a feedthrough filter capacitor or filter circuit board and a hermetically sealed feedthrough. The present inventions disclosed above also apply to multiple stacked polyimide washers that are co-laminated together.

Figure 53:
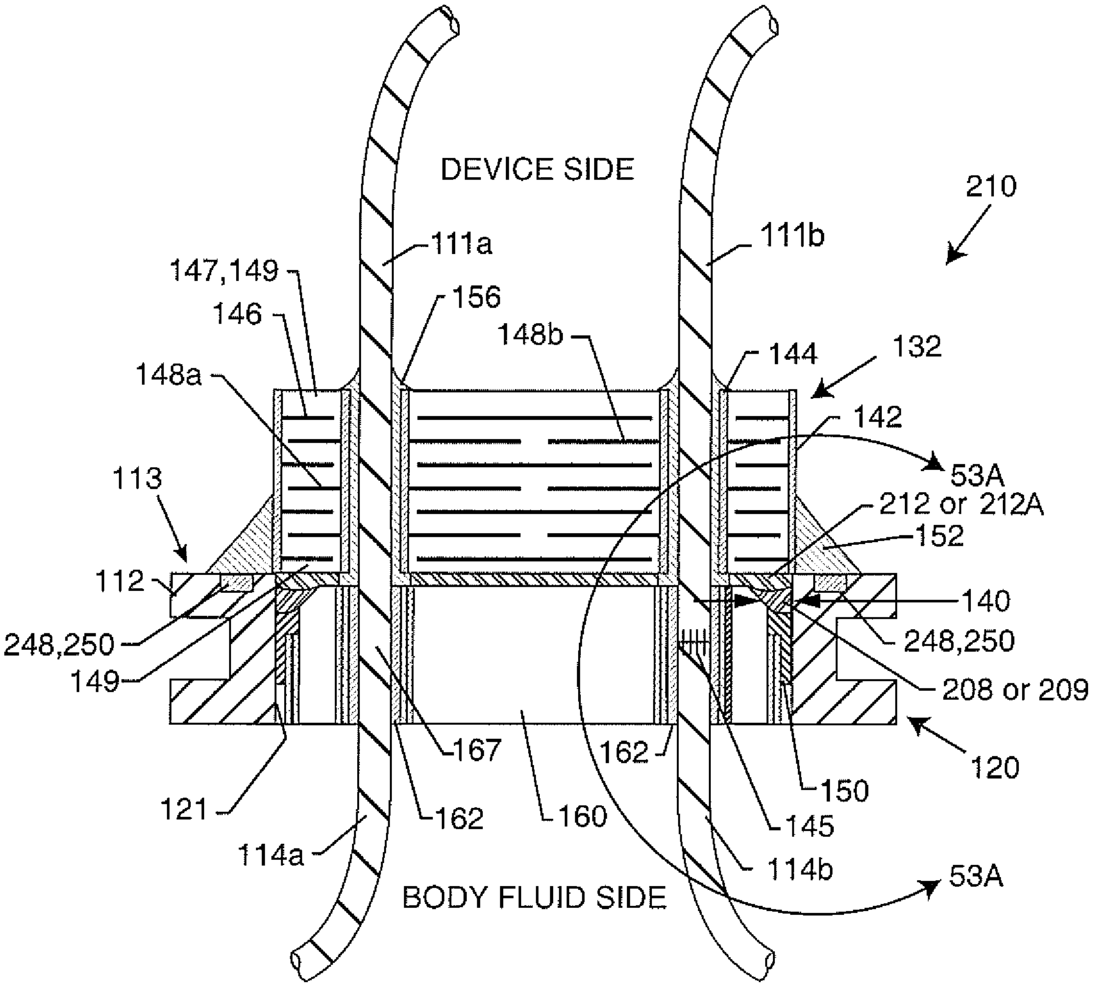
FIG. 53 is similar to FIG. 52, except that the polymeric insulating washer or composite polymeric insulating washer overlays an additional polymeric insulating material, which covers the feedthrough insulator-to-ferrule gold braze.

FIG. 53 is similar to FIG. 52, except that in this embodiment the gold braze 150 is formed below the ferrule surface 113. Forming the gold braze 150 below the ferrule surface 113 creates open space between the ferrule 112 and the insulator 160 so that a second polymeric insulating material 208 can be disposed therein. The second polymeric insulating material 208 provides an additional insulative layer, which further protects against any deficiency of the important active-to-system ground stand-off distance. This second polymeric insulating material 208 can be any one of the insulating materials previously disclosed including a non-conductive thermosetting epoxy or a non-conductive thermosetting polyimide. Additionally, this second polymeric insulating material 208 could comprise any type of adhesive washer, including a Kapton® washer with a non-conductive adhesive, a thermosetting non-conductive material, such as a thermosetting epoxy or a polyimide, and the like.

The polymeric insulating washer 212 of FIG. 53 may comprise any polymeric material including a thermosetting epoxy, a polyimide, and an elastomer. The polymeric insulating washer 212 of FIG. 53 may alternatively comprise a thermoplastic insulating material, a thermoplastic insulating washer, or a thermoplastic coated polymeric insulating washer, with or without insulating nanoparticles 264. The polymeric insulating washer 212 may also comprise a solid insulating structure, for example, mica, nylon, silicone rubber, plastic, ceramic, glass, composite, polytetrafluoroethylene, ethylene tetrafluoroethylene, polycarbonate, polyetherimide, polyoxymethylene, acetal, polyacetal, polyformaldehyde, phenolic, and other similar non-metallic materials, and combinations thereof), or alternatively, a cured liquid insulating material, for example, an epoxy, a polyester, a liquid silicone rubber, a polyurethane, or other similar materials, and combinations thereof. Additionally, the polymeric insulating washer 212 may further comprise an adhesive, such as a polyimide, a silicone polyimide, a polyurethane, a silicone, a polysulfide, and combinations thereof. It is anticipated that other similar adhesive materials can also be used.

Referring again to FIG. 53, it is understood that the polymeric insulating washer 212 can comprise a thermoplastic coated polymeric insulating washer 212A. In an alternative embodiment, the thermoplastic coated polymeric insulating washer 212A contains filler insulating nanoparticles 264 in either the thermoplastic coating, the polymeric insulating washer, or both, and the polymeric insulating washer 212 may be used in combination with any polymeric insulating material 208.

In an ICD application, the ICD may have a high-voltage pulse rise-time generally as fast as 75 nano seconds. When one performs a Fourier transform from the time domain to the frequency domain, this means that the pulse has a high-frequency component typically on the order of 13 MHz. Accordingly, the high-frequency voltage breakdown strength of the polymeric insulating washer 212 and insulating material 208 becomes very important. In summary, even though the conductive terminal pins 111, 114 are each closer to the feedthrough ferrule 112 than illustrated in FIG. 52, the electrical stand-off distance remains relatively the same due to covering of the gold braze 150 and to the second polymeric insulating material 208.

Figure 53A:
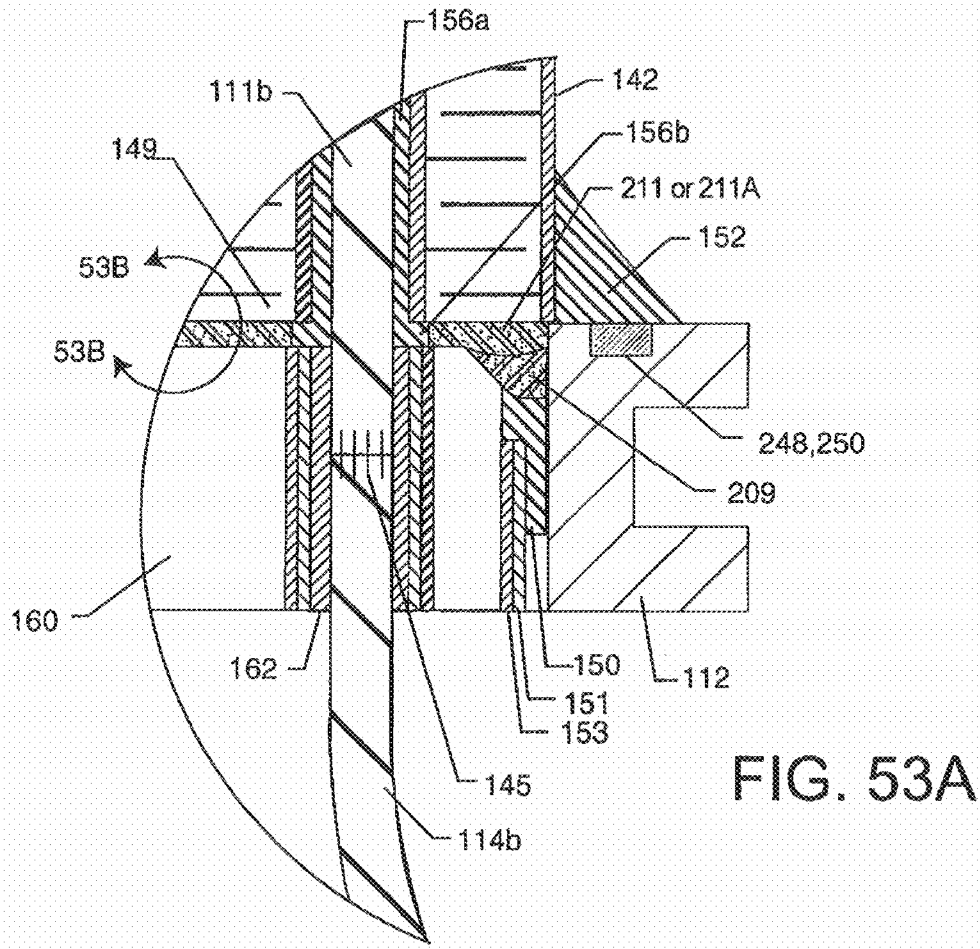
FIG. 53A is a blown-up partial view taken along 53A-53A of FIG. 53 illustrating nanoparticle-filled 264 polymeric insulating washer and an additional insulating material overlaying the feedthrough insulator-to-ferrule gold braze.

The polymeric insulating materials 208 and 209 of FIGS. 53 and 53A can be dispensed robotically, by a hand syringe or as a pre-staged preform. The polymeric insulative materials 208 or 209 can be cured before the polymeric insulating washer 212 is placed. The EMI filter capacitor 132 can then be placed on top of the polymeric insulating washer 212, which is then adhesively bonded or co-cured with the polymeric insulating material 208 or 209. As previously disclosed, the polymeric insulating washer 212 may comprise any of the materials disclosed earlier. In an embodiment, the polymeric insulating washer 212 is either an adhesive washer or a polyimide washer, such as a Kapton® washer, which has a non-conductive epoxy or a non-conductive polyimide adhesive on at least one of its top and bottom surfaces. The polymeric insulating washer 212 may alternatively be a flowable polymer, which is dispensed by a robot or by a hand syringe, and then cured.

Referring once again to FIG. 53, one or more layers of additional insulating material 208 or 209 may be disposed over the gold braze 150 in conjunction with the polymeric insulating washer 212 to further cover and prevent electrical shorting due to leakage of the electrically conductive material 156, 156' into the voltage stand-off areas. The term "voltage stand-off" is understood to mean a minimum dielectric strength or breakdown voltage, whereby avalanche breakdown, flashover or arc-over does not occur between the active terminal pin pairs 111*a*, 114*a* and 111*b*, 114*b* and the system ground 124. Hence, the one or more additional insulating material layers provide enhanced protection should the polymeric insulator washer 212 exhibit any delamination or air gaps (135 in FIG. 29B) as previously disclosed. The embodiment of FIG. 53 illustrates a delamination free, well-bonded polymeric insulating washer 212, which effectively protects (meaning prevents or favorably limits the physical leakage penetration of the electrical connection material 152 or 156') the ground electrical connections, thereby providing a robust and reliable active-to-system ground 124 stand-off distance.

Referring once again to FIG. 53, for a high-voltage application, such as in an ICD, therapeutic delivery of high-voltage pulses can cause significant piezoelectric effects to the ceramic feedthrough filter capacitor 132. That is, during high-voltage pulsing, a rapidly changing electric field is induced between the capacitor electrodes of a multilayer ceramic filter feedthrough capacitor 132, which causes significant changes in the ceramic dielectric crystal lattice, and which also results in substantial subsequent mechanical movement of the multilayer ceramic feedthrough filter capacitor 132 itself. Consequently, the feedthrough filter capacitor 132 flexes against the polymeric insulating washer 212 and the polymeric insulating material 208, which can lead to the creation of open space. Accordingly, it is very important that adhesion between the polymeric insulating washer 212/polymeric insulation material 209 (or optionally 208) and the feedthrough filter capacitor 132 and between the polymeric insulating washer 212/polymeric insulating material 208 and the hermetic seal insulator 160 and/or the ferrule 112 and/or the gold braze 150 be very robust. As disclosed above, any open space, gap, crack, delamination, separation, or other previously listed defect condition in this area can lead to HV field enhancement and subsequent catastrophic high-voltage avalanche breakdowns or flashovers.

Also, the additional insulating material 209 (or optionally 208) covering the gold braze 150 as taught herein can be added to any of the embodiments disclosed throughout the specification of the present application, including all the figures illustrated therewithin. For example, referring to FIG. 22, the gold braze 150, and/or the insulator 160 and its associated insulator metallization's 151, 153 (FIGS. 10C, 10D, 16, 51A and 51B), can optionally be disposed sufficiently lower than the device side surface of the ferrule 112, thereby creating space for the secondary insulating material

209 (or optionally 208). The secondary insulating material 209 (or optionally 208) can comprise a non-conductive epoxy or any of the other previously disclosed materials. As such, the secondary insulating material 209 (or optionally 208) provides an additional layer of protection so that the electrical connection material 156, 156' (FIGS. 41C, 51 and 51B) is precluded from either shorting to the gold braze 150 or to the ferrule 112.

Figure 22:
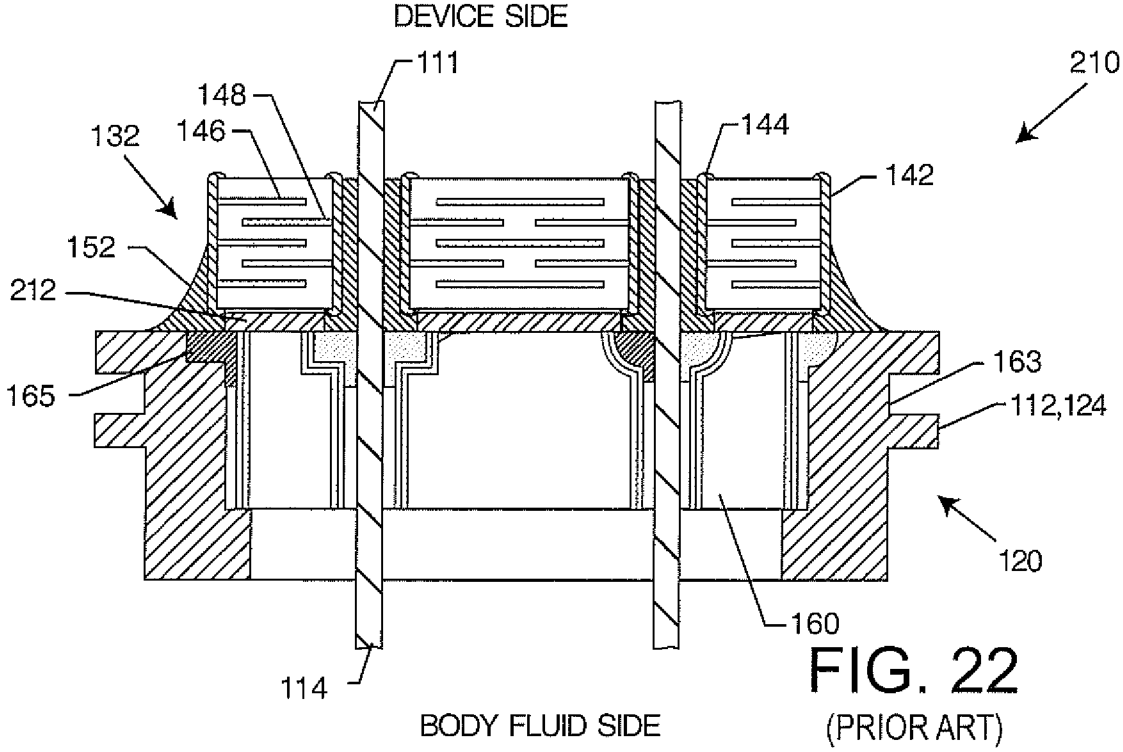
FIG. 22 (PRIOR ART)
FIG. 22 is prior art taken from section 22-22 of FIG. 23 of U.S. Pat. No. 6,765,779, illustrating a cross-sectional view of the discoidal quadpolar filtered feedthrough of FIG. 21.
Figure 23:
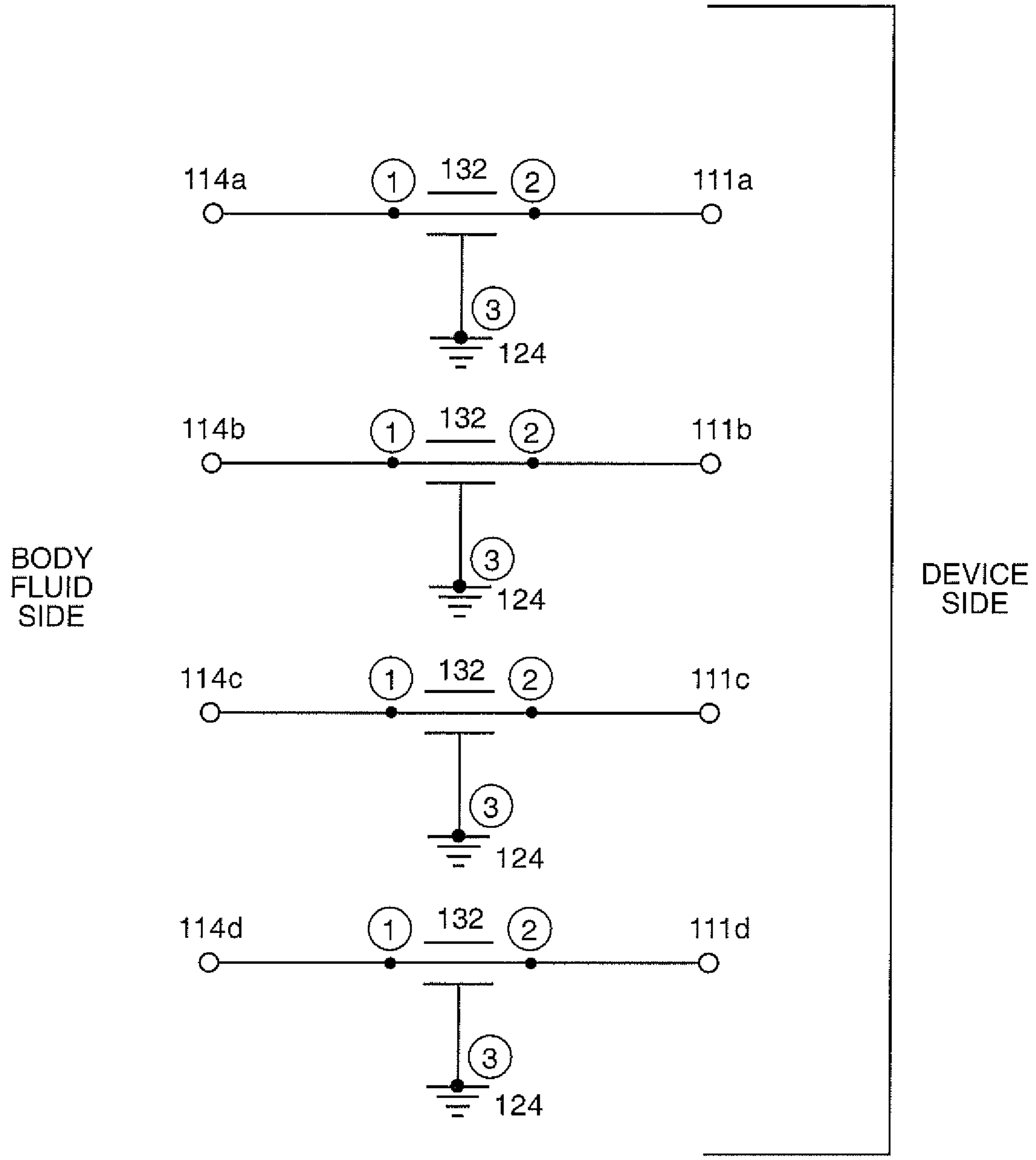
FIG. 23 (PRIOR ART)
FIG. 23 is an electrical schematic representative of the prior art discoidal quadpolar filtered feedthrough of FIGS. 21 and 22.
Figure 24:
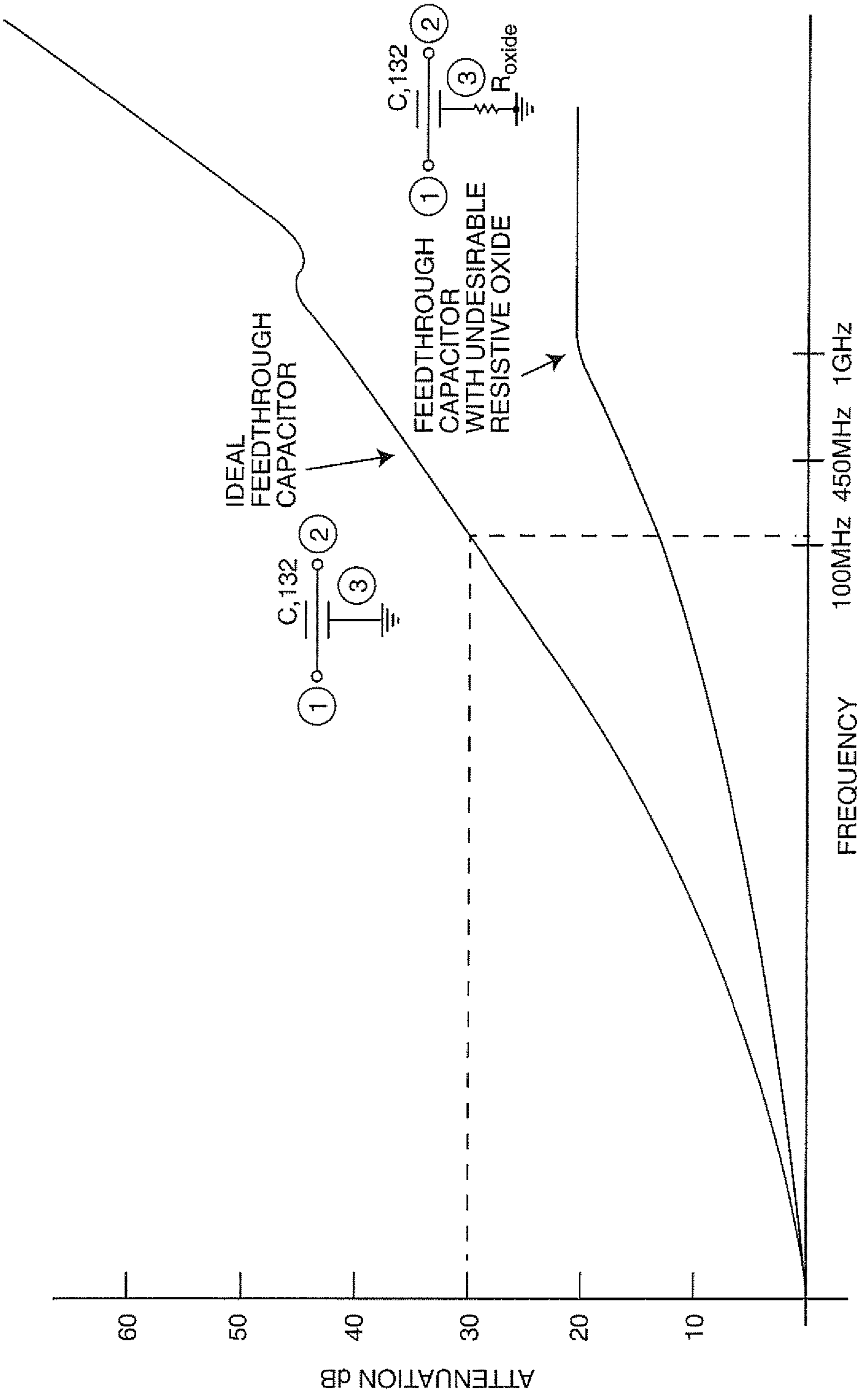
FIG. 24 (PRIOR ART)
FIG. 24 compares the attenuation vs. frequency graph for a feedthrough capacitor that is properly grounded compared to the insertion loss performance of a filter capacitor that has undesirable $R_{OXIDE}$.
Figure 25:
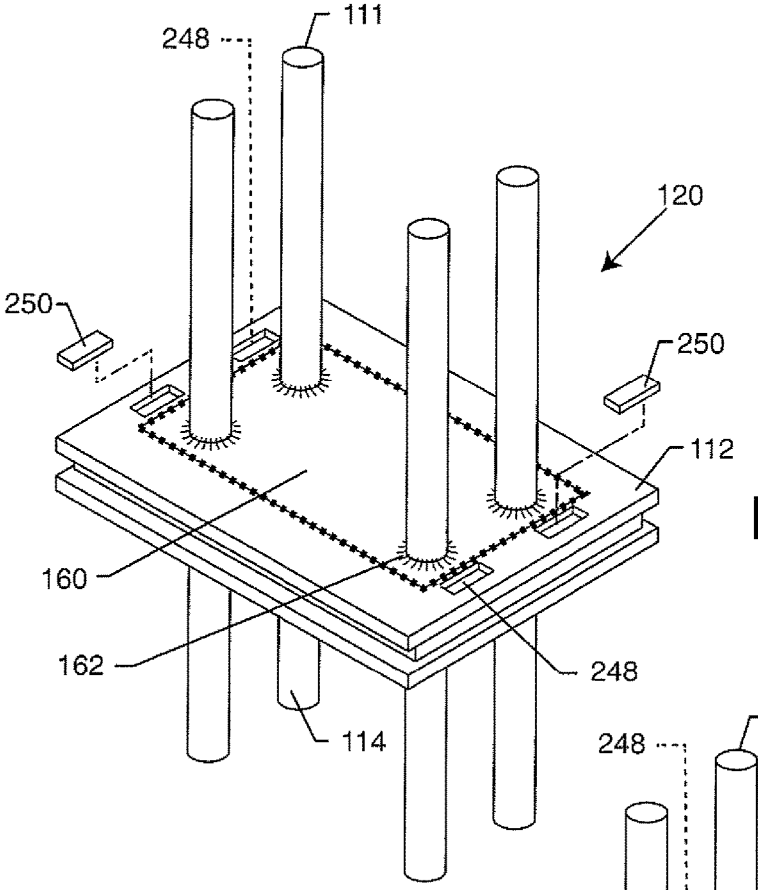
FIG. 25 (PRIOR ART)
FIG. 25 is prior art taken from FIG. 48 of U.S. Pat. No. 9,427,596, which illustrates a hermetically sealed feedthrough, wherein the ferrule of the hermetically sealed feedthrough has four rectangular pockets into which an oxide-resistant material is disposed.
Figure 26:
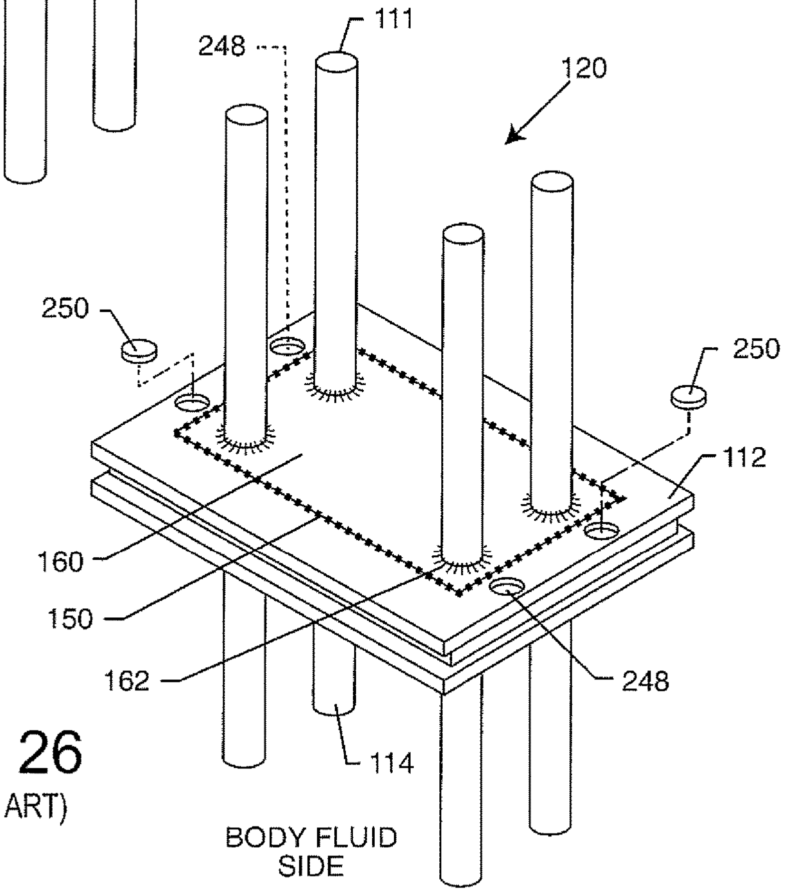
FIG. 26 (PRIOR ART)
FIG. 26 is prior art taken from FIG. 49 of U.S. Pat. No. 9,427,596 which is similar to FIG. 24, however, now shows four round ferrule pockets into which an oxide-resistant material is disposed.
Figure 27:
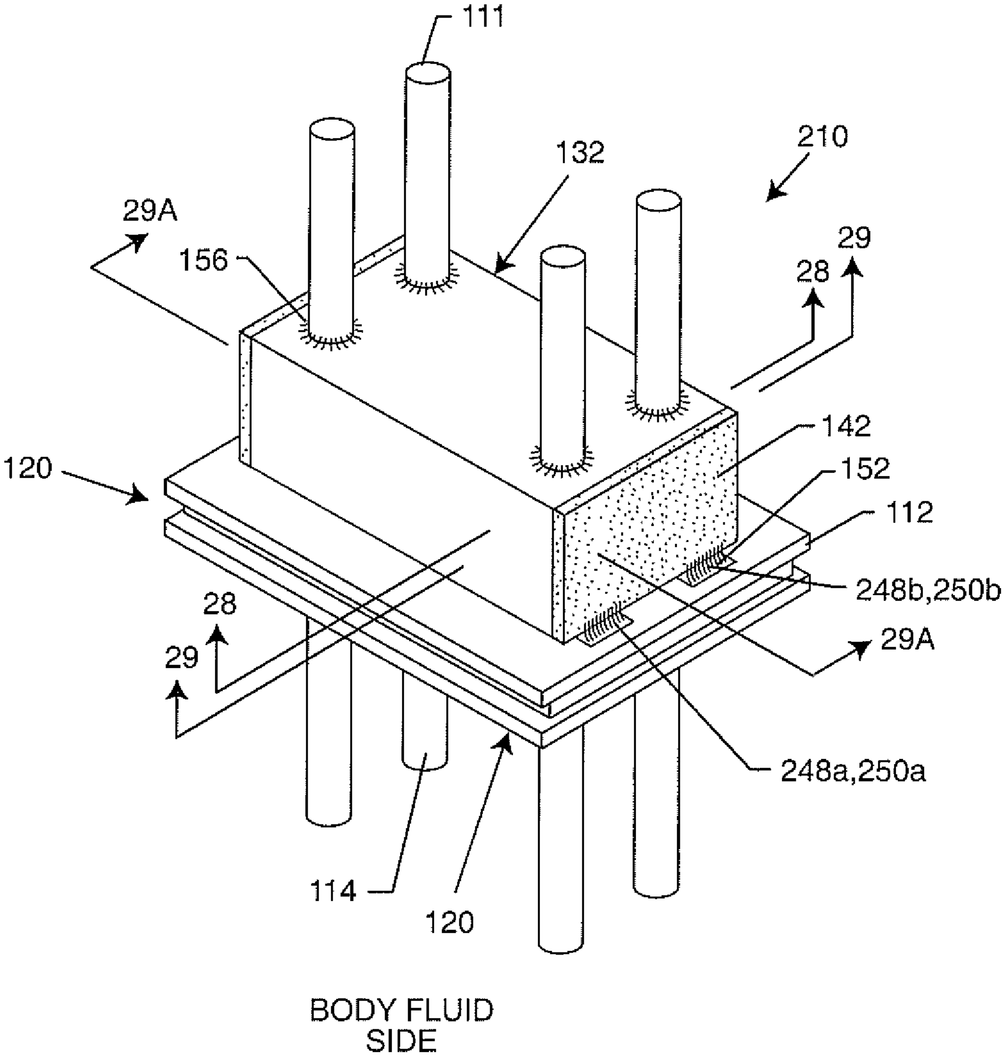
FIG. 27 (PRIOR ART)
FIG. 27 is prior art taken from FIG. 50 of U.S. Pat. No. 9,427,596 illustrating a rectangular quadpolar filtered feedthrough, wherein the feedthrough filter capacitor is attached to rectangular oxide-resistant pocket pads.

Referring again to FIG. 53, it is also very important that the electrically conductive material 152 be prevented from shorting to the active terminal pin pairs 111*a*, 114*a* and 111*b*, 114*b* and their associated gold brazes 162. To emphasize the importance of preventing unintended electrical shorts, it is stressed that the electrical connection material 156, 156' must be prohibited from physically penetrating and contacting gold braze 150 or ferrule 112. Unintended short circuiting due to electrical connection material 152 or 156, 156' leakage can be prevented by (1) a well-bonded polymeric insulating washer 212 as shown in FIG. 22, or by (2) a well-bonded polymeric insulating washer 212 and an additional polymeric insulating material 209 (or optionally 208) disposed in a created open space in addition to the polymeric insulating washer 212 shown in FIG. 53.

Figure 29B:
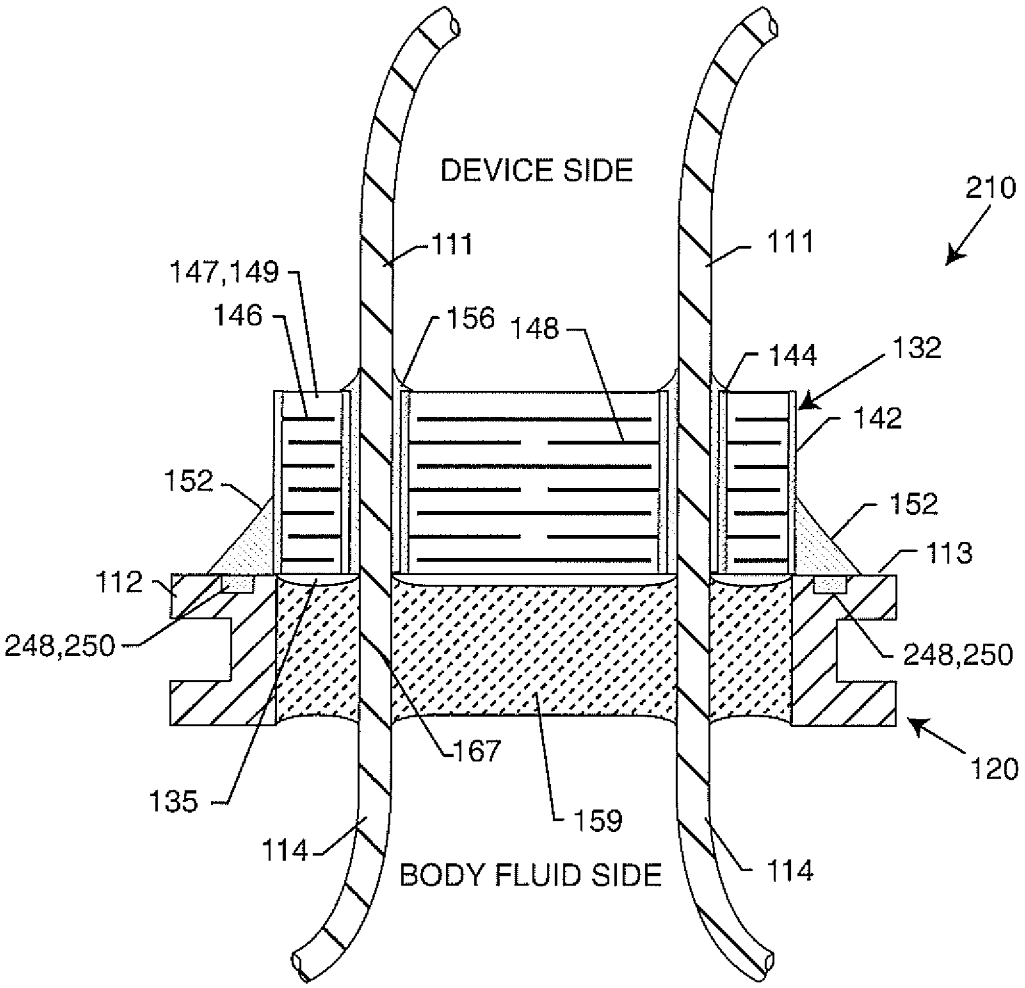
FIG. 29B (PRIOR ART)
FIG. 29B is a cross-sectional view generally taken along 29B-29B of prior art FIG. 27 illustrating that the insulator of the hermetically sealed feedthrough comprises glass.
Figure 30:
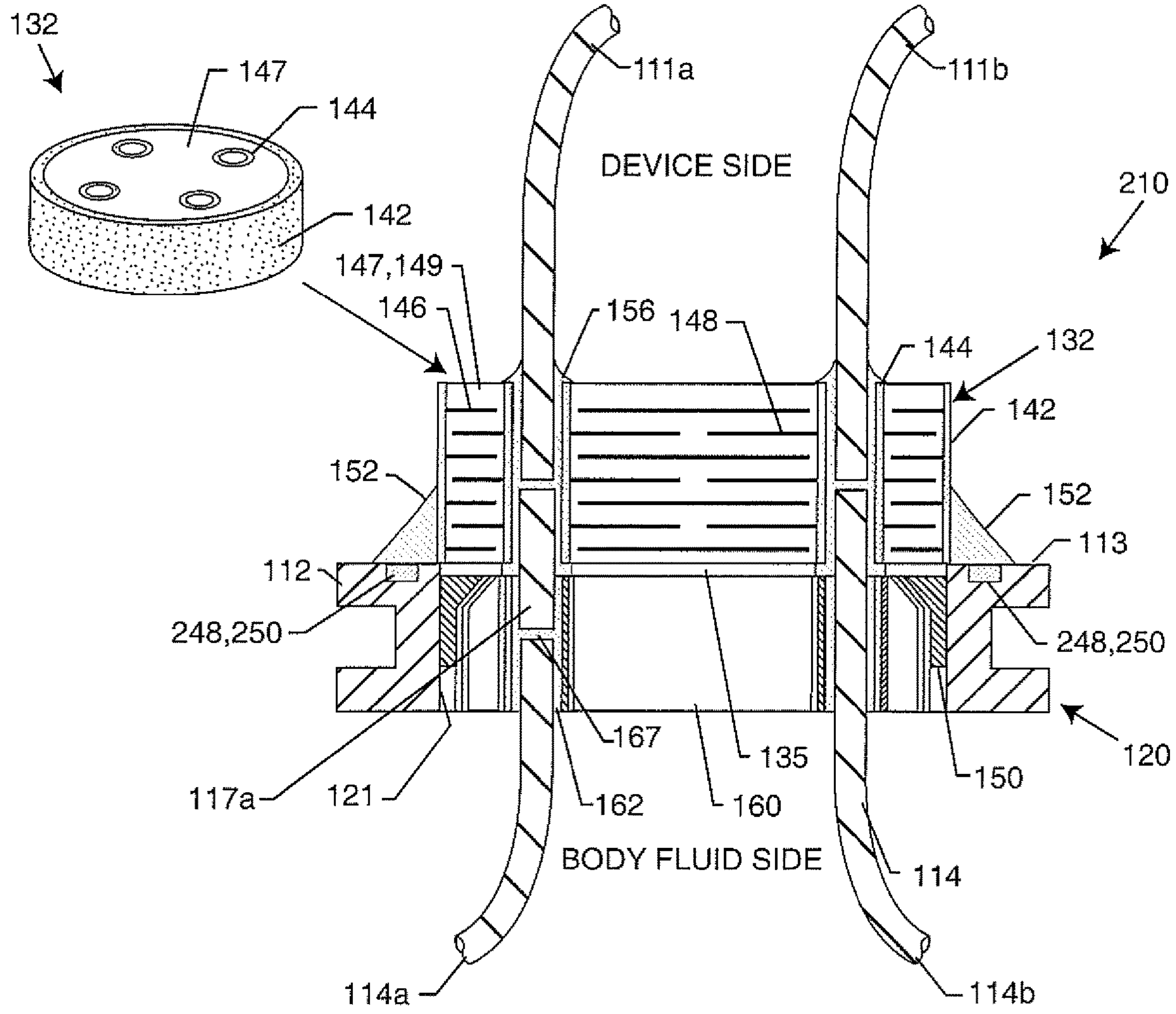
FIG. 30 (PRIOR ART)
FIG. 30 is a cross-sectional view illustrating a prior art hermetically sealed filtered feedthrough.
Figure 31:
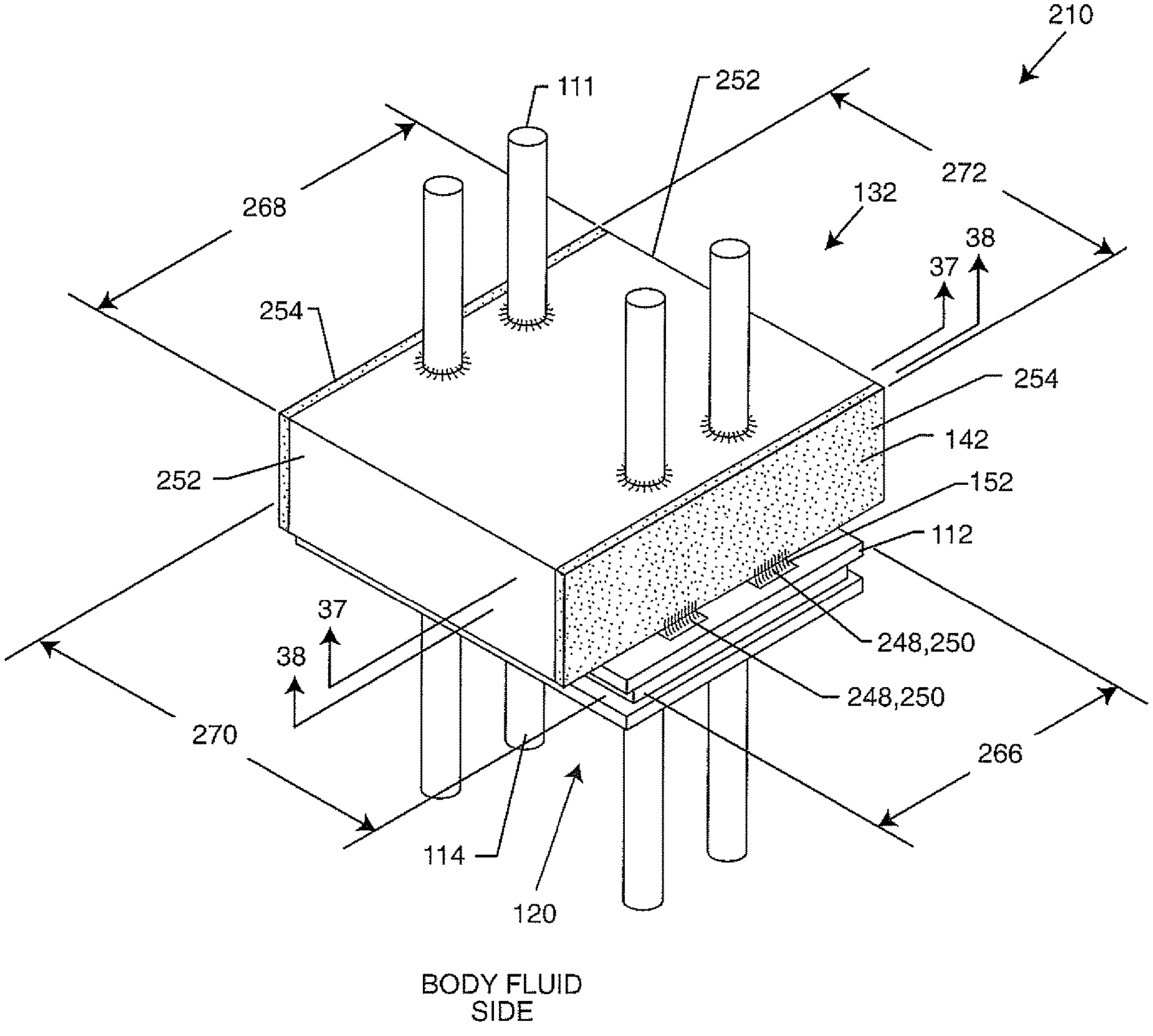
FIG. 31 (PRIOR ART)
FIG. 31 is similar to the hermetically sealed discoidal filtered feedthrough of prior art FIG. 27, except in this case, the feedthrough filter capacitor is substantially wider than the ferrule.
Figure 32A:
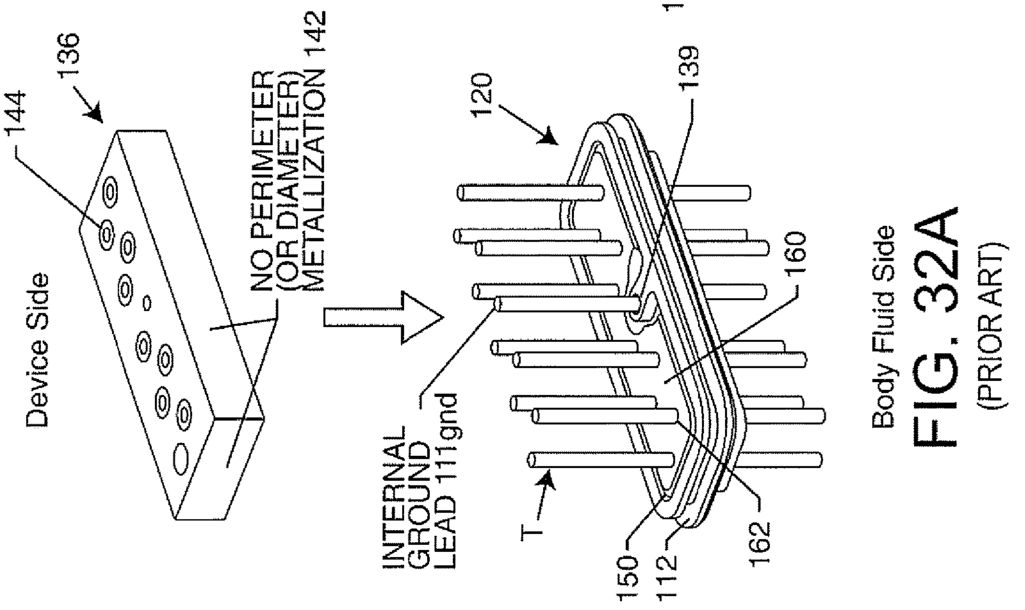
FIG. 32A (PRIOR ART)
FIG. 32A illustrates a partially exploded view of a prior art hermetically sealed feedthrough on which an internally grounded feedthrough filter capacitor is ready to be mounted.
Figure 32B:
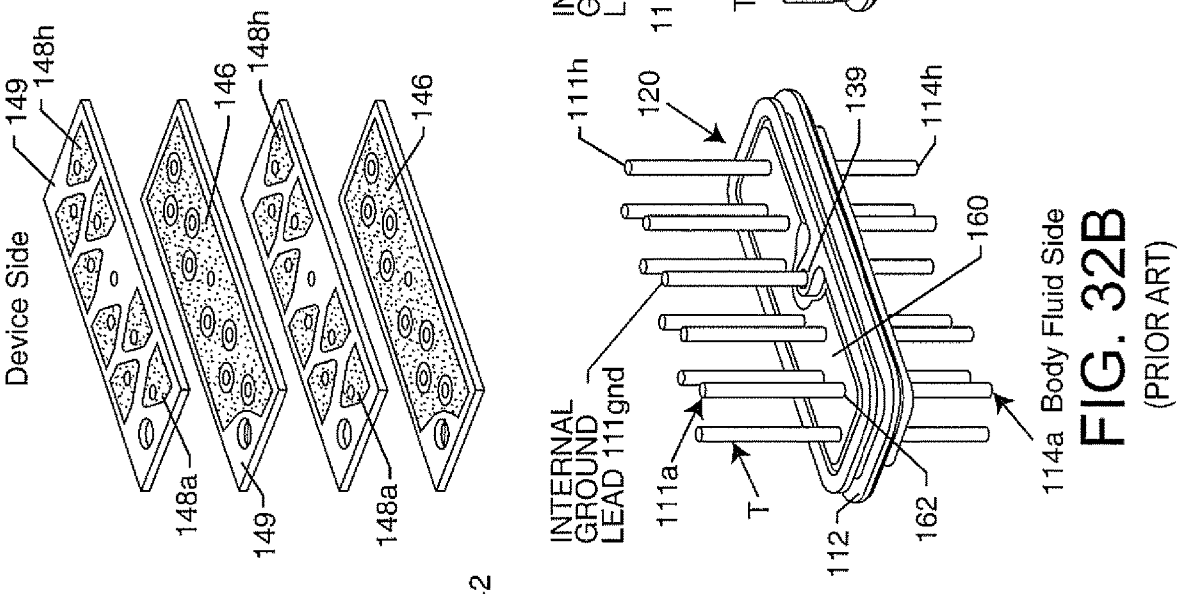
FIG. 32B (PRIOR ART)
FIG. 32B is similar to prior art FIG. 32A, except the feedthrough filter capacitor is further exploded so that the electrode plate structure of the feedthrough filter capacitor is visible.
Figure 32C:
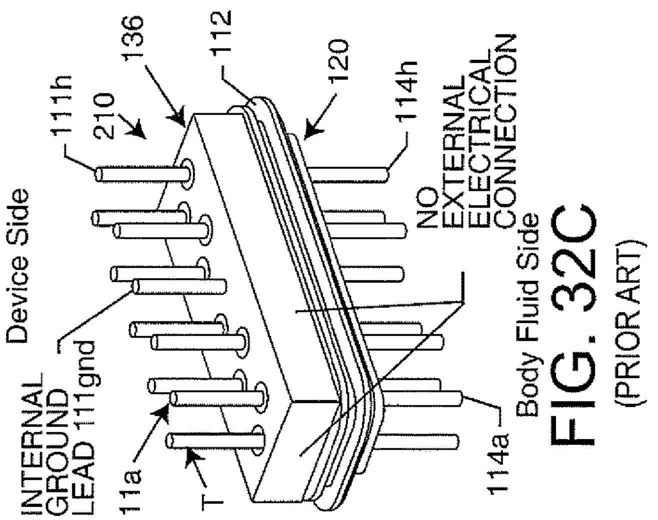
FIG. 32C (PRIOR ART)
FIG. 32C illustrates the fully assembled prior art hermetically sealed internally grounded filtered feedthrough of FIG. 32A.
Figure 32D:
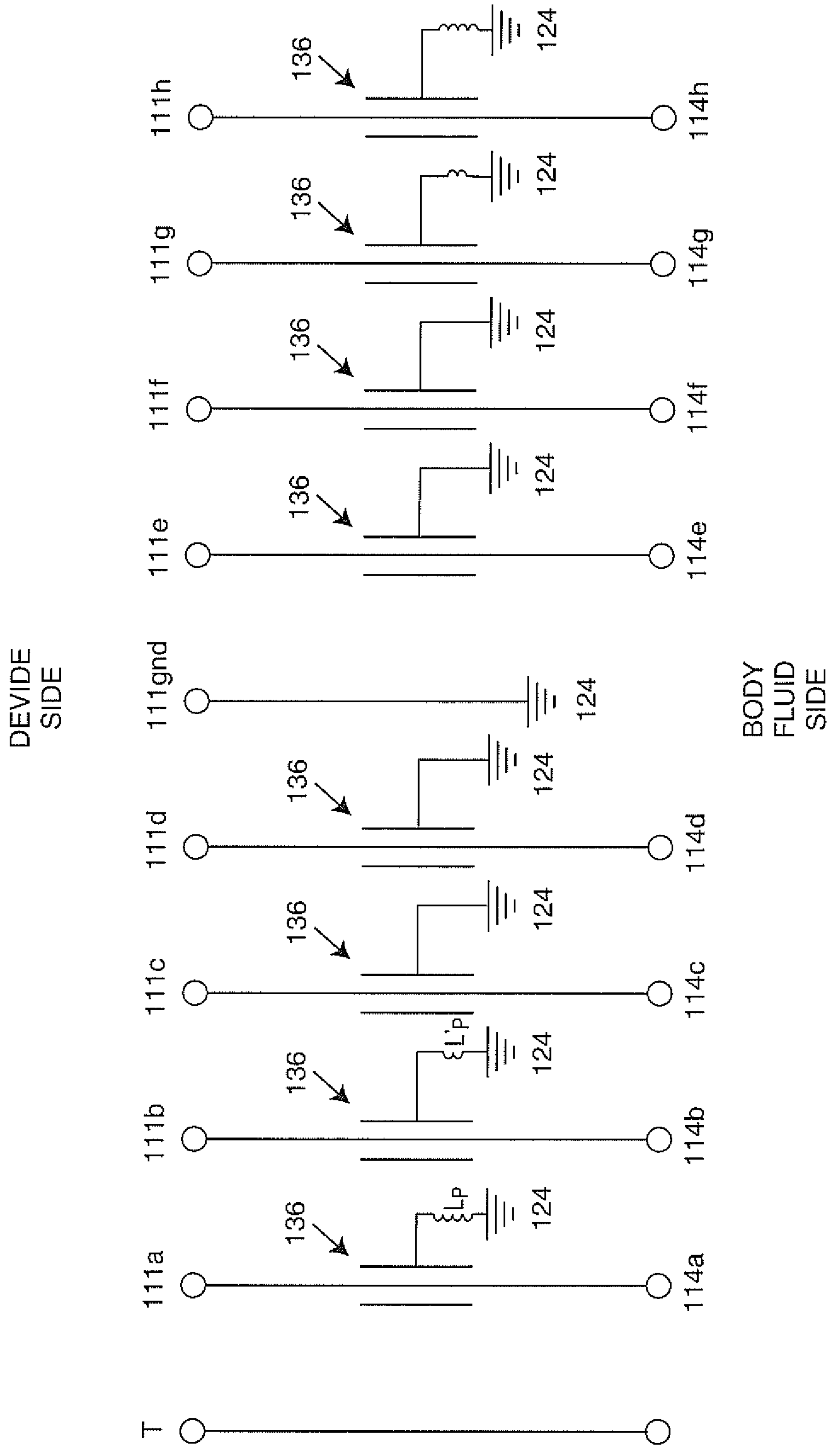
FIG. 32D (PRIOR ART)
FIG. 32D is an electrical schematic representative of the prior art hermetically sealed filtered feedthrough of FIG. 32C.
Figure 33:
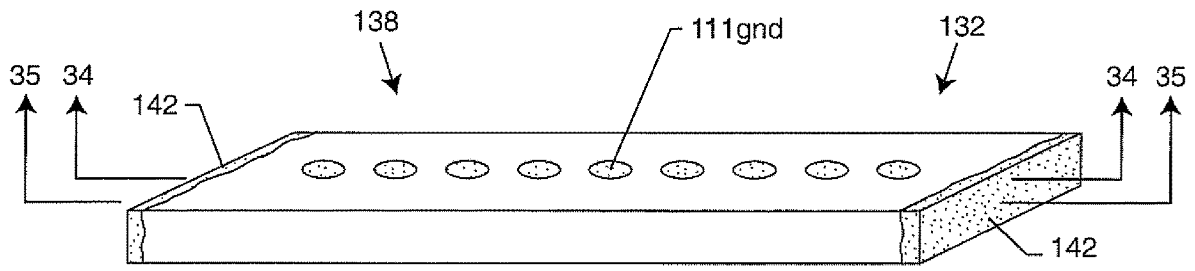
FIG. 33 (PRIOR ART)
FIG. 33 is prior art taken from FIG. 37 of U.S. Pat. No. 6,765,780 illustrating an isometric view of a hybrid rectangular feedthrough filter capacitor designed for both internal and external grounding.
Figure 34:
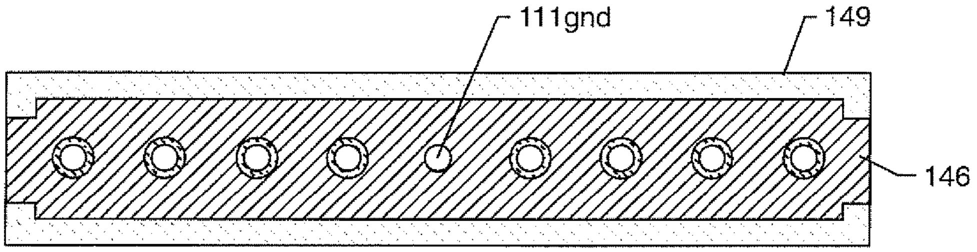
FIG. 34 (PRIOR ART)
FIG. 34 is a cross-sectional view generally taken along section 34-34 of prior art FIG. 33 illustrating a ground electrode plate.
Figure 35:
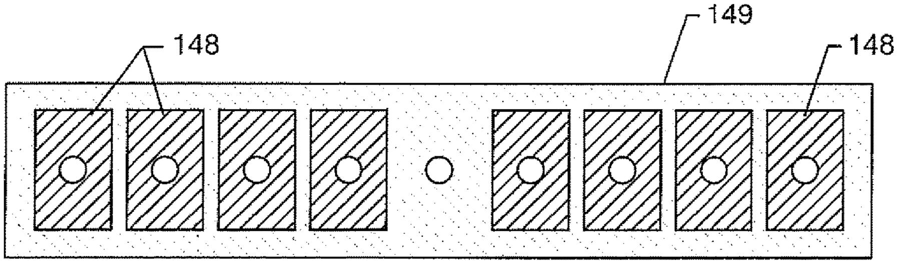
FIG. 35 (PRIOR ART)
FIG. 35 is a cross-sectional view generally taken along section 35-35 of prior art FIG. 33 illustrating eight active electrode plates on a single layer of a capacitor dielectric substrate.
Figure 36:
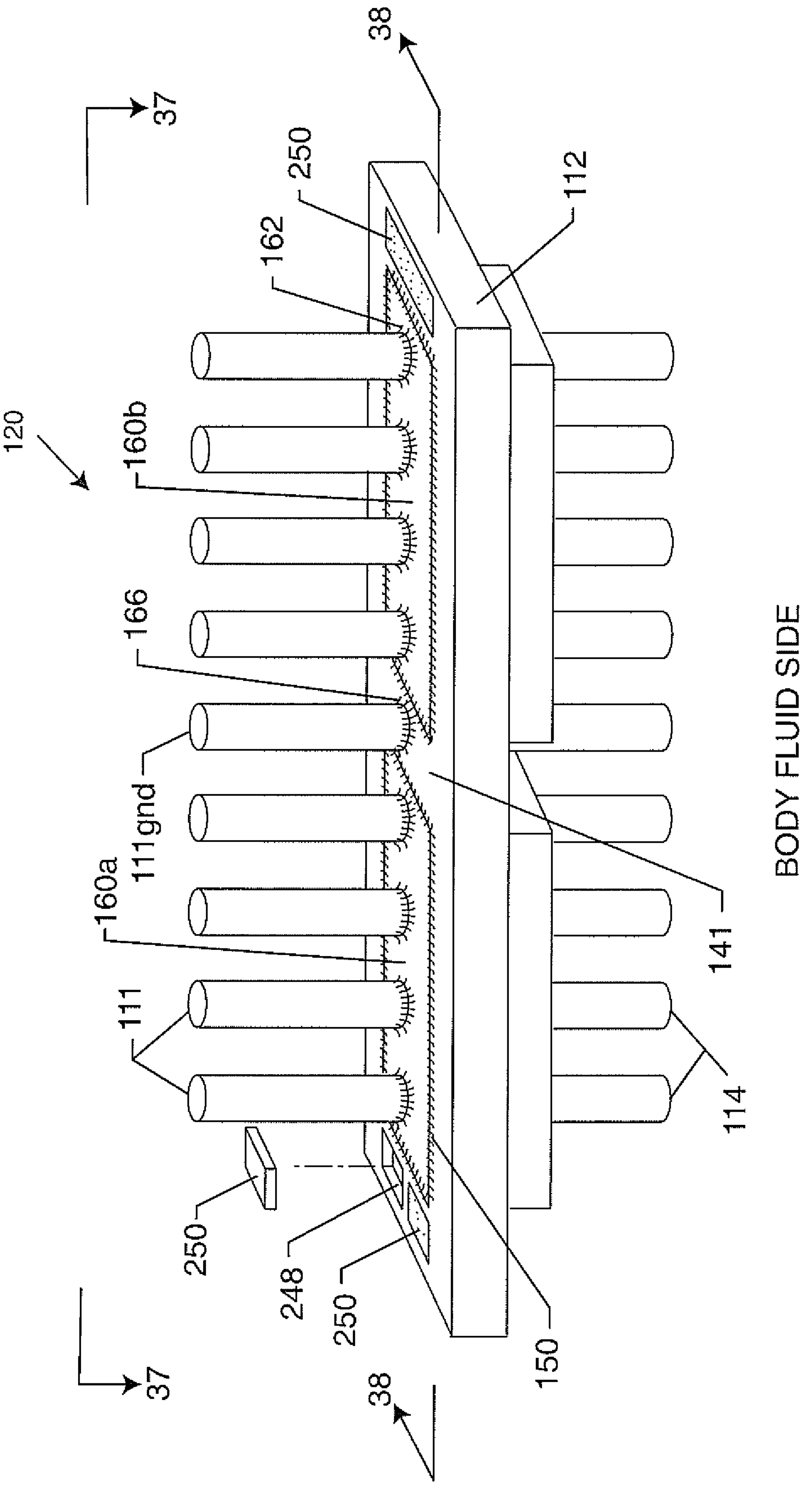
FIG. 36 (PRIOR ART)
FIG. 36 illustrates an isometric view of a prior art hybrid hermetically sealed feedthrough having two feedthrough insulators separated by a ferrule bridge.
Figure 37:
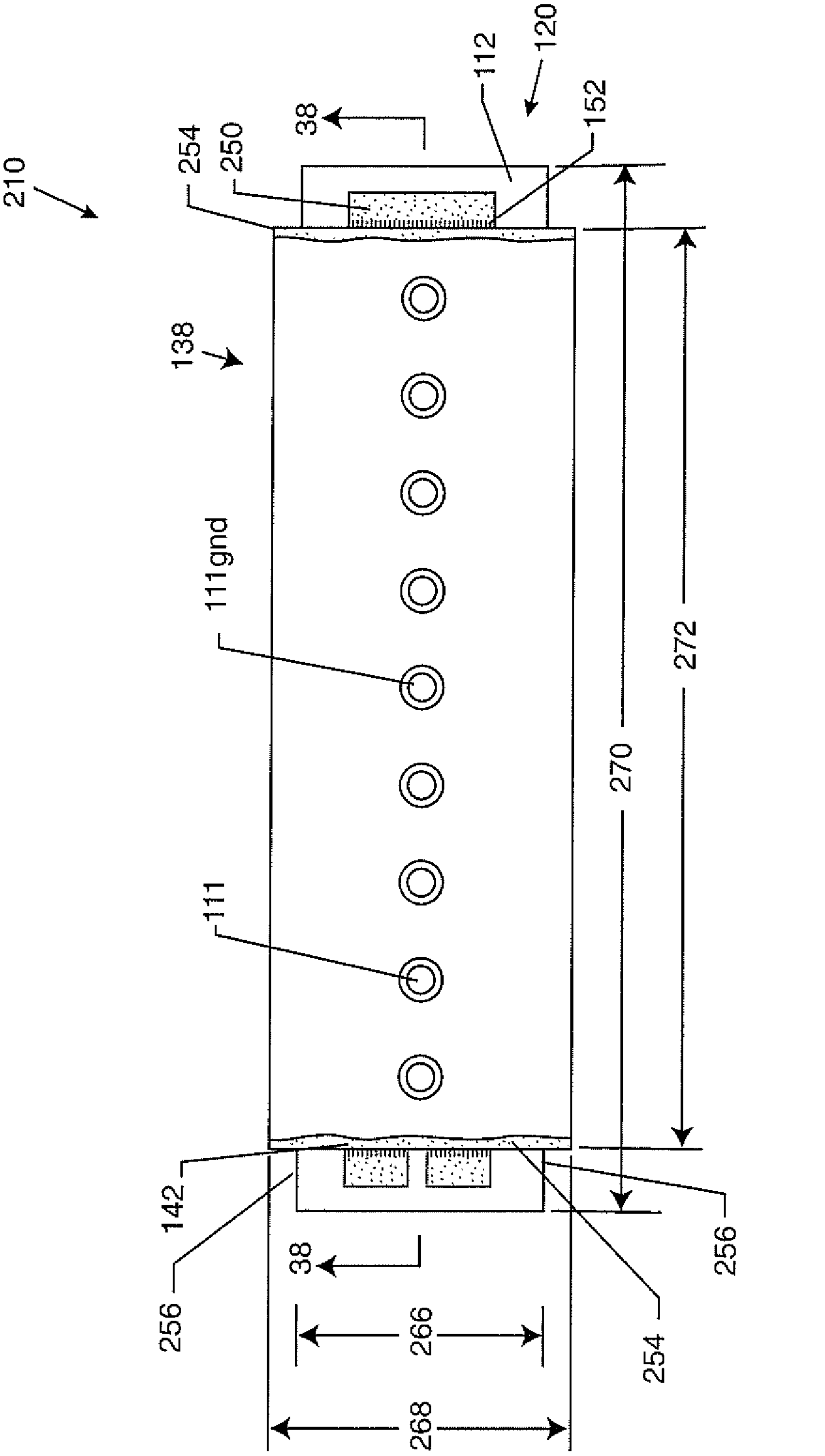
FIG. 37 (PRIOR ART)
FIG. 37 illustrates a prior art plan view of the hybrid feedthrough filter capacitor of FIG. 33 mounted on the hermetically sealed feedthrough of prior art FIG. 36.

The embodiments of FIGS. 29A, 29B and 30 illustrate configurations that are only suitable for low-voltage applications, for example, neurostimulation, such as spinal cord or deep brain stimulation, among others. In FIGS. 29A, 29B and 30, the polymeric insulating washer 212 is absent. For a high-voltage application, the air or gas gap between the EMI filter capacitor 132 and the insulator 160 is a site for potential flashover and breakdown that could lead to catastrophic failure of the active implantable medical device. More specifically, when the polymeric insulator 212 is not disposed between the feedthrough filter capacitor 132 and the insulator 160, the active area (i.e., terminal pin pairs 111*a*, 114*a* and 111*b*, 114*b* and/or gold braze 162) are positioned very close to the system ground 124, 112, 250, 248, 116, which can include gold braze 150, ferrule 112 and pocket-pads 259, 248. For a high-voltage device, such as an ICD 100I, a short distance, such as the illustrated open space or air gap area between the active area and system ground 124, predisposes the ICD 100I to immediate arc over and electrically shorting during high-voltage therapy delivery, which, as previously disclosed, could dangerously destroy functionality of the ICD, thereby becoming life-threatening for an implant patient.

Referring once again to FIG. 53A, two metallization layers applied to the surface of the insulator 160 are illustrated. They are an adhesion layer 153 and a wetting layer 151; however, it is understood that a single metallization layer that promotes both adhesion and wetting may alternately be used. It is also understood, that if the gold braze 150 is disposed below the device side surfaces of the ferrule 112 or the insulator 160 so that an open space is created to provide space for an additional secondary insulation material 209 (or optionally 208), then the insulator surface metallization layers 153 and 151 are typically positioned similarly to gold braze 150. Otherwise, the metallization layers 153 and 151 extending to the device side surface of the insulator 160 could undesirably shorten the voltage breakdown/stand-off distance between the active area and the system ground 124. The two metallization layers 153 and 151 are better understood by referring to FIG. 4 where the metallization layers 153 and 151 are enlarged and are more clearly delineated.

In an embodiment, the insulator 160 comprises two metallization layers, a first metallization layer comprising an adhesion layer 153 and a second wetting metallization layer 151 disposed on top of the first metallization layer 153. A gold braze 150 wets and bonds with wetting metallization layer 151 to form a hermetic seal between the insulator 160 and the ferrule 112. Metallization layers 153 and 151 can be similarly applied to gold braze 162 to hermetically seal the insulator 160 to the terminal pin pairs 111*a*, 114*a* and 111*b*, 114*b*.

FIG. 53A is a blown-up partial view taken from section 53A-53A of FIG. 53 illustrating the nanoparticle-filled 264 polymeric insulating washer 211 and the second nanoparticle-filled 264 polymeric insulating material 209. By adding insulating nanoparticle 264 fillers, like metal oxides (a non-limiting example is nano-scale alumina), the dielectric breakdown strength of the polymeric insulating washer 211 or 211A or the second polymeric insulating material 209 is significantly increased. Importantly, the novel insulating nanoparticle 264 fillers of the present invention are of a sufficient quantity and are uniformly dispersed throughout the polymeric insulating washer 211 or 211A or the second polymeric insulating material 209 so that dielectric breakdown strength is correspondingly uniformly increased. In general, the smaller the uniformly dispersed insulating nanoparticles 264, the higher the breakdown strength will be.

Figure 20:
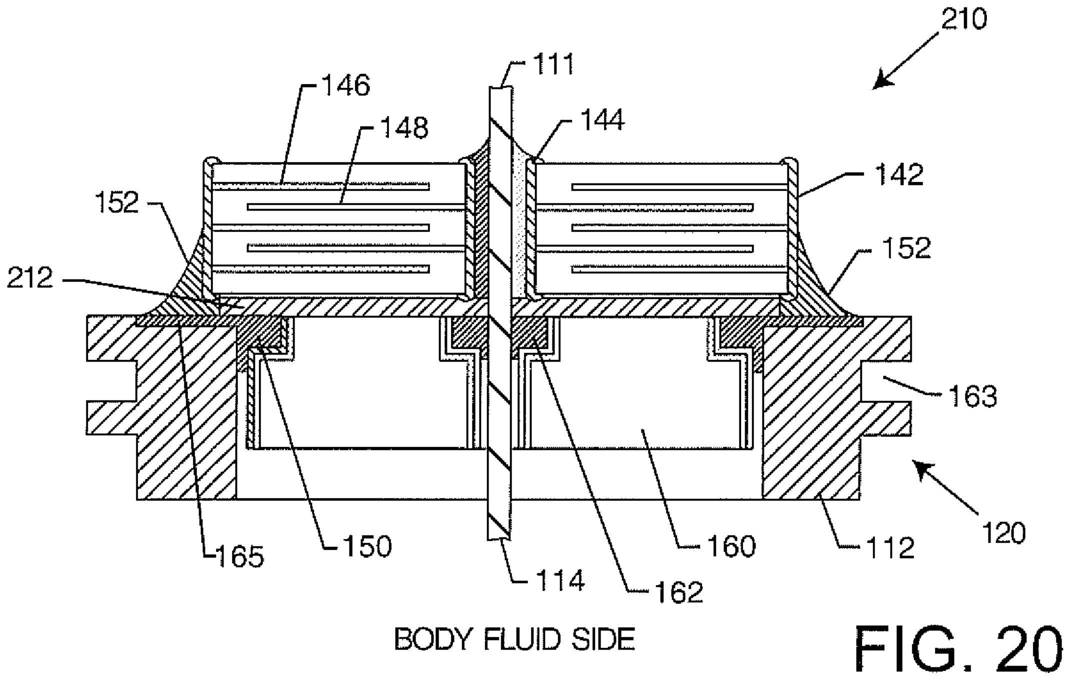
FIG. 20 (PRIOR ART)
FIG. 20 is prior art taken from FIG. 22 of U.S. Pat. No. 6,765,779. Illustrated is a cross-sectional view generally taken along section 20-20 of FIG. 19.

Referring now back to FIG. 20, which is labelled prior art, it will be appreciated that the polymeric insulating washer 212 can be replaced with the novel composite polymeric insulating washer 211 comprising the nano-scale dielectric additives or metal oxides, thereby increasing its insulator dielectric strength, which is particularly important in a high-voltage ICD application. The novel composite polymeric insulating washer 211 or novel composite polymeric insulating material 208, 209 are also applicable to FIGS. 20, 20A, 22, 22A, 38, 41, 41A, 41B, 41C,48, 48A, 49, 50, 50A, 51, 52, 54, 54A, 54B, 55, 56, 57 and 58. By adding nano-scale metal oxides or nano-metal oxides to the polymeric, such as an epoxy or non-conductive polyimide, one achieves a superior dielectric breakdown strength. The highest breakdown strengths are achieved by adding nano-scale dielectric powder additives into the polymeric serving as the matrix. These added nano-insulative particles particularly increase the high-voltage breakdown for fast rise-time (high-frequency) applications, such as those produced by implantable cardioverter defibrillators. Voltage and rise-time (frequency) can vary from one ICD manufacturer to another; therefore, each high-voltage stand-off polymeric insulator application should be individually tailored by adding the right amount of nano-scale dielectric additive. One has to achieve a balance, as adding too much nano-scale alumina powder, could, for example, compromise the insulating polymeric composite adhesive properties, which can result in delamination from the adjoining structures. For retention of adhesive properties, preferred insulating nanoparticle 264 filler volume % ranges from about >0% to about ≤30%. When adhesive properties are not of concern, the insulating nanoparticle 264 filler volume % can be increased to a range from about >0% to about ≤99%. The smaller the nanoparticle 264, the higher the volume % can be.

An alternative to a nanoparticle-filled 264 polymeric insulating washer is an insulating nanolaminate polymeric insulating washer having layers of high dielectric constant nano-materials interlayered with insulating polymeric layers. High dielectric constant nanolaminate layers are fully dense, ultra-fine-grained solids that exhibit a relatively high concentration of interfacial defects, which encourage adhesion to the interlayered insulating polymeric layers. Multilayer nanolaminates comprising interlayering of high dielectric constant and insulating polymeric layers can be grown using atom-by-atom deposition techniques that are designed with different stacking sequences and layer thicknesses. The properties of such fabricated nanolaminates depend on their compositions and thicknesses. These can be demonstrated within the synthesis process by thickness control of each layer and interfacial chemical reaction between layers. Multilayer laminates exhibit high strength efficient dielectric constants with high insulation characteristics. The electrical properties of such laminates may further be modified by incorporating dopants and site-engineering techniques, as well as layer-by-layer structure order and arrangement, which can both be suitable for improving insulative or dielectric properties of the nanolaminates.

It is further appreciated that any of the other materials discussed above can have their dielectric properties improved by adding metal oxides and in particular, nanoscale metal oxides (excellent insulators) into the polymeric matrix. As such, while a polymeric insulating washer 212 and a polymeric insulating material 208 are illustrated, it is anticipated that these polymeric insulators may be a unitary structure comprising a single insulating material. For example, the polymeric insulating washer 212 can be configured as a solid, rigid, or flexible polymeric insulator comprising a double-sided adhesive backing. Upon assembly, the adhesive backing facing the feedthrough insulator 160 may have a thickness and sufficient elastic deformation properties to flow into the open space between the feedthrough insulator 160 and the ferrule 112, mirroring the filled open space occupied by the polymeric insulating material 208, thereby increasing the dielectric breakdown strength to an equivalent level to that of the polymeric insulating washer 212 plus the polymeric insulating material 208. Similarly, the polymeric insulating material 208 may alternatively be applied as a single material that conformally fills the open space between not only the filter capacitor 132 and feedthrough insulator 160 but also between the feedthrough insulator 160 and the ferrule 112.

Figure 53B:
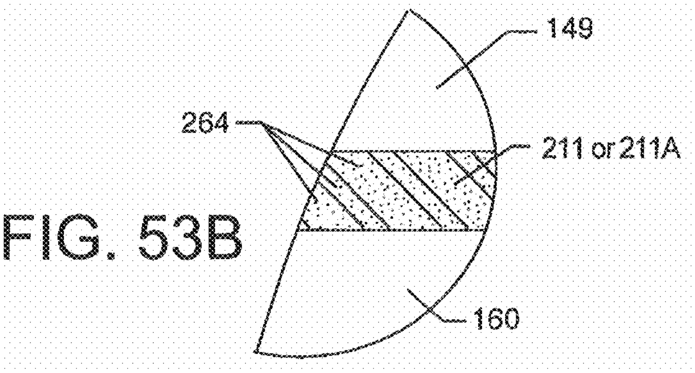
FIG. 53B is a blown-up partial view taken along section 53B-53B of FIG. 53A to more clearly illustrate the novel nanoparticles 264 within the polymeric insulating washer of FIG. 53A.

FIG. 53B is a blown-up sectional view generally taken from section 53B-53B of FIG. 53A of the novel insulating nanoparticles 264 filled into the polymeric insulating washer 211, 2121A. As previously disclosed, while the dots are meant to represent the nanoparticle filler 164, such nanoparticles are actually not visible to the naked eye. The insulating nanoparticles 264 are homogeneously dispersed throughout the polymeric insulating washer 211, 211A so that the washer's dielectric breakdown strength is correspondingly uniformly increased.

Insulating nanoparticle fillers enhance various polymeric insulating material electrical and thermal properties, like increasing dielectric breakdown strength (DBS) and maximizing the dielectric breakdown field (EBD). Other material property enhancements include: minimizing electric current leakage, increasing high-temperature electrical insulation breakdown, improving thermal conductivity, advantageously adjusting the coefficient of the thermal expansion, managing elasticity and/or flexibility, and boosting the mechanical and/or thermal endurance of the composite (hybrid) polymeric insulating material. The primary advantage of insulating nanoparticles is their small size, which provides a large nanoparticle surface area, which, in turn, imparts to the nanoparticle filled polymeric insulating material, a large interfacial area per unit volume. The large interfacial area per unit volume of the nanoparticle filled polymeric insulating material can thereby afford advantageous dielectric response and breakdown strength. The insulating nanoparticles may have various morphologies, including spherical, fiber-like, irregular, or custom shapes, or can be thin, flattened, elongated in shape, where, for example, there is dimensional prominence in one particular dimension similar to a disk, a flake, or potato chip-like shape, or an essentially nano-sized two-dimensional sheet-like shape. The filler nanoparticles may all be of the same size or, alternatively, may comprise a blend of different nanoparticle sizes and/or shapes.

Methods for forming homogenously dispersed nanoparticle filled polymeric insulating materials include: sonication/ultrasonication, extrusion, three-roll milling, blowing, injection, in situ reactive blending, sol-gel processing, melt-mixing, thermo-kinetic (sheared) mixing, polymeric or pre-polymeric solution intercalation, in situ intercalative polymerization, melt intercalation, liquid crystal polymeric alloy formation, or nanofiller direct dispersion, among others.

In general, the smaller the nanoparticles, the higher the increase in insulator DBS (assuming a sufficient quantity of nanoparticles and uniform distribution of the nanoparticles throughout the polymeric or plastic insulators or insulating materials and that the insulating material adequately wets the nanoparticles). The nanoparticles of the present invention range in size from 1 nm (0.001 μm) to 40,000 nm (40 μm). In an embodiment, the nanoparticles of the present invention range in size from 1 nm (0.001 μm) to 4000 nm (4 μm). In another embodiment, the nanoparticles of the present invention range in size from 1 nm (0.001 μm) to 1000 nm (1 μm). The nanoparticles of the present invention may further have at least one dimension less than or equal to 100 nm. A nanoparticle size range for a polymeric or plastic insulator or insulating material can be determined by the maximum voltage of the application.

When the size of the nanoparticles decreases below 100 nm, a markedly higher particle surface area-to-volume ratio is achieved compared with nanoparticle sizes above 100 nm. This high surface area-to-volume ratio means that, for the same particle loading, nanoparticle filled polymeric insulating materials having particle size less than or equal to 100 nm have a much greater interfacial area than polymeric insulating materials filled with nanoparticles greater than 100 nm in size. Higher interfacial area translates into higher dielectric breakdown strength. In contrast, nanoparticle filled polymeric insulating materials having particle size greater than 100 nm have lower high surface are-to-volume ration, therefore lower interfacial area, and, in turn, lower dielectric breakdown. In an embodiment, a nanoparticle filled polymeric insulating material comprises a particle size less than or equal to 100 nm.

Incorporating an insulating nanoparticle filler into a polymeric insulating material is an efficient approach to improving the breakdown strength of an insulation material. Depending on the size and morphology of the nanoparticles, nanoparticle loadings can range from >0% to ≤90% by weight. Related to particle size is the particle surface area. As particle specific surface area increases with decreasing particle size, hence, depending the requirements of an application, nanoparticle loading may depend on nanoparticle size. In an embodiment, the nanoparticle loading of a nanoparticle filled polymeric insulating material having particle size ranging from 1 nm to <1000 nm is >0 to 40% by weight. In an embodiment, the nanoparticle loading of a nanoparticle filled polymeric insulating material having particle size ranging from 1000 nm to 40,000 nm is >40% to ≤90% by weight.

Nanoparticle filled polymeric insulating materials may be flexible, semi-rigid, or rigid. Nanoparticle filled polymeric insulating materials may further be thin film, thick film, dispensable, moldable, stampable or similarly formed. The nanoparticle size and concentration influence the final properties of the nanoparticle filled polymeric insulating materials. Nanoparticle size and concentration can influence the glass transition temperature (Tg) of the nanoparticle filled polymeric insulating material. The Tg of the filled polymeric material relates to its mechanical properties, which include: tensile strength, impact resistance, modulus of elasticity, and its operational temperature range. For example, if the polymeric insulating material wets the surface of the nanoparticle, the insulation material Tg increases with increasing nanoparticle loading, which is likely due to the polymeric insulating material on the surface of the filler nanoparticles becoming immobilized. Similarly, if the polymeric insulating material does not wet the surface of the nanoparticle, the insulation material Tg decreases with increasing nanoparticle loading.

The insulating nanoparticle filler may be subjected to various chemical, mechanical, or thermal treatments to modify the nanoparticle surface, which can be made in situ or post-synthesis, and which provide another way to customize the thermal, mechanical and/or electrical properties of the nanoparticle filled polymeric insulating material. Surface modification methods may incorporate surfactants, dopants, dispersants, emulsifiers, among others, and can. Modification methods include grafting, coupling, deposition, radiation, ion implantation, or other conventionally known surface treatment technologies. Example surface modifications include: surface coatings, which promote miscibility with the polymeric insulation material, decrease the tension between the insulating nanoparticle and the polymeric insulation material, promotes wetting of the nanoparticles by the polymeric insulating material, and encourage surfactant-like dispersion through the polymeric insulating material; functionalization, which changes the surface chemistry of the nanoparticle to form surface functional groups that promote cross-linking between the nanoparticles and the polymeric insulating material; and grafting, which adds another material like "branches" to the surface of the nanoparticle to inhibit aggregation of the nanoparticles (particle aggregation affects efficacy of homogenously dispersing the nanoparticle the polymeric insulating material). The following are examples that show how some of these parameters affect dielectric breakdown strength of polymeric insulating materials.

Example 1—Effect of Surface Modification on DBS

FIG. 53C is TABLE 1, which contains various alumina ($Al_2O_3$) nanoparticle filled epoxy composite polymeric insulating materials. The base epoxy is a cycloaliphatic resin with a methyl-hexahydrophthalic anhydridene hardener, which is used as the control (DBS=30.7 kV/mm). The alumina nanoparticle powder used to make the composite epoxies has an average particle size of 30 nm. The alumina nanoparticle powder was divided into three groups: untreated. γ-aminopropyl-triethoxysilane (APS) treated, and hyperbranched aromatic polyamide grafted (HPB). APS is used for surface functionalization, mostly as a dispersant. HPB grafting of polymers is an effective way to prevent particle aggregation. The particle sizes of TABLE 1 reflect nanoparticle size of after forming the composite epoxy. The dielectric breakdown strength of the composite epoxies is compared to the dielectric breakdown strength of the neat epoxy (no nanoparticle filler). TABLE 1 shows the following:

- DBS decreases with increasing concentration (loading in wt. %)
- Untreated $Al_2O_3$ nanoparticles result in decreased DBS
- APS surface modified $Al_2O_3$ nanoparticles result in decreased DBS compared with neat epoxy
- HPB surface modified $Al_2O_3$ nanoparticles result in increased DBS compared with neat epoxy
- Untreated $Al_2O_3$ nanoparticles result in larger particle size (600 nm-800 nm due to aggregation)
- Surface modified $Al_2O_3$ nanoparticles result in smaller particle sizes compared to the untreated $Al_2O_3$ nanoparticles (100 nm-200 nm due to inhibiting aggregation)

The data indicate that particle size impacts composite epoxy dielectric breakdown strength, nanoparticle surface modification can improve nanoparticle dispersion and aggregation. Specifically for $Al_2O_3$ nanoparticles, both APS and HPB are effective inhibitors to nanoparticle aggregation, therefore are effective in reducing $Al_2O_3$ aggregate particle size, and HPB is more effective for homogenously dispersing the $Al_2O_3$ nanoparticles in epoxy.

Example 2—Effect of Polymorphic Form on DBS

FIG. 53D is TABLE 2, which contains various $Al_2O_3$-epoxy composite polymeric insulating materials having boron nitride (BN) nanoparticle fillers. The base composite epoxy is a bisphenol-A diglycidyl resin with an anhydrite hardener having 60 wt. % $Al_2O_3$ filler containing a 4 μm average particle size. The DBS of the base $Al_2O_3$-epoxy composite is 156 kV/mm. Two different polymorphs of BN were used to make the BN composite $Al_2O_3$-epoxies: cubic BN and hexagonal BN. The particle size of the cubic BN is 150 nm. The concentrations (in Vol. %) of the cubic BN is 0.2 Vol. %. The particle size of the hexagonal BN is 70 nm. Two hexagonal BN concentrations were used: 0.2 Vol. % and 0.6 Vol. %. The dielectric breakdown strengths of the $Al_2O_3$—BN-epoxy composites are compared to the dielectric breakdown strength of the base $Al_2O_3$-epoxy composite. TABLE 2 shows the following:

- DBS increases with decreasing particle size
- DBS decreases with increasing concentration (Vol. %)
- Cubic BN results in larger average particle size than hexagonal BN
- At the same concentration (Vol. %), cubic BN has lower DBS than hexagonal BN
- Both cubic and hexagonal BN increase DBS compared to the $Al_2O_3$-epoxy composite insulating polymer The data indicate that the polymorphic form of boron nitride affects average BN particle size, with a cubic crystal form yielding the larger BN particle size, and, regardless of crystal form, BN favorably increases the DBS of $Al_2O_3$-epoxy composite insulating polymers.

Dielectric properties are material thickness dependent. Thicker dielectric materials mostly exhibit a lowered dielectric strength. Experimental evidence suggests that bipolar charge injection and the formation of charge packets under higher electric fields is the cause, and so, it is believed that the thickness dependence is the result of charge dynamics in the material. Additionally, the operational voltage stress is the fundamental design limitation relative to any advantageous impact nanofillers have on the dielectric breakdown strength of composite polymer insulating materials. It is known that charge carriers transport not only electrical current, but also heat. The fast dissipation of thermal energy through nanoparticle fillers is favorable for the improving breakdown failures at higher voltages. High thermal conductive nanoparticle fillers can transport the heat out more effectively so that the local temperature rise induced by the localized electric field around the nanoparticle fillers is minimal, and thus the local regions maintain a higher voltage withstanding capability. Moreover, both low dimensional nanoparticle filler selection and particle surface modification are substantial enablers or increasing DBS of nanoparticle filled polymer insulating materials. In particular to surface modification, thermally conductive fillers such as boron nitride nanosheets with a polydopamine surface modification not only has good thermal conductivity, but also provides interfacial compatibility between the nanoparticle filler and the base polymer insulating material, thereby enabling higher dielectric strength.

Referring back to FIG. 53D, TABLE 2 shows the following:

Thermal conductivity increases with increasing concentration (Vol. %)

Cubic BN, having larger particle size (150 nm) results in higher thermal conductivity than hexagonal BN having smaller particle size (70 nm) at the same concentration (0.2 Vo. %)

Figure 53E:
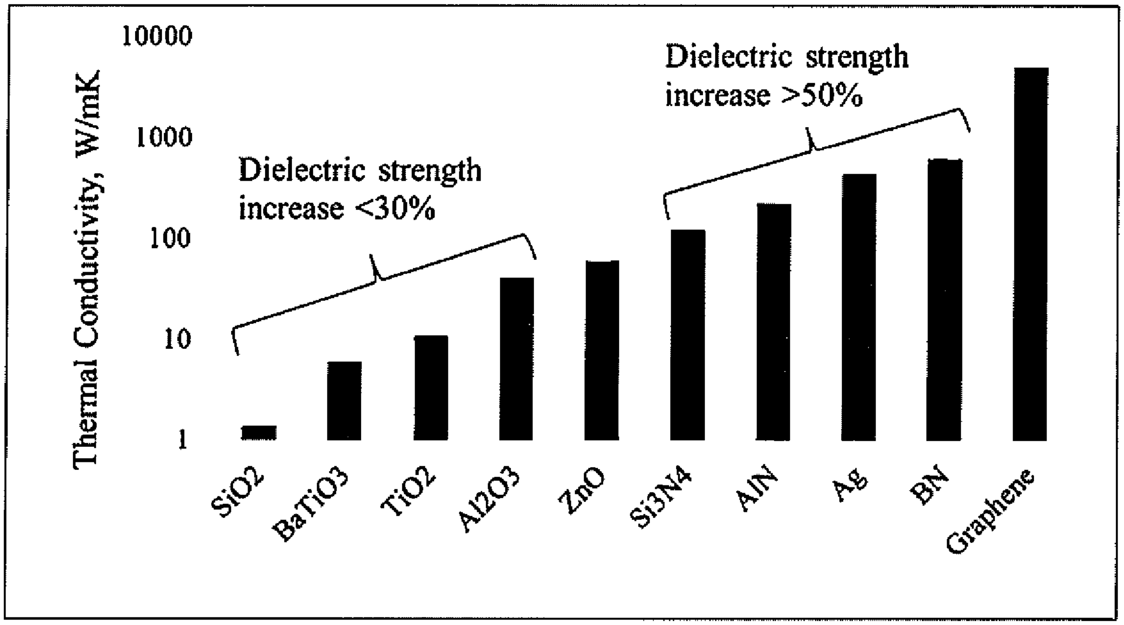
FIG. 53E is GRAPH 1 showing the relationship between thermal conductivity and increased dielectric strength for various nanoparticle fillers.

For the same particle size, higher concentration (Vol. %) results in higher thermal conductivity FIG. 53E is GRAPH 1, which shows the relationship between thermal conductivity and increased dielectric strength for various nanoparticle fillers. For base insulating polymeric materials having thermal conductivity ≥1 W/mK to ≤100 W/mK, insulating nanoparticle fillers can increase the dielectric strength of the composite insulating polymeric material up to 30%. For base insulating polymeric materials having thermal conductivity >100 W/mK to ≤10000 W/mK, insulating nanoparticle fillers can increase the dielectric strength of the composite insulating polymeric material to ≥50%.

Figure 53F:
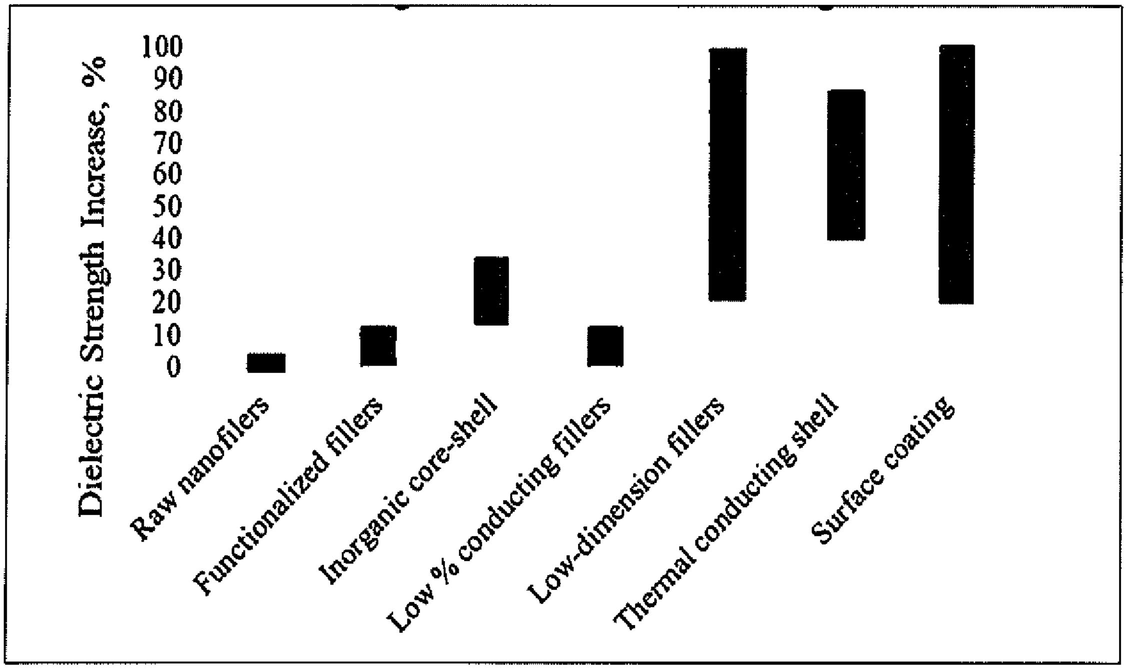
FIG. 53F is GRAPH 2 showing the relationship of particle morphology and surface modification on increased dielectric strength of insulating polymeric materials.

FIG. 53F is GRAPH 2, which shows the relationship of particle morphology and surface modification on increased dielectric strength of insulating polymeric materials. Surface coating and low-dimension fillers have the broadest range for DBS percent increase, with thermal conducting shells second broadest for DBS percent increase range.

FIG. 54 illustrates the present invention applied to prior art FIG. 29B disclosing a thermoplastic insulating washer 212A disposed between the EMI filter capacitor 132 and the hermetically sealed insulator 160 comprising a glass, a glass-ceramic or a glass fritted ceramic. The glass, glass-ceramic or glass fritted ceramic of the glass-containing hermetically sealed insulator 160 is directly bonded and hermetically sealed to the ferrule 112 and the terminal pins 111*a*, 114*a* and 111*b*, 114*b*. As thermoplastics are melt-processible insulating materials so that during assembly the thermoplastic coated polymeric insulating washer 212A conforms to the surface of the insulator 160, which is particularly noticeable at the menisci 160*m*. Solid polymeric insulating washers are generally not able to conform well to such menisci 160*m*. However, with sufficient adhesive backing, the solid polymeric insulating washer 212 becomes an option. In a preferred embodiment, the solid polymeric insulating washer 212 is coated with a melt-processible thermoplastic, for example, a thermoplastic coated polymeric insulating washer 224A (FIG. 52). As a result, as taught by the present invention, the thermoplastic coated insulating washer 212A desirably covers and insulates the glass-containing hermetically sealed insulator 160, which includes the direct bond area at ferrule 112. It is understood that the thermoplastic coated polymeric insulating washer 212A may instead be a nanoparticle-filled 264 thermoplastic insulating washer 211A or a dispensed polymeric insulating material 208, 209 (FIG. 53) with or without insulating nanoparticle 264, respectively. The thermoplastic coated polymeric insulating washer may have nanoparticles 264 in the coating or in the solid polymeric itself. Additionally, the melt-processible thermoplastic coated insulating washer 212A, in comparison with the air or gas gap 135 of FIG. 29B, provides a much higher voltage breakdown strength, thereby favorably increasing the filtered feedthrough 210 active-to-system ground stand-off distance.

FIG. 54A is similar to FIG. 54, except in this embodiment, fixturing or tooling was used during the hermetic sealing process so that the surface of the glass-containing insulator 160 facing the thermoplastic coated polymeric insulating washer 212A is flat (without significant meniscus at and near the terminal pins 111, 114 or the ferrule 112). A flat glass-containing surface enables the use of a stamped or pre-formed solid polymeric insulating washer 212 instead of a dispensable polymeric insulating material. It is understood that the nanoparticle-filled 264 thermoplastic coated polymeric insulating washer 212 or the nanoparticle-filled 264 thermoplastic coated polymeric insulating washers 224A (FIG. 52) may also be used accordingly.

FIG. 54B is similar to FIG. 54A, except that the thermoplastic coated polymeric insulating washer 212A now comprises two thermoplastic coated insulating washers 212A-1 and 212A-2, which are bonded to each other, to the EMI filter capacitor 132 and to the glass-containing insulator 160. It is understood that a nanoparticle-filled 264 polymeric insulating washer 211A may alternatively be used. It is understood that, while two thermoplastic coated polymeric insulating washers 212A-1 and 212A-2 are illustrated, "n" number of polymeric insulating washers 212A or a nanoparticle-filled 264 polymeric insulating washers 211A may be used instead, and in any combination with each other. Multiple thermoplastic coated polymeric insulating washers 212A or 211A or homogeneous thermoplastic washers 224A enhance the high-voltage stand-off distance of the filtered feedthrough 210.

FIG. 54C is very similar to FIG. 54A, except that in this embodiment, a top thermoplastic coated polymeric insulating washer 214A is added. The top thermoplastic coated polymeric insulating washer 214A may be flexible, rigid, or semi-rigid. The top thermoplastic coated polymeric insulating washer 214A may comprise thermoplastic coatings on a solid insulating material, such as a polyimide. In addition to polyimide, the solid insulating material may be mica, nylon, silicone rubber, plastic, ceramic, glass, polytetrafluoroethylene, ethylene tetrafluoroethylene, polycarbonate, polyetherimide, polyoxymethylene, acetal, polyacetal, polyformaldehyde, phenolic, and other similar non-metallic materials, and combinations thereof, or a curable insulating material such as epoxy, polyester, liquid silicone rubber, polyurethane, or other similar materials, and combinations thereof). The top thermoplastic coated polymeric insulating washer 214A may further have an alumina ceramic or a thermosetting plastic or polymeric cover sheet. The thermosetting plastic or polymeric cover sheet may optionally be coated with a thermoplastic or polymeric material, with or without insulating nanoparticles 264. The top thermoplastic insulating washer 214A may alternatively be a top thermoplastic coated polymeric insulating layer with insulating nanoparticles 264.

The top thermoplastic coated polymeric insulating washer 214A is bonded to the top surface of the EMI filter capacitor 132 as shown. In this embodiment, the top thermoplastic insulating washer 214A was not subjected to heat, consequently, it does not conform to the terminal pins 111*a*, 111*b*.

However, the top thermoplastic coated polymeric insulating washer 214A does conform about the terminal pins 111*a*, 111*b* with heat or heat and pressure. For a high-voltage ICD application, the top thermoplastic coated polymeric insulating washer 214A (or alternatively a top nanoparticle-filled 264 polymeric insulating layer) provides several important electrical stand-off qualities: First, this polymeric or alumina washer has a dielectric constant that is much lower than the dielectric constant of the body of the dielectric 147, 149 of the feedthrough capacitor 132. For example, the washer 214A typically has a dielectric constant of about 3 to as high as 10. In contrast, the feedthrough capacitor 132 has a dielectric constant that ranges from a dielectric constant of about 50 up to as high as >2500 k. The thermoplastic coated polymeric insulating washer 214A grades the high-voltage electric field so that there is less electrical stress between the two active terminal pins 111*a*, 111*b* and the capacitor ground metallization 142. Also, less charge pooling occurs by relaxing the HV electric field into air or gas. Charge pooling is the accumulation of pools or micro-coulombs of charge that could result in discharges into the surrounding air or gas. These can be heard as tiny snaps or visualized on a special type of high-voltage dielectric withstanding voltage apparatus that looks for non-linearities in the current during capacitor charging. These current non-linearities are consistent with microcoulomb discharges from such electron charge pools or puddles.

Second, an electrical insulating washer 214 provides additional insulation between the two terminal pins 111*a*, 111*b* themselves, and between the terminal pins 111*a*, 111*b* and capacitor ground metallization 142. In the present invention, one is often referred to the active (terminal pin 111) to ground 142, 112, 248, 250 dielectric stand-off distance or voltage breakdown. In an ICD application, it is often the case that a biphasic pulse is applied between adjacent terminal pins 111*a*, 111*b* where one of them represents the pulse polarity and the other a pulse system ground, which varies with device programming and device electrical engineering architecture. All one really needs to know is that there could be a substantial voltage difference between the two terminal pins 111*a*, 111*b* where arcing can occur from terminal pin to terminal pin or a substantial voltage from any one of the terminal pins 111*a*, 111*b* to the ferrule 112 ground. So, in summary, the thermoplastic coated polymeric insulating washer 214A provides high dielectric breakdown protection between adjacent terminal pins 111*a*, 111*b* and also from any terminal pin to the electrical system ground 124.

Third, insulating layer 214 also helps to protect the capacitor surface 132 against handling marks, scratches or defects that could occur during manufacturing.

Lastly, the top insulating washer 214A provides a pleasing cosmetic appearance to the top of the feedthrough capacitor 132.

Figure 1:
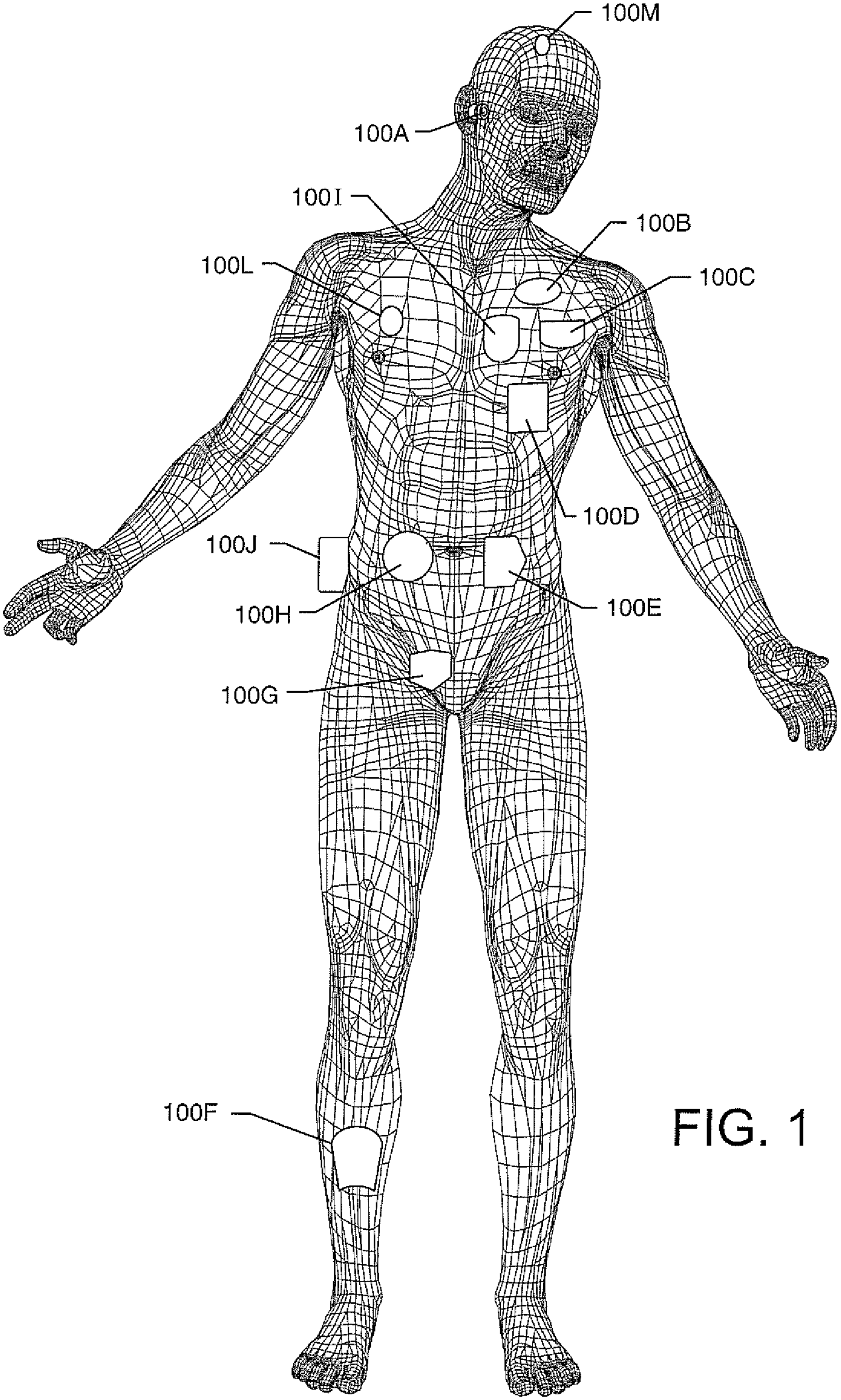
FIG. 1 is a wire-form diagram of a generic human body showing a number of exemplary implantable medical devices.
Figure 4:
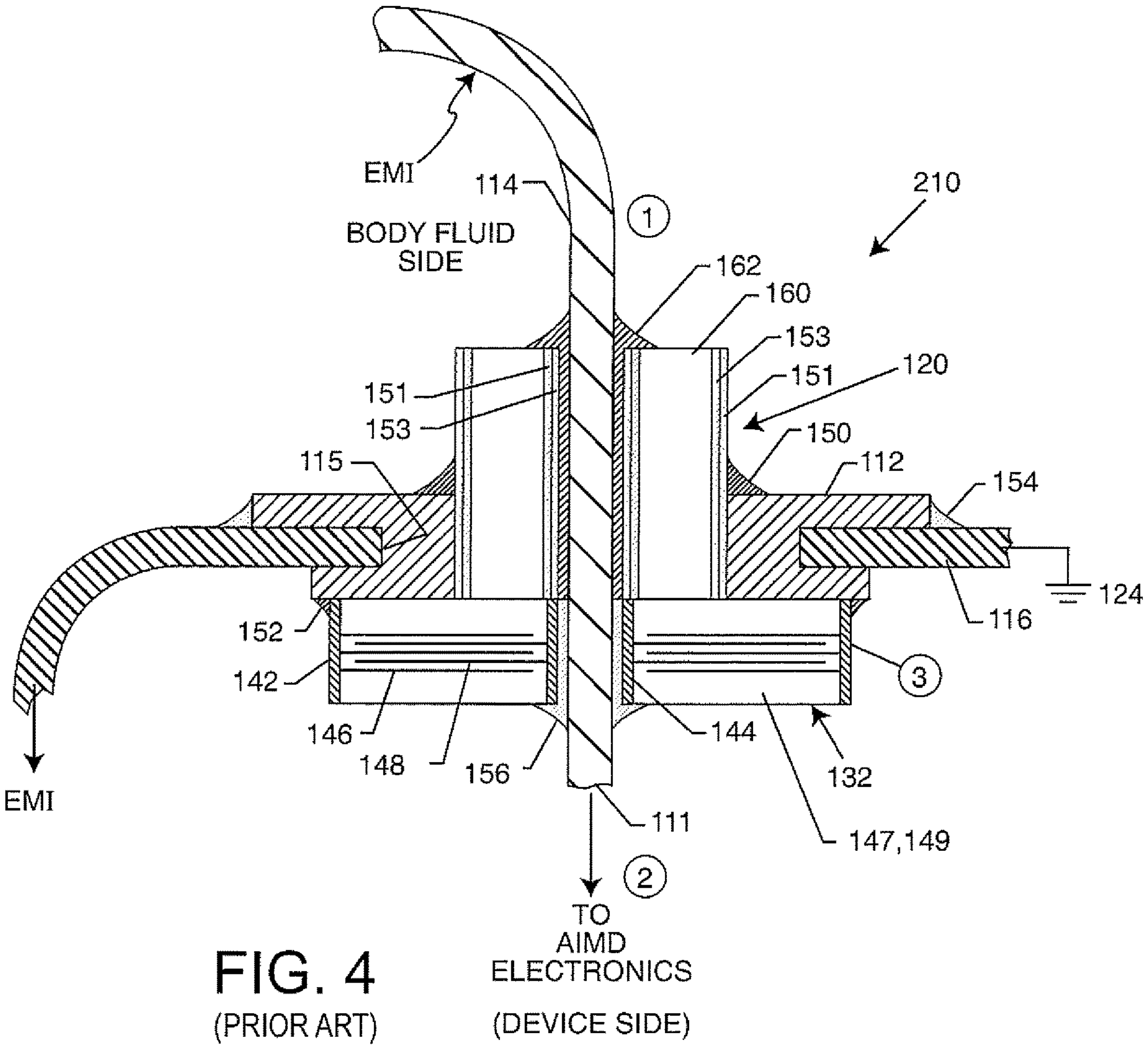
FIG. 4 (PRIOR ART)
FIG. 4 is a cross-sectional view of a prior art hermetically sealed filtered feedthrough.
Figure 4A:
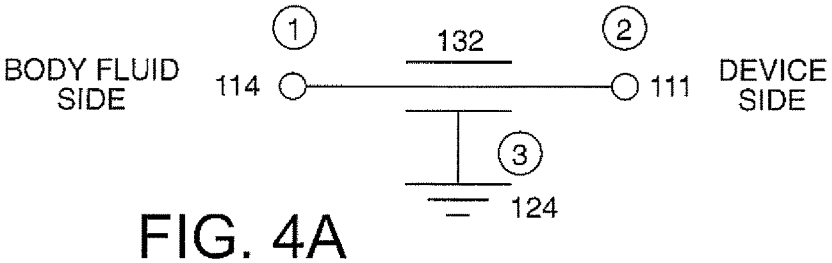
FIG. 4A (PRIOR ART)
FIG. 4A is an electrical schematic representative of the prior art hermetically sealed filtered feedthrough of FIG. 4.

FIGS. 54C-1 through 54C-4 illustrate various embodiments of the filter capacitor composite polymeric insulating washer 214A of FIG. 54C. The insulating washer of FIG. 54 shows double cross-hatching, which is consistent for insulators. The insulative washers and/or adhesives of the blown-up sectional views of FIGS. 54C-1 to 54C-6 show single cross hatching for simplicity. While these embodiments illustrate top or upper washers for an EMI filter capacitor without insulating nanoparticles 264, it is understood that any of the layers within each of these embodiments, individually or in combination, may optionally comprise the insulating nanoparticles 264 previously disclosed by FIG. 51.

FIG. 54C-1 is a blown-up partial view taken from section 54C-1 of FIG. 54C illustrating an embodiment of the composite polymeric insulating washer 214A on top of the ceramic cover sheet 147 of the EMI filter capacitor 132. The structure of the composite polymeric insulating washer 214A has a core polymeric insulating layer 214 to which a bottom thermoplastic coating layer 214*x* is laminated. When the composite polymeric insulating washer 214A is placed against the ceramic cover sheet 147, heat and pressure are applied to the assembly so that the melt-processible thermoplastic coating layer 214*x* melts, acting like an adhesive so that the composite polymeric insulating washer 214A adheres to the filter capacitor ceramic cover sheet 147.

Figure 2:
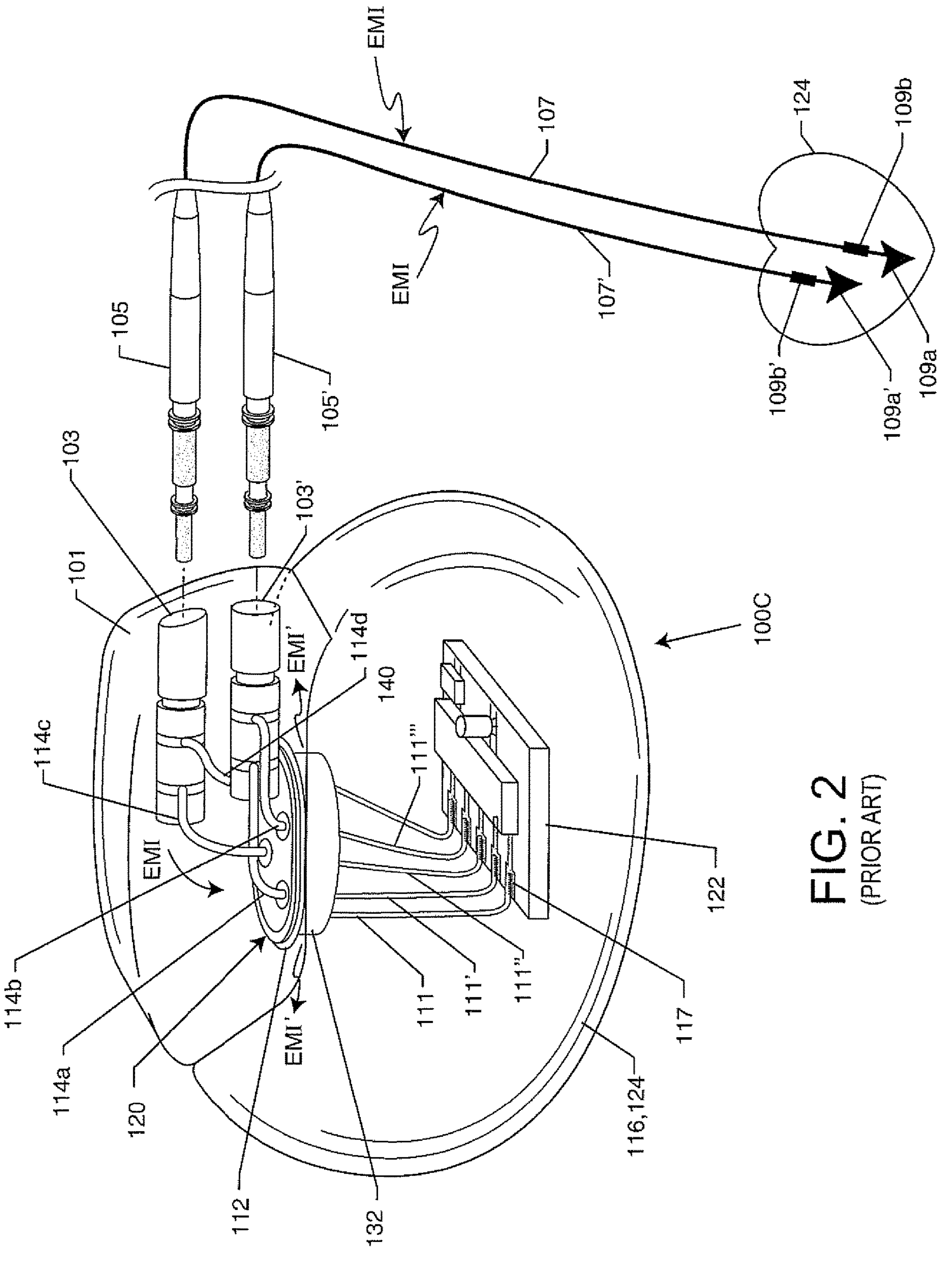
FIG. 2 (PRIOR ART)
FIG. 2 is a side view cutaway of a prior art cardiac pacemaker.

FIG. 54C-2 is a blown-up partial view taken from section 54C-2 illustrating another embodiment of the composite polymeric insulating washer 214A. In this embodiment, the composite polymeric insulating washer 214A has a core polymeric insulating layer 214 to which an optional top thermoplastic coating layer 214*y* and a bottom thermoplastic coating layer 214*x* are laminated. The optional top thermoplastic coating layer 214*y* is recommended for high-voltage applications because it provides for additional high-voltage field relaxation through the surrounding air or gas within the AIMD housing to augment the electric field relaxation already provided by the filter capacitor cover sheet 147. To a high-voltage electrical engineer, this is known as "further grading the field".

Figure 3:
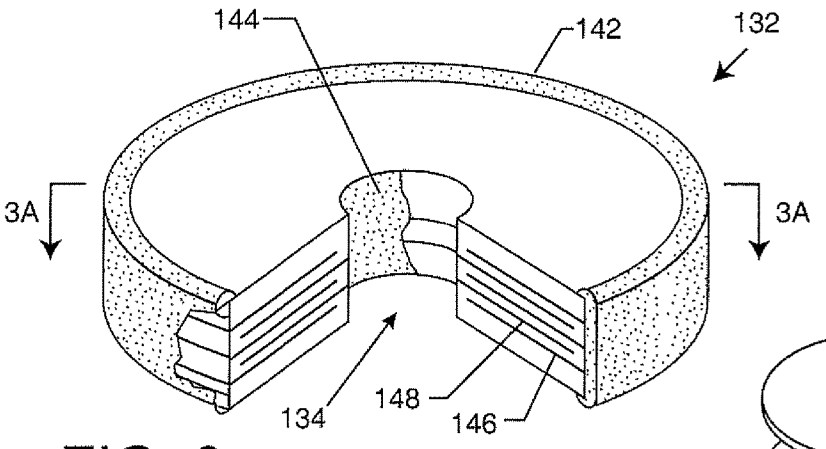
FIG. 3 (PRIOR ART)
FIG. 3 is an isometric cutaway view of a prior art unipolar feedthrough filter capacitor.
Figure 3A:
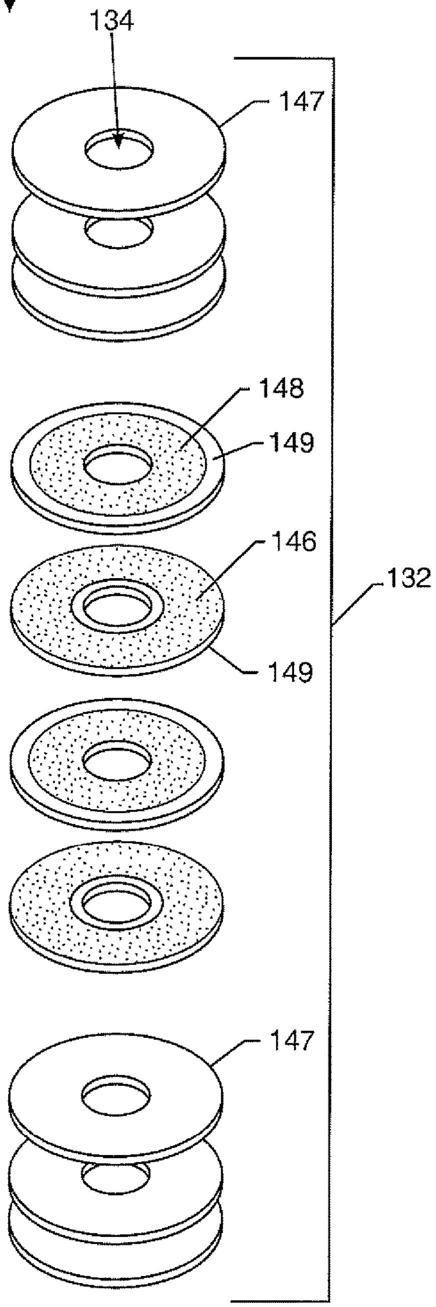
FIG. 3A (PRIOR ART)
FIG. 3A is an isometric exploded view taken generally from section 3A-3A of prior art unipolar feedthrough filter capacitor of FIG. 3.

FIG. 54C-3 is a blown-up partial view taken from section 54C-3 illustrating another embodiment of the composite polymeric insulating washer 214A. In this embodiment, the composite polymeric insulating washer 214A has two polymeric insulating washer layers 214-1 and 214-2, each layer having a different laminated structure. It is understood that while only two polymeric insulating washer layers 214-1 and 214-2 are shown, the filtered feedthrough 210 of FIG. 554C may have any number of polymeric insulating washer layers, including "n" layers. Polymeric insulating washer layer 214-1 has a laminated bottom thermoplastic coating layer 214*x*. The polymeric insulating washer layer 214-2 also has a laminated bottom thermoplastic coating layer 214*y* and an optional laminated top thermoplastic coating layer 214*z*. The assembly process includes placing the first laminated polymeric insulating washer layer 214-1 on top of the EMI filter capacitor 132 of FIG. 52. Then, a second laminated polymeric insulating washer layer 214-2 is disposed on top of the first washer 214-1 so that the surface without the thermoplastic coating layer contacts the first laminated polymeric insulating washer. Heat and pressure are then applied to the assembly to form the multilayer washer structure while at the same time adhering the polymeric insulating washer 214A to the EMI filter capacitor 132 to thereby form the filtered feedthrough 210. It is understood that the order in which the laminated polymeric insulating washer layers 212-1 and 212-2 are disposed may be reversed; however, when the laminated polymeric insulating washer layer 212-2 is the first washer, the surface without the thermoplastic coating layer 212*z* must be oriented to contact the EMI filter capacitor 132. The top thermoplastic coating layer 212*z* is optional for the same reasons as described for FIG. 54C-2.

FIG. 54C-4 is a blown-up partial view taken along section 54C-4 illustrating another embodiment of the composite polymeric insulating washer 214A. In this embodiment, an insulating cover sheet 226, which may be a rigid polymeric or a ceramic, such as alumina, is adhered to the composite polymeric insulating washer 214A. The laminated polymeric insulating washer 214A is disposed on top of the EMI filter capacitor 132 of FIG. 52. Then, the insulating cover sheet 147 is disposed on top of the laminated composite polymeric insulating washer 214A. Heat and pressure are then applied to the assembly so that the insulating cover sheet 226 adheres to the composite washer's thermoplastic coating layer 214$y$ to thereby form the filtered feedthrough 210. Adding the insulating cover sheet 226 further grades a high-voltage electric field as previously disclosed, and also adds substantial protection from mechanical or assembly insults, such as by laser welding, and the like. An example of assembly insult may occur during an AIMD circuit attachment process, such as by soldering, welding, or brazing. Such assembly processes may create spatter or slag. An alumina ceramic insulating cover sheet 226 is protective in that spatter or slag, which is potentially damaging to polymerics, will not penetrate the alumina protecting the composite polymeric insulating washer 214A.

Referring again the FIGS. 54C-1 through 54C-4, the core polymeric insulating layer 214 of the composite polymeric insulating washer 214A may be any of the previously disclosed suitable insulating polymeric materials. The composite polymeric insulating washer 214A may also be an insulating polymeric material having a coefficient of thermal expansion that closely matches the coefficient of thermal expansion of the EMI filter capacitor 132. For example, the core polymeric insulating layer 214 may be the thermoplastic coated polymeric insulating film previously disclosed, which has a CTE of about $21\times10^{-6}/°$ C.

Figure 5:
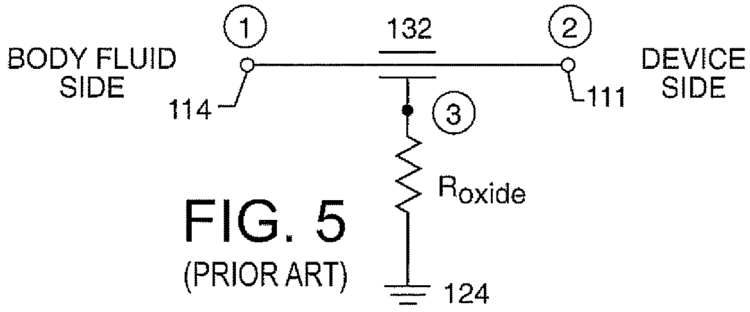
FIG. 5 (PRIOR ART)
FIG. 5 is similar to the electrical schematic of FIG. 4A, except in this case, undesirable an oxide $R_{OXIDE}$ characteristically present on the prior art oxidizable ferrule surface is represented.

FIG. 54C-5 is a blown-up partial view taken from section 54C-5 of FIG. 54C illustrating a homogeneous thermoplastic polymeric insulating washer 228A that has been laminated to an EMI filter capacitor 132 by applying heat and pressure.

FIG. 54C-6 is a blown-up partial view taken from section 54C-6 of FIG. 54C illustrating a homogeneous nanoparticle-filled 264 polymeric insulating washer 227A that has been laminated to an EMI filter capacitor 132 by applying heat and pressure.

FIG. 54D is similar to FIG. 54C except now a top nanoparticle-filled 264 polymeric insulating material 215 or 215A is used to cover the EMI filter capacitor 132 instead of a solid polymeric insulating washer. It is understood that the top polymeric insulating material may alternatively be a top polymeric insulating material 215 or 215A without insulating nanoparticles. The flowability of a dispensable polymeric insulating material permits full coating of the EMI filter capacitor 132 in addition to the area around the hermetically sealed terminal pins 111$a$ and 111$b$, which increases the electrical stand-off distance between terminal pins 111$a$ and 111$b$ and each of the filtered feedthrough terminal pins 111$a$, 111$b$ to the external capacitor ground metallization 142, which is part of system ground 124. Dispensable insulating polymeric materials may be liquid, thermoplastic or B-staged materials, which are cured at elevated temperature or by UV exposure.

FIG. 54E is similar to FIG. 54C except that now two top thermoplastic coated polymeric insulating washers 214A-1 and 214A-2 are disposed. It is understood that two top homogenous nanoparticle-filled 264 insulating washers 227A-1 and 227A-2 may alternatively be used. The two top polymeric insulating washers may further be any insulating polymeric washer material previously disclosed. While two top polymeric insulating washers are illustrated, any number "n" of top polymeric insulating washers may be used. It is understood that the "n" top polymeric insulating washers may be the same material or different materials. It is understood that the "n" top polymeric insulating washers may be the same material or a different material as the polymeric insulating washer between the EMI filter capacitor 132 and the hermetically sealed feedthrough 120. In an embodiment, the top polymeric insulating washers comprise one of an adhesive coated epoxy, a thermoplastic or polymeric material, a thermosetting plastic or polymeric material, a fluorinated polymeric material, a polyimide, a thermoplastic coated polymeric insulating washer, or combinations thereof. In an embodiment, the top polymeric insulating washers are the same material as the polymeric insulating washer between the EMI filter capacitor 132 and the hermetically sealed feedthrough 120.

Referring once again to FIG. 54E, an additional insulating material 235 is shown that both fills the space within the circular washer openings 115 (not labelled) and covers the areas at and about terminal pins 111$a$ and 111$b$. This additional insulating material 235 can comprise any of the insulating polymeric materials previously disclosed including polymeric materials as illustrated, either with or without an insulating nanoparticle 264 filler. The additional insulating material 235 increases the high-voltage stand-off distance between the active terminal pins 111$a$ and 111$b$, and between each active terminal pin 111$a$, 111$b$ and the external capacitor ground metallization 142. Accordingly, the additional insulating material 235 helps prevent active-to-active and/or active-to-ground flashovers or high-voltage arc overs.

FIG. 54F is generally taken from section 54F-54F of FIG. 54E, however, now, instead of the additional insulating material 235, a polymeric insulating tube 222 is disposed about the feedthrough terminal pin after the two top thermoplastic coated polymeric insulating washers 214A-1 and 214A-2 are disposed between the EMI filter capacitor 132 and the hermetically sealed feedthrough 120. Also illustrated is a polymeric insulating tube/washer bond 220 between the polymeric insulating tube 222 and the thermoplastic coated polymeric insulating washer 214A-1. While the polymeric insulating tube 222 may be any polymeric material, because the top thermoplastic insulating washer 216A-1 of the embodiment of FIG. 54F is a melt-processable thermoplastic, a thermoplastic coated polymeric insulating tube is preferred so that both the top thermoplastic coated insulating washers 214A-1 and 214A-2 are bonded to each other and the polymeric insulating tube/washer bond 220 is bonded to the thermoplastic coated polymeric insulating washer 214A-1. By bonding a tube to the top thermoplastic coated polymeric insulating washer, the high-voltage stand-off distances between the active terminal pins 111$a$, 111$b$, and between each active terminal pin 111$a$, 111$b$ and the external capacitor ground metallization 142 are significantly increased. The height of the polymeric insulator tube 222 further increases the stand-off distance, which is desirable for preventing undesirable flashovers or high-voltage arc overs.

FIG. 54G is also generally taken from section 54F-54F of FIG. 54E, however, now, instead of the additional insulating material 235, a polymeric insulating tube 218 is disposed about the feedthrough terminal pin before the two top thermoplastic coated polymeric insulating washers 214A-1 and 214A-2 are disposed between the EMI filter capacitor 132 and the hermetically sealed feedthrough 120. The polymeric insulating tube/washer bond 220 formed at elevated temperature between the polymeric insulating tube 218 and the two top thermoplastic coated polymeric insulating washers 214A-1 and 214A-2 is also illustrated. In this embodiment, the polymeric insulating tube 218 is first placed near or adjacent to the electrical connection material 156, which electrically connects the terminal pin 111$b$ to the passageway capacitor active metallization 144. The polymeric insulating tube 218 has an inside diameter closely matched to the outside diameter of terminal pin 111*b* so that it can easily slip onto the terminal pin 111*b* to seat relatively close to the electrical connection material 156. Once the polymeric insulating tube 118 is in place, the two top thermoplastic coated polymeric insulating washers 216A-1 and 216A-2 are disposed. The inside diameter of the circular washer openings 115 (not labelled) of the two top thermoplastic coated polymeric insulating washers are closely matched to the outside diameter of the polymeric insulating tube 118. During application of heat and/or heat and pressure to the top thermoplastic coated polymeric insulating washers 216A-1 and 216A-2, the polymeric insulating tube/washer bond 220 is made, which significantly increases the high-voltage stand-off distance between the active terminal pins 111*a*, 111*b*, and between each active terminal pin 111*a*, 111*b* and the external capacitor ground metallization 142. The height of the polymeric insulator tube 218 further increases the conductive path, which is desirable in prevention of undesirable flashovers or high-voltage arc overs.

Referring back to FIG. 54G, in an embodiment, the top insulating washer 214A-1 and the side insulating washer 232 (FIG. 54H) can be dispensed in one conformal coating operation. In an embodiment, the side insulation 232 comprises vapor deposited Parylene™ D. The application of Parylene™ D would require masking of the terminal pins 111*a*, 111*b*.

FIG. 54H is similar to FIG. 54A except that an additional polymeric insulating material 232 (231 in FIG. 54I) is disposed about the outside diameter or perimeter of the EMI filter capacitor 132. The additional polymeric insulating material 232 231 in FIG. 54I) fully covers the external capacitor ground metallization 142 and, optionally, the corresponding filter-to-ferrule electrical connection material 152 and gold oxide-resistant pocket pad 248, 250, also as shown. Covering the external ground capacitor metallization 142 using the additional polymeric insulating material 232 (231 in FIG. 54I) desirably increases the high-voltage flashover distance between the active terminal pins 111*a*, 111*b* and 114*a*, 114*b* and the external capacitor ground metallization 142. As previously disclosed, the external capacitor ground metallization 142, the electrical connection material 152, gold oxide-resistant pocket pads 248, 250, and the ferrule 112 are all electrically connected, therefore, when installed into an AIMD housing 116 (not shown), they are at the same potential as the system ground 124. It is understood that the additional polymeric insulating material 232 (231 in FIG. 54I), with or without insulating nanoparticles, respectively, may alternatively be any of the insulating polymeric materials previously disclosed.

FIG. 54I adds two top thermoplastic coated polymeric insulating washers 213*a* and 213*b* to the embodiment of FIG. 54H. Any previously disclosed polymeric insulating materials may be used in combination with or instead of the two thermoplastic coated polymeric insulating washers 213*a* and 2153. The thermoplastic coated polymeric insulating washers are also an option. In an embodiment, the top polymeric insulating washers are polyimide washers may or may not be filled with insulating nanoparticles 264. In an embodiment, the top polymeric insulating washers have an adhesive that is also filled with insulating nanoparticles 264. In a preferred embodiment, the top polymeric insulating washers are adhesively or thermally bonded to the outside diameter or perimeter polymeric insulating material 231. An additional insulating material 235 is disposed within the circular washer openings 115 (not labelled in FIG. 54I) of the two or "n" top polymeric insulating washers to fill washer opening void space and to cover the electrical connection material 156 of the terminal pins 111*a*, 111*b* and 114*a*, 114*b*.

Alternatively, instead of additional insulating material 235, insulating tubes 218 or 222 may be used in a similar manner as shown in FIGS. 54F and 54G. While only two thermoplastic coated polymeric insulating washers are illustrated, it is understood that the top insulating washer of the filtered feedthrough 210 of FIG. 54I can be two washers 213*a* and 213*b* as shown, or "n" number of top insulating washers. In an embodiment, when n is greater than two, thermoplastic coated polymeric insulating washers are co-bonded to each other in a melt process with elevated temperature while applying pressure. In an alternative embodiment, when n is two or greater, the polymeric insulating washers are co-bonded to each other with an adhesive.

FIGS. 55 and 56 illustrate the present invention applied to prior art FIGS. 21 and 22, the specific features of which are best viewed in the cross-sectional view of FIG. 56. FIG. 56 is taken from section 56-56 of FIG. 55 and reveals that the filtered feedthrough 210 comprises an EMI filter capacitor 132 having a top thermoplastic coated polymeric insulating washer 216A, an outside diameter insulating material 232, and a nanoparticle-filled 264 polymeric insulating washer 211 positioned between the EMI filter capacitor 132 and the hermetically sealed feedthrough 120. Because the entire EMI filter capacitor 132 of the filtered feedthrough 210 of FIG. 56 is almost completely surrounded by polymeric insulating materials, the active-to-active and active-to-ground voltage stand-off distances are significantly increased, which, in turn, significantly increases the voltage breakdown strength of filtered feedthrough 210. Voltage breakdown strength may be determined about the exterior of an EMI filter capacitor 132 or interior of a filtered feedthrough 210. The top thermoplastic coated polymeric insulating washer 216A and the outside diameter insulating material 232 of FIG. 56 act together to provide superior high-voltage breakdown strength about the exterior of an EMI filter capacitor 132. The exterior of an EMI filter capacitor 132 of FIG. 56 is also the device side of the filtered feedthrough 210. The nanoparticle-filled 264 polymeric insulating washer 211 positioned between the EMI filter capacitor 132 and the hermetically sealed feedthrough 120 provides the filtered feedthrough 210 with superior high-voltage breakdown strength between the EMI filter capacitor 132 and the hermetically sealed feedthrough 120, which is defined as the interior high-voltage breakdown. The interior high-voltage breakdown strength of the filtered feedthrough 210 occurs between the body fluid side of the EMI filter capacitor 132 and the device side of the hermetically sealed feedthrough 120 of the filtered feedthrough 210. The active-to-active and active-to-ground voltage stand-off distances are better understood by examining the insulating materials between the designated plus (+) and minus (−) signs of FIG. 56. The active-to-active HV stand-off distance is equally important for example between terminal pins 111*a* and 111*c*, which is improved by the top washer 216A.

The interior active-to-ground increased stand-off distance of FIG. 56 spans from the plus (+) sign at the device side terminal pin 111*c* to the minus (−) sign at the gold braze 150 at the surface of ferrule 112. The exterior HV stand-off distance extends from the top thermoplastic coated polymeric insulating washer 216A at the OD of terminal pin 111*c*, across the capacitor passageway electrical connection material 156, the passageway active capacitor metallization 144 and the external ground capacitor metallization 142, continuing with the insulating material 232 extending along the surface of the filter-to-ferrule electrical connection material 152 until the surface of the ferrule 112 is reached.

In contrast, FIG. 22 has no top or perimeter insulating materials on the filtered feedthrough 210 illustrated; consequently, without any insulating materials on and about the external device side surfaces of EMI filter capacitor 132, the passageway active filter capacitor metallization 144 is actually positioned physically closer to the external ground capacitor metallization 142, thus providing a much shorter active-to-ground stand-off distance. Applying the present invention to the prior art filtered feedthrough of FIG. 22 substantially increases the high-voltage stand-off distance, which correspondingly significantly increases the flashover and/or arcing high-voltage breakdown strength of the filtered feedthrough 210 of FIG. 56.

Regarding the interior active-to-ground stand-off distance of the filtered feedthrough 210 of FIG. 56, which spans from the plus (+) sign at the gold braze 162 hermetically sealing the terminal pin 111_c_, 114_c_ and the feedthrough insulator 160 to the minus (−) sign at the gold braze 150 hermetically sealing the feedthrough ferrule 112 and insulator 160. The interior stand-off distance extends from the edge of the insulating nanoparticle-filled 264 polymeric insulating washer 211 at the terminal pin-to-insulator gold braze 162, continuing along the feedthrough surface covering the feedthrough insulator pathway metallizations (not labelled), the device side surface of the feedthrough insulator 160, the perimeter insulator metallizations (not labelled), and the portion of ferrule-to-insulator gold braze 150 to the opposite edge of the nanoparticle-filled 264 polymeric insulating washer 211 at electrical connection material 152. In the embodiment of FIG. 56, the nanoparticle-filled 264 polymeric insulating washer 211 is fully adhered (that is, free of defects, particularly delamination or separation) to the body fluid side surface of EMI filter capacitor 132 and to the device side surface of the hermetically sealed feedthrough 120 of the filtered feedthrough 210. More importantly, even though the interior active-to-ground stand-off distance of the embodiment of FIG. 56 is equivalent to that of the prior art embodiment of FIG. 22, because the insulating washer between the EMI filter capacitor 132 and the hermetically sealed feedthrough 120 of FIG. 56 is a nanoparticle-filled 264 polymeric insulating washer 211 instead of the conventional polymeric insulating washer 212 of FIG. 22, the high-voltage breakdown strength of the filtered feedthrough 210 of FIG. 56 will be greater than the high-voltage breakdown strength of FIG. 22.

Moreover, as previously disclosed, the presence of the uniformly dispersed insulating nanoparticles 264 of the filled polymeric insulating washer 211 substantially decreases catastrophic high-voltage pulse breakdown, which can lead to high-voltage arcing, flashovers, or avalanche breakdown. In contrast, high-voltage ICD pulses have been known to form carbon tracks within conventional polymeric insulating washers, such as the polymeric insulating washer 212 of FIG. 22. When such carbon tracks do form, they have experimentally been shown to initiate high-voltage arcing, flashovers and/or avalanche breakdown. It is understood that high-voltage ICD pulses may have opposite polarity from terminal pin 111_a_, 111_c_ to the ground ferrule 112 or from a first terminal pin 111_a_ to a second terminal pin 111_c_. Accordingly, the stand-off distance and the integrity of the polymeric insulating washer 212 between any two terminal pins 111_a_, 111_c_ is equally as important as the stand-off distance from terminal pin 111_a_, 111_c_ to ground ferrule 112.

FIG. 56A is taken from section 56A-56A of FIG. 56 and illustrates an alumina or other ceramic insulating cover sheet 226 bonded to the top surface of a homogenous thermoplastic insulating washer 216A. The insulating cover sheet 226 may also be a polymeric material instead of a ceramic. The addition of an insulating cover sheet 226 further grades high-voltage electric fields and provides a high degree of physical protection to the EMI filter capacitor 132.

FIGS. 57 and 58 illustrate a second polymeric insulating material 208 and an oxide-resistant metal addition 218. The second polymeric insulating material 208 may alternatively comprise a nanoparticle-filled 264 second polymeric insulating material 209 (FIG. 59). In each embodiment, the gold braze 150 and the associated metallizations 151, 153 are positioned below the ferrule surface 113 so that an open space 140 is formed for the second polymeric insulating material 208 (or 209) to be disposed therein. The additional insulating polymeric material (with or without insulating nanoparticles) works in concert with the polymeric insulating washers 212 (FIG. 57) or 212A (FIG. 58) to increase the dielectric breakdown strength and/or stand-off distance of the filtered feedthroughs 210 so that electrical breakdown and/or flashover do not undesirably occur.

Regarding metal additions, the metal addition 218 of FIG. 57 is round, while the metal addition 218 of FIG. 58 is rectangular. The metal addition 218 is attached to the ferrule 112 by a laser weld 154 as illustrated. Alternatively, the metal addition 218 may be gold brazed to the ferrule 112 (not shown). The metal addition 218 may comprise any of the oxide-resistant materials previously disclosed, such as, but not limited to, platinum, palladium, gold, rhodium, and their alloys. The metal addition 218 may also comprise platinum-iridium alloys, palladium-iridium alloys, nitinol, titanium nitride, cobalt-chromium alloys, and combinations thereof. The use of an oxide-resistant metal addition 218 allows low impedance, low resistance electrical ground connections to the EMI filter capacitor 132. Oxide-resistant metal additions are disclosed in U.S. Pat. No. 9,427,596, the contents of which are fully incorporated herein by this reference.

FIG. 59 illustrates a cross section similar to that of FIG. 57 except now a polymeric insulating material 232 covers the perimeter or diameter of the attached EMI filter capacitor 132, a nanoparticle-filled 264 polymeric insulating washer 211 and the additional insulating material 209. It is understood that a nanoparticle-filled 264 polymeric insulating material 231 may alternatively be used instead of the perimeter or diameter polymeric insulating material 232. The nanoparticle-filled 264 polymeric insulating washer 211, which is located between the EMI filter capacitor 132 and the hermetically sealed feedthrough 120, is used instead of the polymeric insulating washer 212 of FIG. 57 to increase the breakdown strength of the filtered feedthrough 210. The nanoparticle-filled 264 additional insulating material 209, which is located between the feedthrough insulator 160 and the feedthrough ferrule 112, is used instead of the additional insulating material 208 of FIG. 57 to further increase the breakdown strength of the filtered feedthrough 210. The perimeter or diameter polymeric insulating materials 231 (FIG. 54I) and 232, polymeric insulating washers 211 (FIG. 54I) and 212, and the additional insulating materials 209 (FIG. 53) and 208, with or without insulating nanoparticles, respectively, apply to all embodiments having a hermetically sealed ferrule-to-insulator gold braze 150 and a reduced active-to-system ground 124 stand-off distance and/or are susceptible of direct electrical shorting, regardless of the application.

FIG. 59A shows a characteristic ICD pulse, which is typically biphasic, and which occurs very quickly. The ICD pulse exhibits a $V_{MAX}$ at the plus (+) sign along with some overshoot with ringing. Such high-frequency ringing is due to an inductance between the uncharged EMI filter capacitor 132 and the high-energy storage capacitor (not shown) of the ICD. The plus (+) sign is indicated at the first phase of the biphasic pulse (which, as shown, is positive), while a minus (−) sign is indicated at the second phase of the biphasic pulse (which, as shown, is a negative). In general, the use of plus (+) and minus (−) signs is arbitrary because implanted biphasic ICDs deliver current in two directions. In the first phase, current moves from one implanted electrode along the cells of heart tissue to the other implanted electrode. During the second phase, the current flow in a reverse direction. As such, in the embodiments of the present application, it is understood that a plus (+) sign assigned, for example, to an active terminal pin or terminal pin and a minus (−) sign assigned, for example, to system ground, are also arbitrary due to the fact that biphasic ICDs deliver current in two directions. This means that when a patient's heart is subjected to a defibrillation cycle, the active terminal pin or terminal pin and the system ground change positive (+) and negative (−) polarities when the direction of the current in the first phase of the pulse reverses direction in the second phase, thereby completing one biphasic defibrillation cycle. It is appreciated that device programming and device architecture can define which terminal pin or pins (active or ground) are positive (+) and which are negative (−) at any particular time and in any particular filtered feedthrough embodiment.

FIG. 59B is a blown-up partial view generally taken from section 59B-59B of FIG. 59 except that now delamination gaps 234, 236 and 238 are shown between the EMI filter capacitor 132 and the nanoparticle-filled 264 polymeric insulating washer 211, between the nanoparticle-filled 264 additional polymeric insulating material 209 and the nanoparticle-filled 264 polymeric insulating washer 211, and between the nanoparticle-filled 264 additional polymeric insulating material 209 and the nanoparticle-filled 264 polymeric insulating washer 211 and ferrule 112, respectively. It is understood that while the embodiment of FIG. 59B illustrates delamination gaps associated with the nanoparticle-filled 264 polymeric insulating washer 211 and the nanoparticle-filled 264 additional polymeric insulating material 209, such delamination gaps 234, 236 and 238 can form with any of the polymeric insulating materials disclosed herein and within any filtered feedthrough, including any of the filtered feedthrough 210 embodiments disclosed herein.

As previously disclosed, for medical implantable devices, electrical shorting can particularly be dangerous and life-threatening to implant patients. The electrical connection materials 152 or 156 do not need to make direct electrical contact (short) to be dangerous because, for high-voltage applications, a reduced active-to-system ground 124 stand-off distance can result in a gas gap avalanche causing breakdown or arcing through the gas (air or nitrogen). As shown in FIG. 59B, with partial delamination 234 or 238 around insulating washer 211, there can be a combination of gas gap avalanches and bulk material breakdown. In other words, if the stand-off distance across the insulating washer is too short, a high-voltage breakdown through the material of the insulating washer 211 itself can occur. In summary, there can be gas gap avalanches or arcs or a combination of a gas gap avalanche and a high-voltage material breakdown. The open space or gap in an active-to-system ground 124 stand-off distance can be a separation, a delamination, a disconnection, a disjunction, a hole, an opening, a break, a cavity, a space, a gas bubble, or any such interruption that functions as a gap through which electrical breakdown or arcing between the bottom of the filter capacitor 132 and the polymeric insulating washer 211 and/or between the polymeric insulating washer 211 and/or the ferrule 112 can occur.

Particularly noteworthy is that high volts per mil or enhanced electric field intensities can occur in these thin open spaces (air gaps), particularly during high-voltage biphasic ICD pulsing therapy, resulting in a catastrophic avalanche breakdown that essentially destroys an implanted life-saving therapy delivery device. This is why the additional insulating material 209 (or optionally 208 shown in FIGS. 57 and 58) becomes very important since it adds a second protective layer of insulation over the gold braze 150. It is appreciated that both insulating materials 208 and 209 independently provide an additional layer of protection, however, two or more additional insulating layers 208 and 209 in any combination can also be added. In other words, there could be "n" layers of additional insulation. The polymeric insulating washer 211 or 212 and polymeric insulating material 208 or 209 acting together make catastrophic electrical shorting due to open space or delamination gaps much more unlikely. When resistance to delamination is unknown, it is preferred that nanoparticle-filled 264 polymeric insulating materials and washers be used instead of conventional polymeric insulating materials, as the addition of nanoparticles 264 to a polymeric insulating material or washer substantially increase electrical breakdowns in the remaining non-delaminated section.

Delamination gaps can occur during filtered feedthrough assembly and/or testing, implantable device manufacturing and/or testing, or, latently, while delivering high-voltage therapy. Delamination gaps may be caused by high temperature exposure or large swings in temperature. For example, installing a filtered feedthrough by laser welding the feedthrough ferrule 112 into an opening of the AIMD housing 116 subjects the filtered feedthrough to high temperatures, which can cause substantial heating of the filtered feedthrough 210. CTE mismatches within a filtered feedthrough 210 worsens any thermally induced stresses, particularly between mating materials that have mismatched CTEs. The delamination gaps can result, for example, from shrinkage rate differences caused by such CTE mismatches, particularly shrinkage rate differences between the insulating material and the material to which the insulating material is adhered. Delamination gaps may also result from mechanical stresses that are either applied or develop within the filtered feedthrough from therapy delivery. For example, mechanical stresses can develop within the EMI filter capacitor 132 when a high-voltage pulse having a fast rise-time induces a piezoelectric effect therewithin. A ceramic EMI filter capacitor, such as those described throughout this specification, generally undergoes mechanical expansion and contraction due to piezoelectric effects, which are directly resultant from high-voltage therapy delivery. Delamination gaps may be partial, as shown by FIG. 59B, or full, meaning across the entire surface to which the insulating material is adhered. Partial delamination, such as the delamination gaps 234, 236, and 238 are characterized by a thin physical separation of the polymeric insulating washer (such as the nanoparticle-filled 264 polymeric insulating washer 211 of FIG. 59B) or cured polymeric insulating material (such as the nanoparticle-filled 264 polymeric insulating material 209 of FIG. 59B) from the mating material surface, creating a gap, in other words, a void space, that subsequently becomes filled by either air or a gas. Even partial delamination gaps at the terminal pin due to high-voltage electric field concentration can lead to catastrophic failure due to high-voltage arcing or avalanche breakdown. A full delamination gap imparts a higher high-voltage gas avalanche breakdown risk.

Referring again to the biphasic ICD pulse of FIG. 59A, the fast rise-time of the high-voltage biphasic pulse during therapy delivery induces a piezoelectric mechanical stress response of the ceramic EMI filter capacitor 132, which may cause one or more delamination gaps illustrated in FIG. 59B. The induced piezoelectric mechanical stress response during the application of the high-voltage pulse mechanically moves the ceramic EMI filter capacitor 132 when the ceramic capacitor expands and contracts. Expansion and contraction can occur in only one axis or in multiple axes; nonetheless, the expansion and contractions can sufficiently mechanically stress the bond between the EMI filter capacitor 132 and one or more of the nanoparticle-filled 264 polymeric insulating materials 211 and 231, or between the nanoparticle-filled 264 polymeric insulating washer 211 still adhered to the EMI filter capacitor 132 and the additional nanoparticle-filled 264 polymeric insulating material 209, as illustrated. Furthermore, as the current delivered by a biphasic ICD pulse is reversible, the induced piezoelectric mechanical expansion and contraction action can violently occur during current flow reversal (meaning as current flow changes positive (+) and negative pulse phases) due to such sudden and rapid pulse phase reversal.

Regardless of the type of insulating materials used, the effect of the delamination gaps of FIG. 59B on the breakdown strength of the filtered feedthrough 210 is better understood by examining the impact each delamination gap 234, 236 and 238 has on its corresponding active-to-ground voltage stand-off distance, which is indicated between corresponding plus (+) and minus (−) signs. The plus (+) sign indicates positive (+) potential, and the minus (−) sign indicates negative potential. As such, the EMI filter capacitor 132 active electrode plates 148, the EMI filter capacitor 132 passageway active capacitor metallization 144, the capacitor passageway electrical connection material 156, the feedthrough insulator 160 adhesion and wetting metallizations 153*a*, 151*a*, the terminal pin-to-insulator gold braze 162 and the terminal pins 111*b*, 114*b* are all at a positive (+) potential. Similarly, the EMI filter capacitor 132 ground electrode plates 146, the EMI filter capacitor 132 external ground capacitor metallization 142, the EMI filter capacitor 132 perimeter metallization electrical connection material 152, the metal addition 218, the ferrule 112, the ferrule-to-insulator gold braze 150, and the feedthrough insulator 160 adhesion and wetting metallizations 153*b*, 151 *b* are all at negative (−) potential.

Further regarding delamination gaps, the inventors have performed high-frequency Fourier analysis of the pulse rise-time converting the biphasic pulse from the time domain into the frequency domain. In mathematical terms, this results in the first sinusoidal component of the Fourier transform being about 13 MHz. Such a high-frequency pulse will arc over or break down at a lower voltage than the voltage of a low frequency pulse or a DC high-voltage application. Accordingly, the high-frequency components and ring up of a fast rise time ICD pulse has a greater tendency to flashover or arc over in enhanced electric field stress areas formed by any gaps, for example, the delamination gaps 234, 236 or 238 shown in FIG. 59B. The delamination gaps illustrated in FIG. 59B are dangerous because the air or gas in the gaps has orders of magnitude lower HV breakdown strength than the nanoparticle-filled 264 polymeric insulating materials 211, 209. However, the HV breakdown strength of the nanoparticle-filled 264 polymeric insulating materials 211, 209 is much greater (even orders of magnitude greater) than non-nanoparticle filled polymeric materials so that that even if partial delamination exists, as illustrated, the increased breakdown strength can mitigate catastrophic avalanche breakdown.

It is understood that the second insulating material with or without nanoparticles 264 applies to all embodiments having a hermetically sealed ferrule-to-insulator gold braze 150 and a reduced active-to-system ground 124 stand-off distance and/or susceptibility of direct electrical shorting, regardless of the application.

FIG. 60 is very similar to FIG. 58 except now distances x and y are illustrated. The x and y distances indicate the electrical stand-off distances between positive (+) and negative (−) potentials. This is ideal since insulation materials 209 and 211 are bonded very well and have no delamination gaps.

FIG. 61 illustrates the present invention applied to a prior art EMI filter circuit board 155 demonstrating that a top polymeric insulating material 215 or 216, with or without insulating nanoparticles 264, respectively, may be disposed on top of the circuit board 155. In the embodiment of FIG. 61, the top polymeric insulating material 215 or 216 is disposed over both the surface of the EMI filter circuit board 155 and the exposed surfaces of each MLCC chip capacitor 194, thereby insulating not only between each active terminal pin 111*a* through 111*f*, but also between each MLCC chip capacitor 194 and its vias and circuit traces (not shown) to increase the electrical breakdown strength of the EMI filter circuit board 155, particularly against any high-voltage insult, such as an external cardiac defibrillation or from an implanted high-voltage ICD therapy delivery. By coating both the surfaces at the active terminal pins 111*a* through 111*f* of the EMI filter circuit board 155 and the exposed surfaces of each MLCC chip capacitor 194, the electrical stand-off distance between the active terminal pins 111*a* through 111*f* (active-to-active stand-off distance) and between the active terminal pins 111*a* and 111*f* and ground, which in this embodiment is the ground terminal pin 111 and system ground 124 (active-to-ground stand-off distance), is significantly increased. As previously disclosed, the presence of the top polymeric insulating material 215 or 216 relaxes the high-voltage electric fields of the relatively high dielectric constant MLCC chip capacitors 194 so that the high-voltage electric fields are spread through the surrounding air or gas. It is understood that the embodiment taught by FIG. 61 equally applies to all EMI filter circuit board configurations. In addition to the illustrated EMI filter circuit board 155 having MLCC chip capacitors 194, other EMI filter circuit board configurations include all EMI filter circuit boards 155 having X2Y attenuators 198 and/or flat-thru capacitors 196. EMI filter circuit boards having X2Y attenuators 198 and/or flat-thru capacitors 196 are more thoroughly described in U.S. Pat. No. 11,406,817, the contents of which are fully incorporated herein by this reference.

FIG. 62 is a cross-sectional view of a novel hybrid filtered feedthrough 210 comprising an asymmetrical hybrid internally grounded filter capacitor 138 that is electrically connected to a hermetically sealed feedthrough 120. In this embodiment, the hermetically sealed feedthrough 120 has two feedthrough insulators 160*a* and 160*b* separated by a ferrule bridge 141. Feedthrough insulator 160*a* residing on the left side of the novel hybrid filtered feedthrough 210 has three active terminal pins 111*a* through 111*c* that are hermetically sealed by gold braze 162, while feedthrough insulator 160*b* residing on the right side of the novel hybrid filtered feedthrough 210 has four active terminal pins 111*d* through 111 *g* that are hermetically sealed by gold braze 162. A ground terminal pin 111*gnd* is electrically connected to the ferrule bridge 141 of the feedthrough ferrule 112 by a ground terminal pin-to-ferrule gold braze 150'.

Accordingly, EMI filter capacitor 138 has seven corresponding active capacitor passageways, each having a passageway active capacitor metallization 144 and one ground capacitor passageway having a passageway ground capacitor metallization 142. The three active capacitor passageways on the left side of EMI filter capacitor 132 receive active terminal pins 111*a*-111*c* hermetically sealed to feedthrough insulator 160*a*, and the four active passageways on the right side of EMI filter capacitor 132 receive active terminal pins 111*d*-111*g* hermetically sealed to feedthrough insulator 160*b*. The one ground capacitor passageway between the active capacitor passageways in which active terminal pin 111*c* (on the left) and active terminal pin 111*d* (on the right) are disposed, receives ground terminal pin 111*gnd*.

All the active terminal pins 111*a* through 111*g* are electrically connected to their corresponding passageway active capacitor metallizations 144 and the internal ground terminal pin 111*gnd* is electrically connected to its corresponding passageway ground capacitor metallization 142 by electrical connection material 156. The left and right sides of the EMI filter capacitor 132 are asymmetric in that the distance between the active capacitor passageway electrically connected to terminal pin 111*a* and the edge ground capacitor metallization 142 on the left side is notably greater than the distance between the active capacitor passageway electrically connected to terminal pin 111*g* and the edge ground capacitor metallization 142 on the right side. Additionally, the right side of the EMI filter capacitor 132 extends beyond the edge of the feedthrough insulator 160*b*, over the ferrule-to-insulator gold braze 150 and a portion of the ferrule 112, while the left side of the EMI filter capacitor 132 approximately ends at the edge of the feedthrough filter insulator 160*a* and is aligned on top of the ferrule-to-insulator gold braze 150.

To provide oxide-resistant ground electrical connections between the asymmetric EMI filter capacitor 132 and the hermetically sealed feedthrough 120, the right-side edge ground capacitor metallization 142 is electrically connected to a gold oxide-resistant pocket-pad 250, while the left side edge ground capacitor metallization 142 is electrically connected to the ferrule-to-insulator gold braze. Both sides use electrical connection material 152. In addition to enabling oxide-resistant ground electrical connections using the illustrated asymmetrical hybrid internally grounded filter capacitor 138, such ground electrical connections (meaning the internal ground electrical connection of feedthrough terminal pin 111*gnd* and passageway ground capacitor metallization 142, and the external ground electrical connections of the right side edge ground capacitor metallization 142 and the gold oxide-resistant pocket-pad 250, and the left side edge ground capacitor metallization 142 and the ferrule-to-insulator gold braze 150) provide the novel hybrid filtered feedthrough 210 of FIG. 62.

Furthermore, when the ferrule-to-insulator gold braze 150 is particularly close to a feedthrough active terminal pin, for example, the relatively close distance between the active terminal pin 111*g* of FIG. 62 and the ferrule-to-insulator gold braze 150, then, irrespective of capacitor symmetry, electrically connecting the edge ground capacitor metallization 142 of the EMI filter capacitor 132 to an oxide-resistant pocket-pad 250 to form a ground electrical connection becomes particularly useful. That is, electrically connecting to the oxide-resistant pocket-pad 250, such as shown by the hybrid filtered feedthrough 210 of FIG. 62, increases the active-to-ground stand-off distance.

Further regarding the novel hybrid filtered feedthrough 210 of FIG. 62, different polymeric insulating washers are shown residing between the EMI filter capacitor 132 and the hermetically sealed feedthrough 120. A prior art polymeric insulating washer 212 or novel 212A thermoplastic coated polymeric insulating washer resides on the left side of the hybrid filtered feedthrough 210, while a polymeric insulating washer 211 or 211A with insulating nanoparticles 264 resides on the right side. The use of the nanoparticle-filled 264 polymeric insulating washers 211 or 211A on the right side further increases dielectric breakdown, which can be important depending on the length of the active-to-ground stand-off distance (particularly in the case when partial delamination as shown in FIG. 59B has occurred).

Figure 39:
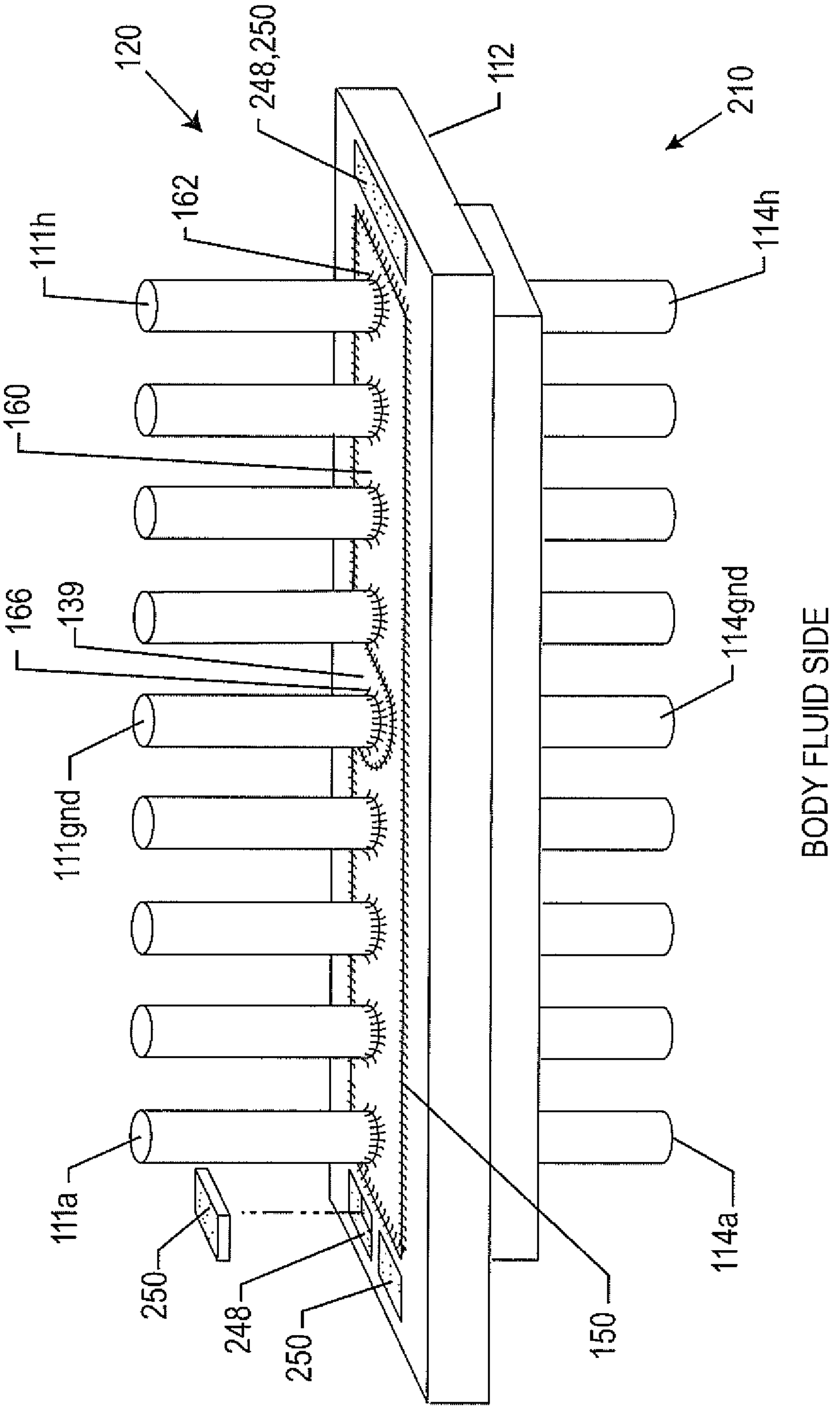
FIG. 39 (PRIOR ART)
FIG. 39 is similar to FIG. 36, except that the central feedthrough ground terminal pin is electrically attached to a ferrule peninsula.
Figure 40:
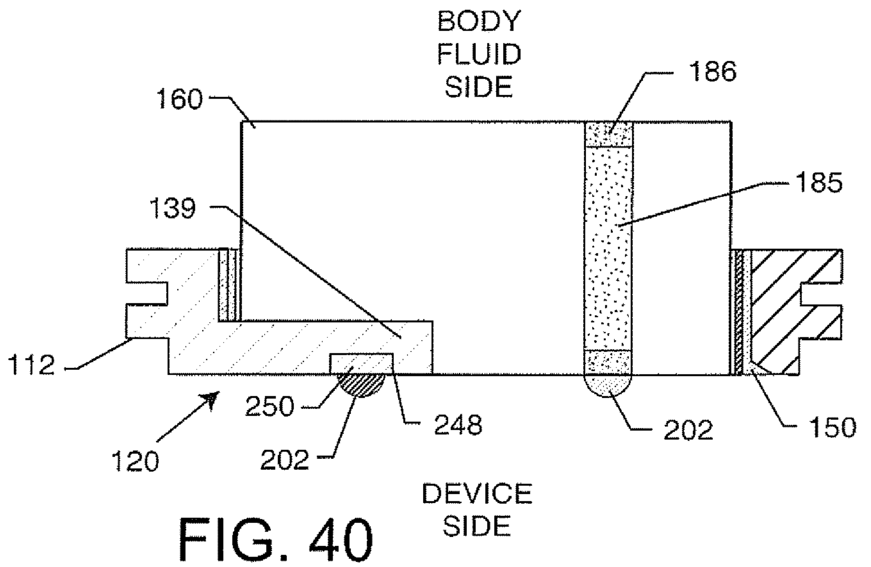
FIG. 40 (PRIOR ART)
FIG. 40 is a cross-sectional view illustrating a prior art oxide-resistant pocket pad in a ferrule peninsula and a co-sintered filled via conductive pathway extending through the insulator of the hermetically sealed feedthrough.

It is understood that the ferrule 112 of the hermetically sealed feedthrough 120 of the hybrid filtered feedthrough 210 of FIG. 62 may have a ferrule peninsula 139 (FIG. 39) instead of a ferrule bridge 141. Accordingly, the hermetically sealed feedthrough 120 of the hybrid filtered feedthrough 210 would likely have only one feedthrough insulator 160 instead of two 160*a* and 160*b*. Whether the hybrid filtered feedthrough 210 of FIG. 62 comprises two feedthrough insulators 160*a* and 160*b* or just one 160, either a symmetrical or an asymmetrical hybrid internally grounded filter capacitor 138 may be used to form the hybrid filtered feedthrough 210 or, the hybrid filtered feedthrough 210 may comprise a symmetrical or an asymmetrical hybrid grounded EMI filter capacitor 132 (edge ground ferrule-to-insulator gold braze 150 and gold oxide-resistant pocket 250 electrical connections but absent an internal ground terminal pin-to-ferrule electrical connection).

Additionally, since the hybrid filtered feedthrough 210 may comprise a feedthrough ferrule 112 having either a ferrule bridge 141 (therefore two feedthrough insulators 160*a* and 160*b*) or a ferrule peninsula 139 (therefore one feedthrough insulator 160), when there are disparate active-to-ground stand-off distances (i.e., the length of one active-to-ground stand-off distance is less than the other active-to-ground stand-off distance), both ferrule embodiments may embody different insulating washers in order to enhance the electrical breakdown strength depending on the length of each active-to-ground stand-off distance. FIG. 62 addresses ferrule bridge 141 filtered feedthrough 210 embodiments. Regarding filtered feedthrough 210 embodiments comprising a hermetically sealed feedthrough 120 with only one feedthrough insulator 160, either the first or the second insulating washer must be custom cut to mate with the other so as to fully cover the feedthrough insulator 160 including the insulator portion at the ferrule peninsula 139.

FIGS. 62A, 62B and 62C are cross-sectional edge views illustrating various configurations that impart asymmetry to a filtered feedthrough 210. FIG. 62A shows a cross-sectional edge view of an asymmetric hybrid filtered feedthrough 210 illustrating an EMI filter capacitor 132 electrically connected to an asymmetrical hermetically sealed feedthrough 120 comprising an asymmetrical ferrule 112 and an asymmetrical insulator 160. The asymmetrical insulator 160 has a feedthrough terminal pin 111 that is much closer to the right side of the ferrule 112 than it is to the left side of the ferrule 112 (which renders an asymmetric feedthrough insulator 160). The right side of the ferrule 112 is wider than the left side (which renders an asymmetric feedthrough ferrule 112) with a ferrule pocket-pad 250 so that an electrical connection material 152 can electrically connect the external ground capacitor metallization 142 of the EMI filter capacitor 132 to the ferrule 112 gold oxide-resistant pocket-pad 250, thereby increasing the right side active-to-ground stand-off distance.

The filtered feedthrough electrical breakdown resistance is also enhanced by using a nanoparticle-filled 264 polymeric insulating washer 211 or 211A. It is understood that a polymeric insulating washer 212 or 212A without insulating nanoparticles may be used instead of the nanoparticle-filled 264 polymeric insulating washer 211 or 211A. The thermoplastics disclosed herein, in general, comprise either a thermoplastic coated polymeric insulating washer or a homogeneous polymeric insulating washer. In this embodiment, the nanoparticle-filled 264 polymeric insulating washer 211 completely covers the right-side gold braze 150 so that the active-to-ground stand-off distance extends from the active terminal pin-to-insulator gold braze 162 to the ground gold oxide-resistant pocket-pad 250 instead of to the ferrule-to-insulator gold braze 150. On the left side, the external ground capacitor metallization 142 is electrically connected to the gold braze 150 using electrical connection material 152, thereby forming an asymmetrical hybrid filtered feedthrough 210.

FIG. 62B is similar to FIG. 62A except that the ferrule 112 on the left side is wider. FIG. 62B shows a cross-sectional edge view of an asymmetric hybrid filtered feedthrough 210 illustrating an EMI filter capacitor 132 electrically connected to an asymmetrical hermetically sealed feedthrough 120 comprising an asymmetrical insulator 160. The asymmetrical insulator 160 has a feedthrough terminal pin 111 that is much closer to the right side of the ferrule 112 than it is to left side of the ferrule 112 (which renders an asymmetric feedthrough insulator 160). Similar to FIG. 62A, the right side of the ferrule has a ferrule pocket-pad 250 formed therein so that an electrical connection material 152 can electrically connect the external ground capacitor metallization 142 of the EMI filter capacitor 132 to the ferrule 112 gold oxide-resistant pocket-pad 250. This increases the right side active-to-ground stand-off distance. The filtered feedthrough electrical breakdown resistance, similar to that shown FIG. 62A, is also increased by using a nanoparticle-filled 264 polymeric insulating washer 211 or 211A. It is understood that a polymeric insulating washer 212 or 212A without insulating nanoparticles may be used instead of the nanoparticle-filled 264 polymeric insulating washer 211 or 211A. Like FIG. 62A, the nanoparticle-filled 264 polymeric insulating washer 211 completely covers the right-side gold braze 150 so that the active-to-ground stand-off distance extends from the active terminal pin-to-insulator gold braze 162 to the ground gold oxide-resistant pocket-pad 250 instead of to the ferrule-to-insulator gold braze 150. On the left side, the external ground capacitor metallization 142 is electrically connected to the gold braze 150 using electrical connection material 152. This forms an asymmetrical hybrid filtered feedthrough 210.

FIG. 62C shows a cross-sectional view that is similar to FIG. 62B except that it illustrates an asymmetric EMI filter capacitor 132 that is electrically connected to a hermetically sealed feedthrough 120. In this embodiment, recessed gold oxide-resistant pocket pads 250 reside on both the left and right sides of ferrule 112. In this embodiment, the gold brazes 150 on both the left and right sides of ferrule 112 are completely covered by a nanoparticle-filled 264 polymeric insulating washer 211 or 211A. This increases both the left and the right side active-to-ground stand-off distances. It is understood that a polymeric insulating washer 212 or 212A without insulating nanoparticles may be used instead of the nanoparticle-filled 264 polymeric insulating washer 211 or 211A. The nanoparticle-filled 264 polymeric insulating washer 211 or 211A also increases the electrical breakdown strength of the asymmetric filtered feedthrough 210. The embodiments of FIGS. 62 to 62C are all robust high-voltage filtered feedthrough design options.

Figure 50:
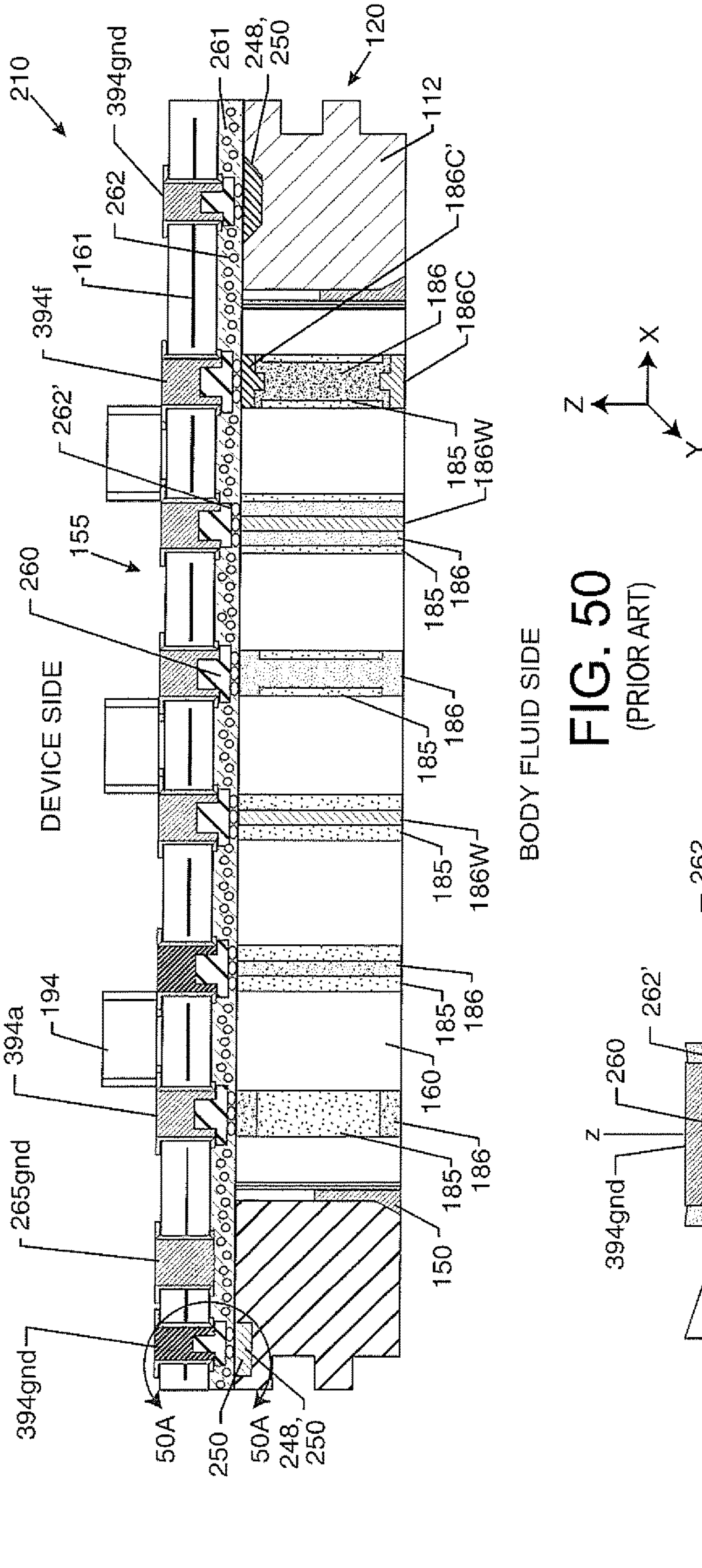
FIG. 50 (PRIOR ART)
FIG. 50 is a similar cross-sectional view to prior art FIG. 49 except that now the filled EMI filter circuit board conductive passageways incorporate proud structures for electrical connections.
Figure 50A:
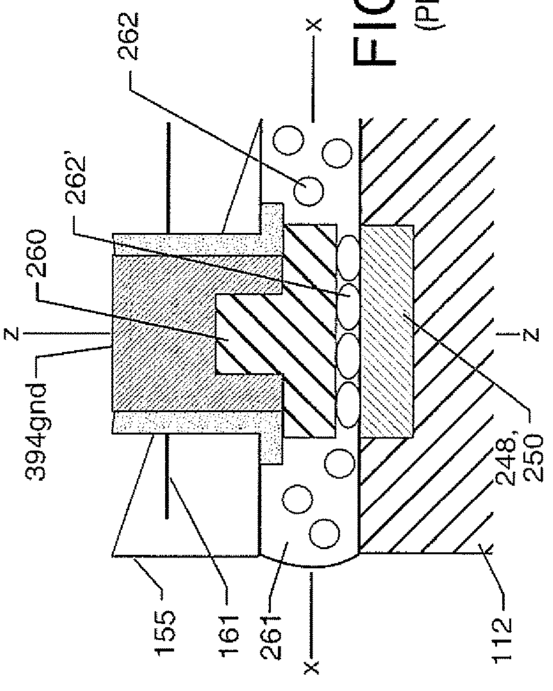
FIG. 50A (PRIOR ART)
FIG. 50A is a blown-up partial view taken from section 50A-50A of prior art FIG. 50 illustrating the ACF compressed electrically conductive particles providing the electrical connection.

FIG. 63 illustrates the present invention applied to prior art FIG. 50A, except in this instance, the insulating nanoparticles 264 of the present invention have been added to the anisotropic conductive film 263. The insulating nanoparticle-filled 264 anisotropic conductive film 263 comprises uniformly dispersed insulating nanoparticle 264 and conductive spheres 262. The insulating nanoparticles 264 increase the dielectric breakdown of the filtered feedthrough 210. Where the conductive spheres 262 are desirably compressed conductive spheres 262', conductivity occurs. In the embodiment of FIG. 63, the compressed conductive spheres 262' electrically connect the ferrule 112 gold oxide-resistant pocket pad 248, 250 and the nail head proud feature 260 of the EMI filter circuit board 155, thereby providing a low impedance, low resistance oxide-resistant electrical connection.

FIG. 64 illustrates the present invention applied to prior art terminal pin connectors 366. Seven terminal pin connectors are illustrated, five of which are active terminal pin connectors 366 and two are ground terminal pin connectors 366*gnd* and 366*gnd'*. Since their corresponding feedthrough terminal pins 111*gnd* and 111*gnd'* are directly electrically and mechanically connected to the feedthrough ferrule 112, both ground terminal pin connectors 366*gnd* and 366*gnd'* are at system ground 124 potential, which, as previously disclosed, may be done by gold brazing, laser welding, or a similar such processes. Terminal pin connectors 366 are more thoroughly disclosed in U.S. Pat. No. 11,211,741, the contents of which are fully incorporated herein by this reference.

Referring once again to FIG. 64, a cutaway view of an exemplary implantable cardioverter defibrillator (ICD) 100I having a terminal pin connector 366 covered with a nanoparticle-filled 264 polymeric insulating material 379 is illustrated. The insulating nanoparticle-filled 264 polymeric insulating material 379 illustrated in the ICD of FIG. 64 is not intended to be limiting, as the nanoparticle-filled 264 polymeric insulating material 379 may also be applied to terminal pin connectors 366 of any AIMD 100. The FIG. 64 cutaway view of ICD 100I reveals the battery 302 and the main AIMD electronic circuit board 122, which characteristically has various electronic circuits including battery charging circuits, high-energy storage capacitor charging circuits, biological sensing circuits, and therapy delivery circuits, among others. For simplicity, only one AIMD circuit board 122 is illustrated, however, it is understood that an AIMD may have a multiplicity of rigid and/or flexible (flex) circuit boards. Today's ICDs generally have several thousand programmable functions, so at least one microprocessor would also be included on the AIMD circuit board 122.

Referring now to the header block 101 of the exemplary ICD 100I of FIG. 64, a polymeric insulating material with or without insulating nanoparticles 264 is dispensed about the body fluid side of the hermetically sealed feedthrough 120 as indicated by arrow 314. Immediately after dispensing the polymeric insulating material with or without insulating nanoparticles 264 (that is, before curing), the header block 101 is seated so that the header block slot 316 exposes feedthrough terminal pins 114. The header block 101 is then anchored to the AIMD housing 116 by various fastening methods. In this embodiment, set screws 312 are inserted into a threaded set screw hole 313 of each screw block 310*a* and 310*b*, which are generally laser welded to the AIMD housing 116. Each set screw 312 is then torqued to anchor the header block 101 to the AIMD housing 116. Once the header block 101 is anchored, an additional polymeric insulating material with or without insulating nanoparticles 264 is dispensed through the header block slot 316 (as indicated by arrow 318) about the active and ground terminal pins (114 and 111*gnd*, 111*gnd'*, respectively) to completely fill (without any voids or cavities) around and between all the terminal pins 114, 111*gnd*, 111*gnd'* including over the body fluid side feedthrough top surfaces. It is understood that buses and/or wires may be disposed within the header block 101, for example, to electrically connect the connector ports 103 and implant leads (not shown), which are also suitably covered and insulated with the additional polymeric insulating material, with or without insulating nanoparticles 264. Importantly, in embodiments having feedthrough ground terminal pins 111*gnd*, 111*gnd'* placed closely to, for example, the active terminal pins 111, the additional nanoparticle-filled 264 polymeric insulating material 209 is preferably disposed to increase electrical breakdown strength.

FIG. 64A is a blown-up partial view generally taken from section 64A-64A of the header block 101 shown in FIG. 64. This drawing illustrates a preferred header block embodiment with the header block 101 being made from an insulating nanoparticle-filled 264 polymeric or plastic material 301. The nanoparticle-filled 264 polymeric insulating material 301 may be an elastomer, a polymeric, or a plastic. The nanoparticle-filled 264 polymeric insulating material 301 may be an epoxy, a liquid silicone rubber, a polyester, a polyurethane, a polyimide, or a polyamide. The insulating nanoparticle-filled 264 polymeric or plastic material 301 may be a thermoplastic material filled with uniformly dispersed insulating nanoparticles 264. The insulating nanoparticle-filled 264 polymeric or plastic material 301 may be one of a thermoplastic polyurethane, an aliphatic polyester-based thermoplastic polyurethane, an aliphatic and aromatic polycarbonate-based thermoplastic polyurethane, an aromatic polyether-based thermoplastic polyurethane, each of which are insulating nanoparticle-filled 264. Additionally, the insulating nanoparticle-filled 264 polymeric or plastic material 301 may be formed by filling commercially available polymeric materials, such as, but not limited to, the following specialty medical polymerics from Lubrizol Corporation: Carbothane™ Tecoflex™, Tecophilic™, Isoplast®, Pellethane® Tecoplast™, Tecothane™ and Tecobax™, each including the uniformly dispersed insulating nanoparticles 264 of the present invention. Due to the resultant greatly increased DC and high-frequency breakdown strength of the insulating nanoparticle-filled 264 header block 101, the insulating nanoparticle-filled 264 polymeric or plastic materials 301 of the present invention are particularly useful for ICD applications.

FIG. 64B illustrates a syringe 350 with a plunger 356 that contains an uncured nanoparticle-filled 264 polymeric insulating material 353. The uncured nanoparticle-filled 264 polymeric insulating materials may be an elastomer, a polymeric, or a plastic. The uncured nanoparticle-filled 264 polymeric insulating materials may be an epoxy, a liquid silicone rubber, a polycarbonate, a polyester, a polyether, a polyurethane, a polyimide, or a polyamide. FIG. 64B indicates the plunger 356 being depressed so that the uncured nanoparticle-filled 264 polymeric insulating material 353 is being dispensed through a needle or a nozzle 352 attached to the syringe end (which in FIG. 64B is the smaller diameter extension of the syringe). It is understood that any suitable syringe configuration may be used to dispense the uncured nanoparticle-filled 264 polymeric insulating material 353. The syringe 350 or an automated dispensing system (not shown) may be used to dispense the uncured nanoparticle-filled 264 polymeric insulating material 353 through the header block slot 316 of FIG. 64. The syringe 350 may also be used to dispense the uncured nanoparticle-filled 264 polymeric insulating material 353 about the terminal pin connector 366, which, when cured, becomes the nanoparticle-filled 264 polymeric insulating material 379 covering terminal pin connector 366.

FIG. 64C is a table listing various polymeric insulating materials, which include an uncured or flowable nanoparticle-filled 264 polymeric insulating material 353, an uncured or flowable polymeric insulating material 354 without a polymeric nanoparticle 264 fill, a cured or solid nanoparticle-filled 264 polymeric insulating material 379, and a cured or solid 378 without insulating polymeric nanoparticle 264 fill, The symbol column in the table has location markers that indicate where polymeric insulating material should or should not be placed. Location marker 360 having no shading indicates that the areas to which this marker points has no polymeric insulating material, as the polymeric insulating material is not appropriate or is even highly undesirable in these areas. Location marker 359 is shape-filled with high density dots indicating the location where nanoparticle-filled 264 polymeric insulating material (uncured being element 353 and cured being element 379) is desirably placed. Location marker 358 is shape-filled with diagonal paired cross-hatch lines and indicates the location where polymeric insulating material without nanoparticle 264 fill (uncured being element 354 and cured being element 378) is desirably placed.

FIG. 65 is a blown-up partial view taken from section 65-65 of FIG. 64. This drawing illustrates terminal pin connectors 366 and 366*gnd'*. An active terminal pin 111 is inserted into the active terminal pin connector 366 (+) and a ground terminal pin 111*gnd'* is inserted into the ground terminal pin connector 366*gnd'* (−). The distal housing ends 382 of the terminal pin connectors 366 and 366*gnd'* are open, thereby exposing their respective terminal pins 111 and 111*gnd'*. This has the advantage of facilitating visual inspection of the electrical connection of each terminal pin 111 and 111*gnd'* within the body of its corresponding terminal pin connector 366 and 366*gnd'*. The distal housing end 382 may optionally be closed. The housing planar surface 377 of each terminal pin connector 366 and 366*gnd* is electrically connected to a corresponding circuit board land 392 and 392*gnd* using an electrical connection material 395. The electrical connection material 395 may comprise a thermosetting conductive adhesive, a solder, a laser weld, or equivalent.

In an alternative embodiment, instead of having the electrical connection material 395 electrically connecting the housing planar surface 377 of the terminal pin connectors 366 and 366*gnd* to circuit board lands 392 and 392*gnd*, respectively, a BGA dot, a solder dot, a thermosetting epoxy dot (not shown) may be used for electrical connection. It is understood that the circuit board lands 392 and 392*gnd* are electrically connected to electrical traces, circuits, circuitry and/or other electrical components within or on the AIMD circuit board 122. As previously disclosed by the table of FIG. 64C, the high-density dot-filled location markers 359 indicate the location where uncured nanoparticle-filled 264 polymeric insulating material 353 is desirably dispensed and later cured to form a solid nanoparticle-filled 264 polymeric insulating material 379.

In this embodiment, a nanoparticle-filled 264 polymeric insulating material is used to increase the active-to-ground high-voltage stand-off distance between the plus (+) and minus (−) signs. It is understood that the polymeric material may comprise an epoxy, a polyimide or even a vapor deposited insulation, such as a Parylene D. The polymeric material may also comprise any of the insulating materials for increasing dielectric breakdown strength that have been previously disclosed. The high-voltage stand-off distance is important, even between adjacent positive terminals. That is because, as previously disclosed, the current flow of a biphasic pulse delivered by an ICD reverses, which means that the positive (+) and negative (−) polarities of the terminal pin connectors 366, 366*gnd*' will change in accordance with the direction of the delivered current. Noteworthy is that the polymeric insulating material of the present invention must be sufficiently disposed between the circuit board lands 392, including along the facing housing surfaces of each terminal pin connector 366 and 366*gnd*'. As the active-to-ground stand-off distance therebetween is relatively close, without such polymeric insulating material, the electrical breakdown risk may be undesirably high. The embodiment of FIG. 65 applies to both high-voltage (HV) and low-voltage (LV) devices. Both HV and LV devices may be subjected to high-voltage and, as previously disclosed, depending on AED paddle placement, inadvertent electrostatic discharge (ESD) or an automatic external defibrillator (AED) event could induce a high voltage across a patient's chest.

FIG. 65 also provides location markers 360, which indicates desired locations where no polymeric insulating material is to be applied. It is especially important for terminal pin connectors having open distal housing ends 382, such as the terminal pin connectors 366 and 366*gnd*' of FIG. 65, that no polymeric insulating material enters through the open distal housing end 382 to the area of terminal pins 111 or 111*gnd*'. Since each terminal pin is removably engaged by the prongs of a clip (not visible in this view), should the polymeric insulating material enter through the open distal housing end 382 to the removably engaged terminal pins 111 or 111*gnd*', the prongs of the connector clip may become permanently secured to the terminal pins 111 or 111*gnd*', which defeats the purpose of a removable terminal pin connector.

Figure 6A:
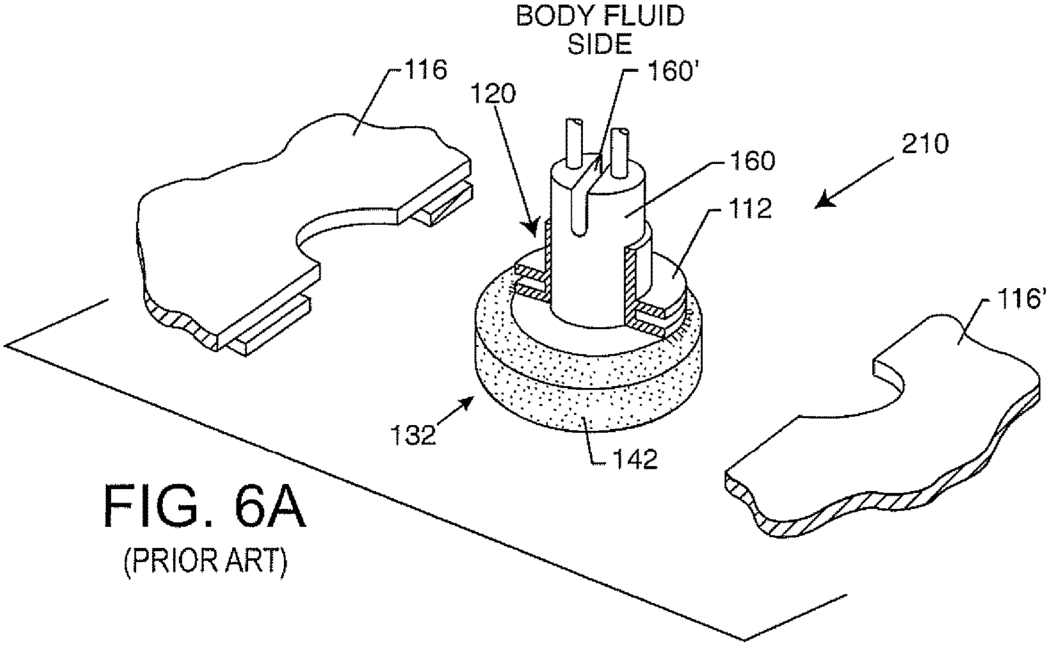
FIG. 6A (PRIOR ART)
FIG. 6A is prior art taken from FIG. 21 of U.S. Pat. No. 5,333,095, which is a fragmented exploded view of a hermetically sealed bipolar filtered feedthrough showing a cutaway sectional view of a bipolar feedthrough filter capacitor mounted on a ferrule of the bipolar feedthrough.
Figure 6B:
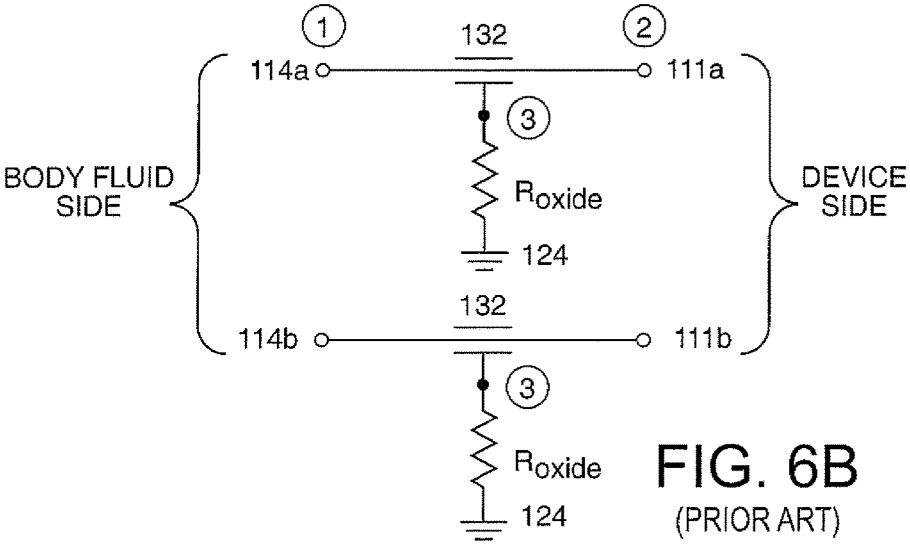
FIG. 6B (PRIOR ART)
FIG. 6B is an electrical schematic of the bipolar feedthrough filter capacitor mounted on the ferrule of the prior art bipolar feedthrough of FIG. 6A.
Figure 7A:
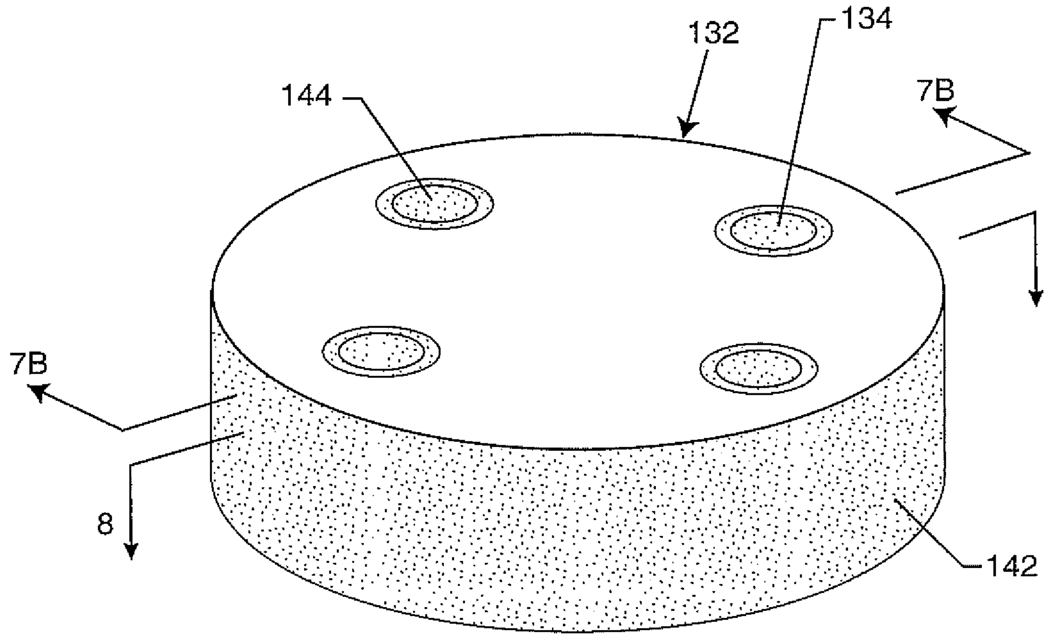
FIG. 7A (PRIOR ART)
FIG. 7A illustrates a prior art quadpolar discoidal feedthrough filter capacitor.
Figure 7B:
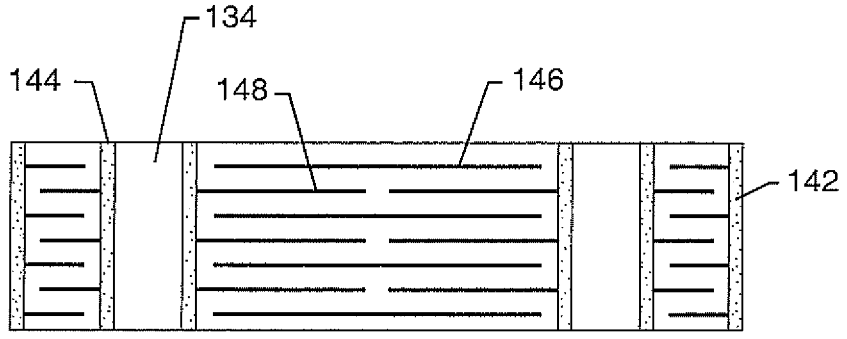
FIG. 7B (PRIOR ART)
FIG. 7B is a cross-sectional view of the prior art quadpolar feedthrough filter capacitor of FIG. 7A.
Figure 8:
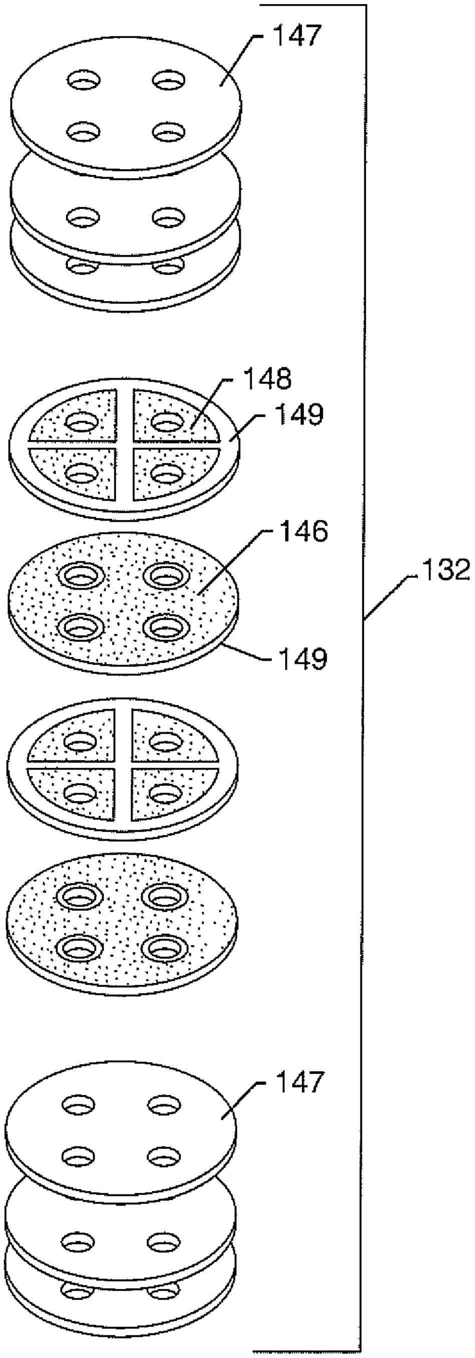
FIG. 8 (PRIOR ART)
FIG. 8 is an isometric exploded view of the prior art quadpolar feedthrough filter capacitor of FIG. 7A.
Figure 9:
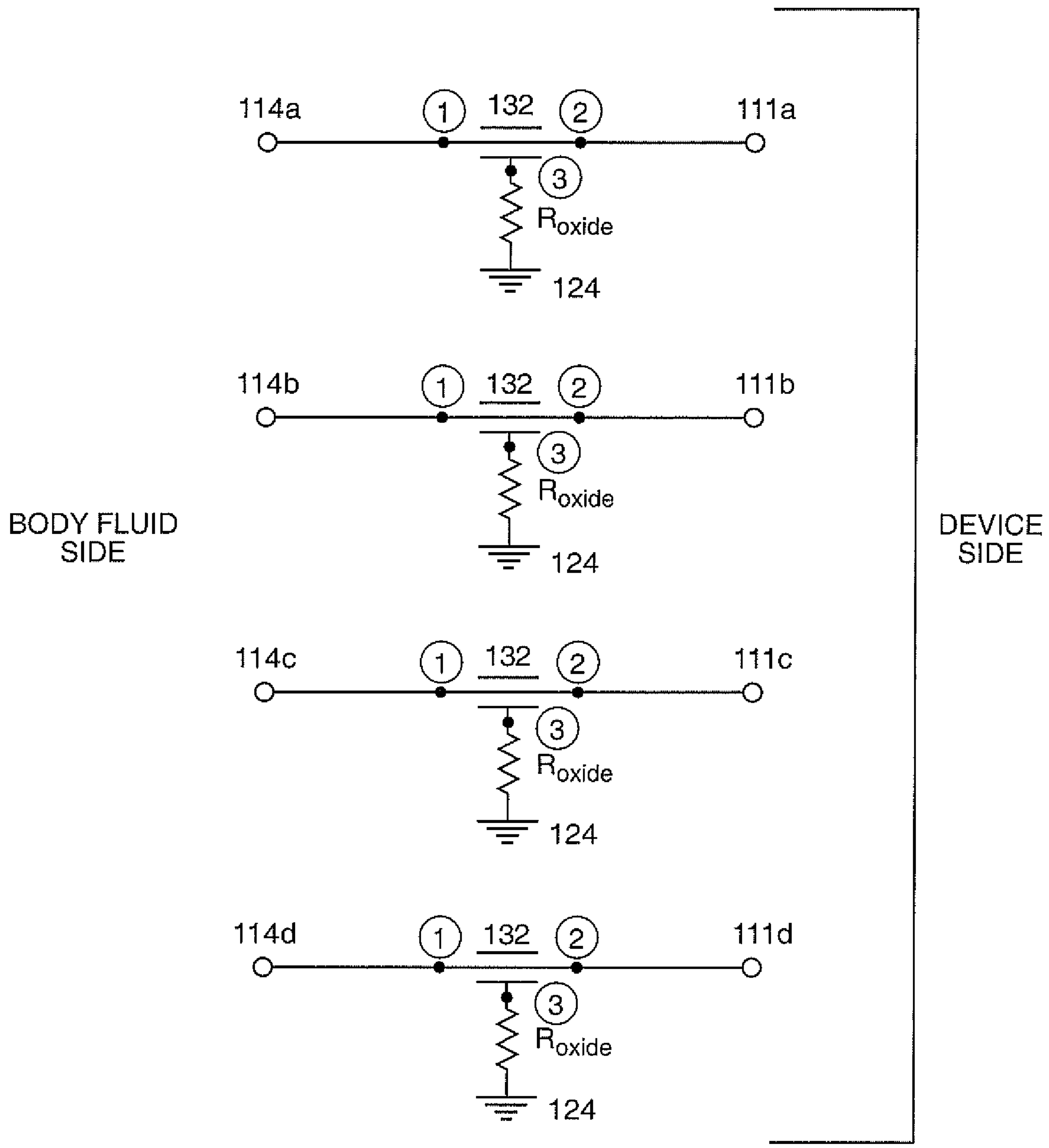
FIG. 9 (PRIOR ART)
FIG. 9 is an electrical schematic representative of the prior art quadpolar feedthrough filter capacitor of FIG. 8 after being mounted to a hermetically sealed feedthrough ferrule and insulator with terminal pins.

FIGS. 65A, 65B and 65C are taken from FIGS. 6A, 6B and 6C of previously referenced and incorporated by reference U.S. Pat. No. 11,211,741, illustrating the present invention applied accordingly. The element numbers within the parenthesis of FIGS. 65A, 65B and 65C are the element numbers taken from the original FIGS. 6A, 6B and 6C of the patent '741, while those that are not in parenthesis represent the element numbers of the present invention. It is understood that the present invention may apply to any of the embodiments disclosed by the '741 patent. FIGS. 65A, 65B and 65C each reveal the internal complexity of terminal pin connector 366 (16). As previously disclosed, the polymeric insulating material preferably does not enter through the open distal housing end 382 (82) of the terminal pin connector 366 (16), for example, to the throughbore 374 (74) of the clip 368 (68) or in and about the prongs 370 (70). Should the polymeric insulating material enter through the open distal housing end 382 (82) of the terminal pin connector 366 (16), rework and/or replacement of a defective ICD circuit boards 122 might be precluded, which could be prohibitively costly.

In a preferred embodiment, the uncured polymeric insulating material 353 or 354, with and without insulating nanoparticle 264 fill, respectively, is or is not dispensed as indicated by the location markers 358, 359, or 360 and then cured to form the solid polymeric insulating material 379 or 378, with and without insulating nanoparticle 264 fill, respectively. Accordingly, FIG. 65A illustrates a proximal end view of the terminal pin connector 366 (16) having the cured nanoparticle-filled 264 insulating polymeric material 379 on the surface of the proximal housing end 380 (80), which corresponds to the left side of the terminal pin connector 366 (16) of FIG. 65B. Location markers 360 show where there should not be any cured insulating polymeric material of any kind.

FIG. 65C illustrates a distal end view of the terminal pin connector 366 (16) having the cured nanoparticle-filled 264 insulating polymeric material 379 on the surface of the distal housing end 382 (82), which corresponds to the right side of the terminal pin connector 366 (16) of FIG. 65B. The location markers 360 show where there should not be any cured insulating polymeric material of any kind.

FIG. 65B is a cross-sectional view of the terminal pin connector 366 (16), illustrating the cured nanoparticle-filled 264 insulating polymeric material 379 on all external connector surfaces, except external connector surface 389, which has no cured nanoparticle filled insulating polymeric material 379 so that the terminal connector 366 (16) can be mounted to a circuit board land 392 (not shown). Location markers 360 show where there should not be any cured insulating polymeric material of any kind.

In summary, it is undesirable to have any polymeric insulating material in the areas indicated by location markers 360. Any polymeric insulating material in these areas could compromise the removability of a defective AIMD circuit board 122 from a feedthrough active and/or ground terminal pin 111, 111*gnd*'. It is understood that either open or closed distal housing end 382 may be used in the terminal pin connector 366 embodiments of the present invention. A closed distal housing ends 382 would prevent dispensed polymeric insulating material from getting inside the body of a connector housing 376 of the terminal pin connectors 366 and 366*gnd*, thereby ensuring terminal pin connector removability.

FIG. 66 illustrates the present invention applied to a prior art ICD 100I. The cutaway view of FIG. 66 reveals the ICD battery 302, the ICD circuit board 122, and a cross-sectional view of one of two ICD ground terminal pin connectors 366*gnd*, including the molded insulated connector block 396. The cross-sectional view of the ground terminal pin connector 366*gnd* shows that the ground terminal pin 111*gnd* is electrically connected to the prong 370 of the ground terminal pin connector 366*gnd*. The molded insulated connector block 396 has individual openings 393 into which terminal pin connectors 366 and 366*gnd* are embedded. The molded insulated connector block openings 393 are more clearly understood by examining FIG. 68A.

Depending on the terminal pin connector design, the molded insulated connector block 396 can be over-molded with the connector housings embedded therein or pre-molded and then subsequently inserted onto the connector housings. The individual terminal pin connectors 366 and 366*gnd* are each separated by a molded polymeric material 383. The molded polymeric material 383 is more clearly understood by examining FIGS. 68A and 68B. FIGS. 68A and 68B show that the molded polymeric material 383 is a monolithic construct of the molded insulating block 396 that separates and insulates each terminal pin connector 366, one from another. The molded insulating block 396 is configured with an opening 393 for either inserting a terminal pin connector 366 therewithin if pre-molded, or exposing the proximal housing end 380 of a terminal pin connectors 366 if over-molded. The molded insulating block 396 further embodies a ledge 385 (FIG. 66) for positioning against the edge of an AIMD circuit board 122. The ledge 385 aligns the connector insulating block 396 with the terminal pin connectors 366 and 366*gnd* therewithin over the circuit board lands 392 (FIG. 65).

Referring back to FIG. 66, the molded insulating block 396 illustrated is over-molded. The ledge 385 of the molded insulating block 396 is L-shaped and has a hook-like feature 387 that captures and secures each terminal pin connector 366, 366*gnd*. In a pre-molded embodiment, depending on the elasticity of the polymeric insulating material used to form the insulating block 396, the hook-like feature 387 may or may not be present. Higher elasticity allows a pre-molded insulating block 396 to stretch more so that, during insertion, the opening 393 can stretch about the terminal pin connector 366 until the connector is fully inserted, whereupon the hook-like feature 387 emerges about the proximal housing end 380 to clasp its cone-shaped countersink-like opening. Lower elasticity materials do not have much stretchability, hence, a pre-molded insulating block 396 made from a low elasticity material will likely not have the hook-like feature 387 illustrated in FIG. 66. For both the over-molded and the pre-molded connector insulating block 396, the connector housing 366*gnd* is electrically connected using an electrical connection material 395 to their respective circuit board lands 392, 392*gnd* (FIG. 65). The molded insulating block 396 comprises an insulating polymeric material selected from any of the insulating materials previously disclosed, including polymeric insulating materials having insulating nanoparticles 264.

FIG. 67 is an isometric cutaway view similar to FIG. 66; however, it is rotated to show a plan view of the terminal pin connector 366 with the molded insulating block 396 electrically attached to the AIMD circuit board 122.

Referring again to FIGS. 68A and 68B, these drawings illustrate tilted pictorial views of the unattached over-molded insulating block 396 of FIG. 67. FIG. 68A is rotated so that the surface of the molded insulating block 396 monolithically covers the terminal pin connectors 366, 366*gnd*. The proximal housing ends 380 of each terminal pin connector 366, 366*gnd* are visible. FIG. 68B is rotated so that the surfaces of the terminal pin connectors 366, 366*gnd* that will be mounted to the circuit board lands 392 (FIG. 65) are visible in addition to the proximal housing ends 380 of each terminal pin connector 366, 366*gnd*. Also visible is that the mounting surface of the terminal pin connector 366, 366*gnd* is flush with the surface of the molded insulating block 396. As such, each terminal pin connector 366, 366*gnd* resides within their own molded insulating block cavity 391, separated by the monolithic constructs of the molded polymeric material 383, which insulates each terminal pin connector 366, 366*gnd* one from another. While the molded polymeric material 383 of FIG. 68B is over-molded, it is understood that in an alternative embodiment, a highly elastic pre-molded insulating block 396 could be made with such insulating block cavities 391.

In addition to polymeric materials with or without insulating nanoparticles 264, the molded insulating block 396 of the present invention may comprise any formable insulating material, for example, a moldable plastic, a ceramic, a glass-ceramic, or composite materials. Moldable insulating polymeric materials may comprise polymeric-based materials, copolymers, thermosetting plastics, thermoplastics, epoxies, or elastomers. The filler insulating nanoparticles 264 may be configured as particulates, short fibers, long fibers, spheres, flakes, submicron fibers, which are isotropically dispersed within the moldable insulating materials. Suitable electrically insulative materials include acrylics, phenolics, polyimides, and fluoropolymers. For example, the electrically insulative material may be selected from the group consisting of silicone, polyurethane, polyester, polyethylene, polypropylene, polyamide (also known as nylon), acrylic, and combinations thereof. Additional electrically insulative materials include perfluoroalkoxy (PFA), fluorinated ethylene-propylene (FEP), polyetheretherketone (PEEK), polyamidimide (PAI), polyphenylsulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), among others. The insulated connector block 396 may molded by one of injection molding, compression molding or thermoforming. Depending on the block design, rotational, blow and extrusion molding may be used. It is appreciated that molded insulated connector block 396 may alternatively be made by a 3D printing process such as, stereolithography, digital light processing, two-photon polymerization processes, or other commercially available polymerization reaction processes.

In an alternative embodiment of the insulated connector block 396, an insulating ceramic material can be used instead of an insulating polymeric material. The insulating ceramic material may be a green (pre-sintered) ceramic that is machined or similarly formed by other applicable techniques to form the connector insulating block 396. The insulator connector block 396 can also be formed by a molding process, like injection molding process or a compression molding process, among others, or by a 3D printing process, such as, selective laser sintering, selective laser melting, laminated object manufacturing, fused deposition modeling, among others. Suitable ceramic materials include alumina, baria, calcia, ceria, magnesia, silica, strontia, titania, and zirconia ceramic families. Non-limiting examples of some nanoscale metal oxides that can be used include: $Al_2O_3$, BaO, CaO, $CeO_2$, MgO, $ZrO_2$, $SiO_2$, $TiO_2$, $Al_2SiO_{53}$, $BaTiO_3$, $SrTiO_2$, and combinations thereof. Various stabilized or partially stabilized zirconia may be used including zirconia toughened alumina (ZTA) and alumina toughened zirconia (ATZ), yttrium stabilized zirconia (YSZ), yttrium-toughened zirconia (YTZP), and combinations thereof. Additionally, nitrides may also be used, such as, aluminum nitride (AlN), silicon nitride ($Si_3N_4$), boron nitride (BN), carbon nitride (CN), and combinations thereof.

FIG. 69 is a cross-sectional view illustrating a unipolar feedthrough EMI filter capacitor 132 disposed within the walls of the internal diameter (ID) of ferrule 112. The EMI filter capacitor 132 is not surface mounted, so ferrule 112 acts like a container that holds the EMI filter capacitor, the insulating materials and electrical connection materials. In this embodiment, the EMI filter capacitor 132 is covered by a top nanoparticle-filled 264 polymeric insulating material 215 and also has a nanoparticle-filled 264 polymeric insulating material 211 disposed between the EMI filter capacitor 132 and the feedthrough insulator 160. The nanoparticle-filled 264 polymeric insulating materials 211 and 215 may be a B-staged polymeric insulating material preform, a thermoplastic insulating material, or a thermoplastic coated polymeric insulating preform that is configured to expose gold brazes 150 and 162 for low impedance, low resistance oxide-resistant electrical connections using electrical connection materials 156 and 152, respectively.

FIG. 69A is generally taken from section 69A-69A of FIG. 69 and illustrates that the electrical connection material 152 electrically connects the external ground capacitor metallization 142 to the ferrule-to-insulator gold braze 150. The nanoparticle-filled 264 polymeric insulating material 211 is configured to expose the gold braze 150 to form a low impedance, low resistance essentially oxide-free electrical connection.

FIG. 69B is generally taken from section 69B-69B of FIG. 69 and illustrates that the electrical connection material 156 electrically connects the passageway active capacitor metallization 144 to the terminal pin-to-insulator gold braze 162. The nanoparticle-filled 264 polymeric insulating material 211 is configured to expose the gold braze 162 to form a low impedance, low resistance essentially oxide-free electrical connection.

FIG. 69C is generally taken from section 69C-69C of FIG. 69 and illustrates that the top nanoparticle-filled 264 polymeric insulating material 215 completely covers the EMI filter capacitor 132 all the way to the ID of the ferrule 112. The use of nanoparticle-filled 264 polymeric insulating material 211, as illustrated by FIGS. 69A and 69B, and the top nanoparticle-filled 264 polymeric insulating material 215 illustrated in FIG. 69C renders the embodiment of FIG. 69 suitable for high-voltage applications, such as for use in an implantable cardioverter defibrillator (ICD).

FIG. 70 illustrates the present invention applied to a prior art flat-thru capacitor 196. Flat-thru capacitors are more thoroughly disclosed in U.S. Pat. Nos. 7,957,806, 8,095,224, 8,321,032, 8,433,410, 8,437,865, 8,483,840, 8,670,841, 8,712,544, 8,761,895, 8,868,189, 8,918,189, 8,996,126, 9,031,670, 9,071,221, 9,463,329, 9,895,534, 10,016,595, 10,016,596, 10,080,889, 10,099,051, 10,124,164, 10,722,706, 10,857,369, 10,874,866, 11,013,928, 11,147,977, and 11,241,581, the contents of which are fully incorporated herein by these references. The location markers in FIG. 70 indicate where and where not to place polymeric insulating materials. Location marker 359 indicates where nanoparticle-filled 264 polymeric insulating materials should be present. Location markers 360 indicate where a polymeric insulating material does not need to be present. For the flat-thru capacitor 196 of FIG. 70, location marker 359 indicates that nanoparticle-filled 264 polymeric insulating materials should be placed over the flat-thru active capacitor metallizations 144*a*, 144*b* and the flat-thru ground capacitor metallizations 142*a*, 142*b*. Location markers 360 indicate that nanoparticle-filled 264 polymeric insulating materials can, but need not, be placed over the active circuit board traces 178*a*, 178*b* and the ground circuit board traces 182*a*, 182*b*. It is understood that the presence of nanoparticle-filled 264 polymeric insulating materials over the active circuit board traces 178*a*, 178*b* and the ground circuit board traces 182*a*, 182*b* is optional.

FIG. 70A illustrates the ground and active electrode plates 146 and 148, respectively, of the flat-thru capacitor 196 of FIG. 70. Flat-thru capacitors are unique three-terminal devices that let AIMD circuit current, for example, pacing pulses or therapeutic pulses, to pass through the active electrode plate 148, as shown by arrows 11*a* to 11*b*.

FIG. 71 illustrates a filtered feedthrough 210 having three of the flat-thru capacitors 196 of FIG. 70 disposed on an EMI filter circuit board 155 mounted on top of a hermetically sealed feedthrough 120. In this embodiment, the location markers indicate where polymeric insulating material 358 (without insulating nanoparticles) can be strategically placed in locations that will either develop high-voltage stress or where increased high-voltage stand-off distance is required. It is understood that all three of the flat-thru capacitors 196*a*, 196*b* and 196*c* would have insulation materials displaced in the locations, as indicated in the right capacitor. In fact, location markers 358 indicate that all of the exterior surfaces and metallizations of the flat-thru capacitors 196*a*, 196*b* and 196*c* are coated with the insulation material. Location markers 360 point to areas distant from ground potential (111*gnd*) or adjacent to terminal pins 111 where insulative material is not necessary.

FIG. 72 is taken from section 72-72 of FIG. 71 and illustrates a cross-sectional view of several flat-thru capacitors 196*a*, 196*b* and 196*c*. It should be noted that this is a tripolar configuration and is not particularly volumetrically efficient. Each of the terminal pins 111*a*, 111*b*, 111*c* is broken so that the current can flow through the active electrode plates from the body fluid side to the device side of the respective flat-thru capacitor 196*a*, 196*b* and 196*c*.

FIG. 73 illustrates a quadpolar flat-thru capacitor disposed in a tombstone position on top of a hermetic seal subassembly that is much more volumetrically efficient that the design shown in FIG. 72. The location marker 359 dots illustrate where nanoparticle-filled 264 insulating material would be disposed over all of the surfaces to provide a very suitable high-voltage stand-off, for example, for use in an ICD application.

FIG. 73A is a sectional view taken from section 73A-73A of FIG. 73. This drawing is taken through one of the ground electrode plates and shows on the right where the ground plate is connected to a gold pocket pad 248, 250 and on the left where the ground plate is connected to a grounded terminal pin 111*gnd*. The grounded terminal pin 111*gnd* is either gold brazed, or laser welded to the ferrule 112. Starting on the left side of the drawing, various hermetically sealed conductors are illustrated including a gold brazed terminal pin 114*a*, a CRMC electrically conductive pathway 185 with co-sintered platinum caps 186, a cylindrically-shaped CRMC conductive pathway 185 with a pure platinum 186 inner core, and the dumbbell-shaped platinum conductive pathway 186 with a CRMC sleeve 185 giving the platinum pathway 186 a dumbbell shape. All but the terminal pin are co-sintered at the same time that the insulator 160 is fired. FIG. 73A is illustrative; one is not likely going to do all of the conductive pathway variations at the same time. For example, on the left-hand side where terminal pin 114*a* is located, one would normally not do a gold braze 162 at the same time that they were co-sintering adjacent terminals. So, these show exemplary embodiments.

FIG. 74A shows a different type of filter capacitor called an X2Y attenuator. X2Y attenuators are more thoroughly described in U.S. Pat. Nos. 8,095,224; 8,855,768; 9,014,808; 9,757,558; 9,764,129; 10,092,749; 10,350,421; 10,561,837; 10,596,369; 10,828,498; 10,905,888; 11,071,858; 11,185,705; and 11,198,014, the contents of which are fully incorporated herein by these references.

FIG. 74A illustrates the left-hand active electrode plate set 146*a*, the ground electrode plate set 146 and the right-hand electrode plate set 146*b*. Referring back to FIG. 74, one can see placement location symbols for a non-nano-insulative material 358 that would generally be disposed over all of the surfaces of the X2Y attenuator to thereby provide a high-voltage stand-off for high-voltage applications. Optionally, any of the non-nano-insulative materials 358 could be replaced by nanoparticle-filled 264 insulating materials 359. One is referred once again to the table of FIG. 64C for the explanation of these symbols.

FIG. 75A is a cross-sectional view through a hermetic seal including a circuit board with X2Y attenuators 198*a*, 198*b* and 198*c* mounted on it. This is very similar to FIG. 72, except that in this case, the terminal pin pairs 111*a*/114*a*, 111*b*/114*b*, 111*c*/114*c*, 111*d*/114*d*, 111*e*/114*e* and 111*f*/114*f* are continuous from the body fluid side to the device side. In this case, each X2Y attenuator 198 filters a pair of terminal pins, for example, 111*a*/114 and 111*b*/114*b*, which is being filtered by X2Y attenuator 198*a*. X2Y attenuators can provide both differential and common-mode attenuation. This means that the X2Y attenuator 198*a* can provide both differential mode filtering between terminal pins 111*a*/114*a* and 111*b*/114*b* and also common mode attenuation from both terminal pins 111*a*/114*a* and 111*b*/114*b* to system ground, which in this case, is the ferrule 112. Compared to FIG. 73, the X2Y attenuators of FIG. 75A have higher volumetric efficiency because they provide a 6-pole EMI filter in a comparable amount of space that a tripolar filter requires. Moreover, an insulative coating 378 is disposed over all of the X2Y attenuators and the circuit board on which they are disposed. This provides a high stand-off distance for high voltage as previously indicated.

FIG. 76 illustrates four X2Y attenuators mounted directly on a hermetic seal subassembly standing on edge. The X2Y attenuators are grounded as indicated and also connected between adjacent pairs of terminal pins. In this case, an X2Y attenuator 198*a* is disposed between terminal pins 111*a* and 111*b*. The dot-filled symbols 359 indicate where nanoparticle insulating material is desirably placed to provide high-voltage stand-off between the active electrodes and active terminations and ground, and also between adjacent X2Y attenuators.

FIG. 77 is a plan view of a hermetically sealed feedthrough 120 on which a prior art insulating washer 212 with round-shaped insulating washer openings 403 (which is typical) for receiving feedthrough terminal pins is undesirably mis-located. Because the insulating washer 212 has round-shaped insulating washer openings, the round-shaped openings undesirably permit the insulating washer 212 to move about the terminal pins 111*a* through 111*e*, mis-locating the position of the insulating washer on top of the hermetically sealed feedthrough 120. For example, using the x-y axis of FIG. 77 for directional referencing, the insulating washer 212 has undesirably moved upward along the y-axis as shown. However, insulating washer 212 can also undesirably move downward along the y-axis, to the left along the x-axis, or to the right along the x-axis. In other words, a round-shaped opening in an insulating washer permits the washer 212 to mis-locate along the planar surface of the hermetically sealed feedthrough 120 in any direction about the terminal pins 111*a*-111*e*. The misalignment of washer 212 creates a gap 432 between the gold braze 162 for the active terminal pin 111 and the closest ground, which in this embodiment, is the ferrule gold braze 150. The presence of gap 432 can result in the highly undesirable effect of reducing the high-voltage keep-out zone 412, which is also the flashover distance. Gap 432 can be particularly problematic when the feedthrough 120 is exposed to a high volts per mil (V/mil) stress. Partial delamination (such as the insulating washer partial delamination previously disclosed), an air bubble between the + and − poles, and the gap 432 within the keep-out zone 412 of gold braze 150, can undesirably lead to a high-voltage discharge or a catastrophic avalanche discharge.

Commensurate with the amount of mis-location that exists, the mis-located insulating washer 212 will also undesirably cover a portion of the insulator-to-ferrule gold braze 150. The covered portion of the gold braze 150 becomes unavailable for oxide-resistant electrical connection. It is noted that the telemetry terminal pin T in the embodiment of FIG. 77 is not associated with a filter capacitor and is therefore not covered by the insulating washer 212. The reason the insulating washer 212 does not cover the telemetry terminal pin T is that AIMD telemetry terminal pins are not filtered. Instead, they enable high-frequency RF communication between an AIMD programmer and the implanted AIMD. This means that the telemetry terminal pin T must not have any electrical connection to an EMI filter capacitor or an EMI filter circuit board. Otherwise, the RF telemetry signal would be undesirably attenuated. Moreover, telemetry terminal pins are generally disposed in the header block or on the outside of the AIMD itself and are very small compared to an implanted lead. Additionally, telemetry terminal pin T is generally positioned in a separated area inside of the AIMD. Accordingly, telemetry terminal pins do not tend to pick up much EMI, therefore they do not have any need for EMI filtering.

The thermoplastic embodiments of the present invention are particularly problematic when it comes to centering the opening of lubricious (slippery) thermoplastic coated polymeric insulating washers or homogeneous lubricious polymeric insulating washers over gold braze 162. Because polymeric insulating washers must be applied and laminated to adjacent structures under significant pressure and high temperature, they can be easily mis-located.

FIGS. 78 through 81B illustrate various embodiments for novel self-centering insulating washers 400*a* to 400*f* according to the present invention. The novel washer embodiments disclosed herein incorporate uniquely designed non-circular irregular washer openings, which may be symmetrically or asymmetrically formed, to constrain movement of the washer in any x-y direction. The self-centering insulating washers 400*a* to 400*f* can be made using conventional punch and cut methods. In the specific case of self-centering washers 400*a* to 400*f*, the dot fill simply distinguishes each novel self-centering washer from the prior art washers 212. It is understood that the novel self-centering washers 400*a* to 400*f* may or may not have insulating nanoparticles. The self-centering washers 400*a* to 400*f* can be made of any of the materials previously disclosed, such as any polymeric material, whether a thermoplastic material, a thermoset material or a thermoplastic/thermoset polymeric material. The novel self-centering insulating washers 400*a* to 400*f* of the present invention may comprise any of the insulating materials used to make the prior art insulating washers 212 without insulating nanoparticles 264 or, alternatively, may comprise the prior art insulating washers 211 with insulating nanoparticles 264. In addition, the novel self-centering insulating washers 400*a* to 400*f* may alternatively comprise the thermoplastic coated thermosetting polymeric insulating washer 212A without insulating nanoparticles 264 or the thermoplastic coated thermosetting polymeric insulating washer 211A with insulating nanoparticles 264. The novel self-centering insulating washers 400*a* to 400*f* may further comprise more than one co-bonded self-centering insulating washer, either with or without insulating nanoparticles or a combination of both types, each using the same insulating material or at least one self-centering insulating washer may be made of a different insulating material, the combinations of which is unlimited.

FIG. 78 is a plan view of a hermetically sealed feedthrough 120 on which a novel self-centering insulating washer 400*a* is desirably located. As illustrated, the self-centering insulating washer 400*a* according to the present invention is located about terminal pins 111*a* to 111*e*. The self-centering washer has a number of novel baseball field-like shaped openings 404 that receive a corresponding one of terminal pins 111*a* to 111*e*, each opening particularly oriented and having a baseball field-like shape defined by a minor arc 417 spaced apart from a major arc 415. The minor are 417 is the inner arcuate or curved portion and the major arc 415 is the outer arcuate portion of the shaped opening 404. The minor arc 417 is generally characterized as the circular area free of grass that is centered about home plate and the major arc 415 is a continuously curved home run outfield fence line. The minor arc 417 abuts its corresponding terminal pin 111*a*-111*e*. The major arc 415 follows the curve of the gold braze hermetically sealing the terminal pin, which exposes the gold for oxide-resistant electrical connection of the EMI filter. Gold braze 162 individually fully surrounds (360°) each hermetically sealed terminal pin 111*a*-111*e*, which is indicated by a circle, whereby the solid line of major arc 415 circumscribes the portion of the gold braze 162 along the fence line of the outfield and the dashed line circumscribes the portion of the gold braze underneath the self-centering washer 400*a*. Using the clock face insert of FIG. 78 as an orientation guide, the apex of the major curve 415 of the baseball field-like shaped opening 404 about each terminal pin 111*a*-111*e* can be made. Terminal pin 111*a* is oriented (clocked) at 3 o'clock, pin 111*b* at 6 o'clock, pin 111*c* at 12 o'clock, pin 111*d* at 6 o'clock and pin 111*e* at 9 o'clock. The particular shaped opening orientations of FIG. 78 constrains inadvertent movement of the entire insulating washer 400*a* in any x-y planar direction. The clockings of FIG. 78 are only examples. It is understood that the clockings can take any meaningful orientation to prevent inadvertent planar movement of an insulating washer 400*a*.

The clockings of the washer openings 404 can be expressed in degrees. For example, opening 404 about terminal pin 111*a* is clocked centered at 3 o'clock having an outer arcuate portion that extends for about 150° to about 170° around the circular perimeter of the gold braze 162, which resides underneath the washer 400*a* at the terminal pin 111*a*, but can extend for about 90° to about 180°.

Referring once again to FIG. 78, the exposed gold braze 162 allows oxide-resistant electrical connections to be made to an EMI filter capacitor or an EMI filter circuit board. Even though the gold braze 162, which hermetically seals the terminal pin 111*c* to the feedthrough insulator 160, is partially covered by the insulating washer opening 404, there is a sufficient amount of exposed gold braze for a low resistance, low impedance electrical connection. In order for there to be a sufficient high-voltage stand-off distance, a keep-out zone 412*a* as the distance between the inner edge of the gold braze 162 and the closest edge of one of the adjacent openings 404 is illustrated. For example, the insulating washer shaped opening orientation 402 of the five pole inline terminal pins 111*a*-111*e* of FIG. 78 can be a challenge for providing sufficient stand-off distance. In high-voltage AIMDs, such as an ICD, or when low voltage AIMDs are exposed to defibrillation paddles or an automatic external defibrillator (AED), the high-voltage keep-out zone 412*a* becomes very important. It is a well-known principle in high-voltage engineering that any sharp point tends to be an equipotential field line stress concentrator. In fact, a needlepoint-shaped corner is actually one of the worst cases for high-voltage breakdown of air between conductors. In that respect, the sharper the corner, the greater the threat of dielectric breakdown.

For example, with reference to terminal pins 111*a* or 111*e*, the respective openings 404 have exposed gold braze 162 sharp points 162*s* that are oriented at about 12 o'clock and pointed directly into the high-voltage keep-out zone 412*a*. This is where the highest volts per mil (V/mil) stress may occur. On the other hand, the insulating washer shaped opening 404 about terminal pin 111*c* has its major arc 415 having a relatively large radial contour. The large radial contour of the major arc 415 faces the gold braze 150, which is also at the edge of the high-voltage keep-out zone 412*a*, as illustrated. Comparing the sharp corners 162*s* of the insulating washer shaped openings 404 about terminal pins 111*a* and 111*e*, respectively, both of which face the keep-out zone 412*a*, with the large radial contour of the insulating washer shaped opening 404 about terminal pin 111*c*, it is apparent that the latter design reduces the V/mil stress and is more unlikely to exhibit high-voltage breakdown than the sharp corners 162*s* at terminal pins 111*a* and 111*e*. Because the insulating washer openings 404 about terminal pins 111*a* and 111*e* exposes gold braze sharp corners 162*s*, the possibility of dielectric breakdown, which can lead to catastrophic high-voltage avalanche, is greater for the insulating washer opening 404 about terminal pin 111*a* and 111 *e* than it is for the insulating washer opening 404 about terminal pin 111*c*. That is the case even though exposed gold braze 162 of the terminal pins 111*a*, 111*c* and 111 *e* have a same keep-out zone 412*a* of the same distance.

FIG. 79 is an isometric view of a novel self-centering insulating washer 400*b* having an insulating washer thickness 406. The self-centering insulating washer 400*b* illustrates uniquely shaped insulating washer shaped openings 404. Each insulating washer shaped opening 404 comprises two internal tooth-like structures 401, which look similar to commercially available toothed metal washers. The insulating washer shaped openings have opposing tooth-like structures that are oriented in alternating pairs, comprising 3 o'clock and 9 o'clock, and 12 o'clock and 6 o'clock. When the insulator washer is seated on top a hermetically sealed feedthrough, the opening shape and orientation prevents inadvertent insulating washer movement in any planar direction.

FIG. 80 illustrates an alternative embodiment of a self-centering insulating washer 400*c* disposed on a hermetically sealed feedthrough 120. The self-centering insulating washer 400*c* is similar to the self-centering washer 400*b* of FIG. 79, except that, in this embodiment, each insulating washer shaped opening 404 comprises four internal tooth-like structures 401 (instead of two) for receiving corresponding feedthrough terminal pins 111*a* through 111*f*. The internal tooth-like structures create proper positioning of the self-centering insulating washer 400*c*. Additionally, self-centering washer 400*b* requires no clocking because the four tooth-like structures 401, being symmetric, prevent inadvertent lateral mis-alignment. The four tooth-toothed shaped openings 404 of the self-centering insulating washer 400*c* exposes four portions of the gold braze 162, each gold braze portion having exposed gold braze sharp corners 162*s* at the keep-out zone 412*c*. It is anticipated that the illustrated sharp corners 162*s* can be rounded (not shown) at the edge of the keep-out zone 412*c* to minimize electric field stress concentration, thereby increasing high-voltage breakdown strength. As previously disclosed, optimizing high-voltage keep-out area 412*c* is very important in preventing catastrophic electrical breakdown between active terminal pins 111*b*, 111*d*, 111*f*, and gold braze 150, and, in turn, the ferrule 112.

FIG. 81 is a plan view of a novel variation of baseball field-like insulating washer shaped openings 404 of self-centering insulating washer 400*d* disposed on top of a hermetically sealed feedthrough 120. In this embodiment, each baseball field-like insulating washer shaped opening 404 is oriented so that none of the exposed gold brazes 162 encroach into the increased distance keep-out zone 412*d* (i.e., none of these gold brazes 162 extend into the high-voltage keep-out zone 412*d*). Terminal pin 111*a* is generally oriented at 6 o'clock, terminal pin 111*b* at 7:30 o'clock, terminal pin 111*c* at 4:30 o'clock and terminal pin 111*d* at 6 o'clock. The increased keep-out zone 412*d* distance extends ideally to the external surface of each terminal pin 111*a*-111*d* and to the insulator-to-ferrule gold braze 150, thereby providing optimal high-voltage stand-off distance therebetween. Optimal high-voltage stand-off distance greatly improves insulative reliability by providing increased safety margins against high-voltage insults. Each insulating washer shaped opening 404 of the self-centering washer 400*d* has a baseball field-like shaped opening that has a minor arc 417 abutting its corresponding terminal pin 111*a* to 111*d*. At least two insulating washer shaped openings must be selectively oriented to prevent the self-centering insulating washer 400*d* from inadvertently undesirably moving in any lateral direction. As previously disclosed, EMI filter capacitor or EMI filter circuit board electrical connection to the exposed gold braze 162 is important in order to provide an oxide-resistant low impedance low resistance active terminal pin electrical connection.

Referring again to FIG. 81, on the left side, another high-voltage keep-out zone 426 is illustrated. The keep-out zone 426 extends to the exposed gold braze 162 rounded corner 422 and the insulator-to-ferrule gold braze 150. As disclosed earlier, an exposed gold braze 162 at rounded corner 422 is preferred compared to a sharp corner 420, as shown adjacent terminal pin 111*d*.

FIG. 81A is similar to FIG. 81, except that the insulating washer shaped openings 404 of this embodiment are clocked at 6 o'clock for terminal pin 111*a*, at 9 o'clock for terminal pin 111*b*, at 3 o'clock for terminal pin 111*c* and at 6 o'clock relative to terminal pin 111*d*. As can be seen, the clocking wise extent illustrated in this embodiment prevent inadvertent movement of insulating washer 400*e* in any lateral direction. The clock-wise orientations shown in FIG. 81A, however, position the exposed gold braze 162 at a narrower keep-out zone 412*e*, as compared to the wider keep-out zone 412*d* of FIG. 81. The keep-out zone 412*e* shown in FIG. 81A, while reduced, is not reduced as much as, for example, the previous embodiments of FIGS. 78 and 80 (distance 412*e* is less than HV stand-off distance 412*d*). Corners 422 and 424' are both radiused which helps reduce volts/mil stress.

Referring once again to FIG. 81A, one also has to be concerned about the keep-out zone 426, which has been previously discussed. In this case, keep-out zone 426 has rounded corner 422 associated with active terminal pin 111*a* facing system ground gold braze 150. As previously discussed, the rounded corner 426, as opposed to a sharp corner 420, is preferred. That is because the rounded corner 422 has reduced volts/mil stress.

FIG. 81B is very similar to FIG. 81 and illustrates various shaped opening 404 designs and orientations, each providing a unique exposure shape of the gold braze 162. The shaped openings 404 do not provide any uncovered or exposed portions of the gold brazes 162 that reside in the keep-out zone 412*f* (distance 412*f*=distance 412*d* in FIG. 81). The present invention is not limited to any particular shape or radius corner. In other words, additional embodiments could be sketched for FIG. 81B, but in the preferred embodiment, the uncovered or exposed portions of the gold brazes 162 are kept out of the high-voltage breakdown area 412*d*. Referring once again to FIG. 81B, it is also important, at least in a preferred embodiment, that the radius corners 422 and 424 are also incorporated into the shape of the opening 404. For example, a high-voltage keep-out zone 426 is shown where it would be highly undesirable to have a sharp corner 425 facing the gold braze 150. In this case, a radius corner 422, as illustrated on pin 111*c*, would have significantly reduced vols/mil stress as compared to the sharp corner 425 illustrated in the keep-out zone 426 associated with terminal pin 111*a*.

What is claimed is:

1. A filtered feedthrough assembly that is attachable to an active implantable medical device (AIMD), the filtered feedthrough assembly comprising:
- a) a feedthrough, comprising:
  - i) an electrically conductive ferrule comprising a ferrule sidewall defining a ferrule opening, the ferrule sidewall extending to a ferrule body fluid side spaced from a ferrule device side;
  - ii) an insulator hermetically sealed to the ferrule in the ferrule opening, the insulator extending to an insulator body fluid side spaced from an insulator device side, wherein, when the ferrule hermetically sealed to the insulator is attached to an opening in a housing of an AIMD, the ferrule body fluid side adjacent to the insulator body fluid side, and the ferrule device side adjacent to the insulator device side reside outside and inside the AIMD, respectively; and
  - iii) at least a first terminal pin hermetically sealed to the insulator in a first via hole by a first braze, wherein the first terminal pin extends outwardly beyond the insulator device side; and
- b) a filter capacitor, comprising:
  - i) a dielectric substrate comprising a dielectric substrate peripheral surface extending to a dielectric substrate first end surface spaced from a dielectric substrate second end surface, wherein the dielectric substrate supports at least one active electrode plate interleaved in a capacitive relationship with at least one ground electrode plate, and wherein the dielectric substrate first end surface is adjacent to the insulator and the ferrule device sides; and
  - ii) at least a first passageway extending through the dielectric substrate to the dielectric substrate first and second end surfaces, wherein the first terminal pin extend through the first passageway and outwardly beyond the dielectric substrate second end surface,
  - iii) wherein the first terminal pin is electrically connected to one of the active and ground electrode plates in the first passageway; and
- c) a polymeric insulating material comprising one or more layers contacted to the dielectric substrate second end surface, wherein the polymeric insulating material comprises insulating nanoparticles.

2. The filtered feedthrough assembly of claim 1, wherein the dielectric substrate second end surface is recessed below the ferrule device side, and the polymeric insulating material extends to an inner surface of the ferrule sidewall.

3. The filtered feedthrough assembly of claim 1, wherein the dielectric substrate second end surface is spaced above the ferrule device side, and wherein the at least one ground electrode plate extends to the dielectric substrate peripheral surface, and an external ground metallization contacts the ground electrode plate at the peripheral surface, and wherein the polymeric insulating material contacted to the dielectric substrate second end surface contacts the external ground metallization at the dielectric substrate peripheral surface.

4. The filtered feedthrough assembly of claim 1, wherein the polymeric insulating material is selected from silicone, polyurethane, polyester, polyethylene, polypropylene, polyimide, polyamide, acrylic, polyacrylates, perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), polytetrafluoroethylene (PTFE), ethylene tetrafluoroethylene (ETFE), polyoxymethylene (POM) polycarbonate (PC), epoxy, rubber, acetal, polyacetal, polyformaldehyde, phenolic, polysulfide, and combinations thereof.

5. The filtered feedthrough assembly of claim 1, wherein the nanoparticles are selected from $Al_2O_3$, BaO, CaO, $CeO_2$, MgO, ZnO, $ZrO_2$, $SiO_2$, $TiO_2$, $Al_2SiO_{53}$, $BaTiO_3$, $SrTiO_2$, zirconia toughened alumina (ZTA), alumina toughened zirconia (ATZ), yttrium stabilized zirconia (YSZ), yttrium-toughened zirconia (YTZP), aluminum nitride (AlN), silicon nitride ($Si_3N_4$), boron nitride (BN), carbon nitride (CN), and combinations thereof.

6. The filtered feedthrough assembly of claim 5, wherein the nanoparticles range in size from greater than about 100 nanometers (0.1 microns) to about 40,000 nanometers (40 microns).

7. The filtered feedthrough assembly of claim 5, wherein a nanoparticle loading in the polymeric insulating material ranges from >0 to about 40%, by weight.

8. The filtered feedthrough assembly of claim 1, wherein the polymeric insulating material contacted to the dielectric substrate second end surface is a first polymeric insulating washer.

9. The filtered feedthrough assembly of claim 8, wherein the first polymeric insulating washer has opposed first and second sides and a first thermoplastic coating contacts the first side of the first polymeric insulating washer adjacent to the dielectric substrate second end surface.

10. The filtered feedthrough assembly of claim 9, wherein the first thermoplastic coating contacting the first side of the first polymeric insulating washer adjacent to the dielectric substrate second end surface is an insulating adhesive.

11. The filtered feedthrough assembly of claim 9, wherein a second thermoplastic coating contacts the second side of the first polymeric insulating washer spaced from the dielectric substrate second end surface.

12. The filtered feedthrough assembly of claim 1, wherein a second polymeric washer is positioned between the insulator device side and the dielectric substrate first end surface, and wherein the second polymeric washer has at least a washer first opening through which the first terminal pin extends.

13. The filtered feedthrough assembly of claim 1, wherein the first terminal pin is a first active terminal pin, and wherein a first electrical connection material connects the first active terminal pin to a capacitor first metallization electrically connected to the at least one active electrode plate in the first passageway.

14. The filtered feedthrough assembly of claim 1, wherein the first terminal pin is a first ground terminal pin, and wherein a first electrical connection material connects the first ground terminal pin to a capacitor first metallization electrically connected to the at least one ground electrode plate in the first passageway.

15. The filtered feedthrough assembly of claim 5, wherein a nanoparticle loading in the polymeric insulating material ranges from >40% to ≤90% by weight.

16. The filtered feedthrough assembly of claim 5, wherein a nanoparticle loading in the polymeric insulating material ranges from >0% to ≤30% by volume.

17. The filtered feedthrough assembly of claim 5, wherein a nanoparticle loading in the polymeric insulating material ranges from >40% to ≤99% by volume.

* * * * *